United States Patent
Kolluri et al.

(10) Patent No.: US 9,062,068 B2
(45) Date of Patent: Jun. 23, 2015

(54) PROTEIN KINASE C INHIBITORS AND USES THEREOF

(71) Applicant: RIGEL PHARMACEUTICALS, INC., South San Francisco, CA (US)

(72) Inventors: Rao Kolluri, Foster City, CA (US); Esteban Masuda, Menlo Park, CA (US); Kin Tso, San Francisco, CA (US); Salvador Alvarez, Fremont, CA (US); Thilo Heckrodt, San Francisco, CA (US); Sacha Holland, San Francisco, CA (US); Ryan Kelley, Pacifica, CA (US); Matthew Duncton, San Bruno, CA (US); Rajinder Singh, Belmont, CA (US); Darren McMurtrie, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/095,893

(22) Filed: Dec. 3, 2013

(65) Prior Publication Data

US 2014/0163022 A1 Jun. 12, 2014

Related U.S. Application Data

(60) Provisional application No. 61/733,259, filed on Dec. 4, 2012.

(51) Int. Cl.
*C07D 455/02* (2006.01)
*C07D 498/04* (2006.01)

(52) U.S. Cl.
CPC ............ *C07D 498/04* (2013.01); *C07D 455/02* (2013.01)

(58) Field of Classification Search
CPC .................................................... C07D 405/22
USPC ........... 544/323, 325, 330, 334; 514/256, 275
See application file for complete search history.

(56) References Cited

U.S. PATENT DOCUMENTS

| | | | |
|---|---|---|---|
| 5,958,935 | A | 9/1999 | Davis et al. |
| 7,517,886 | B2 | 4/2009 | Singh et al. |
| 2004/0029902 | A1 | 2/2004 | Singh et al. |
| 2005/0234049 | A1 | 10/2005 | Singh et al. |
| 2010/0184755 | A1 | 7/2010 | Zhao et al. |

FOREIGN PATENT DOCUMENTS

| | | |
|---|---|---|
| DE | 493586 | 2/1930 |
| EP | 0379806 | 8/1990 |
| WO | 03063794 | 8/2003 |
| WO | 2004014382 | 2/2004 |
| WO | 2004043386 | 5/2004 |
| WO | 2005016893 | 2/2005 |
| WO | 2005062918 | 7/2005 |
| WO | 2010083207 | 7/2010 |
| WO | 2010090875 | 8/2010 |
| WO | 2011068898 | 6/2011 |
| WO | 2012012619 | 1/2012 |

OTHER PUBLICATIONS

Abboushi, et al., J. Immunol., 173:3193-3200 (2004).
Baumann, et al. "Molecular mechanism of immunosuppressive agents,"Transplant. Proc., 4(2): 4-7 (1992).
Blay, et al., "Protein Kinase C θ Is Highly Expressed in Gastrointestinal Stromal Tumors But Not in Other Mesenchymal Neoplasias" Clinical Cancer Research, 10: 4089-4095 (2004).
Hoyer, et al. "Interleukin-2 in the development and control of inflammatory disease" Immunol Rev 266:19-28 (2008).
Isakov, et al., "Protein Kinase Cθ in T Cell Activation" Annual Review of Immunology, 20, 761-794 (2002).
Kuno, et al., "Constitutive kinase activation of the TEL-Syk fusion gene in myelodysplastic syndrome with t(9;12)(q22; p12)" Blood, 97:1050-1055 (2001).
Michael and Jungmann, Tetrahedron, vol. 48, No. 46, pp. 10211-20220 (1992).
Mondiano, et al. "Protein kinase C regulates both production and secretion of interleukin 2" J Biol Chem 266 (16)10552-10561(1991).
Newton, "Protein kinase C: structure, function, and regulation" J Biol Chem 270(48):28495-28498 (1995).
Turhan, et al., "Highly purified primitive hematopoietic stem cells are PML-RARA negative and generate nonclonal progenitors in acute promyelocytic leukemia," Blood 85(8):2154-2161 (1995).
PCT/US2013/072917 International Search Report 1-13 (2014).
Rusconi, et al. "Synthesis and comparison of antiplasmodial activity of (+), (−) of racemic 7-cloro-4-(n-lupinyl)aminoquinoline" Bior & Med. Chem., 20: 5980-5985 (2012).

*Primary Examiner* — Bruck Kifle
(74) *Attorney, Agent, or Firm* — Rudy J. Ng; Carol L. Francis; Bozicevic, Field & Francis LLP

(57) ABSTRACT

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions that include these compounds, methods of using these compounds in the treatment of various diseases and disorders, processes for preparing these compounds and intermediates useful in these processes.

25 Claims, No Drawings

PROTEIN KINASE C INHIBITORS AND USES THEREOF

INTRODUCTION

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, PKC $\alpha$, $\beta_i$, $\beta_{ii}$ and $\gamma$, contain four homologous domains (C1, C2, C3 and C4) and require calcium, phosphatidylserine, and diacylglycerol or phorbol esters for activation. Members of the "novel" or "nPKC" subfamily, PKC $\delta$, $\epsilon$, $\eta$ and $\theta$, lack the C2 homologous domain and do not require calcium for activation. Finally, members of the "atypical" or "$\alpha$PKC" subfamily, PKC $\zeta$ and $\lambda$/i, lack both the C2 and one-half of the C1 homologous domains and are insensitive to diacylglycerol, phorbol esters and calcium.

SUMMARY

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions that include these compounds, methods of using these compounds in the treatment of various diseases and disorders, processes for preparing these compounds and intermediates useful in these processes.

Embodiments of the chemical structures are provided throughout the disclosure. By way of example, such compounds are represented by the following formula (I):

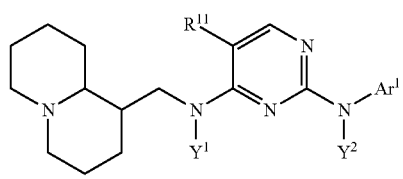

(I)

wherein $R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;

$Y^1$ and $Y^2$ are independently selected from hydrogen and alkyl; and $Ar^1$ is selected from aryl, substituted aryl, heteroaryl, and substituted heteroaryl;

or a salt or stereoisomer thereof.

DETAILED DESCRIPTION

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions that include these compounds, methods of using these compounds in the treatment of various diseases and disorders, processes for preparing these compounds and intermediates useful in these processes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is specifically contemplated. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

Terms

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—$CH_2C$≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, and —$SO_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Acylamino" refers to the groups —$NR^{20}C(O)$alkyl, —$NR^{20}C(O)$substituted alkyl, N $R^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{21}C(O)NR^{22}R^{23}$ where $R^{21}$, $R^{22}$, and $R^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)β-cycloalkyl, —C(O)O-substituted cycloalkyl, —C(O)β-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)β-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, $-R^{60}$, $-O^-M^+$, $-OR^{70}$, $-SR^{70}$, $-S^-M^+$, $-NR^{80}R^{80}$, trihalomethyl, $-CF_3$, $-CN$, $-NO$, $-NO_2$, $-S(O)_2R^{70}$, $-S(O)_2O^-M^+$, $-S(O)_2OR^{70}$, $-OS(O)_2R^{70}$, $-OS(O)_2O^-M^+$, $-OS(O)_2OR^{70}$, $-P(O)(O^-)_2(M^+)_2$, $-P(O)(OR^{70})O^-M^+$, $-P(O)(OR^{70})(OR^{70})$, $-C(O)R^{70}$, $-C(S)R^{70}$, $-C(NR^{70})R^{70}$, $-C(O)OR^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OC(O)OR^{70}$, $-OC(S)OR^{70}$, $-NR^{70}C(O)R^{70}$, $-NR^{70}C(S)R^{70}$, $-NR^{70}C(O)OR^{70}$, $-NR^{70}C(S)OR^{70}$, $-NR^{70}C(O)NR^{80}R^{80}$, $-NR^{70}C(NR^{70})R^{70}$ and $-NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically nonfeasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Representative Embodiments

The following substituents and values are intended to provide representative examples of various aspects and embodiments. These representative values are intended to further define and illustrate such aspects and embodiments and are not intended to exclude other embodiments or to limit the scope of the present disclosure. In this regard, the representation that a particular value or substituent is preferred is not intended in any way to exclude other values or substituents from the present disclosure unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The compositions of the present disclosure include compounds of formulae I-IV, shown below. Pharmaceutical compositions and methods of the present disclosure also contemplate compounds of formulae I-IV.

Formula I

Embodiments of the present disclosure include a compound of formula (I):

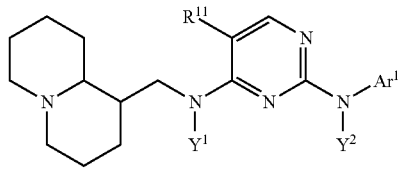

(I)

wherein $R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;

$Y^1$ and $Y^2$ are independently selected from hydrogen and alkyl; and $Ar^1$ is selected from aryl, substituted aryl, heteroaryl, and substituted heteroaryl; or a salt or stereoisomer thereof.

In formula (I), $Ar^1$ is selected from aryl, substituted aryl, heteroaryl, and substituted heteroaryl. In certain embodiments, $Ar^1$ is aryl or substituted aryl. In certain embodiments, $Ar^1$ is aryl. In certain embodiments, $Ar^1$ is substituted aryl. In certain embodiments, $Ar^1$ is heteroaryl or substituted heteroaryl. In certain embodiments, $Ar^1$ is heteroaryl. In certain embodiments, $Ar^1$ is substituted heteroaryl.

Formula II

Embodiments of the present disclosure include a compound of formula (II):

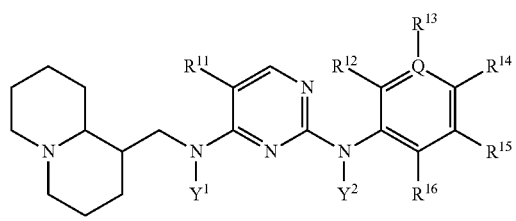

(II)

wherein $R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;

$Y^1$ and $Y^2$ are independently selected from hydrogen and alkyl;

Q is C or N; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

Aspects of the present embodiments also include a compound of formula (IIa):

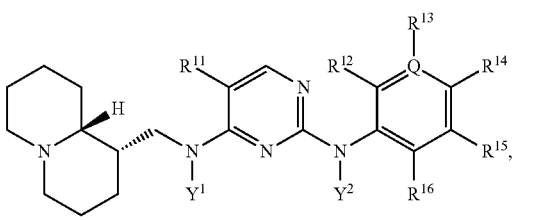

(IIa)

wherein $R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;

$Y^1$ and $Y^2$ are independently selected from hydrogen and alkyl;

Q is C or N; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

Reference to formula (II) is meant to include compounds of formula (II) and (IIa).

In formula (II), Q is C or N. In certain embodiments, Q is C. In certain embodiments, Q is N. In certain embodiments where Q is N, $R^{13}$ is absent.

In formula (II), $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{13}$, $R^{14}$, $R^{15}$, and $R^{16}$ are independently selected from hydrogen, alkyl, substituted alkyl, halogen, cyano, hydroxyl, alkoxy, substituted alkoxy, amino, substituted amino, acylamino, aminocarbonylamino, acyl, aminoacyl, aminocarbonyloxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{13}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{13}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, and substituted heteroaryl, or $R^{14}$ and $R^{15}$ together with the carbon atoms to which they are attached form a heterocyclyl or substituted heterocyclyl 5 to 8-membered ring.

In certain embodiments, $R^{14}$ and $R^{15}$ together with the carbon atoms to which they are attached form a heterocyclyl or substituted heterocyclyl 5 to 8-membered ring. In certain embodiments, $R^{12}$, $R^{13}$, $R^{14}$, $R^{15}$, and $R^{16}$ are independently selected from hydrogen, alkyl, substituted alkyl, halogen, cyano, alkoxy, substituted alkoxy, sulfur pentafluoride, cycloalkyl, substituted, cycloalkyl, substituted cycloalkyl, heteroaryl, substituted heteroaryl, heterocyclyl, and substituted heterocyclyl.

In certain embodiments, $R^{12}$, $R^{13}$, $R^{14}$, $R^{15}$, and $R^{16}$ are independently selected from hydrogen, alkyl, substituted alkyl, and halogen. In certain embodiments, $R^{12}$, $R^{13}$, $R^{14}$, $R^{15}$, and $R^{16}$ are independently selected from hydrogen, halogen, alkoxy, and substituted alkoxy. In certain embodiments, $R^{12}$, $R^{13}$, $R^{14}$, $R^{15}$, and $R^{16}$ are independently selected from hydrogen, alkyl, substituted alkyl, halogen, alkoxy, substituted alkoxy, cycloalkyl, substituted cycloalkyl, heterocyclyl, and substituted heterocyclyl. In certain embodiments, $R^{12}$, $R^{13}$, $R^{14}$, $R^{15}$, and $R^{16}$ are independently selected from hydrogen, alkyl, substituted alkyl, cyano, alkoxy, substituted alkoxy, sulfur pentafluoride, heteroaryl, substituted heteroaryl, heterocyclyl, and substituted heterocyclyl.

In certain embodiments, $R^{12}$ is selected from hydrogen, alkyl, substituted alkyl, and halogen. In certain embodiments, $R^{13}$ is selected from hydrogen, halogen, alkoxy, and substituted alkoxy. In certain embodiments, $R^{14}$ is selected from hydrogen, alkyl, substituted alkyl, halogen, alkoxy, substituted alkoxy, cycloalkyl, substituted cycloalkyl, heterocyclyl, and substituted heterocyclyl. In certain embodiments, $R^{15}$ is selected from hydrogen, alkyl, substituted alkyl, cyano, alkoxy, substituted alkoxy, sulfur pentafluoride, heteroaryl, substituted heteroaryl, heterocyclyl, and substituted heterocyclyl. In certain embodiments, $R^{16}$ is selected from hydrogen, alkyl, substituted alkyl, and halogen.

In formula (IIa), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula III
Embodiments of the present disclosure include a compound of formula (III):

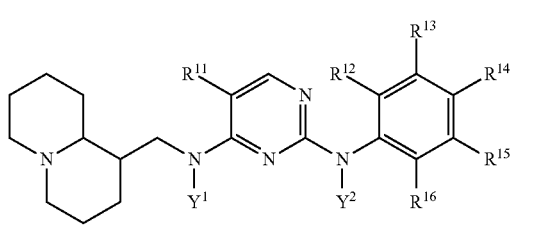

(III)

wherein
$R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;

$Y^1$ and $Y^2$ are independently selected from hydrogen and alkyl; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

Aspects of the present embodiments also include a compound of formula (IIIa):

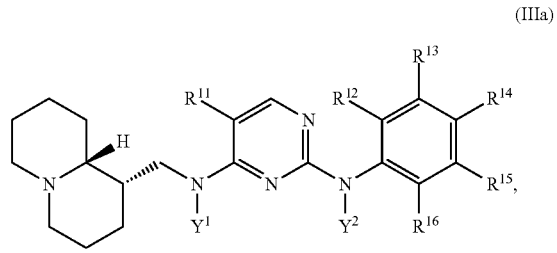

(IIIa)

wherein
$R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;

$Y^1$ and $Y^2$ are independently selected from hydrogen and alkyl; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

Reference to formula (III) is meant to include compounds of formula (III) and (IIIa).

In formula (III), $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{13}$, $R^{14}$, $R^{15}$, and $R^{16}$ are independently selected from hydrogen, alkyl, substituted alkyl, halogen, cyano, hydroxyl, alkoxy, substituted alkoxy, amino, substituted amino, acylamino, aminocarbonylamino, acyl, aminoacyl, aminocarbonyloxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{13}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{13}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, and substituted heteroaryl, or $R^{14}$ and $R^{15}$ together with the carbon atoms to which they are attached form a heterocyclyl or substituted heterocyclyl 5 to 8-membered ring.

In certain embodiments, $R^{14}$ and $R^{15}$ together with the carbon atoms to which they are attached form a heterocyclyl or substituted heterocyclyl 5 to 8-membered ring. In certain embodiments, $R^{12}$, $R^{13}$, $R^{14}$, $R^{15}$, and $R^{16}$ are independently selected from hydrogen, alkyl, substituted alkyl, halogen, cyano, alkoxy, substituted alkoxy, sulfur pentafluoride, cycloalkyl, substituted, cycloalkyl, substituted cycloalkyl, heteroaryl, substituted heteroaryl, heterocyclyl, and substituted heterocyclyl.

In certain embodiments, $R^{12}$, $R^{13}$, $R^{14}$, $R^{15}$, and $R^{16}$ are independently selected from hydrogen, alkyl, substituted alkyl, and halogen. In certain embodiments, $R^{12}$, $R^{13}$, $R^{14}$, $R^{15}$, and $R^{16}$ are independently selected from hydrogen, halogen, alkoxy, and substituted alkoxy. In certain embodiments, $R^{12}$, $R^{13}$, $R^{14}$, $R^{15}$, and $R^{16}$ are independently selected from hydrogen, alkyl, substituted alkyl, halogen, alkoxy, substituted alkoxy, cycloalkyl, substituted cycloalkyl, heterocyclyl, and substituted heterocyclyl. In certain embodiments, $R^{12}$, $R^{13}$, $R^{14}$, $R^{15}$ and $R^{16}$ are independently selected from hydrogen, alkyl, substituted alkyl, cyano, alkoxy, substituted alkoxy, sulfur pentafluoride, heteroaryl, substituted heteroaryl, heterocyclyl, and substituted heterocyclyl.

In certain embodiments, $R^{12}$ is selected from hydrogen, alkyl, substituted alkyl, and halogen. In certain embodiments, $R^{13}$ is selected from hydrogen, halogen, alkoxy, and substituted alkoxy. In certain embodiments, $R^{14}$ is selected from hydrogen, alkyl, substituted alkyl, halogen, alkoxy, substituted alkoxy, cycloalkyl, substituted cycloalkyl, heterocyclyl, and substituted heterocyclyl. In certain embodiments, $R^{15}$ is selected from hydrogen, alkyl, substituted alkyl, cyano, alkoxy, substituted alkoxy, sulfur pentafluoride, heteroaryl, substituted heteroaryl, heterocyclyl, and substituted heterocyclyl. In certain embodiments, $R^{16}$ is selected from hydrogen, alkyl, substituted alkyl, and halogen.

In formula (IIIa), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula IV

Embodiments of the present disclosure include a compound of formula (IV):

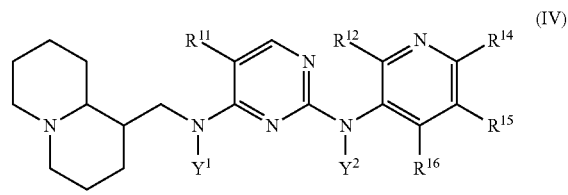

wherein $R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;

$Y^1$ and $Y^2$ are independently selected from hydrogen and alkyl; and $R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

Aspects of the present embodiments also include a compound of formula (IVa):

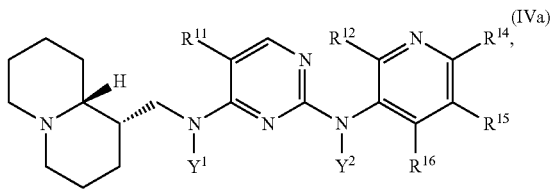

wherein $R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;

$Y^1$ and $Y^2$ are independently selected from hydrogen and alkyl; and $R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

Reference to formula (IV) is meant to include compounds of formula (IV) and (IVa).

In formula (IV), $R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl. In certain embodiments of formula (IV), $R^{13}$ is absent.

In certain embodiments, $R^{12}$, $R^{14}$, $R^{15}$, and $R^{16}$ are independently selected from hydrogen, alkyl, substituted alkyl, halogen, cyano, hydroxyl, alkoxy, substituted alkoxy, amino, substituted amino, acylamino, aminocarbonylamino, acyl, aminoacyl, aminocarbonyloxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments, $R^{12}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, and substituted heteroaryl, or $R^{14}$ and $R^{15}$ together with the carbon atoms to which they are attached form a heterocyclyl or substituted heterocyclyl 5 to 8-membered ring.

In certain embodiments, $R^{14}$ and $R^{15}$ together with the carbon atoms to which they are attached form a heterocyclyl or substituted heterocyclyl 5 to 8-membered ring. In certain embodiments, $R^{12}$, $R^{14}$, $R^{15}$, and $R^{16}$ are independently selected from hydrogen, alkyl, substituted alkyl, halogen, cyano, alkoxy, substituted alkoxy, sulfur pentafluoride, cycloalkyl, substituted, cycloalkyl, substituted cycloalkyl, heteroaryl, substituted heteroaryl, heterocyclyl, and substituted heterocyclyl.

In certain embodiments, $R^{12}$, $R^{14}$, $R^{15}$, and $R^{16}$ are independently selected from hydrogen, alkyl, substituted alkyl, and halogen. In certain embodiments, $R^{12}$, $R^{14}$, $R^{15}$, and $R^{16}$ are independently selected from hydrogen, halogen, alkoxy, and substituted alkoxy. In certain embodiments, $R^{12}$, $R^{14}$, $R^{15}$, and $R^{16}$ are independently selected from hydrogen, alkyl, substituted alkyl, halogen, alkoxy, substituted alkoxy, cycloalkyl, substituted cycloalkyl, heterocyclyl, and substituted heterocyclyl. In certain embodiments, $R^{12}$, $R^{14}$, $R^{15}$, and $R^{16}$ are independently selected from hydrogen, alkyl, substituted alkyl, cyano, alkoxy, substituted alkoxy, sulfur pentafluoride, heteroaryl, substituted heteroaryl, heterocyclyl, and substituted heterocyclyl.

In certain embodiments, $R^{12}$ is selected from hydrogen, alkyl, substituted alkyl, and halogen. In certain embodiments, $R^{13}$ is absent. In certain embodiments, $R^{14}$ is selected from hydrogen, alkyl, substituted alkyl, halogen, alkoxy, substituted alkoxy, cycloalkyl, substituted cycloalkyl, heterocyclyl, and substituted heterocyclyl. In certain embodiments, $R^{15}$ is selected from hydrogen, alkyl, substituted alkyl, cyano, alkoxy, substituted alkoxy, sulfur pentafluoride, heteroaryl, substituted heteroaryl, heterocyclyl, and substituted heterocyclyl. In certain embodiments, $R^{16}$ is selected from hydrogen, alkyl, substituted alkyl, and halogen.

In formula (IVa), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Certain Embodiments of Formulae I-IV

With reference to formulae I-IV, the portion of the compound as shown in the following formula:

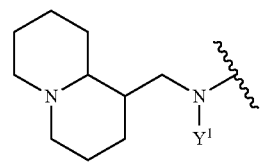

includes at least two chiral centers, and thus at least four stereoisomers. For clarity the numbering of the ring system is shown below with optional substituents omitted.

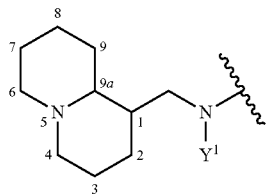

With continued reference to formulae I-IV, the (1,9a) cis diastereomer has the structure:

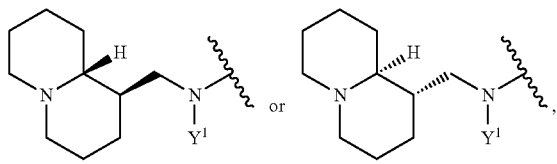

and the (1,9a) trans diastereomer has the structure:

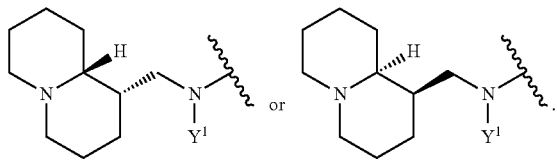

In certain embodiments of formulae I-IV, the (1,9a) trans diastereomer has the structure:

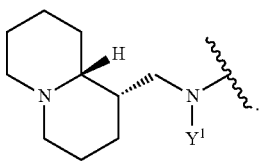

In formulae I-IV, $R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$.

In certain embodiments, $R^{11}$ is selected from hydrogen, alkyl, substituted alkyl, cycloalkyl, substituted cycloalkyl, alkoxy, substituted alkoxy, amino, substituted amino, cyano, halogen, acyl and aminoacyl.

In certain embodiments, $R^{11}$ is hydrogen. In certain embodiments, $R^{11}$ is alkyl or substituted alkyl. In certain embodiments, $R^{11}$ is alkyl, such as a $C_{1-6}$ alkyl, or $C_{1-3}$ alkyl. In certain embodiments, $R^{11}$ is substituted alkyl, such as a substituted $C_{1-6}$ alkyl, or substituted $C_{1-3}$ alkyl. In certain embodiments, $R^{11}$ is methyl. In certain embodiments, $R^{11}$ is trifluoromethyl. In certain embodiments, $R^{11}$ is cycloalkyl or substituted cycloalkyl. In certain embodiments, $R^{11}$ is cycloalkyl, such as a $C_{3-8}$ cycloalkyl, or $C_{3-6}$ cycloalkyl. In certain embodiments, $R^{11}$ is substituted cycloalkyl, such as a substituted $C_{3-8}$ cycloalkyl, or substituted $C_{3-6}$ cycloalkyl. In certain embodiments, $R^{11}$ is alkoxy or substituted alkoxy. In certain embodiments, $R^{11}$ is alkoxy, such as a $C_{1-6}$ alkoxy, or $C_{1-3}$ alkoxy. In certain embodiments, $R^{11}$ is substituted alkoxy, such as a substituted $C_{1-6}$ alkoxy, or substituted $C_{1-3}$ alkoxy. In certain embodiments, $R^{11}$ is methoxy. In certain embodiments, $R^{11}$ is amino or substituted amino. In certain embodiments, $R^{11}$ is dimethylamino. In certain embodiments, $R^{11}$ is cyano. In certain embodiments, $R^{11}$ is halogen. In certain embodiments, $R^{11}$ is fluoro. In certain embodiments, $R^{11}$ is chloro. In certain embodiments, $R^{11}$ is acyl. In certain embodiments, $R^{11}$ is aminoacyl.

In certain embodiments, $R^{11}$ is carboxyl, carboxyl ester, nitro, alkenyl, substituted alkenyl, alkynyl, substituted alkynyl, aryl, substituted aryl, heteroaryl, substituted heteroaryl, sulfide, substituted sulfide, and $SF_5$. In certain embodiments, $R^{11}$ is carboxyl or carboxyl ester. In certain embodiments, $R^{11}$ is nitro. In certain embodiments, $R^{11}$ is alkenyl or substituted alkenyl. In certain embodiments, $R^{11}$ is alkenyl, such as a $C_{2-6}$ alkenyl, or $C_{2-4}$ alkenyl. In certain embodiments, $R^{11}$ is substituted alkenyl, such as a substituted $C_{2-6}$ alkenyl, or substituted $C_{2-4}$ alkenyl. In certain embodiments, $R^{11}$ is alkynyl or substituted alkynyl. In certain embodiments, $R^{11}$ is alkynyl, such as a $C_{2-6}$ alkynyl, or $C_{2-4}$ alkynyl. In certain embodiments, $R^{11}$ is substituted alkynyl, such as a substituted $C_{2-6}$ alkynyl, or substituted $C_{2-4}$ alkynyl. In certain embodiments, $R^{11}$ is aryl or substituted aryl. In certain embodiments, $R^{11}$ is aryl. In certain embodiments, $R^{11}$ is substituted aryl. In certain embodiments, $R^{11}$ is heteroaryl or substituted heteroaryl. In certain embodiments, $R^{11}$ is heteroaryl. In certain embodiments, $R^{11}$ is substituted heteroaryl. In certain embodiments, $R^{11}$ is sulfide, substituted sulfide or $SF_5$. In certain embodiments, $R^{11}$ is sulfide. In certain embodiments, $R^{11}$ is substituted sulfide. In certain embodiments, $R^{11}$ is $SF_5$.

In formulae I-IV, $Y^1$ and $Y^2$ are independently selected from hydrogen and alkyl. In certain embodiments, $Y^1$ and $Y^2$ are hydrogen. In certain embodiments, $Y^1$ and $Y^2$ are alkyl. In certain embodiments, one of $Y^1$ and $Y^2$ is hydrogen and the other of $Y^1$ and $Y^2$ is alkyl.

Embodiments of the compounds of formulae I-IV are shown in the following table.

TABLE 1

| Compound | $R^{11}$ | $Y^1$ | $Y^2$ | $Ar^1$ |
|---|---|---|---|---|
| 1 | F | H | H | |

TABLE 1-continued
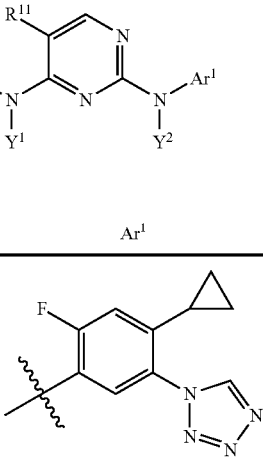
| Compound | R11 | Y1 | Y2 | Ar1 |
|---|---|---|---|---|
| 2 | F | H | H | 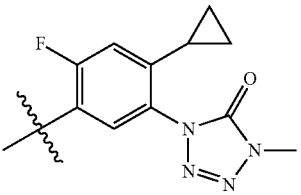 [SMILES: *c1cc(-n2nnn(C)c2=O)c(C2CC2)cc1F] |
| 3 | F | H | H |  |
| 4 | F | H | H | 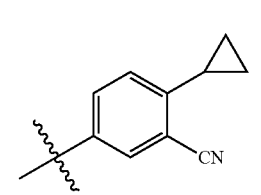 [SMILES: *c1ccc(C2CC2)c(C#N)c1] |
| 5 | Cl | H | H | 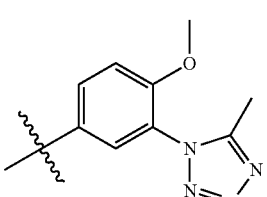 |
| 6 | F | H | H | 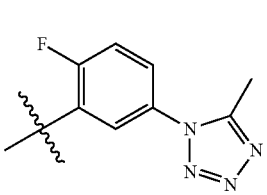 [SMILES: *c1cc(-n2nnnc2C)ccc1F] |
| 7 | F | H | H | 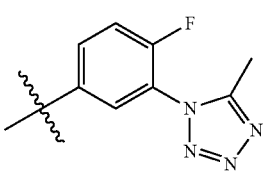 [SMILES: *c1ccc(F)c(-n2nnnc2C)c1] |
| 8 | F | H | H | 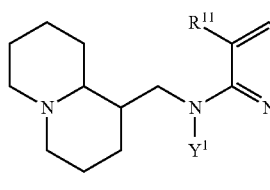 |
| 9 | F | H | H | 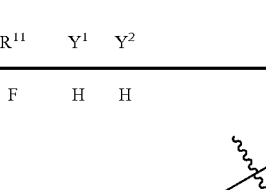 |
| 10 | F | H | H | 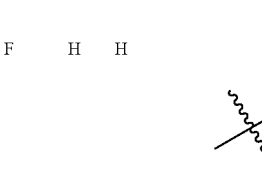 |
| 11 | F | H | H | 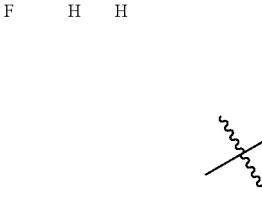 |
| 12 | F | H | H | 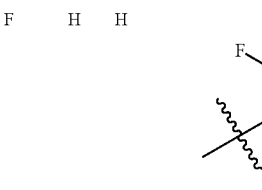 |
| 13 | F | H | H | 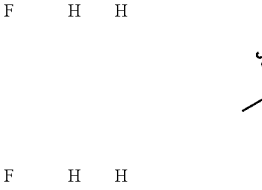 |
| 14 | F | H | H | 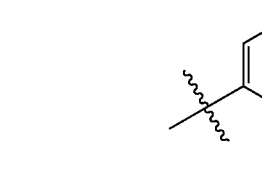 |
| 15 | F | H | H | 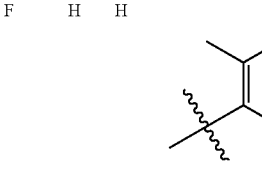 |

TABLE 1-continued
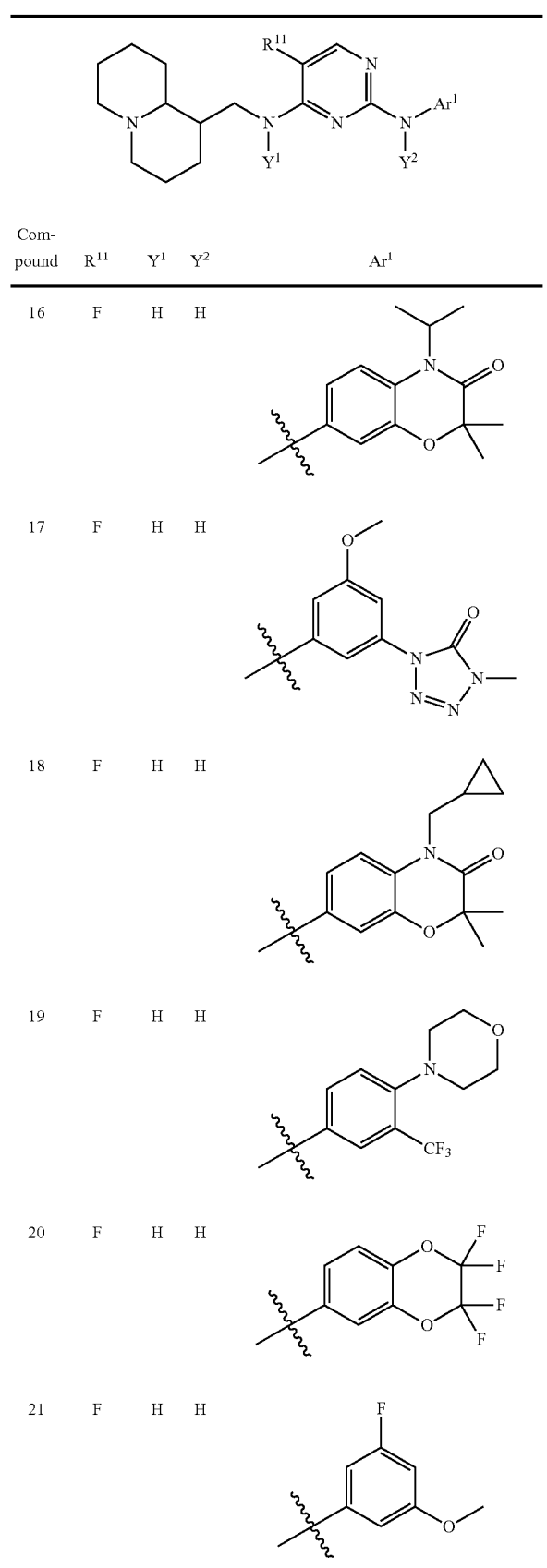
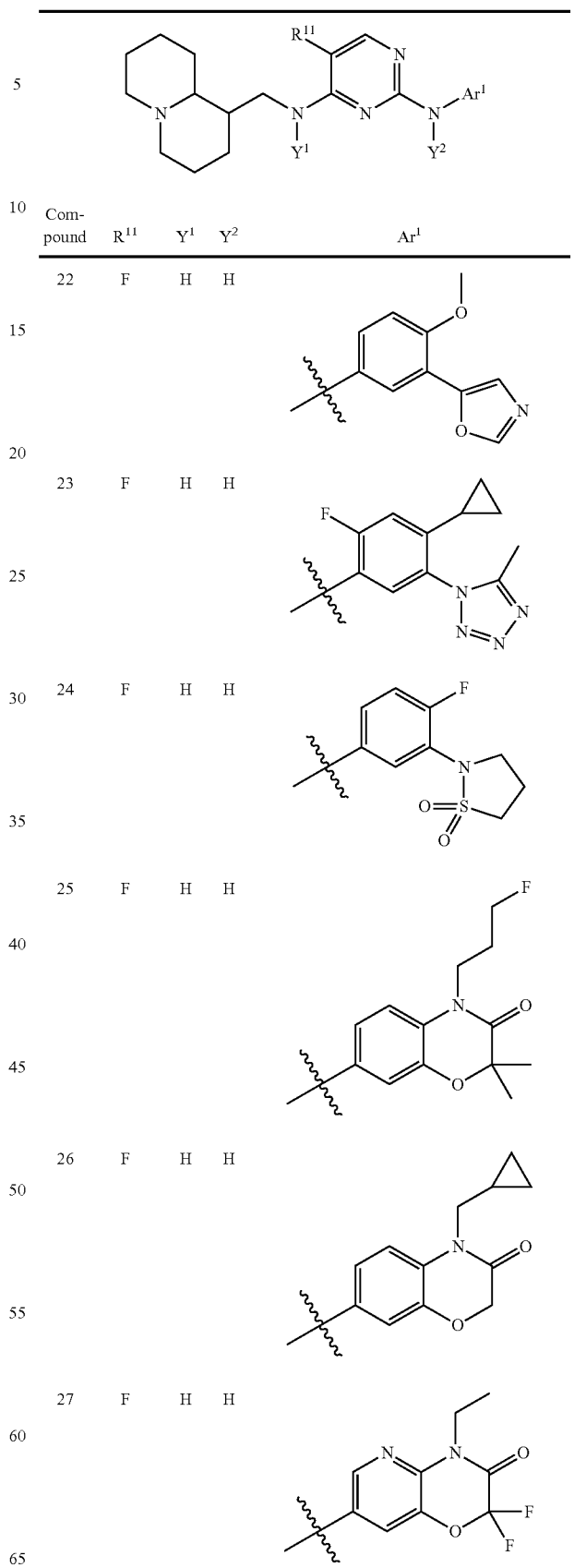

TABLE 1-continued
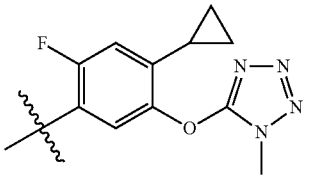 [SMILES: *c1cc(Oc2nnnn2C)c(C2CC2)cc1F]
| Compound | R[11] | Y[1] | Y[2] | Ar[1] |
|---|---|---|---|---|
| 28 | F | H | H | 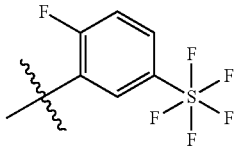 [SMILES: *c1cc(S(F)(F)(F)(F)F)ccc1F] |
| 29 | F | H | H | 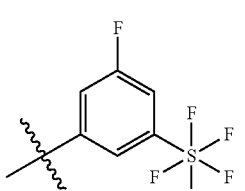 |
| 30 | F | H | H | 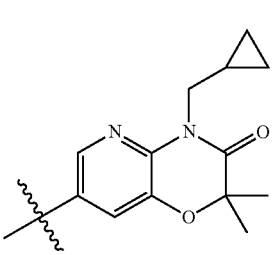 [SMILES: *c1cnc2c(c1)OC(C)(C)C(=O)N2CC1CC1] |
| 31 | F | H | H | 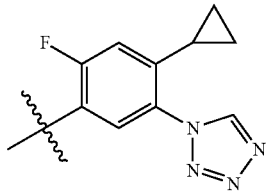 [SMILES: *c1cc(-n2cnnn2)c(C2CC2)cc1F] |
| 32 | Cl | H | H | 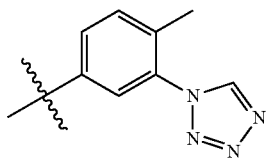 [SMILES: *c1ccc(C)c(-n2cnnn2)c1] |
| 33 | Cl | H | H | 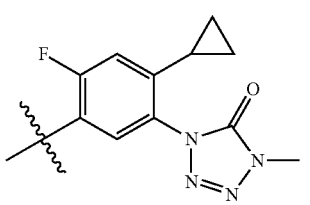 [SMILES: *c1cc(-n2nnn(C)c2=O)c(C2CC2)cc1F] |
| 34 | Cl | H | H | 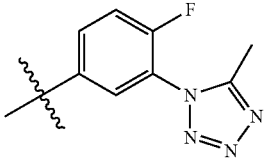 [SMILES: *c1ccc(F)c(-n2nnnc2C)c1] |
TABLE 1-continued
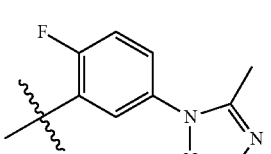
| Compound | R[11] | Y[1] | Y[2] | Ar[1] |
|---|---|---|---|---|
| 35 | Cl | H | H | 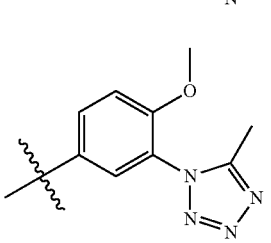 |
| 36 | Cl | H | H | 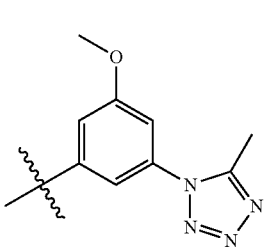 [SMILES: *c1cc(OC)cc(-n2nnnc2C)c1] |
| 37 | Cl | H | H | 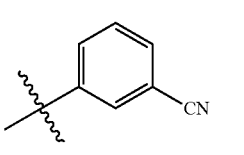 [SMILES: *c1cccc(C#N)c1] |
| 38 | Cl | H | H | 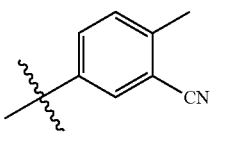 [SMILES: *c1ccc(C)c(C#N)c1] |
| 39 | Cl | H | H | 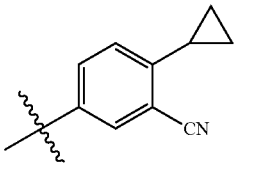 [SMILES: *c1ccc(C2CC2)c(C#N)c1] |
| 40 | Cl | H | H |  |
| 41 | Cl | H | H |  |

TABLE 1-continued

| Compound | R11 | Y1 | Y2 | Ar1 |
|---|---|---|---|---|
| 42 | Cl | H | H | 4-fluoro-2-cyclopropyl-5-cyanophenyl |
| 43 | Cl | H | H | 3,5-dimethoxyphenyl |
| 44 | Cl | H | H | benzoxazol-2(3H)-one-5-yl |
| 45 | F | H | H | 4-fluoro-3-(5-cyclopropyltetrazol-1-yl)phenyl |
| 46 | H | H | H | 4-fluoro-2-cyclopropyl-5-(tetrazol-1-yl)phenyl |
| 47 | H | H | H | 4-methyl-3-(tetrazol-1-yl)phenyl |
| 48 | H | H | H | 4-fluoro-2-cyclopropyl-5-(4-methyl-5-oxo-tetrazol-1-yl)phenyl |
| 49 | H | H | H | 4-fluoro-3-(5-methyltetrazol-1-yl)phenyl |
| 50 | H | H | H | 4-fluoro-3-(5-methyltetrazol-1-yl)phenyl |
| 51 | H | H | H | 4-methoxy-3-(5-methyltetrazol-1-yl)phenyl |
| 52 | H | H | H | 3-methoxy-5-(5-methyltetrazol-1-yl)phenyl |
| 53 | H | H | H | 3-cyanophenyl |
| 54 | H | H | H | 4-methyl-3-cyanophenyl |
| 55 | H | H | H | 4-cyclopropyl-3-cyanophenyl |

TABLE 1-continued

| Compound | R¹¹ | Y¹ | Y² | Ar¹ |
|---|---|---|---|---|
| 56 | H | H | H | 4-fluoro-2-cyano-5-cyclopropylphenyl |
| 57 | H | H | H | 3,5-dimethoxyphenyl |
| 58 | H | H | H | 2-oxo-2,3-dihydrobenzo[d]oxazol-5-yl |
| 59 | CH₃ | H | H | 4-fluoro-2-cyclopropyl-5-(1H-tetrazol-1-yl)phenyl |
| 60 | CH₃ | H | H | 4-methyl-3-(1H-tetrazol-1-yl)phenyl |
| 61 | CH₃ | H | H | 4-fluoro-2-cyclopropyl-5-(4-methyl-5-oxo-4,5-dihydro-1H-tetrazol-1-yl)phenyl |
| 62 | CH₃ | H | H | 4-fluoro-3-(5-methyl-1H-tetrazol-1-yl)phenyl |
| 63 | CH₃ | H | H | 4-fluoro-3-(5-methyl-1H-tetrazol-1-yl)phenyl |
| 64 | CH₃ | H | H | 4-methoxy-3-(5-methyl-1H-tetrazol-1-yl)phenyl |
| 65 | CH₃ | H | H | 3-methoxy-5-(5-methyl-1H-tetrazol-1-yl)phenyl |
| 66 | CH₃ | H | H | 3-cyanophenyl |
| 67 | CH₃ | H | H | 3-cyano-4-methylphenyl |
| 68 | CH₃ | H | H | 3-cyano-4-cyclopropylphenyl |
| 69 | CH₃ | H | H | 4-fluoro-2-cyano-5-cyclopropylphenyl |

TABLE 1-continued
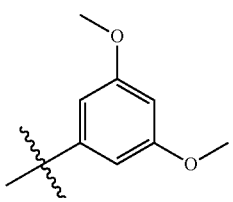 [SMILES: *c1cc(OC)cc(OC)c1]
| Compound | R[11] | Y[1] | Y[2] | Ar[1] |
|---|---|---|---|---|
| 70 | CH₃ | H | H | 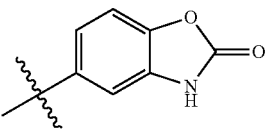 [SMILES: *c1ccc2oc(=O)[nH]c2c1] |
| 71 | CH₃ | H | H | 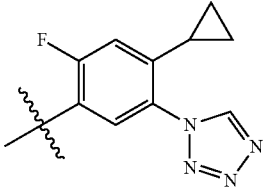 [SMILES: *c1cc(-n2cnnn2)c(C2CC2)cc1F] |
| 72 | OCH₃ | H | H | 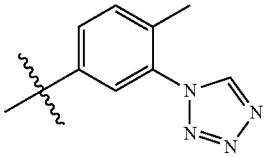 [SMILES: *c1ccc(C)c(-n2cnnn2)c1] |
| 73 | OCH₃ | H | H | 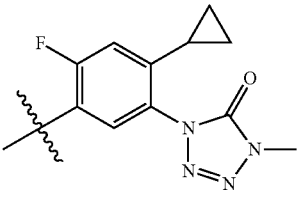 [SMILES: *c1cc(-n2nnn(C)c2=O)c(C2CC2)cc1F] |
| 74 | OCH₃ | H | H | 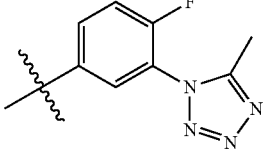 |
| 75 | OCH₃ | H | H | 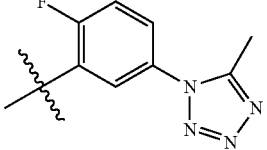 |
| 76 | OCH₃ | H | H | 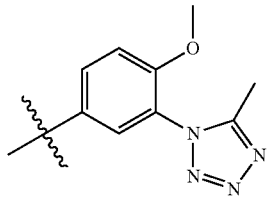 [SMILES: *c1ccc(OC)c(-n2nnnc2C)c1] |
| 77 | OCH₃ | H | H | 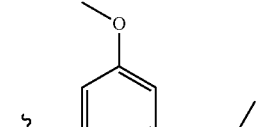 |
| 78 | OCH₃ | H | H | 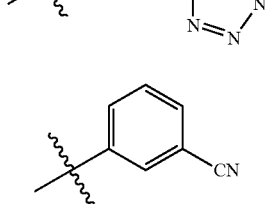 |
| 79 | OCH₃ | H | H | 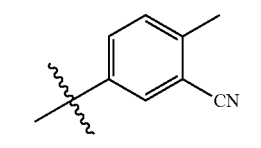 [SMILES: *c1ccc(C)c(C#N)c1] |
| 80 | OCH₃ | H | H | 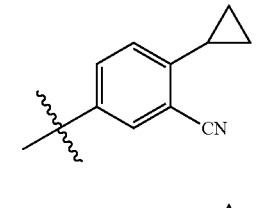 |
| 81 | OCH₃ | H | H | 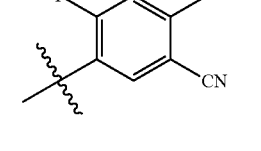 |
| 82 | OCH₃ | H | H | 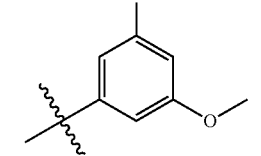 |
| 83 | OCH₃ | H | H |  |

TABLE 1-continued

| Compound | R¹¹ | Y¹ | Y² | Ar¹ |
|---|---|---|---|---|
| 84 | OCH₃ | H | H | 2-oxo-2,3-dihydrobenzoxazol-5-yl |
| 85 | N(CH₃)₂ | H | H | 4-fluoro-2-cyclopropyl-5-(tetrazol-1-yl)phenyl |
| 86 | N(CH₃)₂ | H | H | 4-methyl-3-(tetrazol-1-yl)phenyl |
| 87 | N(CH₃)₂ | H | H | 4-fluoro-2-cyclopropyl-5-(4-methyl-5-oxo-4,5-dihydrotetrazol-1-yl)phenyl |
| 88 | N(CH₃)₂ | H | H | 4-fluoro-3-(5-methyltetrazol-1-yl)phenyl |
| 89 | N(CH₃)₂ | H | H | 4-fluoro-3-(tetrazol-1-yl)phenyl |
| 90 | N(CH₃)₂ | H | H | 4-methoxy-3-(5-methyltetrazol-1-yl)phenyl |
| 91 | N(CH₃)₂ | H | H | 3-methoxy-5-(5-methyltetrazol-1-yl)phenyl |
| 92 | N(CH₃)₂ | H | H | 3-cyanophenyl |
| 93 | N(CH₃)₂ | H | H | 3-cyano-4-methylphenyl |
| 94 | N(CH₃)₂ | H | H | 3-cyano-4-cyclopropylphenyl |
| 95 | N(CH₃)₂ | H | H | 4-fluoro-2-cyclopropyl-5-cyanophenyl |
| 96 | N(CH₃)₂ | H | H | 3,5-dimethoxyphenyl |
| 97 | N(CH₃)₂ | H | H | 2-oxo-2,3-dihydrobenzoxazol-5-yl |
| 98 | F | H | H | 4,4-dimethyl-4H-benzo[b]tetrazolo-fused |

TABLE 1-continued

| Compound | R¹¹ | Y¹ | Y² | Ar¹ |
|---|---|---|---|---|
| 99 | CN | H | H | 4-fluoro-2-cyclopropylphenyl with 4-methyl-5-oxo-tetrazol-1-yl |
| 100 | CF₃ | H | H | 4-fluoro-2-cyclopropylphenyl with tetrazol-1-yl |
| 101 | CF₃ | H | H | 4-methylphenyl with tetrazol-1-yl |
| 102 | CF₃ | H | H | 4-fluoro-2-cyclopropylphenyl with 4-methyl-5-oxo-tetrazol-1-yl |
| 103 | CF₃ | H | H | 4-fluorophenyl with 5-methyltetrazol-1-yl |
| 104 | CF₃ | H | H | 4-fluorophenyl with 5-methyltetrazol-1-yl |
| 105 | CF₃ | H | H | 4-methoxyphenyl with 5-methyltetrazol-1-yl |
| 106 | CF₃ | H | H | 3-methoxyphenyl with 5-methyltetrazol-1-yl |
| 107 | CF₃ | H | H | 3-cyanophenyl |
| 108 | CF₃ | H | H | 4-methyl-3-cyanophenyl |
| 109 | CF₃ | H | H | 4-cyclopropyl-3-cyanophenyl |
| 110 | CF₃ | H | H | 4-fluoro-2-cyclopropyl-5-cyanophenyl |
| 111 | CF₃ | H | H | 3,5-dimethoxyphenyl |
| 112 | CF₃ | H | H | 2-oxo-2,3-dihydrobenzoxazol-5-yl |

TABLE 1-continued

| Compound | R¹¹ | Y¹ | Y² | Ar¹ |
|---|---|---|---|---|
| 113 | CN | H | H | 4-methoxy-3-(5-methyltetrazol-1-yl)phenyl |
| 114 | CN | H | H | 4-fluoro-3-(5-methyltetrazol-1-yl)phenyl |
| 115 | CN | H | H | 3-methoxy-5-(5-methyltetrazol-1-yl)phenyl |
| 116 | CN | H | H | 4-cyclopropyl-5-fluoro-3-(tetrazol-1-yl)phenyl (approx) |
| 117 | CN | H | H | 4-methyl-3-(tetrazol-1-yl)phenyl |
| 118 | CN | H | H | 4-fluoro-3-(5-methyltetrazol-1-yl)phenyl |
| 119 | CN | H | H | 3-cyano-4-methylphenyl |
| 120 | CN | H | H | 3-cyano-4-cyclopropylphenyl |
| 121 | CN | H | H | 3,5-dimethoxyphenyl |
| 122 | CN | H | H | 4-fluoro-3-(5-cyclopropyltetrazol-1-yl)phenyl |
| 123 | CN | H | H | 4-fluoro-3-(5-cyclopropyltetrazol-1-yl)phenyl |
| 124 | CN | H | H | 4-chloro-3-(5-cyclopropyltetrazol-1-yl)phenyl |
| 125 | CONH₂ | H | H | 4-methoxy-3-(5-methyltetrazol-1-yl)phenyl |
| 126 | CONH₂ | H | H | 4-fluoro-3-(5-methyltetrazol-1-yl)phenyl |

TABLE 1-continued
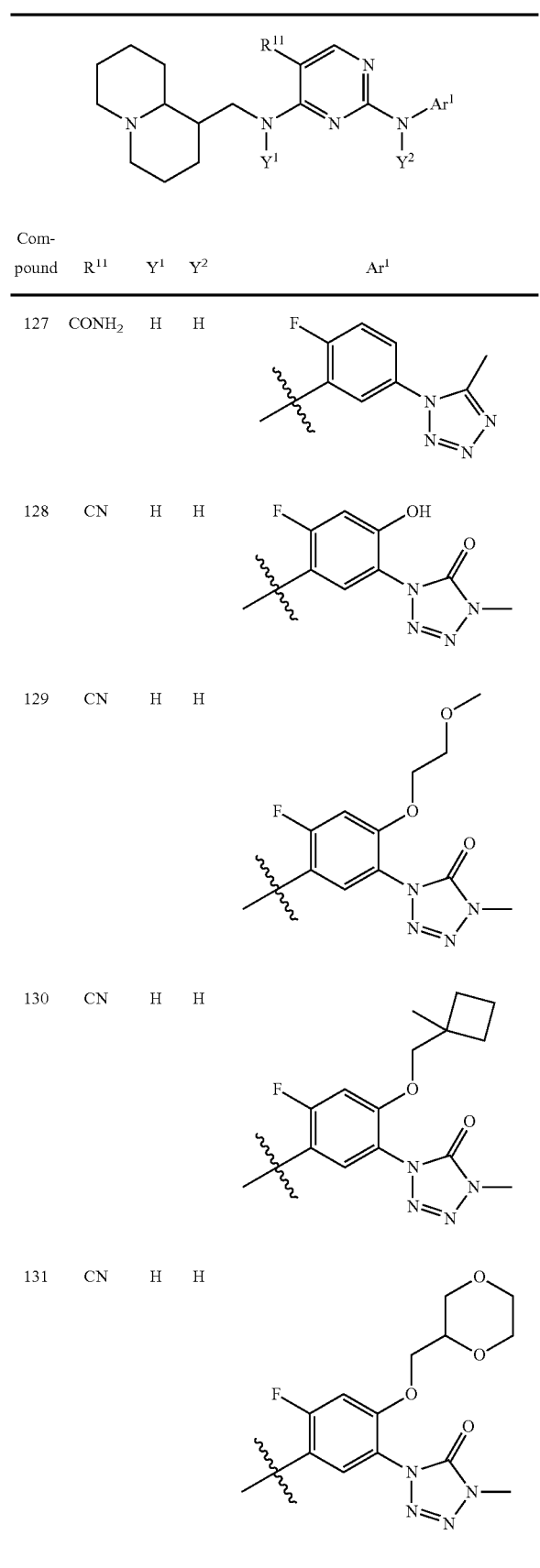
| Compound | $R^{11}$ | $Y^1$ | $Y^2$ | $Ar^1$ |
|---|---|---|---|---|
| 127 | $CONH_2$ | H | H | |
| 128 | CN | H | H | |
| 129 | CN | H | H | |
| 130 | CN | H | H | |
| 131 | CN | H | H | |
TABLE 1-continued
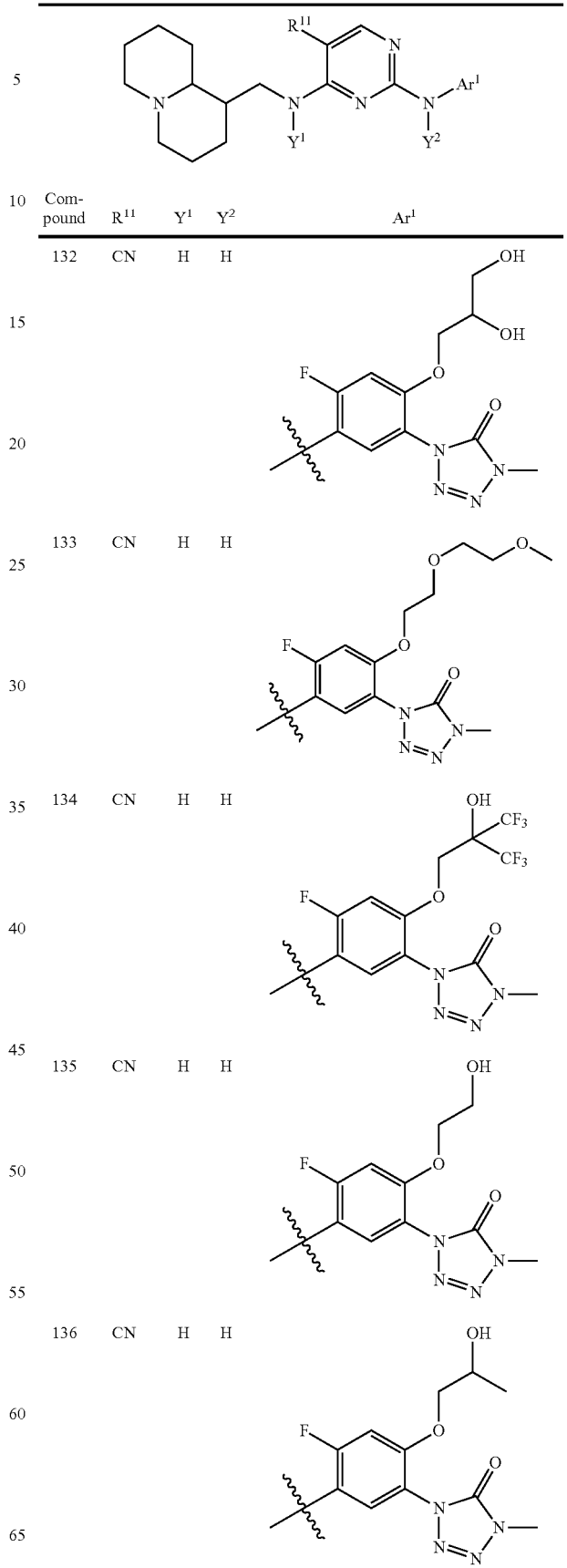
| Compound | $R^{11}$ | $Y^1$ | $Y^2$ | $Ar^1$ |
|---|---|---|---|---|
| 132 | CN | H | H | |
| 133 | CN | H | H | |
| 134 | CN | H | H | |
| 135 | CN | H | H | |
| 136 | CN | H | H | |

TABLE 1-continued

| Compound | R11 | Y1 | Y2 | Ar1 |
|---|---|---|---|---|
| 137 | CN | H | H | (4-fluoro-2-(1,1,2,2-tetradeutero-2-hydroxyethoxy)phenyl)-4-methyl-tetrazol-5-one |
| 138 | F | H | H | 4-(2-hydroxyethoxy)-3-(tetrazol-1-yl)phenyl |
| 139 | Cl | H | H | 4-(2-hydroxyethoxy)-3-(tetrazol-1-yl)phenyl |
| 140 | CN | H | H | 4-(2-hydroxyethoxy)-3-(tetrazol-1-yl)phenyl |
| 141 | H | H | H | 4-(2-hydroxyethoxy)-3-(tetrazol-1-yl)phenyl |
| 142 | CN | H | H | (4-fluoro-2-((S)-2-hydroxypropoxy)phenyl)-4-methyl-tetrazol-5-one |
| 143 | CN | H | H | (4-fluoro-2-((R)-2-hydroxypropoxy)phenyl)-4-methyl-tetrazol-5-one |
| 144 | CN | H | H | 3-cyano-4-(2-hydroxypropoxy)phenyl |
| 145 | F | H | H | 3-cyano-4-(2-hydroxypropoxy)phenyl |
| 146 | Cl | H | H | (4-fluoro-2-hydroxy-phenyl)-4-methyl-tetrazol-5-one |

TABLE 1-continued
| Compound | R11 | Y1 | Y2 | Ar1 |
|---|---|---|---|---|
| 147 | F | H | H | 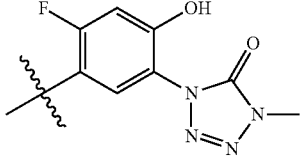 [SMILES: *c1cc(-n2nnn(C)c2=O)c(O)cc1F] |
| 148 | F | H | H | 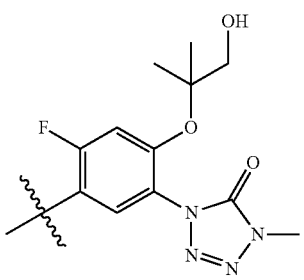 [SMILES: *c1cc(-n2nnn(C)c2=O)c(OC(C)(C)CO)cc1F] |
| 149 | F | H | H | 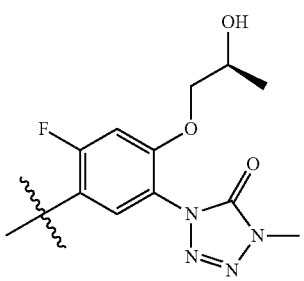 [SMILES: *c1cc(-n2nnn(C)c2=O)c(OC[C@H](C)O)cc1F] |
| 150 | CN | H | H | 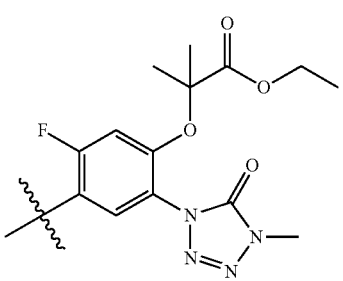 [SMILES: *c1cc(-n2nnn(C)c2=O)c(OC(C)(C)C(=O)OCC)cc1F] |
| 151 | CN | H | H | 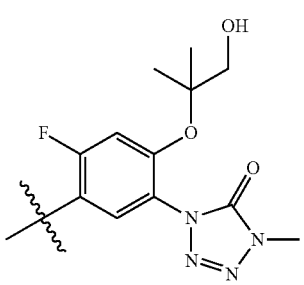 [SMILES: *c1cc(-n2nnn(C)c2=O)c(OC(C)(C)CO)cc1F] |
| 152 | Cl | H | H | 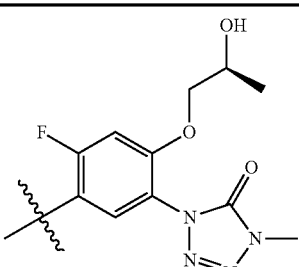 |
| 153 | Cl | H | H | 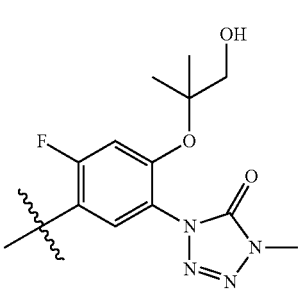 [SMILES: *c1cc(-n2nnn(C)c2=O)c(OC(C)(C)CO)cc1F] |
| 154 | F | H | H | 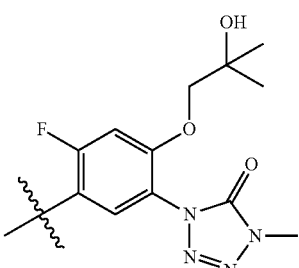 |
| 155 | Cl | H | H | 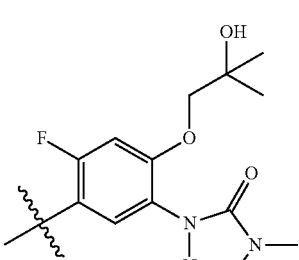 |
| 156 | CN | H | H | 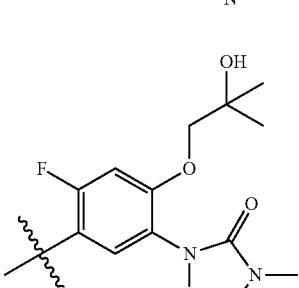 |

Particular compounds of interest, and salts or solvates or stereoisomers thereof, include:

Compound 1: 5-(4-(((1S,9aR)-octahydro-1H-quinolizin-1-yl)methylamino)-5-fluoropyrimidin-2-ylamino)-2-cyclopropylbenzonitrile;

Compound 2: N2-(4-cyclopropyl-2-fluoro-5-(1H-tetrazol-1-yl)phenyl)-5-fluoro-N4-(((1S,9aR)-octahydro-1H-quinolizin-1-yl)methyl)pyrimidine-2,4-diamine;

Compound 3: 1-(5-(4-(((1S,9aR)-octahydro-1H-quinolizin-1-yl)methylamino)-5-fluoropyrimidin-2-ylamino)-2-cyclopropyl-4-fluorophenyl)-4-methyl-1H-tetrazol-5(4H)-one;

Compound 4: 5-fluoro-N4-(((1S,9aR)-octahydro-1H-quinolizin-1-yl)methyl)-N2-(4-methyl-3-(1H-tetrazol-1-yl)phenyl)pyrimidine-2,4-diamine;

Compound 5: 5-(4-(((1S,9aR)-octahydro-1H-quinolizin-9-yl)methylamino)-5-chloropyrimidin-2-ylamino)-2-cyclopropylbenzonitrile;

Compound 6: 5-fluoro-N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine;

Compound 7: 5-fluoro-N2-(2-fluoro-5-(5-methyl-1H-tetrazol-1-yl)phenyl)-N4-(((1S,9aR)-octahydro-1H-quinolizin-1-yl)methyl)pyrimidine-2,4-diamine;

Compound 8: 5-fluoro-N2-(4-fluoro-3-(5-methyl-1H-tetrazol-1-yl)phenyl)-N4-(((1S,9aR)-octahydro-1H-quinolizin-1-yl)methyl)pyrimidine-2,4-diamine;

Compound 9: 5-(4-(((1S,9aR)-octahydro-1H-quinolizin-1-yl)methylamino)-5-fluoropyrimidin-2-ylamino)-2-methylbenzonitrile;

Compound 10: 3-(4-(((1S,9aR)-octahydro-1H-quinolizin-1-yl)methylamino)-5-fluoropyrimidin-2-ylamino)benzonitrile;

Compound 11: 5-fluoro-N4-(((1S,9aR)-octahydro-1H-quinolizin-1-yl)methyl)-N2-(3,5-dimethoxyphenyl)pyrimidine-2,4-diamine;

Compound 12: 5-(4-(((1S,9aR)-octahydro-1H-quinolizin-1-yl)methylamino)-5-fluoropyrimidin-2-ylamino)-2-cyclopropyl-4-fluorobenzonitrile;

Compound 13: 5-fluoro-N4-(((1S,9aR)-octahydro-1H-quinolizin-1-yl)methyl)-N2-phenylpyrimidine-2,4-diamine;

Compound 14: 1-(5-(4-(((1S,9aR)-octahydro-1H-quinolizin-1-yl)methylamino)-5-fluoropyrimidin-2-ylamino)-2-(oxetan-3-yloxy)phenyl)-4-methyl-1H-tetrazol-5(4H)-one;

Compound 15: 1-(5-(4-(((1S,9aR)-octahydro-1H-quinolizin-1-yl)methylamino)-5-fluoropyrimidin-2-ylamino)-2-cyclopropyl-4-methylphenyl)-4-methyl-1H-tetrazol-5(4H)-one;

Compound 16: 7-(4-(((1S,9aR)-octahydro-1H-quinolizin-1-yl)methylamino)-5-fluoropyrimidin-2-ylamino)-4-isopropyl-2,2-dimethyl-2H-benzo[b][1,4]oxazin-3(4H)-one;

Compound 17: 1-(3-(4-(((1S,9aR)-octahydro-1H-quinolizin-1-yl)methylamino)-5-fluoropyrimidin-2-ylamino)-5-methoxyphenyl)-4-methyl-1H-tetrazol-5(4H)-one;

Compound 18: 7-(4-(((1S,9aR)-octahydro-1H-quinolizin-1-yl)methylamino)-5-fluoropyrimidin-2-ylamino)-4-(cyclopropylmethyl)-2,2-dimethyl-2H-benzo[b][1,4]oxazin-3(4H)-one;

Compound 19: 5-fluoro-N2-(3-(trifluoromethyl)-4-morpholinophenyl)-N4-(((1S,9aR)-octahydro-1H-quinolizin-1-yl)methyl)pyrimidine-2,4-diamine;

Compound 20: 5-fluoro-N2-(2,2,3,3-tetrafluoro-2,3-dihydrobenzo[b][1,4]dioxin-7-yl)-N4-(((1S,9aR)-octahydro-1H-quinolizin-1-yl)methyl)pyrimidine-2,4-diamine;

Compound 21: 5-fluoro-N2-(3-fluoro-5-methoxyphenyl)-N4-(((1S,9aR)-octahydro-1H-quinolizin-1-yl)methyl)pyrimidine-2,4-diamine;

Compound 22: 5-fluoro-N4-(((1S,9aR)-octahydro-1H-quinolizin-1-yl)methyl)-N2-(4-methoxy-3-(oxazol-5-yl)phenyl)pyrimidine-2,4-diamine;

Compound 23: N2-(4-cyclopropyl-2-fluoro-5-(5-methyl-1H-tetrazol-1-yl)phenyl)-5-fluoro-N4-(((1S,9aR)-octahydro-1H-quinolizin-1-yl)methyl)pyrimidine-2,4-diamine;

Compound 24: N2-[3-(1,1-dioxo-isothiazolidin-2-yl)-4-fluoro-phenyl]-5-fluoro-N4-(((1S,9aR)-octahydro-1H-quinolizin-1-yl)methyl)-pyrimidine-2,4-diamine;

Compound 25: 7-(4-(((1S,9aR)-octahydro-1H-quinolizin-1-yl)methylamino)-5-fluoropyrimidin-2-ylamino)-4-(3-fluoropropyl)-2,2-dimethyl-2H-benzo[b][1,4]oxazin-3(4H)-one;

Compound 26: 7-(4-(((1S,9aR)-octahydro-1H-quinolizin-1-yl)methylamino)-5-fluoropyrimidin-2-ylamino)-4-(cyclopropylmethyl)-2H-benzo[b][1,4]oxazin-3(4H)-one;

Compound 27: 7-(4-(((1S,9aR)-octahydro-1H-quinolizin-1-yl)methylamino)-5-fluoropyrimidin-2-ylamino)-4-ethyl-2,2-difluoro-2H-pyrido[3,2-b][1,4]oxazin-3(4H)-one;

Compound 28: N2-(5-(1-methyl-1H-tetrazol-5-yloxy)-4-cyclopropyl-2-fluorophenyl)-5-fluoro-N4-(((1S,9aR)-octahydro-1H-quinolizin-1-yl)methyl)pyrimidine-2,4-diamine;

Compound 29: 5-fluoro-N2-(3-pentafluorosulfanyl-6-fluoro-phenyl)-N4-(((1S,9aR)-octahydro-1H-quinolizin-1-yl)methyl)pyrimidine-2,4-diamine;

Compound 30: 5-fluoro-N2-(3-pentafluorosulfanyl-5-fluoro-phenyl)-N4-(((1S,9aR)-octahydro-1H-quinolizin-1-yl)methyl)pyrimidine-2,4-diamine;

Compound 31: 7-(4-(((1S,9aR)-octahydro-1H-quinolizin-1-yl)methylamino)-5-fluoropyrimidin-2-ylamino)-4-(cyclopropylmethyl)-2,2-dimethyl-2H-pyrido[3,2-b][1,4]oxazin-3(4H)-one;

Compound 32: 5-chloro-N2-(4-cyclopropyl-2-fluoro-5-(1H-tetrazol-1-yl)phenyl)-N4-(((1S,9aR)-octahydro-1H-quinolizin-1-yl)methyl)pyrimidine-2,4-diamine;

Compound 33: 5-chloro-N4-(((1S,9aR)-octahydro-1H-quinolizin-1-yl)methyl)-N2-(4-methyl-3-(1H-tetrazol-1-yl)phenyl)pyrimidine-2,4-diamine;

Compound 34: 1-(5-(4-(((1S,9aR)-octahydro-1H-quinolizin-1-yl)methylamino)-5-chloropyrimidin-2-ylamino)-2-cyclopropyl-4-fluorophenyl)-4-methyl-1H-tetrazol-5(4H)-one;

Compound 35: 5-chloro-N2-(4-fluoro-3-(5-methyl-1H-tetrazol-1-yl)phenyl)-N4-(((1S,9aR)-octahydro-1H-quinolizin-1-yl)methyl)pyrimidine-2,4-diamine;

Compound 36: 5-chloro-N2-(2-fluoro-5-(5-methyl-1H-tetrazol-1-yl)phenyl)-N4-(((1S,9aR)-octahydro-1H-quinolizin-1-yl)methyl)pyrimidine-2,4-diamine;

Compound 37: 5-chloro-N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine;

Compound 38: 5-chloro-N4-(((1S,9aR)-octahydro-1H-quinolizin-1-yl)methyl)-N2-(3-methoxy-5-(5-methyl-1H-tetrazol-1-yl)phenyl)pyrimidine-2,4-diamine;

Compound 39: 3-(4-(((1S,9aR)-octahydro-1H-quinolizin-1-yl)methylamino)-5-chloropyrimidin-2-ylamino)benzonitrile;

Compound 40: 5-(4-(((1S,9aR)-octahydro-1H-quinolizin-1-yl)methylamino)-5-chloropyrimidin-2-ylamino)-2-methylbenzonitrile;

Compound 41: 5-(4-(((1S,9aR)-octahydro-1H-quinolizin-1-yl)methylamino)-5-chloropyrimidin-2-ylamino)-2-cyclopropylbenzonitrile;

Compound 42: 5-(4-(((1S,9aR)-octahydro-1H-quinolizin-1-yl)methylamino)-5-chloropyrimidin-2-ylamino)-2-cyclopropyl-4-fluorobenzonitrile;

Compound 43: 5-chloro-N4-(((1S,9aR)-octahydro-1H-quinolizin-1-yl)methyl)-N2-(3,5-dimethoxyphenyl)pyrimidine-2,4-diamine;

Compound 44: 5-(4-(((1S,9aR)-octahydro-1H-quinolizin-1-yl)methylamino)-5-chloropyrimidin-2-ylamino)benzo[d]oxazol-2(3H)-one;

Compound 45: N2-(5-(5-cyclopropyl-1H-tetrazol-1-yl)-2-fluorophenyl)-5-fluoro-N4-(((1S,9aR)-octahydro-1H-quinolizin-1-yl)methyl)pyrimidine-2,4-diamine;

Compound 46: N2-(4-cyclopropyl-2-fluoro-5-(1H-tetrazol-1-yl)phenyl)-N4-(((1S,9aR)-octahydro-1H-quinolizin-1-yl)methyl)pyrimidine-2,4-diamine;

Compound 47: N4-(((1S,9aR)-octahydro-1H-quinolizin-1-yl)methyl)-N2-(4-methyl-3-(1H-tetrazol-1-yl)phenyl)pyrimidine-2,4-diamine;

Compound 48: 1-(5-(4-(((1S,9aR)-octahydro-1H-quinolizin-1-yl)methylamino)pyrimidin-2-ylamino)-2-cyclopropyl-4-fluorophenyl)-4-methyl-1H-tetrazol-5(4H)-one;

Compound 49: N2-(4-fluoro-3-(5-methyl-1H-tetrazol-1-yl)phenyl)-N4-(((1S,9aR)-octahydro-1H-quinolizin-1-yl)methyl)pyrimidine-2,4-diamine;

Compound 50: N2-(2-fluoro-5-(5-methyl-1H-tetrazol-1-yl)phenyl)-N4-(((1S,9aR)-octahydro-1H-quinolizin-1-yl)methyl)pyrimidine-2,4-diamine;

Compound 51: N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine;

Compound 52: N4-(((1S,9aR)-octahydro-1H-quinolizin-1-yl)methyl)-N2-(3-methoxy-5-(5-methyl-1H-tetrazol-1-yl)phenyl)pyrimidine-2,4-diamine;

Compound 53: 3-(4-(((1S,9aR)-octahydro-1H-quinolizin-1-yl)methylamino)pyrimidin-2-ylamino)benzonitrile;

Compound 54: 5-(4-(((1S,9aR)-octahydro-1H-quinolizin-1-yl)methylamino)pyrimidin-2-ylamino)-2-methylbenzonitrile;

Compound 55: 5-(4-(((1S,9aR)-octahydro-1H-quinolizin-1-yl)methylamino)pyrimidin-2-ylamino)-2-cyclopropylbenzonitrile;

Compound 56: 5-(4-(((1S,9aR)-octahydro-1H-quinolizin-1-yl)methylamino)pyrimidin-2-ylamino)-2-cyclopropyl-4-fluorobenzonitrile;

Compound 57: N4-(((1S,9aR)-octahydro-1H-quinolizin-1-yl)methyl)-N2-(3,5-dimethoxyphenyl)pyrimidine-2,4-diamine;

Compound 58: 5-(4-(((1S,9aR)-octahydro-1H-quinolizin-1-yl)methylamino)pyrimidin-2-ylamino)benzo[d]oxazol-2(3H)-one;

Compound 59: N2-(4-cyclopropyl-2-fluoro-5-(1H-tetrazol-1-yl)phenyl)-N4-(((1S,9aR)-octahydro-1H-quinolizin-1-yl)methyl)-5-methylpyrimidine-2,4-diamine;

Compound 60: N4-(((1S,9aR)-octahydro-1H-quinolizin-1-yl)methyl)-5-methyl-N2-(4-methyl-3-(1H-tetrazol-1-yl)phenyl)pyrimidine-2,4-diamine;

Compound 61: 1-(5-(4-(((1S,9aR)-octahydro-1H-quinolizin-1-yl)methylamino)-5-methylpyrimidin-2-ylamino)-2-cyclopropyl-4-fluorophenyl)-4-methyl-1H-tetrazol-5(4H)-one;

Compound 62: N2-(4-fluoro-3-(5-methyl-1H-tetrazol-1-yl)phenyl)-N4-(((1S,9aR)-octahydro-1H-quinolizin-1-yl)methyl)-5-methylpyrimidine-2,4-diamine;

Compound 63: N2-(2-fluoro-5-(5-methyl-1H-tetrazol-1-yl)phenyl)-N4-(((1S,9aR)-octahydro-1H-quinolizin-1-yl)methyl)-5-methylpyrimidine-2,4-diamine;

Compound 64: N4-(((1S,9aR)-octahydro-1H-quinolizin-1-yl)methyl)-N2-(4-methoxy-3-(5-methyl-1H-tetrazol-1-yl)phenyl)-5-methylpyrimidine-2,4-diamine;

Compound 65: N4-(((1S,9aR)-octahydro-1H-quinolizin-1-yl)methyl)-N2-(3-methoxy-5-(5-methyl-1H-tetrazol-1-yl)phenyl)-5-methylpyrimidine-2,4-diamine;

Compound 66: 3-(4-(((1S,9aR)-octahydro-1H-quinolizin-1-yl)methylamino)-5-methylpyrimidin-2-ylamino)benzonitrile;

Compound 67: 5-(4-(((1S,9aR)-octahydro-1H-quinolizin-1-yl)methylamino)-5-methylpyrimidin-2-ylamino)-2-methylbenzonitrile;

Compound 68: 5-(4-(((1S,9aR)-octahydro-1H-quinolizin-1-yl)methylamino)-5-methylpyrimidin-2-ylamino)-2-cyclopropylbenzonitrile;

Compound 69: 5-(4-(((1S,9aR)-octahydro-1H-quinolizin-1-yl)methylamino)-5-methylpyrimidin-2-ylamino)-2-cyclopropyl-4-fluorobenzonitrile;

Compound 70: N4-(((1S,9aR)-octahydro-1H-quinolizin-1-yl)methyl)-N2-(3,5-dimethoxyphenyl)-5-methylpyrimidine-2,4-diamine;

Compound 71: 5-(4-(((1S,9aR)-octahydro-1H-quinolizin-1-yl)methylamino)-5-methylpyrimidin-2-ylamino)benzo[d]oxazol-2(3H)-one;

Compound 72: N2-(4-cyclopropyl-2-fluoro-5-(1H-tetrazol-1-yl)phenyl)-N4-(((1S,9aR)-octahydro-1H-quinolizin-1-yl)methyl)-5-methoxypyrimidine-2,4-diamine;

Compound 73: N4-(((1S,9aR)-octahydro-1H-quinolizin-1-yl)methyl)-5-methoxy-N2-(4-methyl-3-(1H-tetrazol-1-yl)phenyl)pyrimidine-2,4-diamine;

Compound 74: 1-(5-(4-(((1S,9aR)-octahydro-1H-quinolizin-1-yl)methylamino)-5-methoxypyrimidin-2-ylamino)-2-cyclopropyl-4-fluorophenyl)-4-methyl-1H-tetrazol-5(4H)-one;

Compound 75: N2-(4-fluoro-3-(5-methyl-1H-tetrazol-1-yl)phenyl)-N4-(((1S,9aR)-octahydro-1H-quinolizin-1-yl)methyl)-5-methoxypyrimidine-2,4-diamine;

Compound 76: N2-(2-fluoro-5-(5-methyl-1H-tetrazol-1-yl)phenyl)-N4-(((1S,9aR)-octahydro-1H-quinolizin-1-yl)methyl)-5-methoxypyrimidine-2,4-diamine;

Compound 77: N4-(((1S,9aR)-octahydro-1H-quinolizin-1-yl)methyl)-5-methoxy-N2-(4-methoxy-3-(5-methyl-1H-tetrazol-1-yl)phenyl)pyrimidine-2,4-diamine;

Compound 78: N4-(((1S,9aR)-octahydro-1H-quinolizin-1-yl)methyl)-5-methoxy-N2-(3-methoxy-5-(5-methyl-1H-tetrazol-1-yl)phenyl)pyrimidine-2,4-diamine;

Compound 79: 3-(4-(((1S,9aR)-octahydro-1H-quinolizin-1-yl)methylamino)-5-methoxypyrimidin-2-ylamino)benzonitrile;

Compound 80: 5-(4-(((1S,9aR)-octahydro-1H-quinolizin-1-yl)methylamino)-5-methoxypyrimidin-2-ylamino)-2-methylbenzonitrile;

Compound 81: 5-(4-(((1S,9aR)-octahydro-1H-quinolizin-1-yl)methylamino)-5-methoxypyrimidin-2-ylamino)-2-cyclopropylbenzonitrile;

Compound 82: 5-(4-(((1S,9aR)-octahydro-1H-quinolizin-1-yl)methylamino)-5-methoxypyrimidin-2-ylamino)-2-cyclopropyl-4-fluorobenzonitrile;

Compound 83: N4-(((1S,9aR)-octahydro-1H-quinolizin-1-yl)methyl)-5-methoxy-N2-(3,5-dimethoxyphenyl)pyrimidine-2,4-diamine;

Compound 84: 5-(4-(((1S,9aR)-octahydro-1H-quinolizin-1-yl)methylamino)-5-methoxypyrimidin-2-ylamino)benzo[d]oxazol-2(3H)-one;

Compound 85: N2-(4-cyclopropyl-2-fluoro-5-(1H-tetrazol-1-yl)phenyl)-N4-(((1S,9aR)-octahydro-1H-quinolizin-1-yl)methyl)-N5,N5-dimethylpyrimidine-2,4,5-triamine;

Compound 86: N4-(((1S,9aR)-octahydro-1H-quinolizin-1-yl)methyl)-N5,N5-dimethyl-N2-(4-methyl-3-(1H-tetrazol-1-yl)phenyl)pyrimidine-2,4,5-triamine;

Compound 87: 1-(5-(4-(((1S,9aR)-octahydro-1H-quinolizin-1-yl)methylamino)-5-(dimethylamino)pyrimidin-2-ylamino)-2-cyclopropyl-4-fluorophenyl)-4-methyl-1H-tetrazol-5(4H)-one;

Compound 88: N2-(4-fluoro-3-(5-methyl-1H-tetrazol-1-yl)phenyl)-N4-(((1S,9aR)-octahydro-1H-quinolizin-1-yl)methyl)-N5,N5-dimethylpyrimidine-2,4,5-triamine;

Compound 89: N2-(2-fluoro-5-(5-methyl-1H-tetrazol-1-yl)phenyl)-N4-(((1S,9aR)-octahydro-1H-quinolizin-1-yl)methyl)-N5,N5-dimethylpyrimidine-2,4,5-triamine;

Compound 90: N4-(((1S,9aR)-octahydro-1H-quinolizin-1-yl)methyl)-N2-(4-methoxy-3-(5-methyl-1H-tetrazol-1-yl)phenyl)-N5,N5-dimethylpyrimidine-2,4,5-triamine;

Compound 91: N4-(((1S,9aR)-octahydro-1H-quinolizin-1-yl)methyl)-N2-(3-methoxy-5-(5-methyl-1H-tetrazol-1-yl)phenyl)-N5,N5-dimethylpyrimidine-2,4,5-triamine;

Compound 92: 3-(4-(((1S,9aR)-octahydro-1H-quinolizin-1-yl)methylamino)-5-(dimethylamino)pyrimidin-2-ylamino)benzonitrile;

Compound 93: 5-(4-(((1S,9aR)-octahydro-1H-quinolizin-1-yl)methylamino)-5-(dimethylamino)pyrimidin-2-ylamino)-2-methylbenzonitrile;

Compound 94: 5-(4-(((1S,9aR)-octahydro-1H-quinolizin-1-yl)methylamino)-5-(dimethylamino)pyrimidin-2-ylamino)-2-cyclopropylbenzonitrile;

Compound 95: 5-(4-(((1S,9aR)-octahydro-1H-quinolizin-1-yl)methylamino)-5-(dimethylamino)pyrimidin-2-ylamino)-2-cyclopropyl-4-fluorobenzonitrile;

Compound 96: N4-(((1S,9aR)-octahydro-1H-quinolizin-1-yl)methyl)-N2-(3,5-dimethoxyphenyl)-N5,N5-dimethylpyrimidine-2,4,5-triamine;

Compound 97: 5-(4-(((1S,9aR)-octahydro-1H-quinolizin-1-yl)methylamino)-5-(dimethylamino)pyrimidin-2-ylamino)benzo[d]oxazol-2(3H)-one;

Compound 98: N2-(4,4-dimethyl-4H-5-oxa-1,2,3,9b-tetraaza-cyclopenta[a]naphthalen-8-yl)-5-fluoro-N4-(((1S,9aR)-octahydro-1H-quinolizin-1-yl)methyl)-pyrimidine-2,4-diamine;

Compound 99: 4-(((1S,9aR)-octahydro-1H-quinolizin-1-yl)methylamino)-2-(4-cyclopropyl-2-fluoro-5-(4,5-dihydro-4-methyl-5-oxotetrazol-1-yl)phenylamino)pyrimidine-5-carbonitrile;

Compound 100: N2-(4-cyclopropyl-2-fluoro-5-(1H-tetrazol-1-yl)phenyl)-5-(trifluoromethyl)-N4-(((1S,9aR)-octahydro-1H-quinolizin-1-yl)methyl)pyrimidine-2,4-diamine;

Compound 101: 5-(trifluoromethyl)-N4-(((1S,9aR)-octahydro-1H-quinolizin-1-yl)methyl)-N2-(4-methyl-3-(1H-tetrazol-1-yl)phenyl)pyrimidine-2,4-diamine;

Compound 102: 1-(5-(4-(((1S,9aR)-octahydro-1H-quinolizin-1-yl)methylamino)-5-(trifluoromethyl)pyrimidin-2-ylamino)-2-cyclopropyl-4-fluorophenyl)-4-methyl-1H-tetrazol-5(4H)-one;

Compound 103: N2-(4-fluoro-3-(5-methyl-1H-tetrazol-1-yl)phenyl)-5-(trifluoromethyl)-N4-(((1S,9aR)-octahydro-1H-quinolizin-1-yl)methyl)pyrimidine-2,4-diamine;

Compound 104: N2-(2-fluoro-5-(5-methyl-1H-tetrazol-1-yl)phenyl)-5-(trifluoromethyl)-N4-(((1S,9aR)-octahydro-1H-quinolizin-1-yl)methyl)pyrimidine-2,4-diamine;

Compound 105: 5-(trifluoromethyl)-N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine;

Compound 106: 5-(trifluoromethyl)-N4-(((1S,9aR)-octahydro-1H-quinolizin-1-yl)methyl)-N2-(3-methoxy-5-(5-methyl-1H-tetrazol-1-yl)phenyl)pyrimidine-2,4-diamine;

Compound 107: 3-(4-(((1S,9aR)-octahydro-1H-quinolizin-1-yl)methylamino)-5-(trifluoromethyl)pyrimidin-2-ylamino)benzonitrile;

Compound 108: 5-(4-(((1S,9aR)-octahydro-1H-quinolizin-1-yl)methylamino)-5-(trifluoromethyl)pyrimidin-2-ylamino)-2-methylbenzonitrile;

Compound 109: 5-(4-(((1S,9aR)-octahydro-1H-quinolizin-1-yl)methylamino)-5-(trifluoromethyl)pyrimidin-2-ylamino)-2-cyclopropylbenzonitrile;

Compound 110: 5-(4-(((1S,9aR)-octahydro-1H-quinolizin-1-yl)methylamino)-5-(trifluoromethyl)pyrimidin-2-ylamino)-2-cyclopropyl-4-fluorobenzonitrile;

Compound 111: 5-(trifluoromethyl)-N4-(((1S,9aR)-octahydro-1H-quinolizin-1-yl)methyl)-N2-(3,5-dimethoxyphenyl)pyrimidine-2,4-diamine;

Compound 112: 5-(4-(((1S,9aR)-octahydro-1H-quinolizin-1-yl)methylamino)-5-(trifluoromethyl)pyrimidin-2-ylamino)benzo[d]oxazol-2(3H)-one;

Compound 113: 4-(((1S,9aR)-octahydro-1H-quinolizin-1-yl)methylamino)-2-(4-methoxy-3-(5-methyl-1H-tetrazol-1-yl)phenylamino)pyrimidine-5-carbonitrile;

Compound 114: 4-(((1S,9aR)-octahydro-1H-quinolizin-1-yl)methylamino)-2-(4-fluoro-3-(5-methyl-1H-tetrazol-1-yl)phenylamino)pyrimidine-5-carbonitrile;

Compound 115: 4-(((1S,9aR)-octahydro-1H-quinolizin-1-yl)methylamino)-2-(3-methoxy-5-(5-methyl-1H-tetrazol-1-yl)phenylamino)pyrimidine-5-carbonitrile;

Compound 116: 4-(((1S,9aR)-octahydro-1H-quinolizin-1-yl)methylamino)-2-(4-cyclopropyl-2-fluoro-5-(1H-tetrazol-1-yl)phenylamino)pyrimidine-5-carbonitrile;

Compound 117: 4-(((1S,9aR)-octahydro-1H-quinolizin-1-yl)methylamino)-2-(4-methyl-3-(1H-tetrazol-1-yl)phenylamino)pyrimidine-5-carbonitrile;

Compound 118: 4-(((1S,9aR)-octahydro-1H-quinolizin-1-yl)methylamino)-2-(2-fluoro-5-(5-methyl-1H-tetrazol-1-yl)phenylamino)pyrimidine-5-carbonitrile;

Compound 119: 4-(((1S,9aR)-octahydro-1H-quinolizin-1-yl)methylamino)-2-(3-cyano-4-methylphenylamino)pyrimidine-5-carbonitrile;

Compound 120: 4-(((1S,9aR)-octahydro-1H-quinolizin-1-yl)methylamino)-2-(3-cyano-4-cyclopropylphenylamino)pyrimidine-5-carbonitrile;

Compound 121: 4-(((1S,9aR)-octahydro-1H-quinolizin-1-yl)methylamino)-2-(3,5-dimethoxyphenylamino)pyrimidine-5-carbonitrile;

Compound 122: 4-(((1S,9aR)-octahydro-1H-quinolizin-1-yl)methylamino)-2-(3-(5-cyclopropyl-1H-tetrazol-1-yl)-4-fluorophenylamino)pyrimidine-5-carbonitrile;

Compound 123: 4-(((1S,9aR)-octahydro-1H-quinolizin-1-yl)methylamino)-2-(5-(5-cyclopropyl-1H-tetrazol-1-yl)-2-fluorophenylamino)pyrimidine-5-carbonitrile;

Compound 124: 4-(((1S,9aR)-octahydro-1H-quinolizin-1-yl)methylamino)-2-(4-chloro-3-(5-cyclopropyl-1H-tetrazol-1-yl)phenylamino)pyrimidine-5-carbonitrile;

Compound 125: 4-(((1S,9aR)-octahydro-1H-quinolizin-1-yl)methylamino)-2-(4-methoxy-3-(5-methyl-1H-tetrazol-1-yl)phenylamino)pyrimidine-5-carboxamide;

Compound 126: 4-(((1S,9aR)-octahydro-1H-quinolizin-1-yl)methylamino)-2-(4-fluoro-3-(5-methyl-1H-tetrazol-1-yl)phenylamino)pyrimidine-5-carboxamide;

Compound 127: 4-(((1S,9aR)-octahydro-1H-quinolizin-1-yl)methylamino)-2-(2-fluoro-5-(5-methyl-1H-tetrazol-1-yl)phenylamino)pyrimidine-5-carboxamide;

Compound 128: 2-((2-fluoro-4-hydroxy-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 129: 2-((2-fluoro-4-(2-methoxyethoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 130: 2-((2-fluoro-5-(4-methyl-5-oxo-4,5-dihydro-1H-tetrazol-1-yl)-4-((3-methyloxetan-3-yl)methoxy)phenyl)amino)-4-((((1S,9aR)-octahydro-2H-quinolizin-1-yl)methyl)amino)pyrimidine-5-carbonitrile;

Compound 131: 2-((4-((1,4-dioxan-2-yl)methoxy)-2-fluoro-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 132: 2-((4-(2,3-dihydroxypropoxy)-2-fluoro-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 133: 2-((2-fluoro-4-(2-(2-methoxyethoxy)ethoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 134: 2-((2-fluoro-5-(4-methyl-5-oxo-4,5-dihydro-1H-tetrazol-1-yl)-4-(3,3,3-trifluoro-2-hydroxy-2-(trifluoromethyl)propoxy)phenyl)amino)-4-((((1S,9aR)-octahydro-2H-quinolizin-1-yl)methyl)amino)pyrimidine-5-carbonitrile;

Compound 135: 2-((2-fluoro-4-(2-hydroxyethoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 136: 2-((2-fluoro-4-(2-hydroxypropoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 137: 2-((2-fluoro-4-(2-hydroxyethoxy-1,1,2,2-d4)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 138: 2-(4-((5-fluoro-4-((((1S,9aR)-octahydro-2H-quinolizin-1-yl)methyl)amino)pyrimidin-2-yl)amino)-2-(1H-tetrazol-1-yl)phenoxy)ethan-1-ol;

Compound 139: 2-(4-((5-chloro-4-((((1S,9aR)-octahydro-2H-quinolizin-1-yl)methyl)amino)pyrimidin-2-yl)amino)-2-(1H-tetrazol-1-yl)phenoxy)ethan-1-ol;

Compound 140: 2-((4-(2-hydroxyethoxy)-3-(1H-tetrazol-1-yl)phenyl)amino)-4-((((1S,9aR)-octahydro-2H-quinolizin-1-yl)methyl)amino)pyrimidine-5-carbonitrile;

Compound 141: 2-(4-((4-((((1S,9aR)-octahydro-2H-quinolizin-1-yl)methyl)amino)pyrimidin-2-yl)amino)-2-(1H-tetrazol-1-yl)phenoxy)ethan-1-ol;

Compound 142: 2-((2-fluoro-4-((S)-2-hydroxypropoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 143: 2-((2-fluoro-4-((R)-2-hydroxypropoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 144: 2-((3-cyano-4-(2-hydroxypropoxy)phenyl)amino)-4-((((1S,9aR)-octahydro-2H-quinolizin-1-yl)methyl)amino)pyrimidine-5-carbonitrile;

Compound 145: 5-((5-fluoro-4-((((1S,9aR)-octahydro-2H-quinolizin-1-yl)methyl)amino)pyrimidin-2-yl)amino)-2-(2-hydroxypropoxy)benzonitrile;

Compound 146: 1-(5-((5-chloro-4-((((1S,9aR)-octahydro-2H-quinolizin-1-yl)methyl)amino)pyrimidin-2-yl)amino)-4-fluoro-2-hydroxyphenyl)-4-methyl-1,4-dihydro-5H-tetrazol-5-one;

Compound 147: 1-(5-((5-fluoro-4-((((1S,9aR)-octahydro-2H-quinolizin-1-yl)methyl)amino)pyrimidin-2-yl)amino)-4-fluoro-2-hydroxyphenyl)-4-methyl-1,4-dihydro-5H-tetrazol-5-one;

Compound 148: 1-(4-fluoro-5-((5-fluoro-4-((((1S,9aR)-octahydro-2H-quinolizin-1-yl)methyl)amino)pyrimidin-2-yl)amino)-2-((1-hydroxy-2-methylpropan-2-yl)oxy)phenyl)-4-methyl-1,4-dihydro-5H-tetrazol-5-one;

Compound 149: 1-(4-fluoro-5-((5-fluoro-4-((((1S,9aR)-octahydro-2H-quinolizin-1-yl)methyl)amino)pyrimidin-2-yl)amino)-2-((S)-2-hydroxypropoxy)phenyl)-4-methyl-1,4-dihydro-5H-tetrazol-5-one;

Compound 150: ethyl 2-(4-((5-cyano-4-((((1S,9aR)-octahydro-2H-quinolizin-1-yl)methyl)amino)pyrimidin-2-yl)amino)-5-fluoro-2-(4-methyl-5-oxo-4,5-dihydro-1H-tetrazol-1-yl)phenoxy)-2-methylpropanoate;

Compound 151: 2-((2-fluoro-4-((1-hydroxy-2-methylpropan-2-yl)oxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 152: 1-(5-((5-chloro-4-((((1S,9aR)-octahydro-2H-quinolizin-1-yl)methyl)amino)pyrimidin-2-yl)amino)-4-fluoro-2-((S)-2-hydroxypropoxy)phenyl)-4-methyl-1,4-dihydro-5H-tetrazol-5-one;

Compound 153: 1-(5-((5-chloro-4-((((1S,9aR)-octahydro-2H-quinolizin-1-yl)methyl)amino)pyrimidin-2-yl)amino)-4-fluoro-2-((1-hydroxy-2-methylpropan-2-yl)oxy)phenyl)-4-methyl-1,4-dihydro-5H-tetrazol-5-one;

Compound 154: 1-(4-fluoro-5-((5-fluoro-4-((((1S,9aR)-octahydro-2H-quinolizin-1-yl)methyl)amino)pyrimidin-2-yl)amino)-2-(2-hydroxy-2-methylpropoxy)phenyl)-4-methyl-1,4-dihydro-5H-tetrazol-5-one;

Compound 155: 1-(5-((5-chloro-4-((((1S,9aR)-octahydro-2H-quinolizin-1-yl)methyl)amino)pyrimidin-2-yl)amino)-4-fluoro-2-(2-hydroxy-2-methylpropoxy)phenyl)-4-methyl-1,4-dihydro-5H-tetrazol-5-one; and Compound 156: 2-((2-fluoro-4-(2-hydroxy-2-methylpropoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile.

Aspects of the present disclosure also include a compound according to the formula:

(V)

wherein $Z^1$ is $OR^{17}$, $-NR^{17}R^{18}$ or X;

$Z^2$ is H, or $Z^1$ and $Z^2$ together form an oxo, $=NR^{19}$ or $=NNR^{20}R^{21}$;

$R^{17}$ is H, alkyl, substituted alkyl, acyl, acylamino, $-SO_2$-alkyl or $-SO_2$-aryl;

$R^{18}$ is H, alkyl, substituted alkyl, acyl, acylamino, $-SO_2$-alkyl, $-SO_2$-aryl, aryl, substituted aryl, heteroaryl, or substituted heteroaryl;

X is halo or azido; and $R^{19}$, $R^{20}$ and $R^{21}$ are each independently selected from alkyl, substituted alkyl, aryl substituted aryl, heteroaryl and substituted heteroaryl.

In certain embodiments of formula (V), the compound is optically active. In certain embodiments of formula (V), there is an enantiomeric excess of 90% or more. In certain embodiments of formula (V), there is an enantiomeric excess of 95% or more. In certain embodiments of formula (V), there is an enantiomeric excess of 99% or more.

In certain embodiments, in formula (V), $R^{18}$ comprises the formula

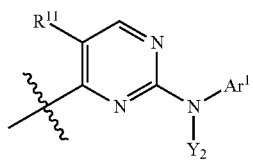

wherein $R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;

$Y^2$ is selected from hydrogen and alkyl; and $Ar^1$ is selected from aryl, substituted aryl, heteroaryl, and substituted heteroaryl.

In certain embodiments, the compound of formula (V) comprises the formula

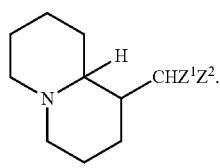

In certain embodiments, the compound of formula (V) comprises the formula

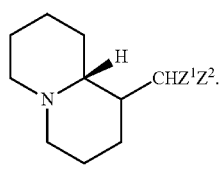

In certain embodiments, the compound of formula (V) comprises the formula

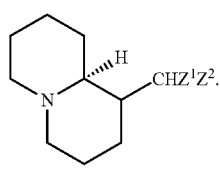

In certain embodiments, the compound of formula (V) comprises the formula

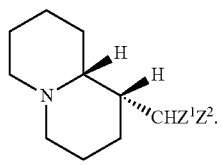

In certain embodiments, the compound of formula (V) comprises the formula

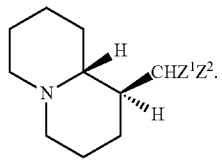

In certain embodiments, the compound of formula (V) comprises the formula

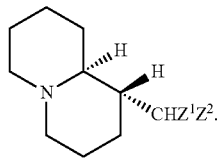

In certain embodiments, the compound of formula (V) comprises the formula

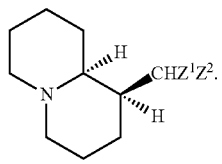

Aspects of the present disclosure also include a compound according to the formula:

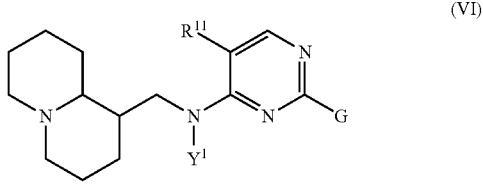

(VI)

wherein $R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$; and $Y^1$ is selected from hydrogen and alkyl.

In formula (VI), G is halogen or —$NY^2Ar^1$. In certain embodiments, G is halogen. In certain embodiments, G is —NY²Ar¹. In certain embodiments, Y² is selected from hydrogen and alkyl. In certain embodiments, Ar¹ is selected from aryl, substituted aryl, heteroaryl, and substituted heteroaryl. In certain embodiments, Ar¹ is aryl or substituted aryl. In certain embodiments, Ar¹ is heteroaryl or substituted heteroaryl.

In certain embodiments, a compound of formula (VI) is of the formula:

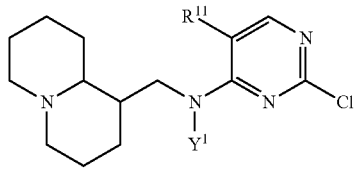

wherein
$R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$; and
$Y^1$ is selected from hydrogen and alkyl.

In certain embodiments, a compound of formula (VI) is of the formula:

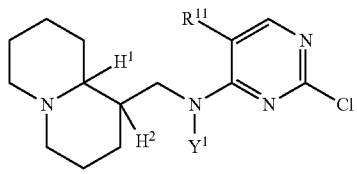

wherein
$R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and $SF_5$;
$Y^1$ is selected from hydrogen and alkyl; and
$H^1$ and $H^2$ are each hydrogen.

In certain embodiments, $H^1$ and $H^2$ are hydrogen with cis relative configuration. In certain embodiments, $H^1$ and $H^2$ are hydrogen with trans relative configuration.

In certain embodiments, $R^{11}$ in formulae (V) and (VI) is as described above in relation to formulae (I)-(IV).

The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{15}N$, $^{18}O$, $^{17}O$, etc. Thus, the disclosed compounds may be enriched in one or more of these isotopes relative to the natural abundance of such isotope. By way of example, deuterium ($^2H$) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

The present disclosure also provides pharmaceutical compositions that include a pharmaceutically acceptable carrier and a therapeutically effective amount of a compound of formula I-IV or a pharmaceutically acceptable salt or solvate or stereoisomer thereof.

A disclosed compound can be administered alone, as the sole active pharmaceutical agent, or in combination with one or more additional compounds of formula I-IV or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of formula I-IV optionally include other therapeutic agents. Accordingly, certain embodiments are directed to such pharmaceutical compositions, where the composition further includes a therapeutically effective amount of an agent selected as is known to those of skill in the art.

The subject compounds can inhibit a protein kinase C (PKC) activity. Accordingly, the compounds are useful for treating a disease or disorder that is mediated through the activity of a PKC activity in a subject. Also, the compounds are useful for treating a disease or disorder that is associated with the activation of T-cells in a subject.

The present disclosure provides a method of treating an inflammatory disease in a subject. In certain embodiments, the method includes administering to the subject (e.g., patient) a compound of formula I-IV or a salt or solvate or stereoisomer thereof.

The present disclosure also provides a method of treating an autoimmune disease in a subject. In certain embodiments, the method includes administering to the subject (e.g., patient) a compound of formula I-IV or a salt or solvate or stereoisomer thereof.

The present disclosure also provides a method of treating an ocular disease or disorder involving inflammatory and/or neovascular events.

The present disclosure also provides a method of treating diseases or conditions of interest including, but are not limited to, atherosclerosis, vascular occlusion due to vascular injury, angioplasty, restenosis, obesity, syndrome X, impaired glucose tolerance, polycystic ovary syndrome, hypertension, heart failure, chronic obstructive pulmonary disease, CNS diseases, Alzheimer disease, amyotrophic lateral sclerosis, bipolar disease, cancer, infectious disease, AIDS, septic shock, adult respiratory distress syndrome, ischemia/reperfusion injury, myocardial infarction, stroke, gut ischemia, renal failure, hemorrhage shock, and traumatic shock, and traumatic brain injury. In certain embodiments, the present compounds are useful in treating muscle diseases or disorders, including inflammatory muscle disease and dystrophic disorders, such as Duchenne muscular dystrophy and myotonic muscular dystrophy.

The present disclosure also provides a method of treating diseases or conditions of interest including, but are not limited to, T-cell mediated acute or chronic inflammatory diseases or disorders or autoimmune diseases, rheumatoid arthritis, osteoarthritis, systemic lupus erythematosus, Hashimoto's thyroiditis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases, psoriasis, atopic dermatitis, allergic contact dermatitis, irritant contact dermatitis and further eczematous dermatitises, seborrhoeic dermatitis, inflammatory eye diseases, Sjoegren's syndrome, keratoconjunctivitis, uveitis, inflammatory bowel disease, Crohn's disease or ulcerative colitis, Guillain-Barre syndrome, and allergies.

The subject compounds can be used for treating a cell proliferative disorder. The present disclosure also provides a method of treating diseases or conditions of interest including, but are not limited to, hematopoietic neoplasm, lymphoid neoplasm, T cell neoplasm, T-lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, and acute myeloid leukemia.

Since embodiments of the subject compounds possess PKC inhibitory properties, such compounds are also useful as research tools. Accordingly, the disclosure also provides for a method for using a compound of formula I-IV or a salt or solvate or stereoisomer thereof as a research tool for studying a biological system or sample, or for discovering new chemical compounds having PKC inhibitory properties.

The embodiments are also directed to a compound of formula I-IV or a salt or solvate or stereoisomer thereof, for use in therapy or as a medicament.

Additionally, the embodiments are directed to the use of a compound of formula I-IV or a salt or solvate or stereoisomer thereof, for the manufacture of a medicament; for example, for the manufacture of a medicament for the inhibition of protein kinase C (PKC) activity. The embodiments are also directed to the use of a compound of formula I-IV or a salt or solvate or stereoisomer thereof for the manufacture of a medicament for the treatment of a disease or disorder mediated or sustained through the activity of PKC activity. The embodiments are also directed to the use of a compound of formula I-IV or a salt or solvate or stereoisomer thereof for the manufacture of a medicament for the treatment of a disease or disorder associated with the activation of T-cells. Diseases or conditions of interest include, but are not limited to, an inflammatory disease, an immunological disorder, an autoimmune disease, an ocular disease or disorder involving inflammatory and/or neovascular events, organ and bone marrow transplant rejection, acute or chronic inflammation, allergies, contact dermatitis, psoriasis, rheumatoid arthritis, multiple sclerosis, type I diabetes, type II diabetes, inflammatory bowel disease, Guillain-Barre syndrome, Crohn's disease, ulcerative colitis, graft versus host disease, and lupus erythematosus.

The embodiments of the present disclosure are also directed to the use of a compound of formula I-IV or a salt or solvate or stereoisomer thereof for the manufacture of a medicament for the treatment of a cell proliferative disorder. Diseases or conditions of interest include, but are not limited to, hematopoietic neoplasm, lymphoid neoplasm, T cell neoplasm, T-lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, acute myeloid leukemia.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Suitable examples of methods that can be adapted to synthesize the 2,4-pyrimidinediamine compounds and prodrugs disclosed herein are found in U.S. Pat. No. 5,958,935, the disclosure of which is incorporated herein by reference. Specific examples describing the synthesis of various 2,4-pyrimidinediamine compounds and prodrugs, as well as intermediates therefore, are described in the U.S. Application Publication No. 2004/0029902, the disclosure of which are incorporated herein by reference. Suitable examples of methods that can be routinely used and/or adapted to synthesize active 2,4-pyrimidinediamine compounds can also be found in WO 03/063794, U.S. application Ser. No. 10/631,029, filed Jul. 29, 2003, WO2004/014382, U.S. Application Publication No. 2005/0234049, and WO2005/016893, the disclosures of each of which are incorporated herein by reference. All of the compounds described herein (including prodrugs) can be prepared by adaptation of these methods.

Exemplary synthetic methods for the 2,4-substituted pyrimidinediamines described herein are described below. Those of skill in the art will also be able to readily adapt these methods for the synthesis of specific 2,4-substituted pyrimidinediamines as described herein.

A variety of examples of synthetic routes that can be used to synthesize the 2,4-pyrimidinediamine compounds disclosed herein are described in the schemes below. These methods can be adapted to synthesize the 2,4-pyrimidinediamine compounds and prodrugs described herein.

Synthesis of Compounds

In certain embodiments, the compounds can be synthesized from substituted or unsubstituted uracils as illustrated in Scheme 1, below:

synthetic conditions (such as temperature), as is well-known in the art.

In certain embodiments, to couple compounds with an electrophilic leaving group, such as halides or pseudohalides, and compounds with an amino group, nucleophilic aromatic substitution can be used. For example, a halogen substituent

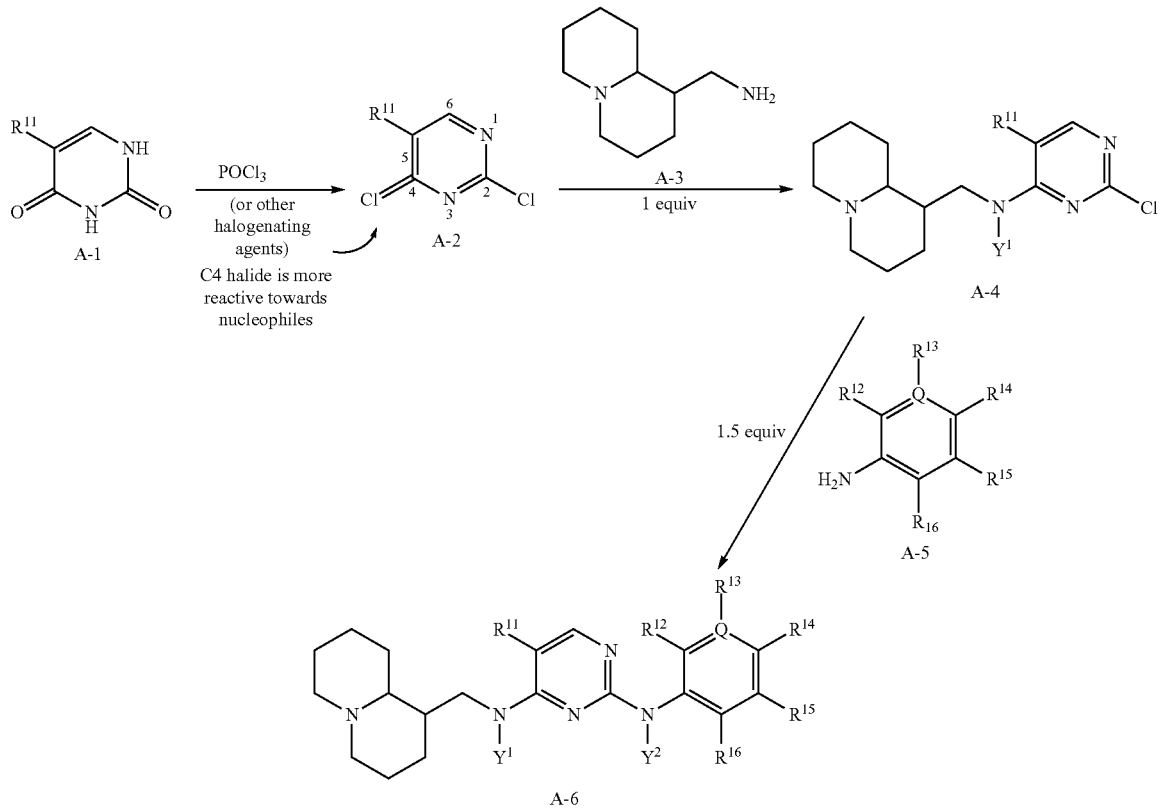

In Scheme 1, $R^{11}$, $R^{12}$, $R^{13}$, $R^{14}$, $R^{15}$, $R^{16}$, $Y^1$, $Y^2$, and Q are as set forth hereinbefore.

According to Scheme 1, uracil A-1 is dihalogenated at the 2- and 4-positions using a standard dehydrating-halogenating agent such as $POCl_3$ (phosphorus oxychloride) (or other standard halogenating agent) to yield 2,4 dichloropyrimidine A-2. Depending upon the substituents in pyrimidinediamine A-2, the chloride at the C4 position is more reactive towards nucleophiles than the chloride at the C2 position. This differential reactivity can be exploited by first reacting 2,4 dichloropyrimidine A-2 with one equivalent of amine A-3, yielding 4N-substituted-2-chloro-4-pyrimidineamine A-4, followed by one or more equivalents of amine A-5 to yield a 2,4-pyrimidinediamine derivative A-6.

Typically, the C4 halide is more reactive towards nucleophiles, as illustrated in the scheme. However, as will be recognized by skilled artisans, the identity of the substituent may alter this reactivity. For example, when the substituent is trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other on Compound A-2 and the amino group on Compound A-3 can react. Also for example, a halogen substituent on Compound A-4 and the amino group on Compound A-5 can react. Conditions for nucleophilic aromatic substitution include the compounds reacting in a polar aprotic solvent or polar protic solvent. Suitable solvents include alcohols (such as isopropanol, methanol, ethanol), formic acid, dimethylsulfoxide, dimethylformamide, dioxane, and tetrahydrofuran. The reaction can be run at room temperature or can be heated.

In certain embodiments, to couple compounds with an electrophilic leaving group, such as halides or pseudohalides, and aryl compounds with an amino group, a coupling reaction, such as a Buchwald coupling reaction, can be used. The Buchwald coupling reaction involves palladium-catalyzed synthesis of aryl amines. Starting materials are aryl halides or pseudohalides (for example, triflates) and primary or secondary amines. Such reaction can be performed using a variety of methods well known in the art and specific examples can be had by reference to the Examples hereunder described.

A specific embodiment of Scheme 1 utilizing 5-fluorouracil (Aldrich #32, 937-1) as a starting material is illustrated in Scheme 2, below.

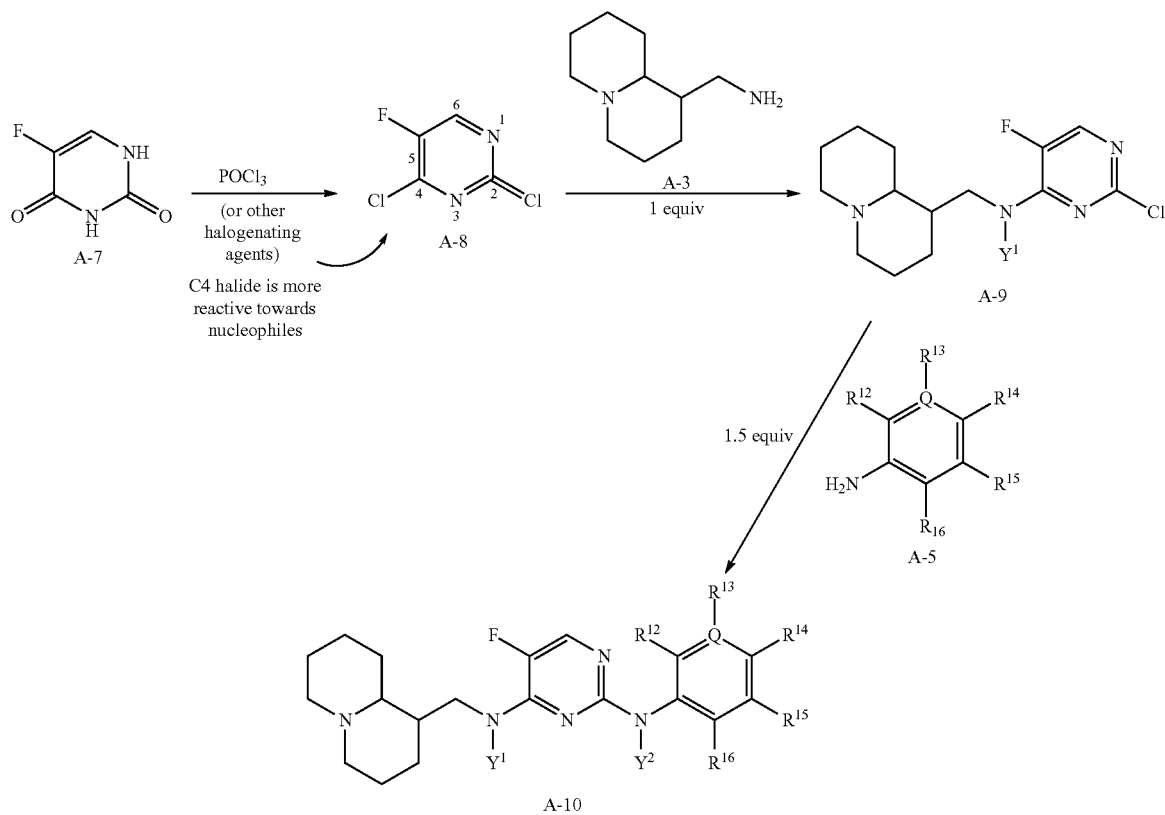

In Scheme 2, $R^{11}$, $R^{12}$, $R^{13}$, $R^{14}$, $R^{15}$, $R^{16}$, $Y^1$, $Y^2$, and Q are as set forth hereinbefore.

Asymmetric 2N,4N-disubstituted-5-fluoro-2,4-pyrimidinediamine A-10 can be obtained by reacting 2,4-dichloro-5-fluoropyrimidine A-8 with one equivalent of amine A-3 (to yield 2-chloro-N4-substituted-5-fluoro-4-pyrimidineamine A-9) followed by one or more equivalents of amine A-5.

In certain embodiments, chloro derivatives of the compounds can be synthesized as illustrated in Scheme 3, below:

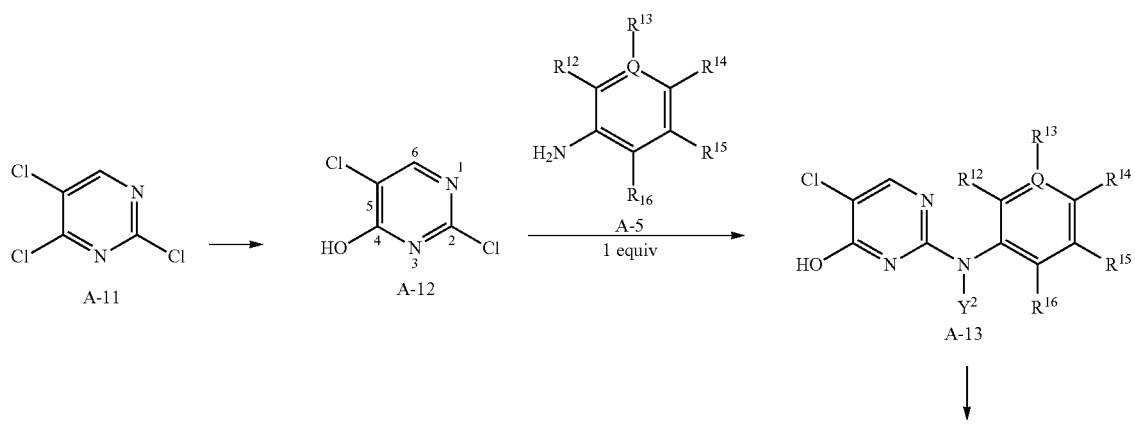

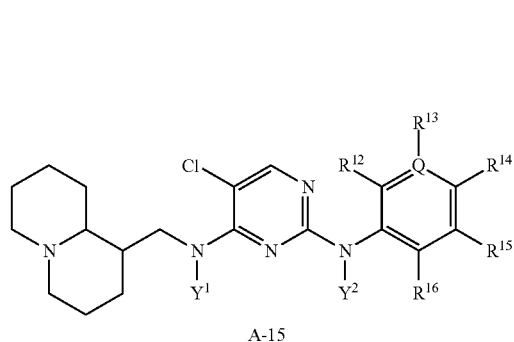

A-15

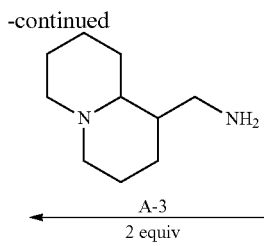

A-3
2 equiv

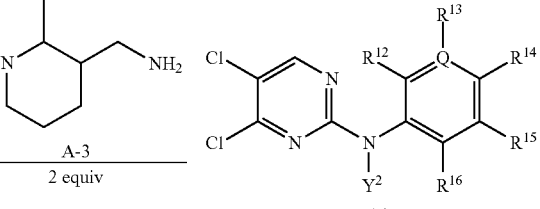

A-14

In Scheme 3, $R^{12}$, $R^{13}$, $R^{14}$, $R^{15}$, $R^{16}$, $Y^1$, $Y^2$, and Q are as set forth hereinbefore.

Asymmetric 2N,4N-disubstituted-5-chloro-2,4-pyrimidinediamine A-15 can be obtained by reacting 2,5-dichloro-pyrimidin-4-ol A-12 with one equivalent of amine A-5 (to yield N2-substituted-5-chloro-pyrimidin-4-ol A-13). The hydroxy group of Compound A-13 is converted to a chloro group to yield Compound A-14, followed by reaction with one or more equivalents of amine A-3. Conversion of the hydroxy group to the chloro group can be accomplished with a dehydrating-halogenating agent such as $POCl_3$ (phosphorus oxychloride) (or other standard halogenating agent).

Uracil Starting Materials and Intermediates

The uracil A-1 and A-7 starting materials can be purchased from commercial sources or prepared using standard techniques of organic chemistry. Commercially available uracils that can be used as starting materials in the schemes disclosed herein include, but are not limited to, uracil (Aldrich #13,078-8; CAS Registry 66-22-8); 5-chlorouracil (Aldrich #224588; CAS Registry 1820-81-1); 5-bromouracil (Aldrich #85, 247-3; CAS Registry 51-20-7); 5-fluorouracil (Aldrich #85, 847-1; CAS Registry 51-21-8); 5-iodouracil (Aldrich #85, 785-8; CAS Registry 696-07-1); 5-nitrouracil (Aldrich #85, 276-7; CAS Registry 611-08-5); 5-methyluracil (thymine, Aldrich #T0376; CAS Registry 65-71-4); 5-(trifluoromethyl)-uracil (Aldrich #22, 327-1; CAS Registry 54-20-6); 5-cyanouracil (Aldrich #AMS000822). Additional 5-substituted uracils are available from General Intermediates of Canada, Inc., Edmonton, Calif. and/or Interchim, Cedex, France, or can be prepared using standard techniques. Various textbook references teaching suitable synthetic methods are provided infra.

Pyrimidine Starting Materials and Intermediates

Pyrimidines, such as A-11 can be purchased from commercial sources or, alternatively, can be synthesized utilizing standard techniques. Commercially available pyrimidines that can be used as starting materials in the schemes disclosed herein include, but are not limited to, 2,4,5-trichloropyrimidine (Aldrich #652032; CAS Registry 5750-76-5).

Amino Starting Materials and Intermediates

Amines, such as A-3 and A-5 can be purchased from commercial sources or, alternatively, can be synthesized utilizing standard techniques. For example, suitable amines can be synthesized from nitro precursors using standard chemistry. See also Vogel, 1989, Practical Organic Chemistry, Addison Wesley Longman, Ltd. and John Wiley & Sons, Inc. For example, amines A-5 can be prepared as described in WO 2010/090875, WO 2010/083207, WO 2011/068898 and WO 2012/012619, the disclosures of each of which are incorporated herein by reference.

In certain embodiments, Compound A-3 can be synthesized as illustrated in Schemes 4 and 5, below.

Scheme 4

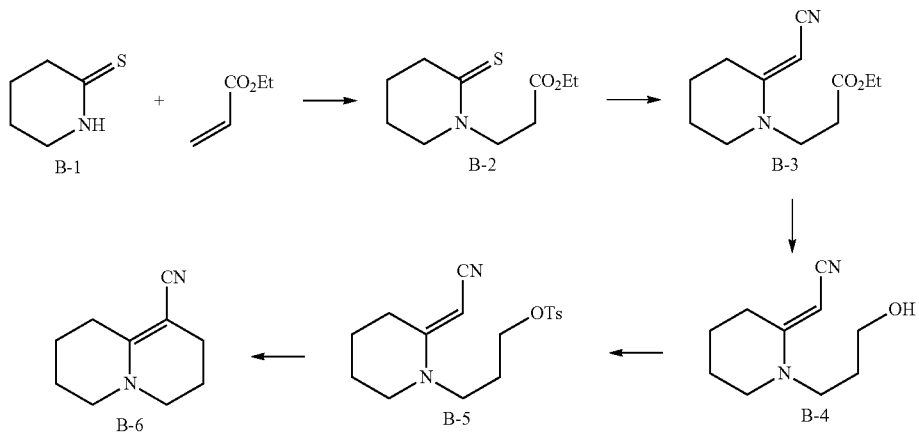

Referring to Scheme 4, thiolactam B-2 can be prepared by conjugate addition of piperidine-2-thione B-1 to ethyl acrylate. Compound B-3 can be prepared as a single geometric isomer by reacting Compound B-2 with bromoacetonitrile in the presence of triphenylphosphine and triethylamine. Selective reduction of the ester group of Compound B-3 affords the alcohol (Compound B-4). Suitable conditions for reduction of the ester group include reaction with lithium aluminum hydride, and the like. Tosylate B-5 can be prepared under standard conditions (e.g., NaH, p-TsCl). Subsequent intramolecular nucleophilic displacement of Compound B-5 affords Compound B-6.

Compound B-6 may serve as an intermediate precursor for the diastereomeric amines (which includes Compound A-3), as shown in Scheme 5 below.

Scheme 5

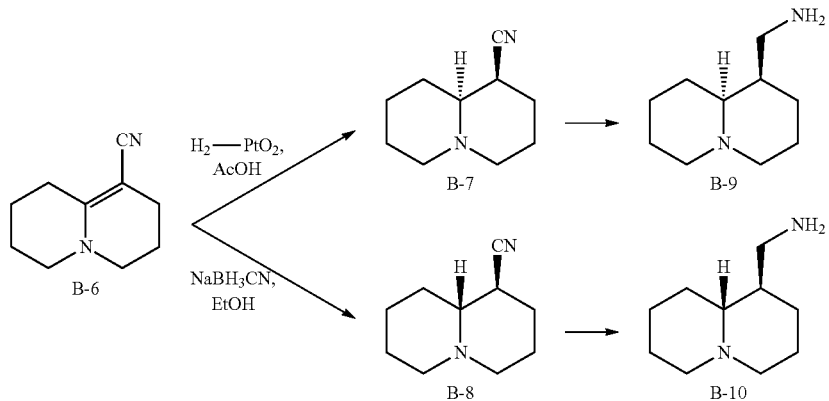

Referring to Scheme 5, intermediate Compound B-6 can be preferentially converted to the cis-hydrogenated cyanoquinolizidine B-7 by catalytic hydrogenation. Alternatively, reduction of Compound B-6 with sodium cyanoborohydride affords an excess of the trans-cyanoquinolizidine B-8. The nitrile group on Compounds B-7 and B-8 can be reduced to afford (±)-lupinamine B-9 and (±)-epilupinamine B-10, respectively. Suitable conditions for reduction of the nitrile group in Compounds B-7 and B-8 include reaction with a catalyst, such as, but not limited to, nickel-aluminum alloy, or reaction with a reducing agent, such as, but not limited to, lithium aluminum hydride, and the like. Additional details of the reactions described in Schemes 4 and 5 may be found in Michael, J. P., and Jungmann, C. M., Tetrahedron, vol. 48, no. 46, pp. 10211-20220 (1992).

The stereoisomers of Compound A-3 can be isolated by procedures known to those skilled in the art. The individual stereoisomers may be obtained, for instance, by a resolution technique or by chromatography techniques (e.g., silica gel chromatography, chiral chromatography, etc.).

Although many of the synthetic schemes discussed above do not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected 2,4-pyrimidinediamine with a suitable progroup. Conditions for carrying out such reactions and for deprotecting the product to yield prodrugs as described herein are well-known.

Various references teaching methods useful for synthesizing pyrimidines generally, as well as starting materials described in the Schemes above, are known in the art. For specific guidance, the reader is referred to Brown, D. J., "The Pyrimidines", in The Chemistry of Heterocyclic Compounds, Volume 16 (Weissberger, A., Ed.), 1962, Interscience Publishers, (A Division of John Wiley & Sons), New York ("Brown I"); Brown, D. J., "The Pyrimidines", in The Chemistry of Heterocyclic Compounds, Volume 16, Supplement I (Weissberger, A. and Taylor, E. C., Ed.), 1970, Wiley-Interscience, (A Division of John Wiley & Sons), New York (Brown II"); Brown, D. J., "The Pyrimidines", in The Chemistry of Heterocyclic Compounds, Volume 16, Supplement II (Weissberger, A. and Taylor, E. C., Ed.), 1985, An Interscience Publication (John Wiley & Sons), New York ("Brown III"); Brown, D. J., "The Pyrimidines" in The Chemistry of Heterocyclic Compounds, Volume 52 (Weissberger, A. and Taylor, E. C., Ed.), 1994, John Wiley & Sons, Inc., New York, pp. 1-1509 (Brown IV"); Kenner, G. W. and Todd, A., in Heterocyclic Compounds, Volume 6, (Elderfield, R. C., Ed.), 1957, John Wiley, New York, Chapter 7 (pyrimidines); Paquette, L. A., Principles of Modern Heterocyclic Chemistry, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., Heterocyclic Chemistry, 3rd Edition, 1995, Chapman and Hall, London, UK, pp. 1-516; Vorbrüggen, H. and Ruh-Pohlenz, C., Handbook of Nucleoside Synthesis, John Wiley & Sons, New York, 2001, pp. 1-631 (protection of pyrimidines by acylation pp. 90-91; silylation of pyrimidines pp. 91-93); Joule, J. A., Mills, K. and Smith, G. F., Heterocyclic Chemistry, 4th Edition, 2000, Blackwell Science, Ltd, Oxford, UK, pp. 1-589; and Comprehensive Organic Synthesis, Volumes 1-9 (Trost, B. M. and Fleming, I., Ed.), 1991, Pergamon Press, Oxford, UK.

The embodiments are also directed to processes and novel intermediates useful for preparing compounds of formula I-IV or a salt or solvate or stereoisomer thereof.

Accordingly, the present disclosure provides a method for making a compound according to the formula

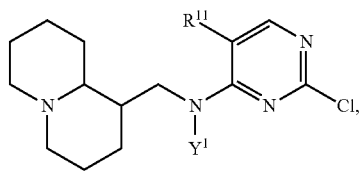

wherein

R¹¹ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and SF₅; and Y¹ is selected from hydrogen and alkyl.

In certain embodiments, the method includes contacting a compound of the formula

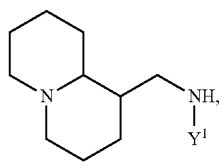

with a compound of the formula:

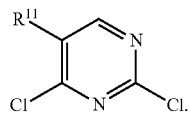

Aspects of the present disclosure include a method for making a compound according to the formula

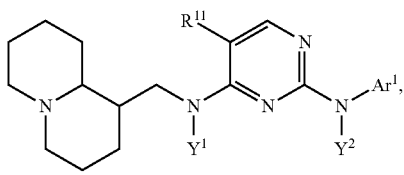

wherein

R¹¹ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, sulfide, substituted sulfide, and SF₅;

Y¹ and Y² are independently selected from hydrogen and alkyl; and

Ar¹ is selected from aryl, substituted aryl, heteroaryl, and substituted heteroaryl.

In certain embodiments, the method includes contacting a compound of the formula

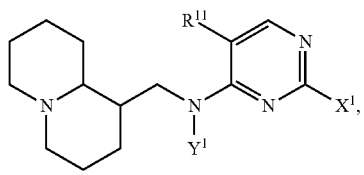

wherein X¹ is a halogen;

with a compound of the formula HNY²Ar¹. R¹¹, Y¹, Y² and Ar¹ are as described hereinbefore.

In certain embodiments, in the above methods, the method further includes separating isomers with a resolution technique. In certain embodiments, in the above methods, the method further includes separating isomers with chiral chromatography. In certain embodiments, the disclosure provides a method for preparing an aptically active compound, for example as shown in Schemes 4 and 5 above.

In some embodiments, the above methods further include the step of forming a salt of a compound of formula I-IV. Embodiments are directed to the other processes described herein, and to the product prepared by any of the processes described herein.

Pharmaceutical Compositions

In certain embodiments, the disclosed compounds are useful for the inhibition of PKC activity and the treatment of a disease or disorder that is mediated through the activity of a PKC activity. Accordingly, pharmaceutical compositions comprising at least one disclosed compound are also described herein.

A pharmaceutical composition that includes a subject compound may be administered to a patient alone, or in combination with other supplementary active agents. The pharmaceutical compositions may be manufactured using any of a variety of processes, including, but not limited to, conventional mixing, dissolving, granulating, dragee-making, levigating, emulsifying, encapsulating, entrapping, lyophilizing, and the like. The pharmaceutical composition can take any of a variety of forms including, but not limited to, a sterile solution, suspension, emulsion, lyophilisate, tablet, pill, pellet, capsule, powder, syrup, elixir or any other dosage form suitable for administration.

A subject compound may be administered to a subject using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, aerosols, and the like Formulations for pharmaceutical compositions are described in, for example, Remington's Pharmaceutical Sciences, by E. W. Martin, Mack Publishing Co., Easton, Pa., 19th Edition, 1995, which describes examples of formulations (and components thereof) suitable for pharmaceutical delivery of disclosed compounds. Pharmaceutical compositions that include at least one of the subject compounds can be formulated for use in human or veterinary medicine. Particular formulations of a disclosed pharmaceutical composition may depend, for example, on the mode of administration and/or on the location of the subject to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the disease or condition being treated can also be included as active ingredients in a pharmaceutical composition.

Pharmaceutically acceptable carriers useful for the disclosed methods and compositions may depend on the particular mode of administration being employed. For example, parenteral formulations may include injectable fluids, such as, but not limited to, pharmaceutically and physiologically acceptable fluids such as water, physiological saline, balanced salt solutions, aqueous dextrose, glycerol or the like as a vehicle. For solid compositions (e.g., powder, pill, tablet, or capsule forms), non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other examples of excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) water (e.g., pyrogen-free water); (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, methyl sulfonic acid, salicylic acid, formic acid, trichloroacetic acid, trifluoroacetic acid, gluconic acid, asparagic acid, aspartic acid, benzenesulfonic acid, para-toluenesulfonic acid, naphthalenesulfonic acid, and the like. In certain embodiments, the pharmaceutically acceptable salt includes formic acid. In certain embodiments, the pharmaceutically acceptable salt includes trifluoroacetic acid. Other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying the compound in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are substantially solid at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition may be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions that include a subject compound may be formulated in unit dosage form suitable for individual administration of precise dosages. The amount of active ingredient administered may depend on the subject being treated, the severity of the affliction, and the manner of administration, and is known to those skilled in the art. In certain instances, the formulation to be administered contains a quantity of the compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Methods of Administration

The subject compounds can inhibit a protein kinase C (PKC) activity. Accordingly, the subject compounds are useful for treating a disease or disorder that is mediated through the activity of a PKC activity in a subject. In certain embodiments, the subject compounds are useful for treating a disease or disorder that is associated with the activation of T-cells in a subject.

The route of administration may be selected according to a variety of factors including, but not limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound may depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (e.g., patient) being treated. For example, this may be the amount of a subject compound necessary to prevent, inhibit, reduce or relieve a disease or disorder that is mediated through the activity of a PKC activity in a subject. Ideally, a therapeutically effective amount of a compound is an amount sufficient to prevent, inhibit, reduce or relieve a disease or disorder that is mediated through the activity of a PKC activity in a subject without causing a substantial cytotoxic effect on host cells.

Therapeutically effective doses of a subject compound or pharmaceutical composition can be determined by one of skill in the art, with a goal of achieving local (e.g., tissue) concentrations that are at least as high as the $IC_{50}$ of an applicable compound disclosed herein.

An example of a dosage range is from 0.1 to 200 mg/kg body weight orally in single or divided doses. In some embodiments, a dosage range is from 1.0 to 100 mg/kg body weight orally in single or divided doses, including from 1.0 to 50 mg/kg body weight, from 1.0 to 25 mg/kg body weight, from 1.0 to 10 mg/kg body weight (assuming an average body weight of approximately 70 kg; values may be adjusted accordingly for persons weighing more or less than average). For oral administration, the compositions are, for example, provided in the form of a tablet containing from about 10 to about 1000 mg of the active ingredient, such as 25 to 750 mg, or 50 to 500 mg, for example 75 mg, 100 mg, 200 mg, 250 mg, 400 mg, 500 mg, 600 mg, 750 mg, or 1000 mg of the active ingredient for the symptomatic adjustment of the dosage to the subject being treated. In certain embodiments of an oral dosage regimen, a tablet containing from 500 mg to 1000 mg active ingredient is administered once (e.g., a loading dose) followed by administration of ½ (i.e., half) dosage tablets (e.g., from 250 to 500 mg) each 6 to 24 hours for 3 days or more.

The specific dose level and frequency of dosage for any particular subject may be varied and may depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

Embodiments of the present disclosure also include combinations of one or more disclosed compounds with one or more other agents or therapies useful in the treatment of a disease or disorder. In certain instances, the disease or disorder is mediated through the activity of a PKC activity in a subject. In certain instances, the disease or disorder is cell proliferative disorder. For example, one or more disclosed compounds may be administered in combination with therapeutically effective doses of other medicinal and pharmaceutical agents, or in combination other non-medicinal therapies, such as hormone or radiation therapy. The term "administration in combination with" refers to both concurrent and sequential administration of the active agents.

Protein Kinase C

Protein Kinase C (PKC)

PKC is a family of enzymes that function as serine/threonine kinases. The isoenzymes of PKC differ in their tissue distribution, enzymatic selectivity, requirement for $Ca^{2+}$, and regulation. PKCs play an important role in cell-cell signaling, gene expression and in the control of cell differentiation and growth.

The subject compound can be a selective inhibitor of PKC, e.g. an inhibitor selective for PKC over one or more other protein kinases, e.g. over one or more tyrosine kinases, for instance, over one or more non-receptor or receptor tyrosine kinases, e.g. over one or more of PKA, PKB, Abl Met, Src, Ins-R, Flt-3, JAK-2, KDR and/or Ret proteins. The selective PKC inhibitors may optionally be selective over one or more serine/threonine kinases, e.g. one or more serine/threonine kinases which do not belong to the CDK family. The subject compounds can exhibit a selectivity of at least 10 fold, or 20 fold, or 100 fold for the PKC over one or more other protein kinases, e.g. over one or more tyrosine kinases, e.g. over Flt-3, JAK-2, KDR and/or Ret proteins, or over one or more serine/threonine kinases which do not belong to the CDK family.

The selectivity of a selective inhibitor of PKC over other protein kinases may be calculated as the ratio of the $IC_{50}$ measured for PKC in an assay described herein over the $IC_{50}$ determined for another kinase. In a certain instance, there is provided a PKC inhibitor for which the ratio of the $IC_{50}$ value as determined in an Allogeneic Mixed Lymphocyte Reaction (MLR) assay to the $IC_{50}$ value as determined in a Bone Marrow Proliferation (BM) assay is higher than 5, 10, 20, or 30. MLR and BM assays can be done according to known methods, e.g. mouse or human MLR and BM assays, such as disclosed herein.

The disclosure provides an inhibitor of PKC, which can be an isozyme-selective PKC inhibitor, wherein the subject compound possesses selectivity for the isoforms θ and α of PKC over one or more of the other PKC isoforms. In a certain instance, the subject compound possesses selectivity for the isoform θ of PKC over one or more of the other PKC isoforms. In a certain instance, the subject compound possesses selectivity for the isoform α of PKC over one or more of the other PKC isoforms. In one embodiment, the disclosed compounds exhibit selectivity for PKC θ and PKC α over at least one PKC isoform.

A subject compound can show a selectivity of at least 10 fold, or 20 fold, or 100 fold for the isoforms θ or α of PKC over one or more of the other PKC isoforms. Selectivity for the isoforms θ or α of PKC over one or more of the other PKC isoforms can be measured by comparing the $IC_{50}$ of the subject compound for the isoforms θ or α of PKC to the $IC_{50}$ of the subject compound for the other PKC isoforms. In certain instances, the selectivity can be determined by calculating the ratio of $IC_{50}$ of the subject compound for the other isoforms of PKC to the $IC_{50}$ of the subject compound for θ or α isoforms of PKC. In certain examples subject compounds exhibit a selectivity for PKC θ, α or both over another PKC isoform of at least about 2-fold, such as from about 3-fold to about 300-fold, from about 10-fold to about 100-fold or from about 5-fold to 50-fold. $IC_{50}$ values are obtained, for example, according to PKC assays described herein. The subject compounds can show an $IC_{50}$ value for the isoforms θ or α of PKC of 1 μM or less, such as less than about 300 nM, such as from about 1 nM to about 250 nM, less than 100 nM or even less than 10 nM in the assays disclosed herein.

The subject compounds can show a selectivity of the isoforms θ or μ of PKC over other isoforms of PKC, as well as a selectivity over one or more of the other protein kinases, e.g. over one or more tyrosine kinases, or over one or more serine/threonine kinases which do not belong to the CDK-family, e.g. over one or more of PKA, PKB, Abl, Met, Src, Ins-it, Flt-3, JAK-2, KDR and Ret proteins, e.g. over one or more of Flt-3, JAK-2, KDR and Ret proteins.

Certain isozymes of PKC have been implicated in the mechanisms of various disease states, including, but not necessarily limited to, the following: cancer (PKC α, βI, βII, and δ); cardiac hypertrophy and heart failure (PKC βI and PKC βII) nociception (PKC γ and ε); ischemia including myocardial infarction (PKC ε and δ); immune response, particularly T-cell mediated (PKC θ and α); and fibroblast growth and memory (PKC δ and ζ). The role of PKC ε is also implicated in pain perception. PKC inhibitors can also be used for treating an ocular disease or disorder involving inflammatory and/or neovascular events.

The subject compounds can be used in the treatment of mammalian (especially human) disease states characterized by aberrant, elevated activity of a PKC isozyme in a tissue as compared to non-disease tissue of the same origin. PKC isozymes and disease states and/or biological functions amenable to therapy by inhibition of activity of the PKC isozyme include, but are not necessarily limited to: PKC α (hyperproliferative cellular diseases, such as cancer); PKC βI and PKC βII (cardiac hypertrophy and heart failure); PKC γ (pain management); PKC δ (ischemia, hypoxia (e.g., such as in myocardial infarction and in stroke); apoptosis induced by UV irradiation; and aberrant fibroblast growth (e.g., as may occur in wound healing)); PKC ε (pain management, myocardial dysfunction); PKC θ (immune system diseases, particularly those involving T-cell mediated responses); and PKC ζ (memory and fibroblast growth).

PKC Theta

PKC θ is expressed predominantly in lymphoid tissue and skeletal muscle. PKC θ is selectively expressed in T-cells and plays a role in mature T-cell activation. It has been shown that PKC θ is involved in T-cell receptor (TCR)-mediated T-cell activation but inessential during TCR-dependent thymocyte development. PKC θ, but not other PKC isoforms, translocates to the site of cell contact between antigen-specific T-cells and antigen presenting cells (APC), where it localizes with the TCR in the central core of the T-cell activation. PKC θ, but not the α, ε, or ζ isoenzymes, can selectively activate a FasL promoter-reporter gene and upregulate the mRNA or cell surface expression of endogenous FasL. On the other hand, PKC θ and ε can promote T-cell survival by protecting the cells from Fas-induced apoptosis, and this protective effect was mediated by promoting p90Rsk-dependent phosphorylation of BCL-2 family member BAD. Thus, PKC θ appears to play a dual regulatory role in T-cell apoptosis.

PKC θ inhibitors can find use in the treatment or prevention of disorders or diseases mediated by T lymphocytes, for example, autoimmune disease such as rheumatoid arthritis, psoriasis and lupus erythematosus, and inflammatory disease such as asthma and inflammatory bowel diseases.

PKC θ is a drug target for immunosuppression in transplantation and autoimmune diseases (Isakov et al. (2002) Annual Review of Immunology, 20, 761-794). PCT Publication WO2004/043386 identifies PKC θ as a target for treatment of transplant rejection and multiple sclerosis. PKC θ also plays a role in inflammatory bowel disease (The Journal of Pharmacology and Experimental Therapeutics (2005), 313 (3), 962-982), asthma (WO 2005062918), and lupus (Current Drug Targets: Inflammation & Allergy (2005), 4 (3), 295-298).

In addition, PKC θ is highly expressed in gastrointestinal stromal tumors (Blay, P. et al. (2004) Clinical Cancer Research, 10, 12, Pt. 1), it has been suggested that PKC θ is a molecular target for treatment of gastrointestinal cancer (Wiedmann, M. et al. (2005) Current Cancer Drug Targets 5(3), 171).

Experiments induced in PKC θ knock-out mice led to the conclusion that PKC θ inactivation prevented fat-induced defects in insulin signalling and glucose transport in skeletal muscle (Kim J. et al, 2004, The J. of Clinical Investigation 114 (6), 823). This data indicates PKC θ is a therapeutic target for the treatment of type 2 diabetes, and hence PKC θ inhibitors can be useful for treating such disease.

Therapeutic Applications

The subject compounds are useful for treating a disease or disorder that is mediated through, or exacerbated by, the activity of a PKC in a subject in need of treatment. Also, the compounds are useful for treating a disease or disorder that is associated with aberrant or otherwise undesirable T cell activation in a subject.

Accordingly, the present disclosure provides methods of treating an inflammatory disease in a subject by administering an effective amount of a subject compound, including a salt or solvate or stereoisomer thereof, so as to treat inflammation. Inflammatory diseases contemplated for therapy include acute and chronic inflammation mediated or exacerbated by PKC activity.

The present disclosure also provides methods of treating an autoimmune disease in a subject by administering to the subject an effective amount of a subject compound, including a salt or solvate or stereoisomer thereof, so as to treat the autoimmune disease.

The present disclosure also provides methods of treating an ocular disease or disorder involving inflammatory and/or neovascular events by administration of a subject compound, including a salt or solvate or stereoisomer thereof, in an effective amount.

Diseases or conditions of interest for treatment according to the present disclosure include, but are not limited to, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as: AIDS, septic shock or adult respiratory distress syndrome, ischemia/reperfusion injury, e.g., myocardial infarction, stroke, gut ischemia, renal failure or hemorrhage shock, and traumatic shock, e.g., traumatic brain injury.

Further diseases or conditions of interest for treatment according to the present disclosure include, but are not limited to, T-cell mediated acute or chronic inflammatory diseases or disorders or autoimmune diseases, rheumatoid arthritis, osteoarthritis, systemic lupus erythematosus, Hashimoto's thyroiditis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases (such as Sjoegren's syndrome, keratoconjunctivitis, uveitis) inflammatory bowel disease, Crohn's disease or ulcerative colitis, Guillain-Barre syndrome, and allergies.

The subject compounds can also be used for preventing or treating or delaying ocular diseases and disorders involving inflammation and/or neovascularization. Ocular diseases or disorders involving inflammatory and/or neovascular events include, but are not limited to, macular degeneration (AMD), diabetic ocular diseases or disorders, uveitis, optic neuritis, ocular edema, ocular angiogenesis, ischemic retinopathy, anterior ischemic optic neuropathy, optic neuropathy and neuritis, macular edema, cystoid macular edema (CME), retinal disease or disorder, such as retinal detachment, retinitis pigmentosa (RP), Stargart's disease, Best's vitelliform retinal degeneration, Leber's congenital amaurosis and other hereditary retinal degenerations, Sorsby's fundus dystrophy, pathologic myopia, retinopathy of prematurity (ROP), Leber's hereditary optic neuropathy, corneal transplantation or refractive corneal surgery, keratoconjunctivitis, or dry eye.

Generally, cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9; 22)(qq34;q11)), chronic neutrophilic leukemia, chronic eosinophilic leukemiahypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12) (q22;p12) (TEL-Syk fusion; see, e.g., Kuno et al., 2001, Blood 97:1050).

In some embodiments, the composition can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16) (p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

In other aspects, cell proliferative disorders comprise virally mediated tumors. These can arise from infection of cells by an oncogenic virus that has the capability of transforming a normal cell into a tumor cell. Because rates of viral infection far exceed the number of actual incidence of cell transformation, viral mediated transformation generally act together with other cellular factors to generate a transformed tumor cell. Thus, a virally mediated tumor does not require the virus to be the sole causative agent of the cell proliferative disorder, but rather that the viral infection or persistent presence of virus is associated with the generation of the tumor. Generally, tumors where the causative agent is a virus typically has continual expression of a limited number of viral genes and that viral these oncogenes, expressed as part of the viral infection or through persistence of the virus, disrupts the normal cellular gene expression and signal transduction pathways. Without being bound by theory, viral oncogenes involved in cell transformation appear to disrupt four main cellular processes: cell surface receptors that interact with growth factors and extracellular matrix, transmembrane signaling networks, cytosolic elements such as soluble proteins and second messengers, and nuclear proteins including DNA binding proteins and factors which function directly and indirectly in gene regulation and replication.

Characterization of Functional Properties

The following are examples of assays useful in characterizing activities of a compound of the present disclosure.

A. In Vitro

1. Protein Kinase C Assay

The inhibition of PKC activity is measured by monitoring the production of phosphorylated peptide by fluorescence polarization at different concentrations of the inhibitor. Reactions are carried out in 96-well plate format with a total volume of 20 μL containing 20 mM HEPES, pH 7.4, 5 mM $MgCl_2$, 0.2 mM $CaCl_2$, 1 mM DTT, 0.02% Brij-35, 0.1 mg/ml phosphatidylserine, 0.02 mg/ml dioleoyl-sn-glycerol and 5 μM each of ATP and the peptide substrate. Compounds are first diluted serially in DMSO and then transferred to a solution containing the above concentrations of HEPES, $MgCl_2$, $CaCl_2$, DTT, and Brij-35 to yield 5× compound solutions in 2% DMSO, which is then added to the reaction solution. Reactions are initiated by the addition of PKC at a typical concentration as described in the table below, and then allowed to incubate at room temperature for 20 minutes. At the end of this time, a combination of quench (EDTA) and detection (peptide tracer and antibody) reagents is added using the protocol of Invitrogen P2748 (Carlsbad, Calif.), a Protein Kinase C Fluorescence polarization Assay Kit. After a 30 minute period of incubation, the amount of phosphorylated peptide generated is measured by fluorescence polarization (Ex=485 nm, Em=535 nm) using a Tecan Polarian instrument (Switzerland).

TABLE 2

| Peptide substrate | SEQ ID | Enzyme source | enzyme concentration |
|---|---|---|---|
| PKC theta | RFARKGSLRQKNV | Seq ID No. 1 | Upstate Bio-technologies, Temecula, CA, cat. #14-444 | 40 ng/ml |
| PKC epsilon | RFARKGSLRQKNV | Seq ID No. 1 | Upstate Bio-technologies, Temecula, CA, cat. #14-518 | 50 ng/ml |

2. IL-2 ELISA, Human Primary T Cell, Anti-CD3+CD28+ Assays

Human Primary T Cell Isolation and Culture: Human primary T cells were prepared as follows. Fresh PBMC's from All Cells (Cat #PB002) were re-suspended in RPMI (RPMI-1640 with L-Glutamine; Mediatech, Inc., Herndon Va., cat. #10-040-CM) with 10% FBS and seeded into flasks and incubated at 37° C. for 2 hours to allow the monocytes to adhere. The non-adherent cells were then centrifuged and re-suspended in RPMI medium containing 40 U/ml IL2 and seeded into a flask pre-coated with 1 μg/ml aCD3 and 5 ug/ml aCD28 (Anti-Human CD3, BD Pharmingen Catalog #555336, Anti-Human CD28, Beckman Coulter Catalog #1M1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/ml IL-2.

Primary T Cell Stimulation and IL2 ELISA: Human primary T cells (100,000 cells per well) were pre-incubated with or without test compound in RPMI-1640 with L-Glutamine and 10% FBS for 1 hour at 37° C. Cells were then stimulated by transferring them to round-bottom 96-well plates pre-coated with 1 μg/ml aCD3 and 5 μg/ml aCD28. For counter assay, cells were instead stimulated by adding 8× stock solutions of PMA and ionomycin in RPMI-1640 with L-Glutamine and 10% FBS (for final concentrations of 0.5 ng/ml PMA and 0.1 μM ionomycin, both from Calbiochem). Cells were incubated at 37° C. for 24 hours before 100 μL supernatants were harvested for quantification of IL-2 by ELISA using Human IL-2 Duoset ELISA Kit from R and D Systems, Cat. #DY202E.

3. Protein Kinase C assay

The subject compounds can be tested for activity on different PKC isoforms according to the following method. Assay is performed in a white with clear bottom 384-well microtiterplate with non-binding surface. The reaction mixture (25 μl) contains 1.5 μM of a tridecapeptide acceptor substrate that mimics the pseudo substrate sequence of PKC α with the Ala→Ser replacement, 10 μM $^{33}$P-ATP, 10 mM Mg(NO$_3$)$_2$, 0.2 mM CaCl$_2$, PKG at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 minutes at room temperature. Reaction is stopped by adding 50 μl of stop mix (100 mM EDTA, 200 μM ATP, 0.1% Triton X-100, 0.375 mg/well streptavidin-coated SPA beads in phosphate buffered saline w/o Ca, Mg. After 10 minutes incubation at room temperature, the suspension is spun down for 10 minutes at 300 g. Incorporated radioactivity is measured in a Trilux counter for 1 minute. IC$_{50}$ measurement is performed on a routine basis by incubating a serial dilution of inhibitor at concentrations ranging between 1-1000 μM. IC$_{50}$ values are calculated from the graph by curve fitting with XL Fit® software.

4. Protein Kinase C α Assay

Human recombinant PKC α is obtained from Oxford Biomedical Research and is used under the assay conditions as described under Section A.1 above.

5. Protein Kinase C β1 Assay

Human recombinant PKC β1 is obtained from Oxford Biomedical Research and is used under the assay conditions as described under Section A.1 above.

6. Protein Kinase C δ Assay

Human recombinant PKC δ is obtained from Oxford Biomedical Research and is used under the assay conditions as described under Section A.1 above.

7. Protein Kinase C ε Assay

Human recombinant PKC ε is obtained from Oxford Biomedical Research and is used under the assay conditions as described under Section A.1 above.

8. Protein Kinase C η Assay

Human recombinant PKC η is obtained from PanVera and is used under the assay conditions as described under Section A.1 above.

9. Protein Kinase C θ Assay

Human recombinant PKC θ is used under the assay conditions as described above.

10. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the Ca$^{++}$ ionophore ionomycin as follows. For antibody-mediated stimulation Microlite TM1 microtiter plates (Dynatech) are coated with 3 μg/ml goat anti-mouse IgG Fc antibodies (Jackson) in 55 μl phosphate-buffered saline (PBS) per well for three hours at room temperature. Plates are blocked after removing the antibodies by incubation with 2% bovine serum albumin (BSA) in PBS (300 μl per well) for 2 hours at room temperature. After washing three times with 300 μl PBS per well, 10 ng/ml anti-T cell receptor antibodies (WT31, Becton & Dickinson) and 300 ng/ml anti-CD28 antibodies (15E8) in 50 μl 2% BSA/PBS are added as stimulating antibodies and incubated overnight at 4° C. Finally the plates are washed three times with 300 μl PBS per well. Seven three-fold serial dilutions of test compounds in duplicates in assay medium (RPMI 1640/10% fetal calf serum (FCS) containing 50 μM 2-mercaptoethanol, 100 units/ml penicillin and 100 μg/ml streptomycin) are prepared in separate plates, mixed with transfected Jurkat cells (clone K22 290_H23) and incubated for 30 minutes at 37° C. in 5% CO$_2$ 100 μl of this mixture containing 1×10$^5$ cells are then transferred to the antibody-coated assay plates. In parallel 100 μl are incubated with 40 ng/ml PMA and 2 μM ionomycin. After incubation for 5.5 hours at 37° C. in 5% CO$_2$, the level of luciferase is determined by bioluminescence measurement. The plates are centrifuged for 10 minutes at 500 g and the supernatant is removed by flicking. Lysis buffer containing 25 mM Tris-phosphate, pH 7.8, 2 mM DTT, 2 mM 1,2-diaminocyclohexane-N,N,N',N-tetraacetic acid, 10% (v/v) glycerol and 1% (v/v) Triton X-100 is added (20 μl per well). The plates are incubated at room temperature for 10 minutes under constant shaking. Luciferase activity is assessed with a bioluminescence reader (Labsystem, Helsinki, Finland) after automatic addition of 50 μl per well luciferase reaction buffer containing 20 mM Tricine, 1.07 mM (MgCO$_3$)$_4$Mg(OH)$_2$×5H$_2$O, 2.67 mM MgSO$_4$, 0.1 mM EDTA, 33.3 mM DTT, 270 μM coenzyme A, 470 μM luciferin (Chemie Brunschwig AG), 530 μM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition (IC$_{50}$) is determined from the dose-response curves.

11. Bone Marrow Proliferation (BM) Assay

Bone marrow cells from CBA mice (2.5×10$^4$ cells per well in flat bottom tissue culture microtiter plates) are incubated in 100 μl RPMI medium containing 10% FCS, 100 U/ml penicillin, 100 μg/ml streptomycin (Gibco BRL, Basel, Switzerland), 50 UM 2-mercaptoethanol (Fluke, Buchs, Switzerland), WEHI-3 conditioned medium (7.5% v/v) and L929 conditioned medium (3% v/v) as a source of growth factors and serially diluted compounds. Seven three-fold dilution steps in duplicates per test compound are performed. After four days of incubation 1 μCi³H-thymidine is added. Cells are harvested after an additional five-hour incubation period, and incorporated ³H-thymidine is determined according to standard procedures. Conditioned media are prepared as follows. WEHI-3 cells 1 (ATCC TIB68) and L929 cells (ATCC CCL 1) are grown in RPMI medium until confluence for 4 days and one week, respectively. Cells are harvested, resuspended in the same culture flasks in medium C containing 1% FCS (Schreier and Tees 1981) for WEHI-3 cells and RPMI medium for L929 cells and incubated for 2 days (WEHI-3) or one week (L929). The supernatant is collected, filtered through 0.2 μm and stored in aliquots at −80° C. Cultures without test compounds and without WEHI-3 and L929 supernatants are used as low control values. Low control values are subtracted from all values. High controls without any sample are taken as 100% proliferation. Percent inhibition by the samples is calculated and the concentrations required for 50% inhibition ($IC_{50}$ values) are determined.

12. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi³H-thymidine is added. Cells are harvested after an additional five-hour incubation period, and incorporated ³H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined.

B. In Vivo

1. Heart Transplantation Model

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 1010 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when-heart beat stops. Graft survival is monitored in animals treated with compounds.

2. Graft v. Host Model

Spleen cells ($2 \times 10^7$) from Wistar/F rats are injected subcutaneously into the right hind footpad of (Wistar/F×Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. In certain instances the test compound is a selective PKC inhibitor. For example, disclosed compounds that are particularly useful for treating graft versus host disease and related disorders are selective PKC α and θ inhibitors.

3. Rat Collagen-Induced Arthritis Model

Rheumatoid arthritis (RA) is characterized by chronic joint inflammation eventually leading to irreversible cartilage destruction. IgG-containing IC are abundant in the synovial tissue of patients with RA. While it is still debated what role these complexes play in the etiology and pathology of the disease, IC communicate with the hematopoetic cells via the FcγR.

CIA is a widely accepted animal model of RA that results in chronic inflammatory synovitis characterized by pannus formation and joint degradation. In this model, intradermal immunization with native type II collagen, emulsified with incomplete Freund's adjuvant, results in an inflammatory polyarthritis within 10 or 11 days and subsequent joint destruction in 3 to 4 weeks.

4. Study Protocol

Syngeneic LOU rats are immunized with native type II collagen on Day 0, and efficacy of a test compound is evaluated in a prevention regimen and a treatment regimen. In the prevention protocol, either vehicle or various doses of a test compound are administered via oral gavage starting on day of immunization (Day 0). In the treatment protocol, after clinical signs of arthritis develop on Day 10, treatment with a test compound is initiated (e.g., 300 mg/kg by oral gavage, qd) and continued until sacrifice on Day 28. In both protocols, clinical scores are obtained daily, and body weights are measured twice weekly. At Day 28, radiographic scores are obtained, and serum levels of collagen II antibody are measured by ELISA.

5. Determination of Results

By 10 days after immunization, rats can develop clinical CIA, as determined by an increase in their arthritis scores. The mean arthritic score gradually increases in the rats treated with vehicle alone after Day 10, and by Day 28 the mean clinical score can reach about 6.75. Mean clinical scores in animals treated from the day of immunization (Day 0) with a test compound can be significantly reduced on Days 10-28 compared with vehicle controls. In the rats treated with a test compound at disease onset, there can be a significantly lower arthritis score beginning around Day 16, and this difference can be observed until the end of the study on Day 28.

Blinded radiographic scores (scale 0-6) can be obtained on Day 28 of CIA and compared between the animals in the vehicle group, animals in the prevention group, and animals in the treatment group.

The groups administered with a test compound, either prophylactically (at immunization) or after disease onset can preclude the development of erosions and reduced soft tissue swelling. Similarly, the groups administered with a test compound can result in reduction of serum anti-collagen II antibody.

6. Mouse Experimental Autoimmune Encephalomyelitis

The in vivo efficacy of a test compound towards autoimmune diseases can be demonstrated in a mouse model of experimental autoimmune encephalomyelitis (EAE).

7. Model Description

EAE is a useful model for multiple sclerosis (MS), an autoimmune disease of the CNS that is caused by immune-cell infiltration of the CNS white matter. Inflammation and subsequent destruction of myelin cause progressive paralysis. Like the human disease, EAE is associated with peripheral activation of T cells autoreactive with myelin proteins, such as myelin basic protein (MBP), proteolipid protein (PLP), or myelin oligodendrocyte protein (MOG). Activated neuroantigen-specific T cells pass the blood-brain barrier, leading to focal mononuclear cell infiltration and demyelination. EAE can be induced in susceptible mouse strains by immunization with myelin-specific proteins in combination with adjuvant. In the SJL mouse model used in these studies, hind limb and tail paralysis is apparent by Day 10 after immunization, the peak of disease severity can be observed between Days 10 and 14, and a cycle of partial spontaneous remission followed by relapse can be observed up to Day 35. The results can demonstrate the potential of the test compound to suppress disease severity and prevent relapse of disease symptoms that may be the result of FcγR-mediated cytokine release from immune cells.

8. Study Protocol

In the SJL murine model of EAE, each mouse is sensitized with PLP/CFA. (150 μg PLP139-151 with 200 μg CFA in 0.05 ml of homogenate on four sites of hind flank for a total of 0.2 ml emulsion is used to induce EAE). In a suppression protocol, either vehicle or various doses of a test compound are administered via oral gavage starting on the day of immunization (Day 0). In a treatment protocol, at onset of disease, animals are separated to achieve groups with a similar mean clinical score at onset and administered vehicle or various dose frequencies of test compounds via oral gavage. In both protocols, clinical scores are monitored daily, and body weights are measured twice weekly.

9. Determination of Results

By 10 days after PLP immunization, SJL mice can develop clinical EAE, as evidenced by an increase in their mean clinical scores. The paralytic score can gradually increase in the animals treated with vehicle only from the day of immunization (Day 0), and by Day 14 the mean score can reach a peak of about 5.1. At disease peak (e.g., Day 14), the mean clinical score in animals treated with either daily or twice daily can be significantly reduced. By Day 16, animals can exhibit a partial remission of mean clinical severity, which is a characteristic of the SJL model. The lower clinical scores in animals treated twice daily with a test compound can remain significant throughout the experiment until the animals are sacrificed on Day 30. These lower scores throughout the treatment period are reflected in the significantly lower cumulative disease index (CDI) and increase in cumulative weight index (CWI).

SJL mice treated with a test compound at disease onset (e.g., Day 11) can show a significant decrease in CDI. Further, there can be a decrease in the number of relapses in animals treated with a test compound compared with the number of relapses in animals treated with vehicle.

Research Applications

Since subject compounds can inhibit a PKC activity, such compounds are also useful as research tools. The present disclosure also provides a method for using subject compounds as a research tool for studying a biological system or sample, or for discovering new chemical compounds that can inhibit a PKC activity.

The disclosure provides for a method of studying a biological system or sample known to comprise PKC, the method comprising: (a) contacting the biological sample with a compound of formula I-IV or a salt or solvate or stereoisomer thereof; and (b) determining the inhibiting effects caused by the compound on the biological sample.

Any suitable biological sample having PKC can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample comprising PKC is typically contacted with a PKC activity-inhibiting amount of a subject compound. After the biological sample is exposed to the compound, the effects of inhibition of a PKC activity are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radioligand binding assays and measuring ligand-mediated changes in functional assays. The assay results can be used to determine the activity level as well as the amount of compound necessary to achieve the desired result, that is, a PKC activity-inhibiting amount.

Additionally, subject compounds can be used as research tools for evaluating other chemical compounds, and thus are also useful in screening assays to discover, for example, new compounds having a PKC inhibiting activity. In this manner, a subject compound can be used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b). The assays that can be used for generation of comparison data are disclosed herein, such as the PKC assays.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. As will be understood, by those of skill in the art of organic synthesis and medicinal chemistry the specific conditions set forth below are exemplary and can be varied or adapted to other reagents and products in routine fashion. Unless indicated otherwise, parts are parts by weight, molecular weight is weight average molecular weight, temperature is in degrees Celsius, and pressure is at or near atmospheric. Standard abbreviations may be used.

As referred to in the Examples, HPLC and LCMS protocols are as follows:

Protocol-1:
HPLC: Waters 2690 Alliance
Diode array detector (210-400 nm)
Column: Phenomenex Gemini 4.6×100 mm, 5um, 110 Å
Column temperature 30° C.
Sample temperature 15° C.
Solvent A—0.05% Formic acid in Water
Solvent B—0.05% Formic acid in Acetonitrile
Flow rate—1.5 ml/min
Gradient:

| Time | A % | B % |
|---|---|---|
| 0 | 95 | 5 |
| 10 | 0 | 100 (curve = 6) |
| 11.1 | 0 | 100 |
| 11.2 | 95 | 5 |
| 12.1 | 95 | 5 |

Protocol-2:
HPLC: Waters 2690 Alliance
Diode array detector (210-400 nm)
Column: Phenomenex Gemini 4.6×100 mm, 5um, 110 Å
Column temperature 30° C.
Sample temperature 15° C.
Solvent A—0.05% Formic acid in Water
Solvent B—0.05% Formic acid in Acetonitrile
Flow rate—1.5 ml/min
Gradient:

| Time | A % | B % |
|---|---|---|
| 0 | 95 | 5 |
| 10 | 0 | 100 (curve = 8) |
| 11.1 | 0 | 100 |
| 11.2 | 95 | 5 |
| 12.1 | 95 | 5 |

Protocol-3:
HPLC: Waters 2695 Alliance
Diode array detector (210-400 nm)
Column: Phenomenex Gemini 4.6×100 mm, 5 um, 110 Å
Column temperature 30° C.
Sample temperature 15° C.
Solvent A—0.05% Formic acid in Water
Solvent B—0.05% Formic acid in Acetonitrile
Flow rate—1.5 ml/min
Gradient:

| Time | A % | B % |
|---|---|---|
| 0 | 95 | 5 |
| 10 | 0 | 100 (curve = 6) |
| 11.1 | 0 | 100 |
| 11.2 | 95 | 5 |
| 12.1 | 95 | 5 |

Chiral HPLC Methods:
Protocol-4:
HPLC: Waters 2695 Alliance
Diode array detector (210-400 nm)
Column: Chiralcel-OJ, 4.6×250 mm, with guard
Mobil phase (isocratic): 40% methanol, 40% ethanol, 19.9% Hexane, 0.1% triethylamine
Flow rate: 0.5 ml/min
Injection volume: 3 µL
Concentration: approx 5 mg/ml
Detection: UV at 254 nm
Run Time: 30 minutes Protocol-5:
HPLC: Waters 2695 Alliance
Diode array detector (210-400 nm)
Column: Chiralcel-OJ, 4.6×250 mm, with guard
Mobil phase (isocratic): 89.9% Hexane, 5% methanol, 5% ethanol 0.1% triethylamine
Flow rate: 0.5 ml/min
Injection volume: 3 µL
Concentration: approx 5 mg/ml
Detection: UV at 254 nm
Run Time: 45 minutes Example 1

General Scheme for the Synthesis of Lupinane PKC Inhibitors

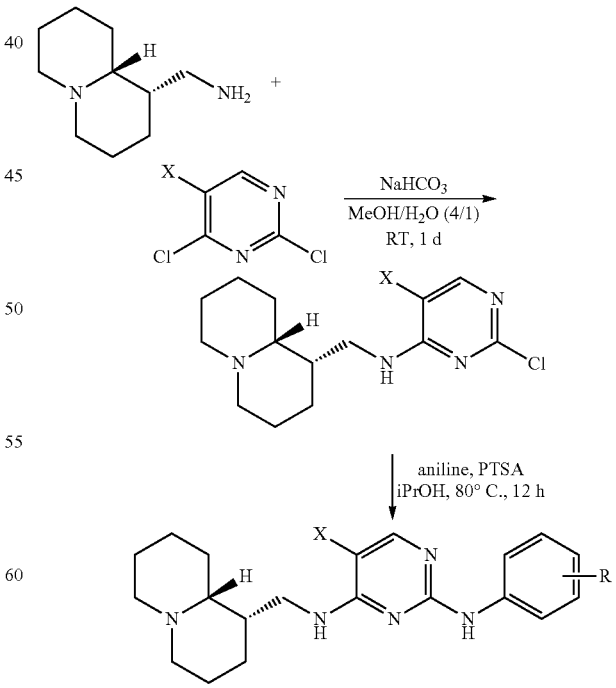

X = H, F, Cl, Me, $CF_3$, CN, $CONH_2$, OMe, $NMe_2$

General Procedure for the Synthesis of the Lupinane Mono-SNAr Product

The lupinane amine.2HCl (1-[(1S,9aR)-octahydro-2H-quinolizin-1-yl]methanamine, CAS #: 75532-84-2, commercially available from ChemBridge, San Diego) (1.0 eq) was combined with 2,4-dichloro-5-X-pyrimidine (X=H, F, Cl, Me, $CF_3$, CN, $CONH_2$, OMe, $NMe_2$) (1.0 eq) and $NaHCO_3$ (1.2 eq). A mixture of $MeOH:H_2O$ (4/1) (concentration of the reaction mixture: ca. 0.1-0.5 M) was added and the resulting suspension was stirred for 1 d at RT. After the completion of the reaction was confirmed by TLC and HPLC, silica gel was added to the reaction mixture and solvents were evaporated under reduced pressure. The resulting solid was loaded on a CombiFlash column and further purified by flash chromatography eluting with DCM/MeOH—$NH_3$ (2M) (gradient 0->10%).

General Procedure for the Installment of the N2 Substituent ($2^{nd}$ $S_NAr$)

The mono-$S_NAr$ product (50.0 mg, 1.0 eq) was dissolved in 4 ml of isopropyl alcohol in a 2 dram vial. p-Toluenesulfonic acid monohydrate (1.2 eq) and the desired aniline (1.5 eq) were added and the vial was sealed. After heating over night at 80° C. using an anodized aluminum heating block the solvent was boiled off by removing the cap. The product was isolated by preparative HPLC eluting with an acetonitrile/water gradient.

Synthesis of Right-Hand Side (RHS) Anilines

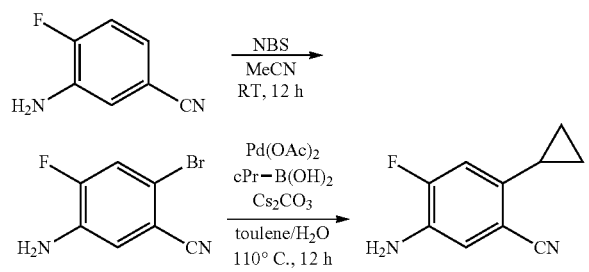

Preparation of 5-amino-2-bromo-4-fluorobenzonitrile

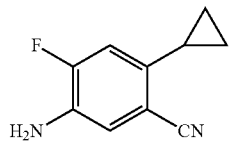

3-amino-4-fluorobenzonitrile (9.82 g, 72.1 mmol) was dissolved in acetonitrile to give a pale yellow solution. NBS (13.5 g, 75.7 mmol) was added in portions; the reaction mixture turned brown-blackish but remained a solution. After the completion of the reaction was confirmed by TLC and HPLC, silica gel was added to the reaction mixture and the solvent was evaporated under reduced pressure. The crude product was leaded on a CombiFlash column (330 g) and the product was eluted with hexanes/ethyl acetate (0→15% gradient). The clean fractions were combined to give 9.63 g (62%) of a yellowish off-white solid. More product was found in mixed fractions which were discarded. $^1$H NMR (300 MHz, dmso) δ 7.57 (d, J=10.9 Hz, 1H), 7.17 (d, J=8.7 Hz, 1H), 5.85 (s br, 2H); MS (ES) 213/215 (M–H).

Preparation of 5-amino-2-cyclopropyl-4-fluorobenzonitrile

The product from the above reaction (5-amino-2-bromo-4-fluorobenzonitrile) (4.0 g, 18.6 mmol), cyclo-propyl boronic acid (3.19 g, 37.2 mmol), $Pd(OAc)_2$ (835 mg, 3.72 mmol), tricyclohexyl phosphine (1.04 g, 3.72 mmol), $Cs_2CO_3$ (36.3 g, 111.6 mmol) were combined in a pressure vessel. A mixture of toluene (110 ml) and $H_2O$ (35 ml) was added. The ensuing yellow-orange suspension was degassed and flushed with nitrogen gas (3×). The pressure vessel was sealed and heated over night (ca. 12 h) at 110° C. After checking the reaction by TLC and HPLC, the precipitate/salts were filtered off, more $H_2O$ was added and the mixture was extracted with ethyl acetate (3×). The combined organic phases were filtered through $Na_2SO_4$, silica gel was added and solvents were removed using a rotary evaporator. Further purification by CombiFlash (120 g column) eluting with hexanes/ethyl acetate (0→20% gradient) yielded 2.01 g (61%) of the desired product in form of a pale yellow, beige solid. $^1$H NMR (300 MHz, cdcl$_3$) δ 6.98 (d, J=8.6 Hz, 1H), 6.58 (d, J=12.0 Hz, 1H), 3.81 (s br, 2H), 2.21-2.06 (m, 1H), 1.11-0.99 (m, 2H), 0.69-0.59 (m, 2H); MS (ES) 177 (M+H).

Example 2

5-(4-(((1S,9aR)-octahydro-1H-quinolizin-1-yl)methylamino)-5-fluoropyrimidin-2-ylamino)-2-cyclopropylbenzonitrile (Compound 1)

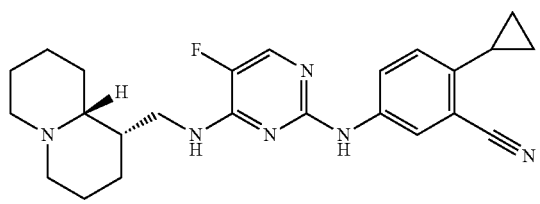 [SMILES: N#Cc1cc(Nc2ncc(F)c(NC[C@@H]3CCCN4CCCC[C@H]34)n2)ccc1C1CC1]

Compound 1 was prepared as described in Example 1.

$^1$H NMR (300 MHz, dmso) δ 9.22 (s, 1H), 8.12 (s, 1H), 7.84 (d, J=3.7 Hz, 1H), 7.79 (d, J=8.7 Hz, 1H), 7.51 (s, 1H), 6.92 (d, J=8.8 Hz, 1H), 3.64-3.44 (m, 2H), 3.41-3.21 (m, 4H), 2.71 (d, J=9.3 Hz, 2H), 2.48 (s, 2H), 2.13-1.98 (m, 1H), 1.98-1.73 (m, 7H), 1.68 (d, J=13.4 Hz, 4H), 1.59-1.33 (m, 4H), 1.33-1.08 (m, 3H), 1.01 (d, J=10.2 Hz, 2H), 0.70 (d, J=4.8 Hz, 2H); MS (ES) 421 (M+H).

Example 3

N2-(4-cyclopropyl-2-fluoro-5-(1H-tetrazol-1-yl)phenyl)-5-fluoro-N4-(((1S,9aR)-octahydro-1H-quinolizin-1-yl)methyl)pyrimidine-2,4-diamine (Compound 2, Formate Salt)

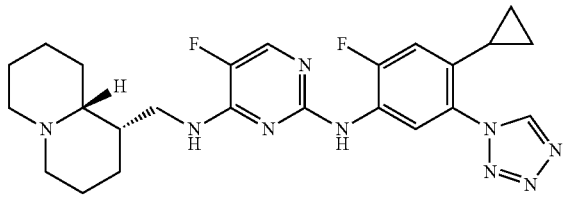

Compound 2 was prepared as described in Example 1.
$^1$H NMR (300 MHz, dmso) δ 9.87 (dd, J=12.6, 0.6 Hz, 1H), 8.10 (dd, J=9.3, 4.1 Hz, 1H), 7.97 (d, J=4.1 Hz, 1H), 7.47 (d, J=8.0 Hz, 1H), 7.13-7.00 (m, 2H), 3.57-3.02 (m, 5H), 3.02-2.74 (m, 2H), 2.33-1.99 (m, 2H), 1.90-1.08 (m, 20H), 0.76 (dd, J=18.3, 9.8 Hz, 2H), 0.72-0.53 (m, 2H); MS (ES) 482 (M+H).

Example 4

1-(5-(4-(((1S,9aR)-octahydro-1H-quinolizin-1-yl)methylamino)-5-fluoropyrimidin-2-ylamino)-2-cyclopropyl-4-fluorophenyl)-4-methyl-1H-tetrazol-5(4H)-one (Compound 3, Formate Salt)

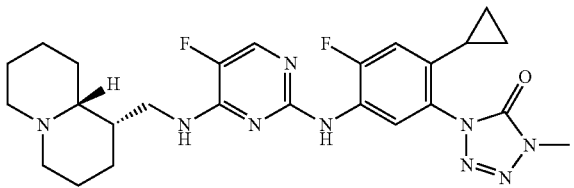 [SMILES: Cn1nnn(-c2cc(Nc3ncc(F)c(NC[C@@H]4CCCN5CCCC[C@H]45)n3)c(F)cc2C2CC2)c1=O]

Compound 3 was prepared as described in Example 1.
$^1$H NMR (300 MHz, dmso) δ 8.16-8.09 (m, 1H), 8.04 (t, J=4.4 Hz, 2H), 7.84 (d, J=7.6 Hz, 1H), 7.62 (d, J=7.5 Hz, 1H), 3.61 (s, 3H), 3.55-3.04 (m, 3H), 3.02-2.73 (m, 2H), 2.55-2.40 (m, 2H), 2.31-1.86 (m, 4H), 1.82-1.10 (m, 4H), 0.88 (t, J=8.0 Hz, 2H), 0.69 (dd, J=12.0, 4.8 Hz, 2H); MS (ES) 512 (M+H).

Example 5

5-fluoro-N4-(((1S,9aR)-octahydro-1H-quinolizin-1-yl)methyl)-N2-(4-methyl-3-(1H-tetrazol-1-yl)phenyl)pyrimidine-2,4-diamine (Compound 4, Formate Salt)

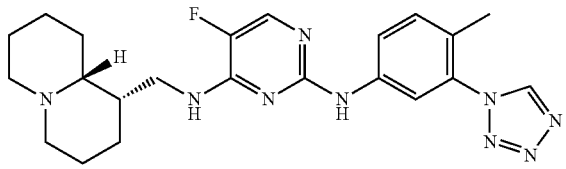 [SMILES: Cc1ccc(Nc2ncc(F)c(NC[C@@H]3CCCN4CCCC[C@H]34)n2)cc1-n1cnnn1]

Compound 4 was prepared as described in Example 1.
$^1$H NMR (300 MHz, dmso) δ 9.94 (d, J=10.0 Hz, 2H), 9.25 (s, 1H), 8.80 (s, 1H), 8.53 (s, 1H), 8.09 (t, J=3.6 Hz, 1H), 7.96-7.85 (m, 1H), 7.62 (d, J=10.6 Hz, 2H), 3.53-3.22 (m, 3H), 3.22-3.07 (m, 2H), 3.03-2.77 (m, 2H), 2.31-2.08 (m, 6H), 2.07 (s, 3H), 1.86-1.10 (m, 5H); MS (ES) 438 (M+H).

Example 6

5-fluoro-N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine (Compound 6, Trifluoroacetate Salt)

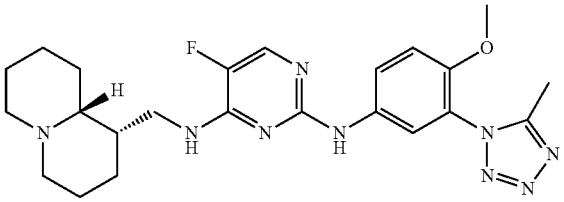 [SMILES: COc1ccc(Nc2ncc(F)c(NC[C@@H]3CCCN4CCCC[C@H]34)n2)cc1-n1nnnc1C]

Compound 6 was prepared as described in Example 1.
$^1$H NMR (300 MHz, dmso) δ 10.08-9.83 (m, 1H), 9.66 (s, 1H), 8.05 (t, J=3.9 Hz, 1H), 7.77 (dd, J=9.0, 2.5 Hz, 1H), 7.68 (dd, J=9.0, 2.6 Hz, 1H), 7.31 (dd, J=9.1, 2.3 Hz, 1H), 3.77 (s, 3H), 3.56-3.04 (m, 3H), 3.03-2.73 (m, 4H), 2.50-2.43 (m, 1H), 2.37 (s, 3H), 2.29-2.07 (m, 4H), 1.89-1.10 (m, 7H); MS (ES) 468 (M+H).

Example 7

5-fluoro-N2-(2-fluoro-5-(5-methyl-1H-tetrazol-1-yl)phenyl)-N4-(((1S,9aR)-octahydro-1H-quinolizin-1-yl)methyl)pyrimidine-2,4-diamine (Compound 7, Trifluoroacetate Salt)

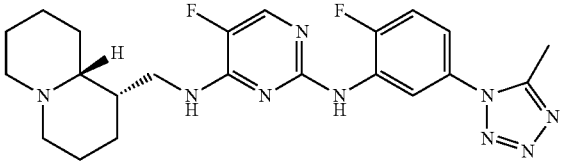 [SMILES: Cc1nnnn1-c1ccc(F)c(Nc2ncc(F)c(NC[C@@H]3CCCN4CCCC[C@H]34)n2)c1]

Compound 7 was prepared as described in Example 1.
MS (ES) 456 (M+H).

Example 8

5-fluoro-N2-(4-fluoro-3-(5-methyl-1H-tetrazol-1-yl)phenyl)-N4-(((1S,9aR)-octahydro-1H-quinolizin-1-yl)methyl)pyrimidine-2,4-diamine (Compound 8, Trifluoroacetate Salt)

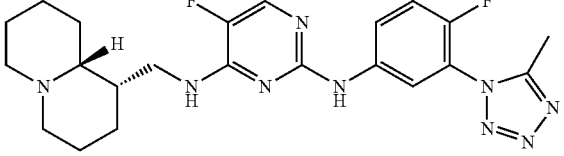

Compound 8 was prepared as described in Example 1.
$^1$H NMR (300 MHz, dmso) δ 10.38-10.13 (m, 1H), 9.92-9.34 (m, 1H), 8.67-8.30 (m, 1H), 8.17-8.03 (m, 1H), 7.97-7.71 (m, 1H), 7.53 (dd, J=23.0, 13.4 Hz, 1H), 3.73-3.06 (m,

Example 9

5-(4-(((1S,9aR)-octahydro-1H-quinolizin-1-yl)methylamino)-5-fluoropyrimidin-2-ylamino)-2-methylbenzonitrile (Compound 9, Formate Salt)

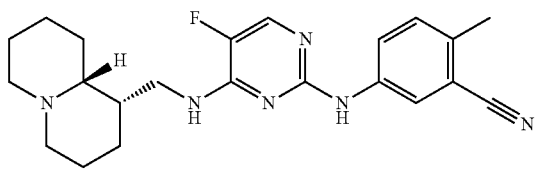 [SMILES: Cc1ccc(Nc2ncc(F)c(NC[C@@H]3CCCN4CCCC[C@H]34)n2)cc1C#N]

Compound 9 was prepared as described in Example 1.
$^1$H NMR (300 MHz, dmso) δ 9.87 (s, 1H), 9.29 (s, 1H), 8.80 (d, J=11.1 Hz, 1H), 8.10 (dd, J=10.3, 3.6 Hz, 1H), 7.69-7.57 (m, 1H), 7.44-7.33 (m, 1H), 3.70-3.56 (m, 2H), 3.54-3.12 (m, 2H), 3.04-2.79 (m, 2H), 2.41 (d, J=4.5 Hz, 1H), 2.27 (s, 3H), 2.20-2.03 (m, 4H), 1.91-1.65 (m, 3H), 1.58 (s, 2H), 1.50-1.20 (m, 2H); MS (ES) 395 (M+H).

Example 10

3-(4-(((1S,9aR)-octahydro-1H-quinolizin-1-yl)methylamino)-5-fluoropyrimidin-2-ylamino)benzonitrile (Compound 10, Formate Salt)

Compound 10 was prepared as described in Example 1. MS (ES) 381 (M+H).

Example 11

5-fluoro-N4-(((1S,9aR)-octahydro-1H-quinolizin-1-yl)methyl)-N2-(3,5-dimethoxyphenyl)pyrimidine-2,4-diamine (Compound 11, Formate Salt)

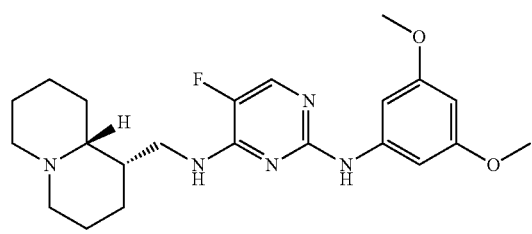 [SMILES: COc1cc(Nc2ncc(F)c(NC[C@@H]3CCCN4CCCC[C@H]34)n2)cc(OC)c1]

Compound 11 was prepared as described in Example 1.
$^1$H NMR (300 MHz, dmso) δ 10.12 (d, J=19.2 Hz, 1H), 9.44-9.16 (m, 2H), 8.28-8.01 (m, 1H), 6.76 (d, J=2.1 Hz, 1H), 6.63 (d, J=2.2 Hz, 1H), 6.42-6.21 (m, 1H), 3.78-3.65 (m, 2H), 3.57-3.34 (m, 2H), 3.34-3.01 (m, 2H), 3.05-2.74 (m, 1H), 2.39-1.98 (m, 3H), 2.00-1.62 (m, 4H), 1.64-1.16 (m, 4H); MS (ES) 416 (M+H).

Example 12

5-(4-(((1S,9aR)-octahydro-1H-quinolizin-1-yl)methylamino)-5-fluoropyrimidin-2-ylamino)-2-cyclopropyl-4-fluorobenzonitrile (Compound 12, Formate Salt)

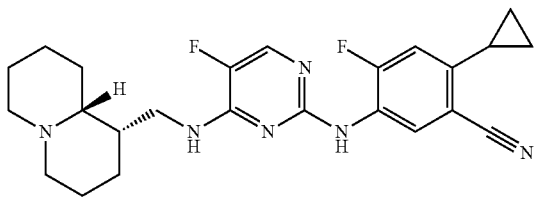

Compound 12 was prepared as described in Example 1.
$^1$H NMR (300 MHz, dmso) δ 8.84 (s, 1H), 7.94 (t, J=3.4 Hz, 1H), 7.01 (d, J=12.2 Hz, 1H), 3.64-3.38 (m, 2H), 3.29 (d, J=6.9 Hz, 2H), 3.17 (d, J=6.3 Hz, 2H), 3.03-2.76 (m, 1H), 2.12 (s, 1H), 1.89-1.66 (m, 6H), 1.65-1.48 (m, 4H), 1.50-1.30 (m, 2H), 1.09 (d, J=8.0 Hz, 2H), 0.91-0.74 (m, 2H); MS (ES) 439 (M+H).

Example 13

5-fluoro-N4-(((1S,9aR)-octahydro-1H-quinolizin-1-yl)methyl)-N2-phenylpyrimidine-2,4-diamine (Compound 13, Formate Salt)

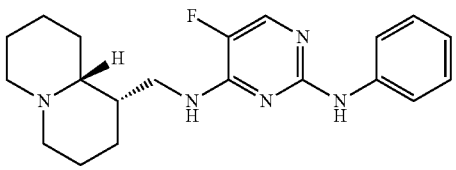 [SMILES: Fc1cnc(Nc2ccccc2)nc1NC[C@@H]1CCCN2CCCC[C@H]12]

Compound 13 was prepared as described in Example 1.
$^1$H NMR (300 MHz, dmso) δ 10.09 (d, J=14.5 Hz, 1H), 9.43-9.10 (m, 1H), 8.16 (td, J=5.4, 1.7 Hz, 1H), 7.48-7.27 (m, 3H), 7.26-7.12 (m, 2H), 3.70-3.08 (m, 2H), 3.03-2.71 (m, 2H), 2.54-2.42 (m, 2H), 2.17-1.98 (m, 1H), 1.93-1.63 (m, 4H), 1.63-1.50 (m, 4H), 1.49-1.19 (m, 3H); MS (ES) 356 (M+H).

Example 14

5-chloro-N2-(4-cyclopropyl-2-fluoro-5-(1H-tetrazol-1-yl)phenyl)-N4-(((1S,9aR)-octahydro-1H-quinolizin-1-yl)methyl)pyrimidine-2,4-diamine (Compound 32, Bis-Formate Salt)

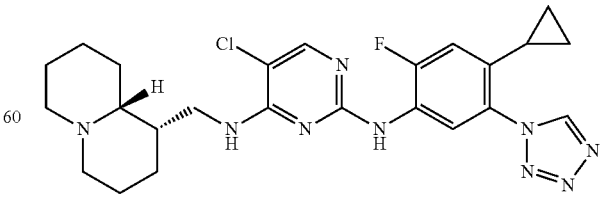

Compound 32 was prepared as described in Example 1.
$^1$H NMR (300 MHz, dmso) δ 9.85 (d, J=14.6 Hz, 1H), 9.00-8.67 (m, 1H), 7.95 (d, J=8.9 Hz, 1H), 7.21-7.11 (m, 1H), 3.50-3.02 (m, 2H), 2.99-2.61 (m, 4H), 2.12 (s, 1H), 1.96-1.25 (m, 6H), 1.22 (dd, J=6.2, 2.6 Hz, 6H), 0.99-0.44 (m, 4H); MS (ES) 498 (M+H).

Example 15

5-chloro-N4-(((1S,9aR)-octahydro-1H-quinolizin-1-yl)methyl)-N2-(4-methyl-3-(1H-tetrazol-1-yl)phenyl)pyrimidine-2,4-diamine (Compound 33, Bis-Formate Salt)

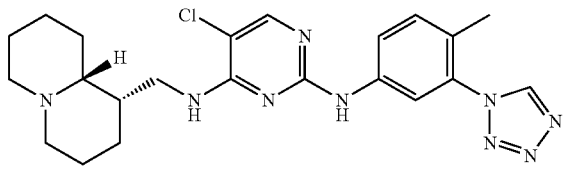 [SMILES: Cc1ccc(Nc2ncc(Cl)c(NC[C@@H]3CCCN4CCCC[C@H]34)n2)cc1-n1cnnn1]

Compound 33 was prepared as described in Example 1.
$^1$H NMR (300 MHz, dmso) δ 9.86 (d, J=9.6 Hz, 1H), 8.06 (d, J=5.1 Hz, 1H), 8.00-7.85 (m, 1H), 7.71 (dd, J=14.1, 5.9 Hz, 1H), 7.41 (d, J=8.5 Hz, 1H), 3.70-3.53 (m, 2H), 3.53-3.06 (m, 4H), 3.04-2.74 (m, 1H), 2.30-2.13 (m, 4H), 2.07 (s, 3H), 1.89-1.62 (m, 3H), 1.62-1.31 (m, 2H), 1.30-1.10 (m, 2H); MS (ES) 454 (M+H).

Example 16

1-(5-(4-(((1S,9aR)-octahydro-1H-quinolizin-1-yl)methylamino)-5-chloropyrimidin-2-ylamino)-2-cyclopropyl-4-fluorophenyl)-4-methyl-1H-tetrazol-5(4H)-one (Compound 34, Bis-Formate Salt)

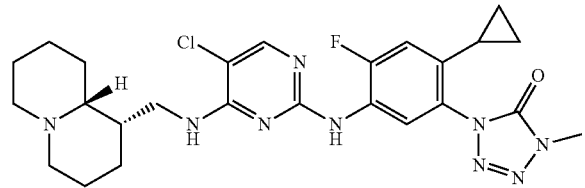 [SMILES: Cn1nnn(-c2cc(Nc3ncc(Cl)c(NC[C@@H]4CCCN5CCCC[C@H]45)n3)c(F)cc2C2CC2)c1=O]

Compound 34 was prepared as described in Example 1.
$^1$H NMR (300 MHz, dmso) δ 8.80 (d, J=23.6 Hz, 1H), 7.91 (d, J=10.5 Hz, 1H), 7.45-7.31 (m, 1H), 7.00 (dd, J=11.9, 7.8 Hz, 1H), 3.62 (s, 3H), 3.56-3.04 (m, 3H), 3.02-2.72 (m, 3H), 2.23-1.98 (m, 1H), 1.94-1.44 (m, 6H), 1.44-1.12 (m, 6H), 0.92-0.77 (m, 2H), 0.66 (dd, J=8.6, 4.3 Hz, 2H); MS (ES) 428 (M+H).

Example 17

5-chloro-N2-(4-fluoro-3-(5-methyl-1H-tetrazol-1-yl)phenyl)-N4-(((1S,9aR)-octahydro-1H-quinolizin-1-yl)methyl)pyrimidine-2,4-diamine (Compound 35, Bis-Formate Salt)

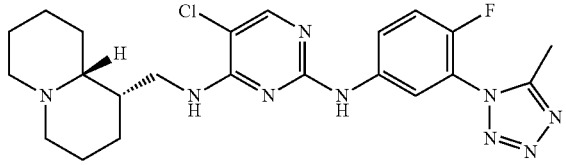 [SMILES: Cc1nnnn1-c1cc(Nc2ncc(Cl)c(NC[C@@H]3CCCN4CCCC[C@H]34)n2)ccc1F]

Compound 35 was prepared as described in Example 1.
$^1$H NMR (300 MHz, dmso) δ 8.18-8.05 (m, 1H), 7.98 (d, J=7.3 Hz, 1H), 7.86 (d, J=9.0 Hz, 1H), 7.40 (s, 1H), 3.53-3.07 (m, 4H), 2.95 (m, 2H), 2.26 (m, 1H), 2.00-1.60 (m, 8H), 1.60-1.13 (m, 6H); MS (ES) 472 (M+H).

Example 18

5-chloro-N2-(2-fluoro-5-(5-methyl-1H-tetrazol-1-yl)phenyl)-N4-(((1S,9aR)-octahydro-1H-quinolizin-1-yl)methyl)pyrimidine-2,4-diamine (Compound 36, Bis-Formate Salt)

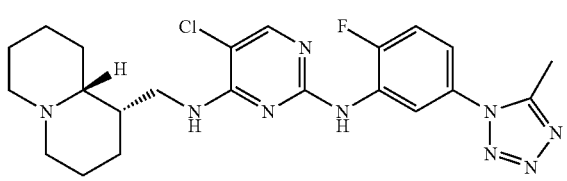 [SMILES: Cc1nnnn1-c1ccc(F)c(Nc2ncc(Cl)c(NC[C@@H]3CCCN4CCCC[C@H]34)n2)c1]

Compound 36 was prepared as described in Example 1.
MS (ES) 472 (M+H).

Example 19

5-chloro-N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine (Compound 37)

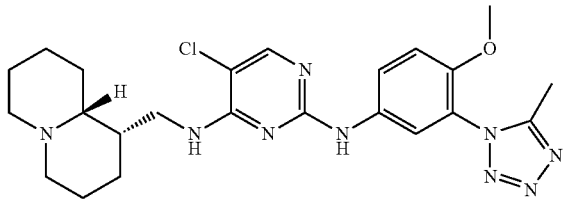 [SMILES: COc1ccc(Nc2ncc(Cl)c(NC[C@@H]3CCCN4CCCC[C@H]34)n2)cc1-n1nnnc1C]

Compound 37 was prepared as described in Example 1.
$^1$H NMR (300 MHz, dmso) δ 9.62-9.41 (m, 1H), 8.01 (d, J=3.5 Hz, 1H), 7.96-7.83 (m, 1H), 7.77 (ddd, J=14.4, 9.1, 2.5 Hz, 1H), 7.70-7.54 (m, 1H), 7.29 (dd, J=9.2, 3.5 Hz, 1H), 3.76 (s, 3H), 3.70-3.34 (m, 3H), 3.36-3.04 (m, 2H), 3.03-2.69 (m, 2H), 2.37 (s, 3H), 2.19-2.03 (m, 2H), 1.98-1.07 (m, 9H); MS (ES) 484 (M+H).

Example 20

5-chloro-N4-(((1S,9aR)-octahydro-1H-quinolizin-1-yl)methyl)-N2-(3-methoxy-5-(5-methyl-1H-tetrazol-1-yl)phenyl)pyrimidine-2,4-diamine (Compound 38)

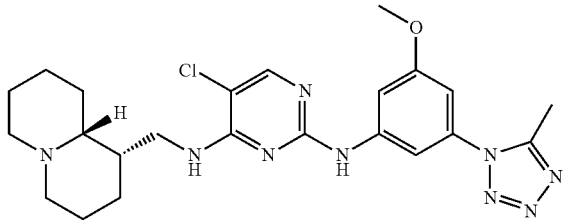 [SMILES: COc1cc(Nc2ncc(Cl)c(NC[C@@H]3CCCN4CCCC[C@H]34)n2)cc(-n2nnnc2C)c1]

Compound 38 was prepared as described in Example 1.
MS (ES) 484 (M+H).

Example 21

3-(4-(((1S,9aR)-octahydro-1H-quinolizin-1-yl)methylamino)-5-chloropyrimidin-2-ylamino)benzonitrile (Compound 39)

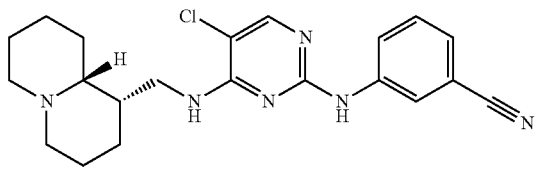 [SMILES: N#Cc1cccc(Nc2ncc(Cl)c(NC[C@@H]3CCCN4CCCC[C@H]34)n2)c1]

Compound 39 was prepared as described in Example 1.

$^1$H NMR (300 MHz, dmso) δ 9.51 (s, 1H), 8.20 (s, 1H), 8.00-7.92 (m, 1H), 7.69 (s, 1H), 7.40 (t, J=8.0 Hz, 1H), 7.30 (d, J=6.3 Hz, 1H), 3.59 (t, J=5.5 Hz, 1H), 3.30 (m, 2H), 2.74 (d, J=10.3 Hz, 2H), 2.48 (dd, J=3.1, 1.8 Hz, 2H), 2.02-1.76 (m, 4H), 1.73-1.58 (m, 2H), 1.57-1.25 (m, 4H), 1.24-1.05 (m, 1H); MS (ES) 397 (M+H).

Example 22

5-(4-(((1S,9aR)-octahydro-1H-quinolizin-1-yl)methylamino)-5-chloropyrimidin-2-ylamino)-2-methylbenzonitrile (Compound 40)

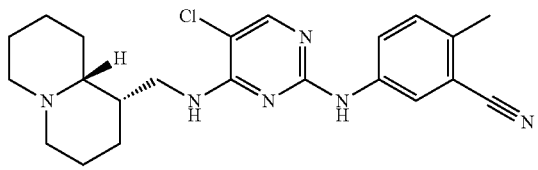 [SMILES: Cc1ccc(Nc2ncc(Cl)c(NC[C@@H]3CCCN4CCCC[C@H]34)n2)cc1C#N]

Compound 40 was prepared as described in Example 1.

$^1$H NMR (300 MHz, dmso) δ 9.37 (s, 1H), 8.12 (d, J=2.2 Hz, 1H), 7.88-7.75 (m, 1H), 7.72-7.61 (m, 1H), 7.26 (d, J=8.8 Hz, 1H), 3.65-3.47 (m, 4H), 2.73 (d, J=9.7 Hz, 4H), 2.53-2.43 (m, 1H), 2.36 (s, 3H), 2.02-1.73 (m, 4H), 1.72-1.56 (m, 2H), 1.58-1.23 (m, 4H), 1.24-1.02 (m, 1H); MS (ES) 411 (M+H).

Example 23

5-(4-(((1S,9aR)-octahydro-1H-quinolizin-1-yl)methylamino)-5-chloropyrimidin-2-ylamino)-2-cyclopropylbenzonitrile (Compound 41)

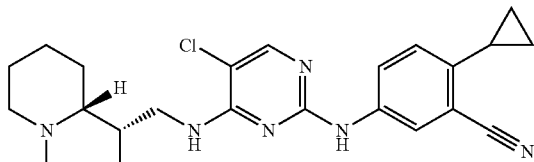

Compound 41 was prepared as described for the corresponding formic acid salt in Example 124.

$^1$H NMR (300 MHz, dmso) δ 9.36 (s, 1H), 8.08 (d, J=2.3 Hz, 1H), 7.91 (d, J=2.5 Hz, 1H), 7.81 (d, J=11.1 Hz, 1H), 7.67 (s, 1H), 6.93 (d, J=8.8 Hz, 1H), 3.56 (t, J=5.4 Hz, 2H), 2.72 (d, J=10.6 Hz, 2H), 2.53-2.41 (m, 1H), 2.14-1.99 (m, 2H), 1.99-1.69 (m, 5H), 1.65 (d, J=12.8 Hz, 2H), 1.60-1.21 (m, 4H), 1.23-1.07 (m, 1H), 1.07-0.90 (m, 2H), 0.80-0.62 (m, 2H); MS (ES) 437 (M+H).

Example 24

5-(4-(((1S,9aR)-octahydro-1H-quinolizin-1-yl)methylamino)-5-chloropyrimidin-2-ylamino)-2-cyclopropyl-4-fluorobenzonitrile (Compound 42)

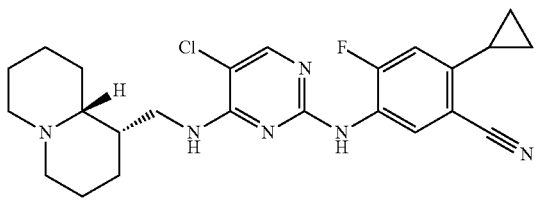

Compound 42 was prepared as described in Example 1.

$^1$H NMR (300 MHz, dmso) δ 8.74 (s, 1H), 8.10 (d, J=7.9 Hz, 1H), 7.88 (d, J=1.1 Hz, 1H), 7.62-7.45 (m, 1H), 6.96 (d, J=12.2 Hz, 1H), 3.58-3.22 (m, 5H), 2.75 (m, 2H), 2.17-1.75 (m, 4H), 1.77-1.32 (m, 5H), 1.34-0.95 (m, 5H), 0.81 (t, J=4.5 Hz, 2H); MS (ES) 455 (M+H).

Example 25

5-chloro-N4-(((1S,9aR)-octahydro-1H-quinolizin-1-yl)methyl)-N2-(3,5-dimethoxyphenyl)pyrimidine-2,4-diamine (Compound 43, Bis-Trifluoroacetate Salt)

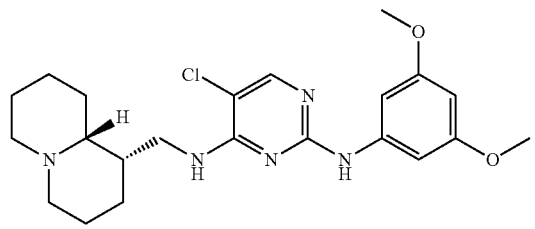 [SMILES: COc1cc(Nc2ncc(Cl)c(NC[C@@H]3CCCN4CCCC[C@H]34)n2)cc(OC)c1]

Compound 43 was prepared as described in Example 1.

$^1$H NMR (300 MHz, dmso) δ 9.81 (d, J=11.5 Hz, 1H), 9.69-9.23 (m, 1H), 8.10-7.98 (m, 1H), 6.89 (d, J=2.2 Hz, 1H), 6.74 (d, J=2.2 Hz, 1H), 6.21 (dt, J=6.2, 2.2 Hz, 1H), 3.70 (s, 6H), 3.56-3.24 (m, 3H), 3.22-3.08 (m, 2H), 3.02-2.75 (m, 1H), 2.43-2.27 (m, 1H), 2.26-2.12 (m, 1H), 2.05-1.68 (m, 7H), 1.67-1.51 (m, 6H), 1.51-1.17 (m, 2H); MS (ES) 432 (M+H).

Example 26

5-(4-(((1S,9aR)-octahydro-1H-quinolizin-1-yl)methylamino)-5-chloropyrimidin-2-ylamino)benzo[d]oxazol-2(3H)-one (Compound 44)

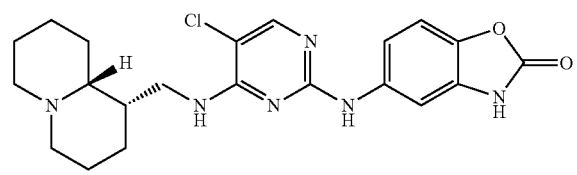

Compound 44 was prepared as described in Example 1. MS (ES) 429 (M+H).

Example 27

N2-(5-(5-cyclopropyl-1H-tetrazol-1-yl)-2-fluorophenyl)-5-fluoro-N4-(((1S,9aR)-octahydro-1H-quinolizin-1-yl)methyl)pyrimidine-2,4-diamine (Compound 45)

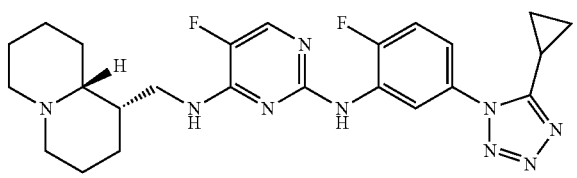 [SMILES: Fc1ccc(-n2nnnc2C2CC2)cc1Nc1ncc(F)c(NC[C@@H]2CCCN3CCCC[C@H]23)n1]

Compound 45 was prepared as described in Example 1.

¹H NMR (300 MHz, dmso) δ 8.67 (s, 1H), 8.40 (dt, J=6.8, 3.4 Hz, 1H), 7.84 (d, J=3.7 Hz, 1H), 7.56 (s, 1H), 7.47 (dd, J=10.7, 8.8 Hz, 1H), 7.30 (dt, J=7.6, 3.4 Hz, 1H), 3.40 (dd, J=11.0, 3.7 Hz, 3H), 2.64 (t, J=10.6 Hz, 3H), 2.11-1.96 (m, 1H), 1.87-1.68 (m, 4H), 1.68-1.51 (m, 3H), 1.50-1.37 (m, 1H), 1.37-0.96 (m, 8H); MS (ES) 482 (M+H).

Example 28

N2-(4-cyclopropyl-2-fluoro-5-(1H-tetrazol-1-yl)phenyl)-N4-(((1S,9aR)-octahydro-1H-quinolizin-1-yl)methyl)pyrimidine-2,4-diamine (Compound 46, Bis-Formate Salt)

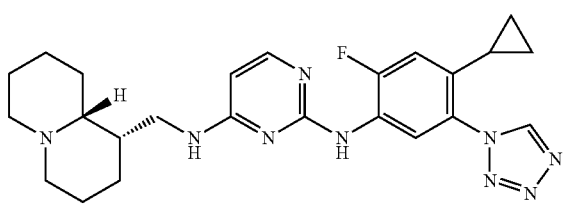 [SMILES: Fc1cc(C2CC2)c(-n2cnnn2)cc1Nc1nccc(NC[C@@H]2CCCN3CCCC[C@H]23)n1]

Compound 46 was prepared as described in Example 1.

¹H NMR (300 MHz, dmso) δ 9.96 (s, 1H), 9.87 (d, J=14.3 Hz, 1H), 9.08-8.66 (m, 1H), 8.15-8.00 (m, 1H), 7.90-7.76 (m, 1H), 7.26 (dd, J=11.6, 8.1 Hz, 1H), 6.24 (d, J=7.1 Hz, 1H), 3.57-3.05 (m, 4H), 3.04-2.76 (m, 2H), 2.13-1.86 (m, 1H), 1.86-1.30 (m, 9H), 1.28-1.06 (m, 3H), 0.84 (t, J=5.8 Hz, 2H), 0.77-0.61 (m, 2H); MS (ES) 464 (M+H).

Example 29

N4-(((1S,9aR)-octahydro-1H-quinolizin-1-yl)methyl)-N2-(4-methyl-3-(1H-tetrazol-1-yl)phenyl)pyrimidine-2,4-diamine (Compound 47, Formate Salt)

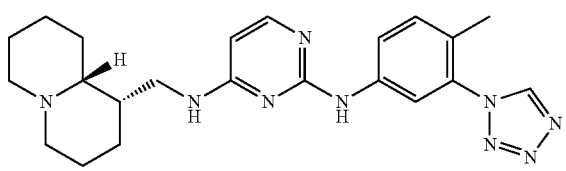 [SMILES: Cc1ccc(Nc2nccc(NC[C@@H]3CCCN4CCCC[C@H]34)n2)cc1-n1cnnn1]

Compound 47 was prepared as described in Example 1.

¹H NMR (300 MHz, dmso) δ 10.58-10.29 (m, 1H), 9.88 (d, J=12.6 Hz, 1H), 9.39-9.09 (m, 1H), 7.90-7.76 (m, 1H), 7.71-7.59 (m, 1H), 7.58-7.51 (m, 1H), 6.29 (dd, J=7.1, 3.9 Hz, 1H), 3.45-3.06 (m, 2H), 3.06-2.75 (m, 3H), 2.37-1.95 (m, 3H), 2.11 (s, 3H) 1.92-1.50 (m, 6H), 1.49-1.10 (m, 5H); MS (ES) 420 (M+H).

Example 30

1-(5-(4-(((1S,9aR)-octahydro-1H-quinolizin-1-yl)methylamino)pyrimidin-2-ylamino)-2-cyclopropyl-4-fluorophenyl)-4-methyl-1H-tetrazol-5(4H)-one (Compound 48)

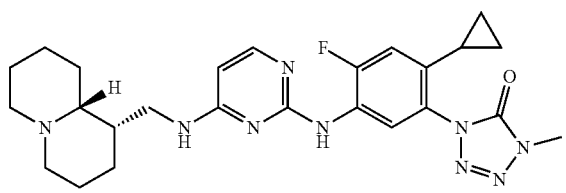 [SMILES: Cn1nnn(-c2cc(Nc3nccc(NC[C@@H]4CCCN5CCCC[C@H]45)n3)c(F)cc2C2CC2)c1=O]

Compound 48 was prepared as described in Example 1.

¹H NMR (300 MHz, dmso) δ 8.24 (d, J=0.8 Hz, 2H), 7.97 (d, J=7.6 Hz, 1H), 7.71 (s, 1H), 7.24 (s, 1H), 6.97 (d, J=12.1 Hz, 1H), 5.94 (dd, J=5.9, 0.7 Hz, 1H), 3.62 (s, 3H), 3.45-3.29 (m, 1H), 3.29-3.12 (m, 1H), 3.03-2.81 (m, 2H), 2.51-2.13 (m, 3H), 1.86 (s br, 1H), 1.76-1.12 (m, 11H), 0.81 (dt, J=5.5, 5.0 Hz, 2H), 0.70-0.55 (m, 2H); MS (ES) 494 (M+H).

Example 31

N2-(4-fluoro-3-(5-methyl-1H-tetrazol-1-yl)phenyl)-N4-(((1S,9aR)-octahydro-1H-quinolizin-1-yl)methyl)pyrimidine-2,4-diamine (Compound 49)

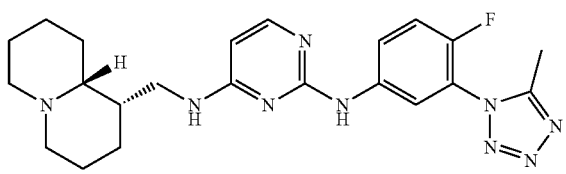 [SMILES: Cc1nnnn1-c1cc(Nc2nccc(NC[C@@H]3CCCN4CCCC[C@H]34)n2)ccc1F]

Compound 49 was prepared as described in Example 1.

¹H NMR (300 MHz, dmso) δ 10.55-10.15 (m, 1H), 9.38-8.95 (m, 1H), 8.02 (s, 1H), 7.91-7.75 (m, 2H), 7.75-7.58 (m, 2H), 6.27 (d, J=6.8 Hz, 1H), 3.65-3.10 (m, 2H), 3.06-2.76 (m, 2H), 2.26 (s, 3H), 2.19-1.90 (m, 1H), 1.90-1.52 (m, 6H), 1.51-1.12 (m, 3H); MS (ES) 438 (M+H).

Example 32

N2-(2-fluoro-5-(5-methyl-1H-tetrazol-1-yl)phenyl)-N4-(((1S,9aR)-octahydro-1H-quinolizin-1-yl)methyl)pyrimidine-2,4-diamine (Compound 50, Bis-Trifluoroacetate Salt)

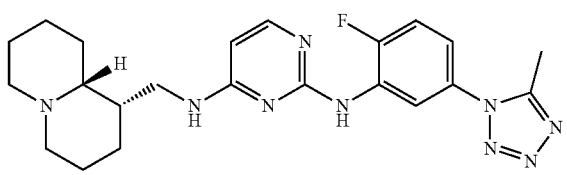 [SMILES: Cc1nnnn1-c1ccc(F)c(Nc2nccc(NC[C@@H]3CCCN4CCCC[C@H]34)n2)c1]

Compound 50 was prepared as described in Example 1.

¹H NMR (300 MHz, dmso) δ 10.73 (s, 1H), 9.40-9.12 (m, 1H), 8.30-7.72 (m, 2H), 7.64 (dd, J=10.3, 4.8 Hz, 2H), 6.29 (t, J=7.5 Hz, 1H), 3.62-2.61 (m, 7H), 2.29 (s, 3H), 2.17-1.83 (m, 2H), 1.85-0.92 (m, 9H); MS (ES) 438 (M+H).

Example 33

N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine (Compound 51, Bis-Trifluoroacetate Salt)

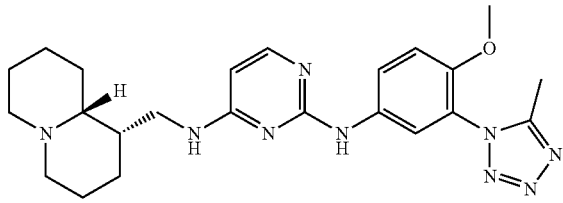 [SMILES: COc1ccc(Nc2nccc(NC[C@@H]3CCCN4CCCC[C@H]34)n2)cc1-n1nnnc1C]

Compound 51 was prepared as described in Example 1.
$^1$H NMR (300 MHz, dmso) δ 11.20-10.53 (m, 1H), 9.84 (s, 1H), 9.50-9.05 (m, 1H), 7.98-7.50 (m, 3H), 7.50-7.23 (m, 1H), 6.22 (dd, J=7.0, 3.4 Hz, 1H), 3.80 (s, 3H), 3.75-3.05 (m, 5H), 3.04-2.62 (m, 2H), 2.38 (s, 3H), 2.21-1.97 (m, 1H), 1.87-1.06 (m, 10H); MS (ES) 450 (M+H).

Example 34

N4-(((1S,9aR)-octahydro-1H-quinolizin-1-yl)methyl)-N2-(3-methoxy-5-(5-methyl-1H-tetrazol-1-yl)phenyl)pyrimidine-2,4-diamine (Compound 52, Bis-Trifluoroacetate Salt)

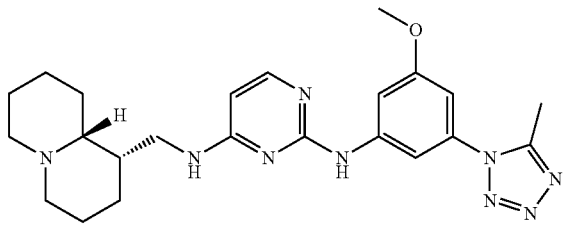 [SMILES: COc1cc(Nc2nccc(NC[C@@H]3CCCN4CCCC[C@H]34)n2)cc(-n2nnnc2C)c1]

Compound 52 was prepared as described in Example 1.
$^1$H NMR (300 MHz, dmso) δ 11.33-10.96 (m, 1H), 9.42-9.24 (m, 1H), 7.87 (t, J=8.1 Hz, 1H), 7.50 (s, 1H), 7.36 (s, 1H), 7.09 (s, 1H), 6.29 (d, J=7.2 Hz, 1H), 3.82 (s, 3H), 3.77-3.61 (m, 1H), 3.57-3.05 (m, 3H), 3.05-2.77 (m, 2H), 2.58 (s, 3H), 2.48 (d, J=1.7 Hz, 1H), 2.31-2.02 (m, 1H), 1.88-1.33 (m, 8H), 1.31-1.09 (m, 1H); MS (ES) 450 (M+H).

Example 35

3-(4-(((1S,9aR)-octahydro-1H-quinolizin-1-yl)methylamino)pyrimidin-2-ylamino)benzonitrile (Compound 53, Bis-Trifluoroacetate Salt)

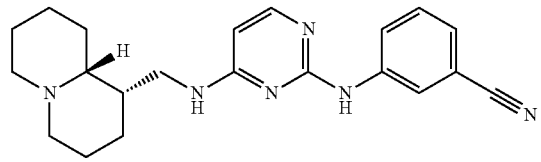 [SMILES: N#Cc1cccc(Nc2nccc(NC[C@@H]3CCCN4CCCC[C@H]34)n2)c1]

Compound 53 was prepared as described in Example 1.
$^1$H NMR (300 MHz, dmso) δ 11.15-10.79 (m, 1H), 10.01-9.57 (m, 1H), 9.20 (s, 1H), 8.24-7.98 (m, 1H), 7.96-7.64 (m, 2H), 7.59 (s, 1H), 6.27 (d, J=7.1 Hz, 1H), 3.28-2.75 (m, 6H), 2.26 (m, 1H), 2.10 (m, 1H), 1.95-1.14 (m, 10H); MS (ES) 463 (M+H).

Example 36

5-(4-(((1S,9aR)-octahydro-1H-quinolizin-1-yl)methylamino)pyrimidin-2-ylamino)-2-methylbenzonitrile (Compound 54, Bis-Trifluoroacetate Salt)

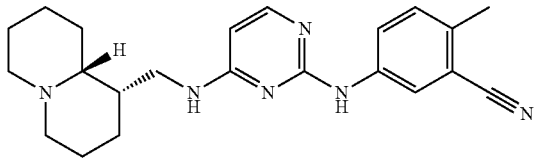 [SMILES: Cc1ccc(Nc2nccc(NC[C@@H]3CCCN4CCCC[C@H]34)n2)cc1C#N]

Compound 54 was prepared as described in Example 1.
$^1$H NMR (300 MHz, dmso) δ 11.23-10.75 (m, 1H), 9.54-8.90 (m, 1H), 8.24-7.91 (m, 1H), 7.86 (t, J=7.6 Hz, 1H), 7.61 (t, J=9.1 Hz, 1H), 7.45 (d, J=8.5 Hz, 1H), 6.34-6.13 (m, 1H), 3.42-3.10 (m, 3H), 3.08-2.93 (m, 2H), 2.95-2.79 (m, 2H), 2.44 (s, 3H), 2.33-2.18 (m, 1H), 2.09 (s, 1H), 1.94-1.20 (m, 9H); MS (ES) 377 (M+H).

Example 37

5-(4-(((1S,9aR)-octahydro-1H-quinolizin-1-yl)methylamino)pyrimidin-2-ylamino)-2-cyclopropylbenzonitrile (Compound 55, Bis-Trifluoroacetate Salt)

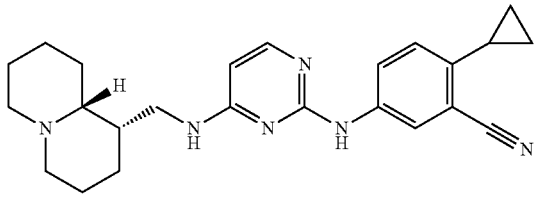 [SMILES: N#Cc1cc(Nc2nccc(NC[C@@H]3CCCN4CCCC[C@H]34)n2)ccc1C1CC1]

Compound 55 was prepared as described in Example 1.
$^1$H NMR (300 MHz, dmso) δ 11.09-10.62 (m, 1H), 9.56-8.95 (m, 1H), 8.19-7.89 (m, 1H), 7.87-7.74 (m, 1H), 7.68-7.46 (m, 1H), 7.10 (d, J=8.8 Hz, 1H), 6.26 (d, J=11.6 Hz, 1H), 3.24-2.72 (m, 4H), 2.34-2.00 (m, 3H), 1.95-1.23 (m, 12H), 1.10 (d, J=7.9 Hz, 2H), 0.90-0.56 (m, 2H); MS (ES) 403 (M+H).

Example 38

5-(4-(((1S,9aR)-octahydro-1H-quinolizin-1-yl)methylamino)pyrimidin-2-ylamino)-2-cyclopropyl-4-fluorobenzonitrile (Compound 56, Bis-Formate Salt)

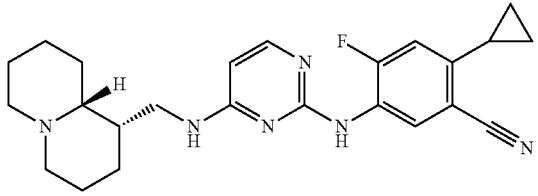 [SMILES: N#Cc1cc(Nc2nccc(NC[C@@H]3CCCN4CCCC[C@H]34)n2)c(F)cc1C1CC1]

Compound 56 was prepared as described in Example 1.
$^1$H NMR (300 MHz, dmso) δ 10.06 (s, 1H), 9.42-9.10 (m, 1H), 8.23-8.02 (m, 1H), 7.83 (dd, J=10.4, 7.4 Hz, 1H), 6.28 (t, J=6.4 Hz, 1H), 3.30-3.04 (m, 4H), 3.05-2.73 (m, 2H), 2.22-

2.07 (m, 2H), 2.00-1.87 (m, 2H), 1.87-1.30 (m, 10H), 1.24-1.05 (m, 2H), 0.95-0.73 (m, 2H); MS (ES) 421 (M+H).

Example 39

N4-(((1S,9aR)-octahydro-1H-quinolizin-1-yl)methyl)-N2-(3,5-dimethoxyphenyl)pyrimidine-2,4-diamine (Compound 57, Bis-Formate Salt)

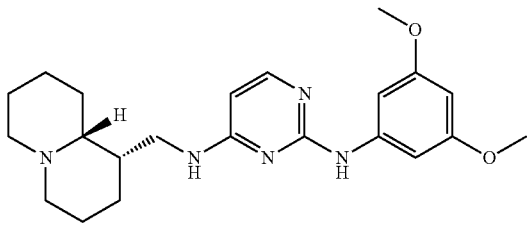 [SMILES: COc1cc(Nc2nccc(NC[C@@H]3CCCN4CCCC[C@H]34)n2)cc(OC)c1]

Compound 57 was prepared as described in Example 1. MS (ES) 398 (M+H).

Example 40

5-(4-(((1S,9aR)-octahydro-1H-quinolizin-1-yl)methylamino)pyrimidin-2-ylamino)benzo[d]oxazol-2(3H)-one (Compound 58, Bis-Formate Salt)

Compound 58 was prepared as described in Example 1.
$^1$H NMR (300 MHz, dmso) δ 11.73 (s, 1H), 10.28-10.04 (m, 1H), 9.21-8.73 (m, 1H), 7.75 (dd, J=7.1, 4.6 Hz, 1H), 7.28 (td, J=8.3, 2.7 Hz, 2H), 7.21-7.13 (m, 1H), 6.31-6.11 (m, 1H), 3.34-3.06 (m, 4H), 3.03-2.69 (m, 3H), 2.21-1.89 (m, 1H), 1.87-1.61 (m, 4H), 1.60-1.34 (m, 5H), 1.37-1.12 (m, 2H); MS (ES) 495 (M+H).

Example 41

N2-(4-cyclopropyl-2-fluoro-5-(1H-tetrazol-1-yl)phenyl)-N4-(((1S,9aR)-octahydro-1H-quinolizin-1-yl)methyl)-5-methylpyrimidine-2,4-diamine (Compound 59, Bis-Trifluoroacetate Salt)

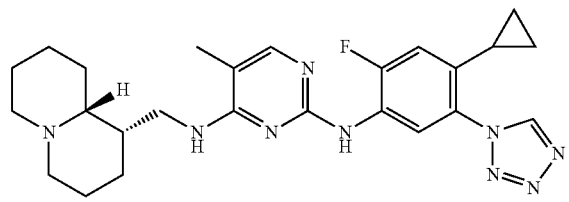

Compound 59 was prepared as described in Example 1.
$^1$H NMR (300 MHz, dmso) δ 10.32-10.08 (m, 1H), 9.86 (dd, J=17.5, 2.3 Hz, 1H), 9.24 (s, 1H), 8.52-8.19 (m, 1H), 7.97 (d, J=7.4 Hz, 1H), 7.82-7.73 (m, 1H), 7.24 (t, J=11.0 Hz, 1H), 3.36-3.03 (m, 4H), 3.02-2.89 (m, 1H), 2.90-2.75 (m, 1H), 2.18-2.03 (m, 1H), 1.96 (s, 3H), 1.84-1.25 (m, 10H), 1.24-1.09 (m, 1H), 1.08-0.95 (m, 1H), 0.84 (t, J=8.0 Hz, 2H), 0.77-0.58 (m, 2H); MS (ES) 478 (M+H).

Example 42

N4-(((1S,9aR)-octahydro-1H-quinolizin-1-yl)methyl)-5-methyl-N2-(4-methyl-3-(1H-tetrazol-1-yl)phenyl)pyrimidine-2,4-diamine (Compound 60, Bis-Formate Salt)

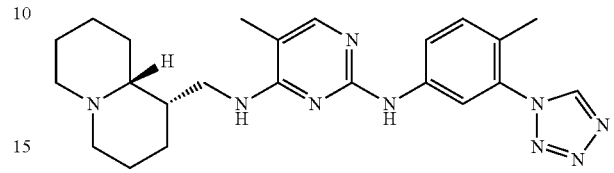

Compound 60 was prepared as described in Example 1.
$^1$H NMR (300 MHz, dmso) δ 10.43-10.10 (m, 1H), 9.93-9.72 (m, 1H), 8.84 (s, 1H), 8.50 (d, J=16.0 Hz, 1H), 7.79-7.68 (m, 1H), 7.65-7.51 (m, 2H), 3.69-3.54 (m, 1H), 3.51-3.03 (m, 4H), 3.02-2.74 (m, 1H), 2.23-2.16 (m, 1H), 2.12 (s, 3H), 1.98 (s, 3H), 1.87-1.51 (m, 7H), 1.42 (m, 3H), 1.27-1.04 (m, 1H); MS (ES) 434 (M+H).

Example 43

1-(5-(4-(((1S,9aR)-octahydro-1H-quinolizin-1-yl)methylamino)-5-methylpyrimidin-2-ylamino)-2-cyclopropyl-4-fluorophenyl)-4-methyl-1H-tetrazol-5(4H)-one (Compound 61, Bis-Formate Salt)

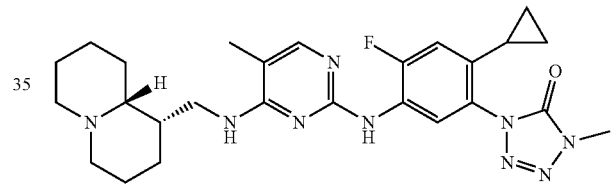

Compound 61 was prepared as described in Example 1.
$^1$H NMR (300 MHz, dmso) δ 9.94 (d, J=26.4 Hz, 1H), 9.24 (s, 1H), 8.75 (s, 1H), 8.52 (d, J=23.2 Hz, 1H), 7.72 (t, J=8.2 Hz, 1H), 7.54 (d, J=8.8 Hz, 1H), 3.61 (s, 3H), 3.55-3.37 (m, 1H), 3.36-3.00 (m, 4H), 3.00-2.86 (m, 1H), 2.87-2.70 (m, 1H), 2.13-1.99 (m, 1H), 1.96 (s, 3H), 1.91-1.05 (m, 11H), 1.00-0.86 (m, 2H), 0.83-0.65 (m, 2H); MS (ES) 508 (M+H).

Example 44

N2-(4-fluoro-3-(5-methyl-1H-tetrazol-1-yl)phenyl)-N4-(((1S,9aR)-octahydro-1H-quinolizin-1-yl)methyl)-5-methylpyrimidine-2,4-diamine (Compound 62, Formate Salt)

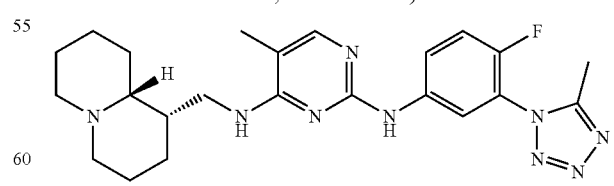

Compound 62 was prepared as described in Example 1.
$^1$H NMR (300 MHz, dmso) δ 10.70-10.11 (m, 1H), 8.67-8.41 (m, 1H), 8.04-7.88 (m, 1H), 7.83-7.52 (m, 2H), 7.32 (t, J=9.5 Hz, 1H), 7.02-6.88 (m, 1H), 3.41-3.20 (m, 3H), 3.20-3.02 (m, 2H), 3.02-2.71 (m, 2H), 2.44 (s, 3H), 2.20-2.04 (m, 1H), 1.98 (s, 3H), 1.88-1.48 (m, 5H), 1.49-1.23 (m, 4H), 1.23-0.98 (m, 1H); MS (ES) 452 (M+H).

Example 45

N2-(2-fluoro-5-(5-methyl-1H-tetrazol-1-yl)phenyl)-N4-(((1S,9aR)-octahydro-1H-quinolizin-1-yl)methyl)-5-methylpyrimidine-2,4-diamine (Compound 63, Formate Salt)

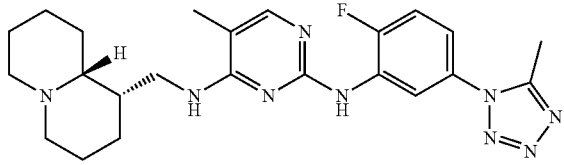 [SMILES: Cc1cnc(Nc2cc(-n3nnnc3C)ccc2F)nc1NC[C@@H]1CCCN2CCCC[C@H]12]

Compound 63 was prepared as described in Example 1.
$^1$H NMR (300 MHz, dmso) δ 10.11 (d, J=14.3 Hz, 1H), 8.81 (s, 1H), 8.64-8.48 (m, 1H), 7.89 (d, J=7.0 Hz, 1H), 7.77 (d, J=15.2 Hz, 1H), 7.70-7.60 (m, 1H), 3.44-3.35 (m, 2H), 3.34-3.17 (m, 2H), 3.09 (d, J=13.4 Hz, 1H), 2.98-2.70 (m, 2H), 2.53 (td, J=4.2, 1.9 Hz, 2H), 2.21-2.03 (m, 1H), 1.98 (s, 3H), 1.92 (s, 1H), 1.86-1.45 (m, 8H), 1.43-1.03 (m, 5H), 1.01-0.81 (m, 1H); MS (ES) 452 (M+H).

Example 46

N4-(((1S,9aR)-octahydro-1H-quinolizin-1-yl)methyl)-N2-(4-methoxy-3-(5-methyl-1H-tetrazol-1-yl)phenyl)-5-methylpyrimidine-2,4-diamine (Compound 64, Bis-Trifluoroacetate Salt)

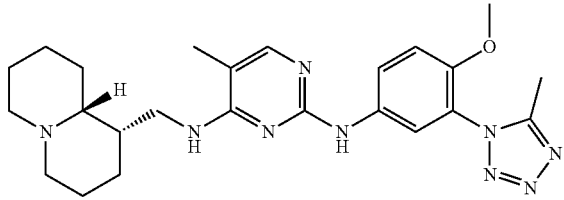 [SMILES: COc1ccc(Nc2ncc(C)c(NC[C@@H]3CCCN4CCCC[C@H]34)n2)cc1-n1nnnc1C]

Compound 64 was prepared as described in Example 1.
$^1$H NMR (300 MHz, dmso) δ 11.13-10.47 (m, 1H), 10.12-9.33 (m, 1H), 8.66-8.34 (m, 1H), 7.93-7.48 (m, 2H), 7.38 (s, 1H), 3.80 (s, 3H), 3.74-3.59 (m, 1H), 3.52-3.21 (m, 2H), 3.19-3.03 (m, 2H), 3.03-2.89 (m, 1H), 2.89-2.68 (m, 1H), 2.38 (s, 3H), 2.30-2.16 (m, 1H), 2.13-2.01 (m, 1H), 1.97 (s, 3H), 1.89-0.99 (m, 9H); MS (ES) 464 (M+H).

Example 47

N4-(((1S,9aR)-octahydro-1H-quinolizin-1-yl)methyl)-N2-(3-methoxy-5-(5-methyl-1H-tetrazol-1-yl)phenyl)-5-methylpyrimidine-2,4-diamine (Compound 65, Bis-Trifluoroacetate Salt)

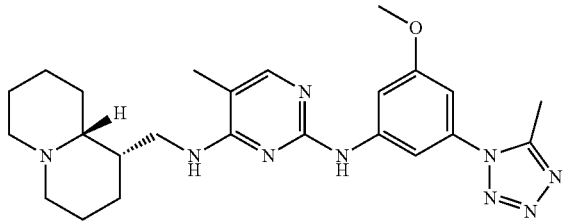 [SMILES: COc1cc(Nc2ncc(C)c(NC[C@@H]3CCCN4CCCC[C@H]34)n2)cc(-n2nnnc2C)c1]

Compound 65 was prepared as described in Example 1.
$^1$H NMR (300 MHz, dmso) δ 11.22-10.77 (m, 1H), 10.06-9.31 (m, J=128.3 Hz, 1H), 8.73-8.42 (m, 1H), 7.82 (d, J=13.1 Hz, 1H), 7.47-7.16 (m, 2H), 7.14-6.90 (m, 1H), 3.82 (s, 3H), 3.76 (d, J=8.0 Hz, 1H), 3.52-3.21 (m, 2H), 3.21-3.05 (m, 2H), 3.02-2.90 (m, 1H), 2.84 (s, 1H), 2.58 (s, 3H), 2.32 (m, 1H), 2.12 (d, J=6.1 Hz, 1H), 2.00 (s, 3H), 1.95-1.48 (m, 7H), 1.48-1.09 (m, 2H); MS (ES) 464 (M+H).

Example 48

3-(4-(((1S,9aR)-octahydro-1H-quinolizin-1-yl)methylamino)-5-methylpyrimidin-2-ylamino)benzonitrile (Compound 66, Bis-Formate Salt)

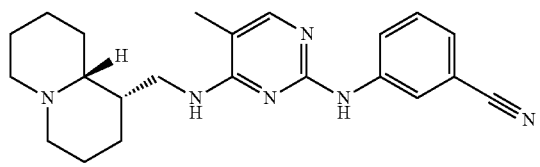 [SMILES: Cc1cnc(Nc2cccc(C#N)c2)nc1NC[C@@H]1CCCN2CCCC[C@H]12]

Compound 66 was prepared as described in Example 1.
$^1$H NMR (300 MHz, dmso) δ 9.17 (s, 1H), 8.23 (d, J=15.6 Hz, 2H), 7.96 (d, J=8.7 Hz, 1H), 7.66 (s, 1H), 7.36 (t, J=7.9 Hz, 1H), 7.23 (d, J=7.2 Hz, 1H), 6.91 (s, 1H), 2.87-2.70 (m, 4H), 2.21-1.92 (m, 3H), 1.90 (s, 3H), 1.86-1.61 (m, 3H), 1.60-1.40 (m, 4H), 1.40-1.28 (m, 2H), 1.26-1.10 (m, 2H); MS (ES) 377 (M+H).

Example 49

5-(4-(((1S,9aR)-octahydro-1H-quinolizin-1-yl)methylamino)-5-methylpyrimidin-2-ylamino)-2-methylbenzonitrile (Compound 67, Bis-Formate Salt)

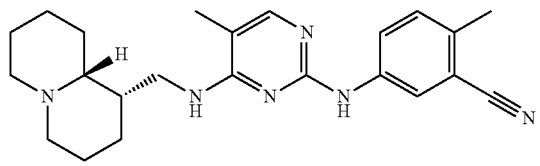 [SMILES: Cc1ccc(Nc2ncc(C)c(NC[C@@H]3CCCN4CCCC[C@H]34)n2)cc1C#N]

Compound 67 was prepared as described in Example 1.
MS (ES) 391 (M+H).

Example 50

5-(4-(((1S,9aR)-octahydro-1H-quinolizin-1-yl)methylamino)-5-methylpyrimidin-2-ylamino)-2-cyclopropylbenzonitrile (Compound 68, Bis-Formate Salt)

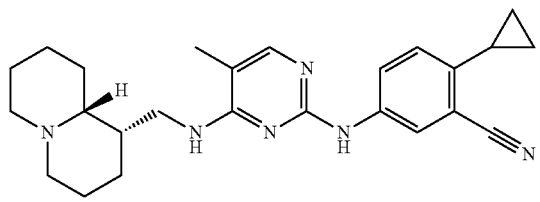

Compound 68 was prepared as described in Example 1.
$^1$H NMR (300 MHz, dmso) δ 10.27-10.05 (m, 1H), 9.38-8.81 (m, 1H), 8.49 (d, J=14.4 Hz, 1H), 8.03-7.79 (m, 1H), 7.75 (d, J=11.1 Hz, 1H), 7.56 (t, J=10.3 Hz, 1H), 3.73-3.58 (m, 1H), 3.31-3.23 (m, 2H), 3.21-3.05 (m, 2H), 3.04-2.74 (m, 1H), 2.21-2.06 (m, 1H), 1.98 (s, 3H), 1.93-1.63 (m, 6H), 1.61-1.25 (m, 6H), 1.24-1.05 (m, 2H), 0.76 (t, J=9.0 Hz, 2H); MS (ES) 417 (M+H).

Example 51

5-(4-(((1S,9aR)-octahydro-1H-quinolizin-1-yl)methylamino)-5-methylpyrimidin-2-ylamino)-2-cyclopropyl-4-fluorobenzonitrile (Compound 69, Bis-Trifluoroacetate Salt)

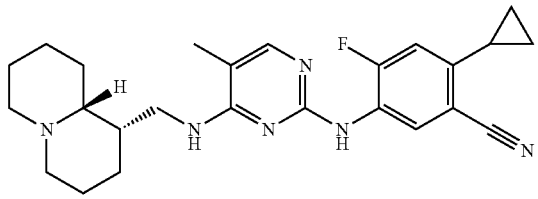 [SMILES: Cc1cnc(Nc2cc(C#N)c(C3CC3)cc2F)nc1NC[C@@H]1CCCN2CCCC[C@H]12]

Compound 69 was prepared as described in Example 1.

$^1$H NMR (300 MHz, dmso) δ 10.38 (s, 1H), 8.67-8.48 (m, 1H), 8.17-7.97 (m, 1H), 7.79 (dd, J=10.5, 0.9 Hz, 1H), 7.13 (dd, J=11.9, 7.1 Hz, 1H), 3.66-3.40 (m, 1H), 3.40-3.21 (m, 2H), 3.14 (d, J=7.5 Hz, 1H), 2.98 (d, J=12.0 Hz, 1H), 2.83 (s, 1H), 2.14 (t, J=12.8 Hz, 1H), 1.98 (s, 3H), 1.87-1.28 (m, 11H), 1.16 (dd, J=10.6, 4.4 Hz, 2H), 1.04-0.77 (m, 3H); MS (ES) 435 (M+H).

Example 52

N4-(((1S,9aR)-octahydro-1H-quinolizin-1-yl)methyl)-N2-(3,5-dimethoxyphenyl)-5-methylpyrimidine-2,4-diamine (Compound 70, Bis-Trifluoroacetate Salt)

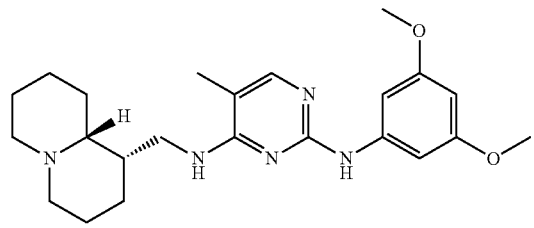

Compound 70 was prepared as described in Example 1.

$^1$H NMR (300 MHz, dmso) δ 10.71-10.35 (m, 1H), 8.63-8.47 (m, 1H), 7.75 (d, J=16.9 Hz, 1H), 6.77 (s, 1H), 6.61 (s, 1H), 6.35 (d, J=1.7 Hz, 1H), 3.73 (s, 6H), 3.58-3.23 (m, 1H), 3.24-3.04 (m, 2H), 2.97 (d, J=11.0 Hz, 1H), 2.92-2.69 (m, 1H), 2.41-2.26 (m, 1H), 2.23-2.04 (m, 1H), 1.98 (s, 3H), 1.93-1.68 (m, 5H), 1.67-1.50 (m, 4H), 1.50-1.19 (m, 2H); MS (ES) 412 (M+H).

Example 53

5-(4-(((1S,9aR)-octahydro-1H-quinolizin-1-yl)methylamino)-5-methylpyrimidin-2-ylamino)benzo[d]oxazol-2(3H)-one (Compound 71, Trifluoroacetate Salt)

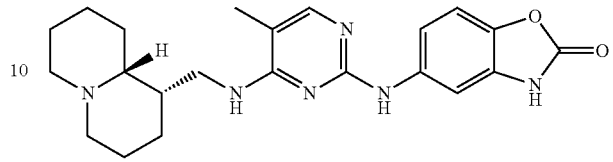

Compound 71 was prepared as described in Example 1.

$^1$H NMR (300 MHz, dmso) δ 11.85 (t, J=7.0 Hz, 1H), 10.81-10.44 (m, 1H), 9.97-9.31 (m, 1H), 8.66-8.36 (m, 1H), 7.81-7.61 (m, 1H), 7.34-6.97 (m, 2H), 3.77-2.61 (m, 6H), 2.34-2.11 (m, 1H), 2.14-2.01 (m, 1H), 1.97 (s, 3H), 1.93-1.60 (m, 4H), 1.61-1.45 (m, 3H), 1.46-0.99 (m, 3H); MS (ES) 409 (M+H).

Example 54

N2-(4-cyclopropyl-2-fluoro-5-(1H-tetrazol-1-yl)phenyl)-N4-(((1S,9aR)-octahydro-1H-quinolizin-1-yl)methyl)-5-methoxypyrimidine-2,4-diamine (Compound 72, Bis-Formate Salt)

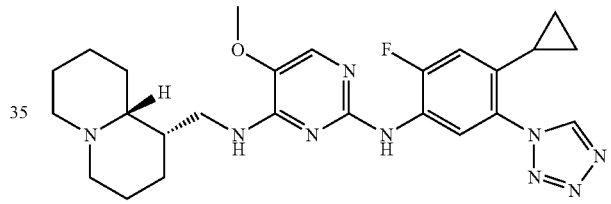

Compound 72 was prepared as described in Example 1.

$^1$H NMR (300 MHz, dmso) δ 9.91-9.77 (m, 1H), 9.00 (dd, J=74.3, 56.6 Hz, 2H), 8.00-7.73 (m, 1H), 7.63-7.50 (m, 1H), 7.33-7.17 (m, 1H), 3.82 (s, 3H), 3.34-3.03 (m, 5H), 3.02-2.70 (m, 2H), 2.21-1.88 (m, 1H), 1.87-1.28 (m, 9H), 1.24-0.92 (m, 2H), 0.86 (d, J=8.0 Hz, 2H), 0.79-0.62 (m, 2H); MS (ES) 494 (M+H).

Example 55

N4-(((1S,9aR)-octahydro-1H-quinolizin-1-yl)methyl)-5-methoxy-N2-(4-methyl-3-(1H-tetrazol-1-yl)phenyl)pyrimidine-2,4-diamine (Compound 73)

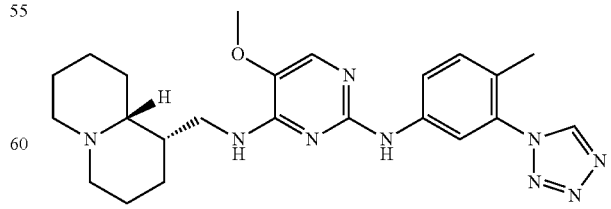

Compound 73 was prepared as described in Example 1.

$^1$H NMR (300 MHz, dmso) δ 9.84 (s, 1H), 9.00 (s, 1H), 8.05 (s, 1H), 7.73 (d, J=8.4 Hz, 1H), 7.54 (s, 1H), 7.27 (d, J=8.5 Hz, 1H), 6.97 (t, J=5.4 Hz, 1H), 3.72 (s, 3H), 3.55-3.35 (m, 4H), 2.69 (t, J=9.6 Hz, 3H), 1.95-1.74 (m, 4H), 1.71-1.53 (m, 3H), 1.52-1.02 (m, 4H); MS (ES) 450 (M+H).

Example 56

1-(5-(4-(((1S,9aR)-octahydro-1H-quinolizin-1-yl)methylamino)-5-methoxypyrimidin-2-ylamino)-2-cyclopropyl-4-fluorophenyl)-4-methyl-1H-tetrazol-5(4H)-one (Compound 74)

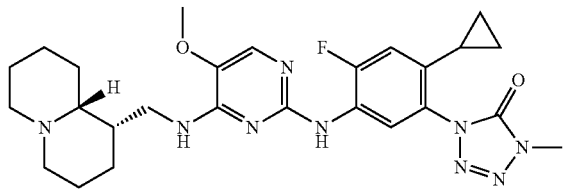 [SMILES: COc1cnc(Nc2cc(-n3nnn(C)c3=O)c(C3CC3)cc2F)nc1NC[C@@H]1CCCN2CCCC[C@H]12]

Compound 74 was prepared as described in Example 1.
$^1$H NMR (300 MHz, dmso) δ 8.10 (dt, J=18.9, 9.5 Hz, 1H), 8.02 (s, 1H), 7.49 (s, 1H), 7.09-6.87 (m, 2H), 3.71 (s, 3H), 3.61 (s, 3H), 3.49-3.35 (m, 4H), 2.67 (m, 3H), 1.91-1.72 (m, 4H), 1.72-1.51 (m, 5H), 1.52-1.00 (m, 3H), 0.87-0.72 (m, 2H), 0.67-0.53 (m, 2H); MS (ES) 524 (M+H).

Example 57

N2-(4-fluoro-3-(5-methyl-1H-tetrazol-1-yl)phenyl)-N4-(((1S,9aR)-octahydro-1H-quinolizin-1-yl)methyl)-5-methoxypyrimidine-2,4-diamine (Compound 75)

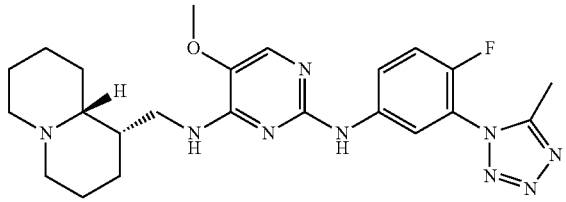 [SMILES: COc1cnc(Nc2ccc(F)c(-n3nnnc3C)c2)nc1NC[C@@H]1CCCN2CCCC[C@H]12]

Compound 75 was prepared as described in Example 1.
$^1$H NMR (300 MHz, dmso) δ 9.12 (s, 1H), 8.21 (dt, J=12.5, 6.3 Hz, 1H), 7.87 (dd, J=8.4, 3.8 Hz, 1H), 7.54 (d, J=1.2 Hz, 1H), 7.41 (t, J=9.5 Hz, 1H), 7.00 (t, J=5.2 Hz, 1H), 3.73 (s, 3H), 3.55-3.39 (m, 4H), 2.76-2.61 (m, 3H), 2.48 (s, 3H), 1.94-1.72 (m, 4H), 1.72-1.53 (m, 3H), 1.54-1.02 (m, 4H); MS (ES) 468 (M+H).

Example 58

N2-(2-fluoro-5-(5-methyl-1H-tetrazol-1-yl)phenyl)-N4-(((1S,9aR)-octahydro-1H-quinolizin-1-yl)methyl)-5-methoxypyrimidine-2,4-diamine (Compound 76)

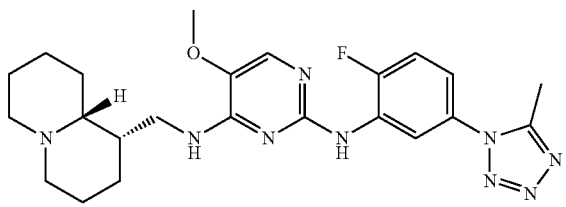 [SMILES: COc1cnc(Nc2cc(-n3nnnc3C)ccc2F)nc1NC[C@@H]1CCCN2CCCC[C@H]12]

Compound 76 was prepared as described in Example 1.
MS (ES) 468 (M+H).

Example 59

N4-(((1S,9aR)-octahydro-1H-quinolizin-1-yl)methyl)-5-methoxy-N2-(4-methoxy-3-(5-methyl-1H-tetrazol-1-yl)phenyl)pyrimidine-2,4-diamine (Compound 77)

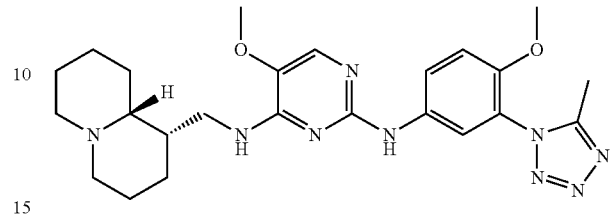

Compound 77 was prepared as described in Example 1.
$^1$H NMR (300 MHz, dmso) δ 8.84 (s, 1H), 8.01 (s, 1H), 7.85 (dd, J=9.1, 1.7 Hz, 1H), 7.52 (s, 1H), 7.19 (d, J=9.2 Hz, 1H), 6.93 (t, J=5.1 Hz, 1H), 3.71 (s, 3H), 3.42 (m, 3H), 3.31 (s, 3H), 2.69 (t, J=8.8 Hz, 4H), 2.37 (s, 3H), 1.96-1.73 (m, 4H), 1.73-1.52 (m, 3H), 1.52-1.01 (m, 4H); MS (ES) 480 (M+H).

Example 60

N4-(((1S,9aR)-octahydro-1H-quinolizin-1-yl)methyl)-5-methoxy-N2-(3-methoxy-5-(5-methyl-1H-tetrazol-1-yl)phenyl)pyrimidine-2,4-diamine (Compound 78)

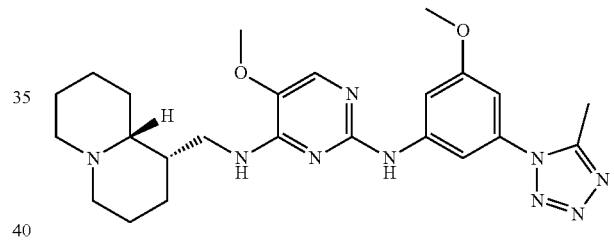

Compound 78 was prepared as described in Example 1.
$^1$H NMR (300 MHz, dmso) δ 9.07 (s, 1H), 7.66 (t, J=1.7 Hz, 1H), 7.62 (t, J=2.0 Hz, 1H), 7.56 (s, 1H), 6.97 (t, J=5.3 Hz, 1H), 6.67 (t, J=2.0 Hz, 1H), 3.78 (s, 3H), 3.74 (s, 3H), 3.48 (td, J=14.0, 8.6 Hz, 2H), 3.43-3.28 (m, 2H), 2.73-2.61 (m, 2H), 2.56 (s, 3H), 2.48 (dd, J=3.6, 1.8 Hz, 1H), 1.93-1.69 (m, 4H), 1.68-1.53 (m, 3H), 1.51-1.03 (m, 4H); MS (ES) 480 (M+H).

Example 61

3-(4-(((1S,9aR)-octahydro-1H-quinolizin-1-yl)methylamino)-5-methoxypyrimidin-2-ylamino)benzonitrile (Compound 79)

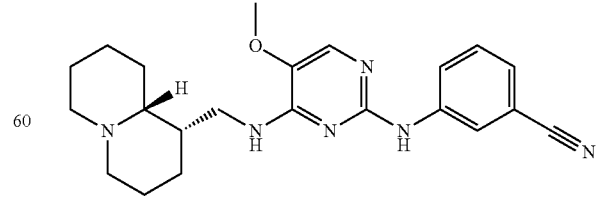

Compound 79 was prepared as described in Example 1.
$^1$H NMR (300 MHz, dmso) δ 9.10 (s, 1H), 8.27 (d, J=1.5 Hz, 1H), 7.93 (d, J=7.5 Hz, 1H), 7.58 (s, 1H), 7.34 (t, J=8.0

Hz, 1H), 7.20 (d, J=7.5 Hz, 1H), 7.03 (t, J=4.8 Hz, 1H), 3.78-3.71 (m, 3H), 3.54 (t, J=5.6 Hz, 2H), 3.40-3.24 (m, 2H), 2.72 (d, J=10.8 Hz, 2H), 2.55-2.43 (m, 1H), 1.98-1.87 (m, 2H), 1.87-1.72 (m, 3H), 1.72-1.59 (m, 2H), 1.57-1.33 (m, 4H), 1.33-1.04 (m, 3H); MS (ES) 393 (M+H).

Example 62

5-(4-(((1S,9aR)-octahydro-1H-quinolizin-1-yl)methylamino)-5-methoxypyrimidin-2-ylamino)-2-methylbenzonitrile (Compound 80)

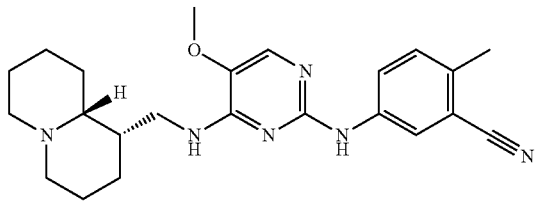 [SMILES: COc1cnc(Nc2ccc(C)c(C#N)c2)nc1NC[C@@H]1CCCN2CCCC[C@H]12]

Compound 80 was prepared as described in Example 1.
¹H NMR (300 MHz, dmso) δ 8.95 (d, J=2.8 Hz, 1H), 8.21 (s, 1H), 7.81 (dd, J=8.5, 2.5 Hz, 1H), 7.56 (d, J=3.5 Hz, 1H), 7.21 (dd, J=8.6, 2.9 Hz, 1H), 7.05-6.93 (m, 1H), 3.79-3.70 (s, 3H), 3.63-3.45 (m, 2H), 3.41-3.26 (m, 2H), 2.71 (d, J=9.8 Hz, 2H), 2.56-2.44 (m, 1H), 2.35 (s, 3H), 1.99-1.59 (m, 5H), 1.59-1.34 (m, 4H), 1.32-1.02 (m, 2H); MS (ES) 407 (M+H).

Example 63

5-(4-(((1S,9aR)-octahydro-1H-quinolizin-1-yl)methylamino)-5-methoxypyrimidin-2-ylamino)-2-cyclopropylbenzonitrile (Compound 81)

Compound 81 was prepared as described in Example 1.
¹H NMR (300 MHz, dmso) δ 8.94 (s, 1H), 8.19 (d, J=2.0 Hz, 1H), 7.79 (d, J=8.8 Hz, 1H), 7.56 (d, J=1.6 Hz, 1H), 7.01 (d, J=5.2 Hz, 1H), 6.90 (d, J=8.7 Hz, 1H), 3.73 (s, 3H), 3.52 (t, J=5.6 Hz, 2H), 3.42-3.22 (m, 2H), 2.71 (d, J=10.2 Hz, 3H), 2.10-1.98 (m, 1H), 1.98-1.59 (m, 4H), 1.58-1.33 (m, 4H), 1.32-1.05 (m, 3H), 1.00 (dd, J=6.4, 1.9 Hz, 2H), 0.68 (d, J=4.9 Hz, 2H); MS (ES) 433 (M+H).

Example 64

5-(4-(((1S,9aR)-octahydro-1H-quinolizin-1-yl)methylamino)-5-methoxypyrimidin-2-ylamino)-2-cyclopropyl-4-fluorobenzonitrile (Compound 82, Bis-Trifluoroacetate Salt)

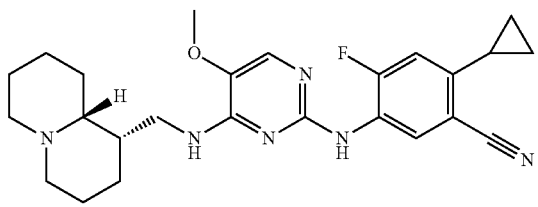 [SMILES: COc1cnc(Nc2cc(C#N)c(C3CC3)cc2F)nc1NC[C@@H]1CCCN2CCCC[C@H]12]

Compound 82 was prepared as described in Example 1.
MS (ES) 451 (M+H).

Example 65

N4-(((1S,9aR)-octahydro-1H-quinolizin-1-yl)methyl)-5-methoxy-N2-(3,5-dimethoxyphenyl)pyrimidine-2,4-diamine (Compound 83, Bis-Trifluoroacetate Salt)

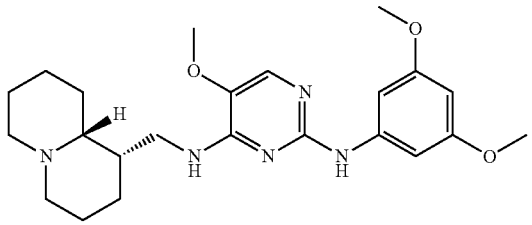 [SMILES: COc1cc(Nc2ncc(OC)c(NC[C@@H]3CCCN4CCCC[C@H]34)n2)cc(OC)c1]

Compound 83 was prepared as described in Example 1.
¹H NMR (300 MHz, dmso) δ 10.87-10.42 (m, 1H), 8.98 (d, J=5.8 Hz, 1H), 7.64 (dd, J=17.1, 1.0 Hz, 1H), 6.77 (s, 1H), 6.62 (s, 1H), 6.32 (s, 1H), 3.81 (s, 3H), 3.72 (s, 6H), 3.56-3.06 (m, 4H), 3.03-2.76 (m, 2H), 2.44-2.27 (m, 1H), 2.25-2.08 (m, 1H), 2.04-1.14 (m, 10H); MS (ES) 428 (M+H).

Example 66

5-(4-(((1S,9aR)-octahydro-1H-quinolizin-1-yl)methylamino)-5-methoxypyrimidin-2-ylamino)benzo[d]oxazol-2(3H)-one (Compound 84, Bis-Trifluoroacetate Salt)

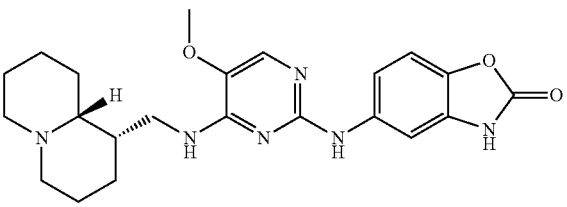

Compound 84 was prepared as described in Example 1.
¹H NMR (300 MHz, dmso) δ 11.79 (d, J=6.1 Hz, 1H), 10.81-10.38 (m, 1H), 9.80-9.24 (m, 1H), 9.03-8.79 (m, J=17.3 Hz, 1H), 7.70-7.53 (m, 1H), 7.36-7.17 (m, 1H), 7.08 (dd, J=13.8, 5.2 Hz, 1H), 3.80 (s, 3H), 3.67-3.02 (m, 4H), 2.99-2.62 (m, 2H), 2.36-2.16 (m, 1H), 2.14-2.00 (m, 1H), 1.99-1.03 (m, 10H); MS (ES) 425 (M+H).

Example 67

N2-(4-cyclopropyl-2-fluoro-5-(1H-tetrazol-1-yl)phenyl)-N4-(((1S,9aR)-octahydro-1H-quinolizin-1-yl)methyl)-N5,N5-dimethylpyrimidine-2,4,5-triamine (Compound 85, Bis-Formate Salt)

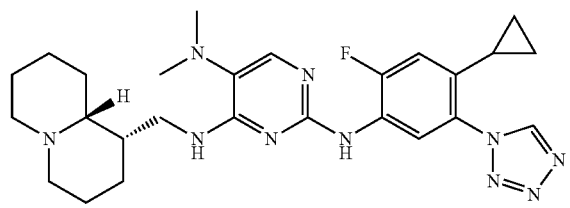

Compound 85 was prepared as described in Example 1.
MS (ES) 507 (M+H).

Example 68

N4-(((1S,9aR)-octahydro-1H-quinolizin-1-yl)methyl)-N5,N5-dimethyl-N2-(4-methyl-3-(1H-tetrazol-1-yl)phenyl)pyrimidine-2,4,5-triamine (Compound 86, Bis-Formate Salt)

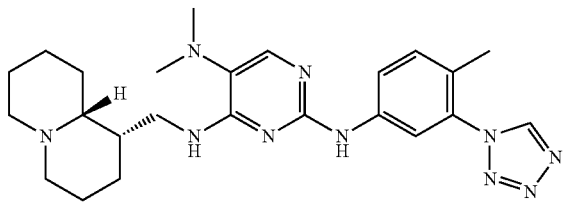 [SMILES: Cc1ccc(Nc2ncc(N(C)C)c(NC[C@@H]3CCCN4CCCC[C@H]34)n2)cc1-n1cnnn1]

Compound 86 was prepared as described in Example 1.
MS (ES) 463 (M+H).

Example 69

1-(5-(4-(((1S,9aR)-octahydro-1H-quinolizin-1-yl)methylamino)-5-(dimethylamino)pyrimidin-2-ylamino)-2-cyclopropyl-4-fluorophenyl)-4-methyl-1H-tetrazol-5(4H)-one (Compound 87, Bis-Formate Salt)

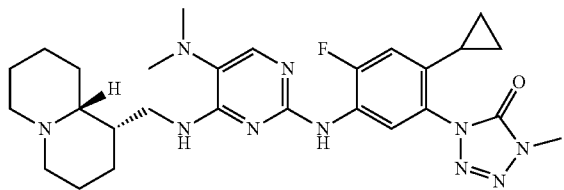 [SMILES: CN(C)c1cnc(Nc2cc(-n3nnn(C)c3=O)c(C3CC3)cc2F)nc1NC[C@@H]1CCCN2CCCC[C@H]12]

Compound 87 was prepared as described in Example 1.
$^1$H NMR (300 MHz, dmso) δ 8.45 (s, 1H), 8.13-7.75 (m, 1H), 7.66 (s, 1H), 7.40-7.13 (m, 1H), 7.00 (d, J=12.0 Hz, 1H), 3.61 (s, 3H), 3.55-3.04 (m, 3H), 3.00-2.74 (m, 4H), 2.52 (s, 6H), 2.23-1.98 (m, 4H), 1.95-1.44 (m, 5H), 1.36 (s, 3H), 0.84 (s, 2H), 0.64 (s, 2H); MS (ES) 537 (M+H).

Example 70

N2-(4-fluoro-3-(5-methyl-1H-tetrazol-1-yl)phenyl)-N4-(((1S,9aR)-octahydro-1H-quinolizin-1-yl)methyl)-N5,N5-dimethylpyrimidine-2,4,5-triamine (Compound 88, Bis-Formate Salt)

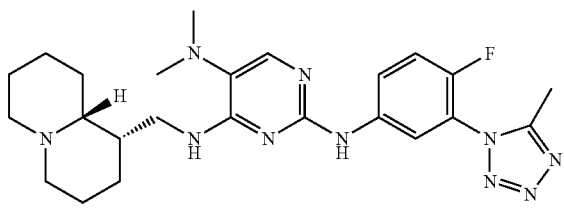 [SMILES: Cc1nnnn1-c1cc(Nc2ncc(N(C)C)c(NC[C@@H]3CCCN4CCCC[C@H]34)n2)ccc1F]

Compound 88 was prepared as described in Example 1.
$^1$H NMR (300 MHz, dmso) δ 9.21 (s, 1H), 8.24 (dd, J=7.1, 2.8 Hz, 1H), 7.93-7.82 (m, 1H), 7.67 (d, J=2.7 Hz, 1H), 7.49-7.35 (m, 1H), 7.09 (d, J=7.7 Hz, 1H), 3.51-3.40 (m, 4H), 2.83-2.67 (m, 3H), 2.48 (s, 6H), 2.26 (s, 3H), 2.08-1.82 (m, 3H), 1.82-1.54 (m, 3H), 1.54-1.02 (m, 5H); MS (ES) 481 (M+H).

Example 71

N2-(2-fluoro-5-(5-methyl-1H-tetrazol-1-yl)phenyl)-N4-(((1S,9aR)-octahydro-1H-quinolizin-1-yl)methyl)-N5,N5-dimethylpyrimidine-2,4,5-triamine (Compound 89, Bis-Formate Salt)

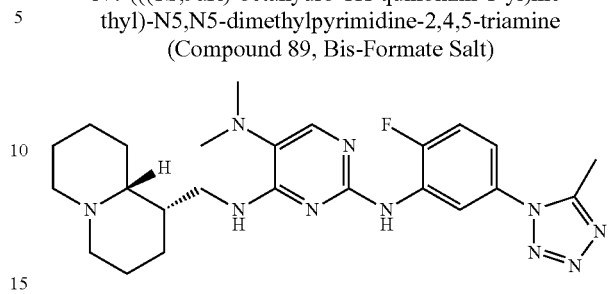

Compound 89 was prepared as described in Example 1.
$^1$H NMR (300 MHz, dmso) δ 10.09-9.98 (m, 1H), 8.89-8.65 (m, 2H), 8.18-7.86 (m, 1H), 7.74-7.54 (m, 2H), 3.29-3.14 (m, 3H), 3.15-3.01 (m, 2H), 2.97-2.73 (m, 2H), 2.53 (s, 6H), 2.26 (s, 3H), 2.21-1.78 (m, 2H), 1.76-0.81 (m, 10H); MS (ES) 481 (M+H).

Example 72

N4-(((1S,9aR)-octahydro-1H-quinolizin-1-yl)methyl)-N2-(4-methoxy-3-(5-methyl-1H-tetrazol-1-yl)phenyl)-N5,N5-dimethylpyrimidine-2,4,5-triamine (Compound 90, Bis-Formate Salt)

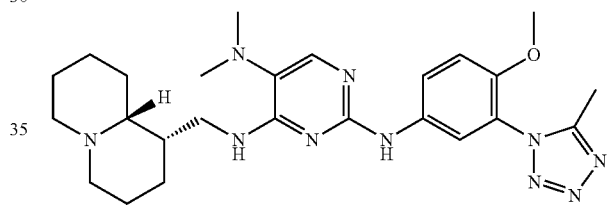

Compound 90 was prepared as described in Example 1.
$^1$H NMR (300 MHz, dmso) δ 10.20-9.81 (m, 1H), 8.89-8.59 (m, 1H), 7.76 (d, J=2.5 Hz, 1H), 7.65 (dt, J=9.0, 3.3 Hz, 1H), 7.53 (dd, J=11.2, 8.7 Hz, 2H), 7.37 (d, J=9.0 Hz, 1H), 3.80 (s, 3H), 3.34-3.19 (m, 3H), 3.20-3.03 (m, 2H), 2.95 (d, J=11.6 Hz, 1H), 2.91-2.72 (m, 1H), 2.53 (s, 6H), 2.26 (s, 3H), 2.15-1.96 (m, 3H), 1.96-1.43 (m, 6H), 1.43-0.99 (m, 2H); MS (ES) 493 (M+H).

Example 73

N4-(((1S,9aR)-octahydro-1H-quinolizin-1-yl)methyl)-N2-(3-methoxy-5-(5-methyl-1H-tetrazol-1-yl)phenyl)-N5,N5-dimethylpyrimidine-2,4,5-triamine (Compound 91, Bis-Formate Salt)

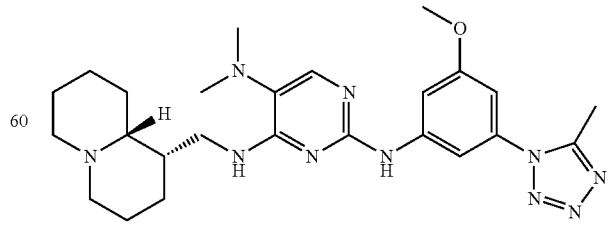

Compound 91 was prepared as described in Example 1.
MS (ES) 493 (M+H).

Example 74

3-(4-(((1S,9aR)-octahydro-1H-quinolizin-1-yl)methylamino)-5-(dimethylamino)pyrimidin-2-ylamino)benzonitrile (Compound 92, Bis-Formate Salt)

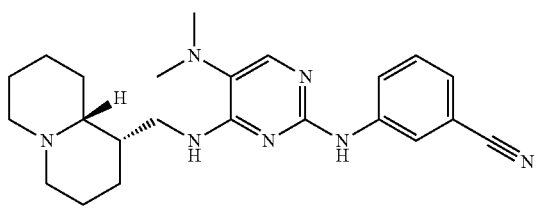 [SMILES: CN(C)c1cnc(Nc2cccc(C#N)c2)nc1NC[C@@H]1CCCN2CCCC[C@H]12]

Compound 92 was prepared as described in Example 1.
MS (ES) 406 (M+H).

Example 75

5-(4-(((1S,9aR)-octahydro-1H-quinolizin-1-yl)methylamino)-5-(dimethylamino)pyrimidin-2-ylamino)-2-methylbenzonitrile (Compound 93, Bis-Formate Salt)

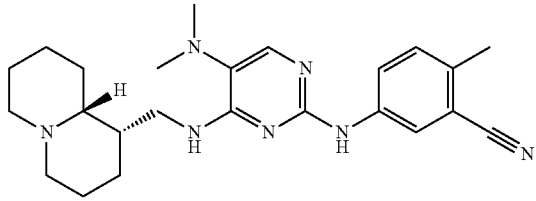 [SMILES: Cc1ccc(Nc2ncc(N(C)C)c(NC[C@@H]3CCCN4CCCC[C@H]34)n2)cc1C#N]

Compound 93 was prepared as described in Example 1.
MS (ES) 420 (M+H).

Example 76

5-(4-(((1S,9aR)-octahydro-1H-quinolizin-1-yl)methylamino)-5-(dimethylamino)pyrimidin-2-ylamino)-2-cyclopropylbenzonitrile (Compound 94, Bis-Trifluoroacetate Salt)

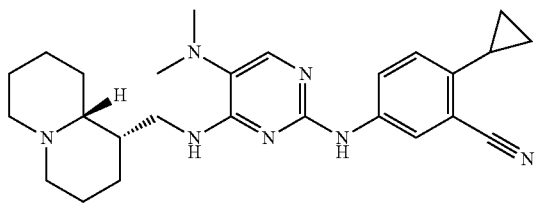 [SMILES: CN(C)c1cnc(Nc2ccc(C3CC3)c(C#N)c2)nc1NC[C@@H]1CCCN2CCCC[C@H]12]

Compound 94 was prepared as described in Example 1.
MS (ES) 446 (M+H).

Example 77

5-(4-(((1S,9aR)-octahydro-1H-quinolizin-1-yl)methylamino)-5-(dimethylamino)pyrimidin-2-ylamino)-2-cyclopropyl-4-fluorobenzonitrile (Compound 95, Bis-Trifluoroacetate Salt)

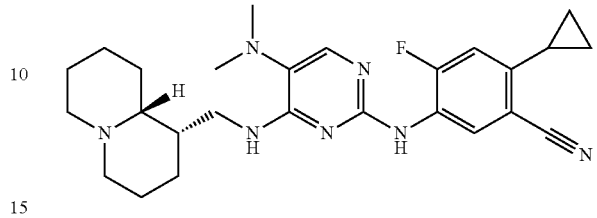

Compound 95 was prepared as described in Example 1.
$^1$H NMR (300 MHz, dmso) δ 10.63-10.42 (m, 1H), 8.88-8.68 (m, 1H), 8.21-7.98 (m, 1H), 7.72 (d, J=8.3 Hz, 1H), 7.11 (dd, J=11.8, 6.8 Hz, 1H), 3.61-3.40 (m, 1H), 3.42-3.20 (m, 3H), 3.21-3.03 (m, 2H), 3.03-2.72 (m, 1H), 2.54 (s, 6H), 2.33-2.07 (m, 2H), 2.07-1.24 (m, 10H), 1.25-1.07 (m, 2H), 1.04-0.79 (m, 2H); MS (ES) 464 (M+H).

Example 78

N4-(((1S,9aR)-octahydro-1H-quinolizin-1-yl)methyl)-N2-(3,5-dimethoxyphenyl)-N5,N5-dimethylpyrimidine-2,4,5-triamine (Compound 96, Bis-Trifluoroacetate Salt)

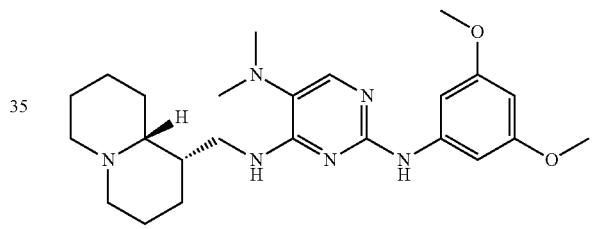

Compound 96 was prepared as described in Example 1.
$^1$H NMR (300 MHz, dmso) δ 10.88-10.42 (m, 1H), 8.85-8.58 (m, 1H), 7.69 (dd, J=13.2, 1.5 Hz, 1H), 6.79 (s, 1H), 6.62 (s, 1H), 6.32 (s, 1H), 3.73 (s, 6H), 3.69-3.60 (m, 1H), 3.55-3.22 (m, 2H), 3.22-3.04 (m, 2H), 3.04-2.73 (m, 2H), 2.53 (s, 6H), 2.45-2.28 (m, 1H), 2.26-2.09 (m, 1H), 2.07-1.16 (m, 9H); MS (ES) 441 (M+H).

Example 79

5-(4-(((1S,9aR)-octahydro-1H-quinolizin-1-yl)methylamino)-5-(dimethylamino)pyrimidin-2-ylamino)benzo[d]oxazol-2(3H)-one (Compound 97, Bis-Trifluoroacetate Salt)

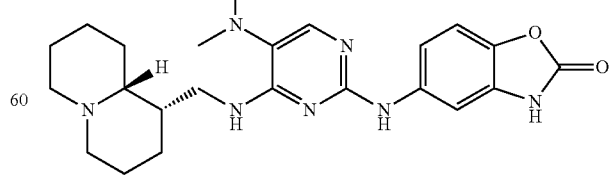

Compound 97 was prepared as described in Example 1.
$^1$H NMR (300 MHz, dmso) δ 11.84 (s, 1H), 10.89-10.51 (m, 1H), 8.86-8.51 (m, 1H), 7.67 (s, 1H), 7.24 (dd, J=14.0, 7.0

Hz, 2H), 7.08 (d, J=8.5 Hz, 1H), 3.66-3.02 (m, 5H), 3.00-2.68 (m, 2H), 2.53 (s, 6H), 2.38-2.20 (m, 1H), 2.18-2.01 (m, 1H), 2.00-1.47 (m, 6H), 1.48-1.01 (m, 3H); MS (ES) 438 (M+H).

Example 80

4-(((1S,9aR)-octahydro-1H-quinolizin-1-yl)methylamino)-2-(4-cyclopropyl-2-fluoro-5-(4,5-dihydro-4-methyl-5-oxotetrazol-1-yl)phenylamino)pyrimidine-5-carbonitrile (Compound 99)

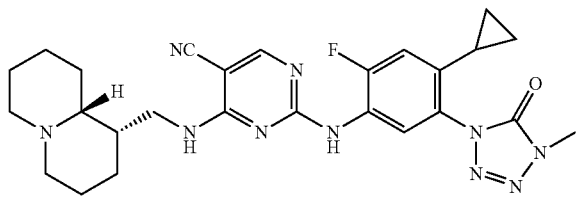 [SMILES: Cn1nnn(-c2cc(Nc3ncc(C#N)c(NC[C@@H]4CCCN5CCCC[C@H]45)n3)c(F)cc2C2CC2)c1=O]

Compound 99 was prepared as described in Example 1.
$^1$H NMR (300 MHz, dmso) δ 9.41 (s, 1H), 8.25 (d, J=2.7 Hz, 1H), 8.18 (s, 1H), 7.60 (dd, J=7.4, 2.4 Hz, 1H), 7.01 (dd, J=11.8, 2.1 Hz, 1H), 3.60 (s, 3H), 3.49-3.32 (m, 2H), 3.49-3.33 (m, 3H), 2.79-2.60 (m, 2H), 2.01-1.00 (m, 11H), 0.96-0.78 (m, 2H), 0.75-0.59 (m, 2H); MS (ES) 519 (M+H).

Example 81

N2-(4-cyclopropyl-2-fluoro-5-(1H-tetrazol-1-yl)phenyl)-N4-(((1S,9aR)-octahydro-1H-quinolizin-1-yl)methyl)-5-(trifluoromethyl)pyrimidine-2,4-diamine (Compound 100, Bis-Formate Salt)

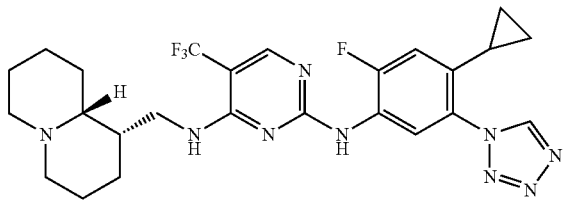 [SMILES: Fc1cc(C2CC2)c(-n2cnnn2)cc1Nc1ncc(C(F)(F)F)c(NC[C@@H]2CCCN3CCCC[C@H]23)n1]

Compound 100 was prepared as described in Example 1.
MS (ES) 532 (M+H).

Example 82

5-(trifluoromethyl)-N4-(((1S,9aR)-octahydro-1H-quinolizin-1-yl)methyl)-N2-(4-methyl-3-(1H-tetrazol-1-yl)phenyl)pyrimidine-2,4-diamine (Compound 101, Formate Salt)

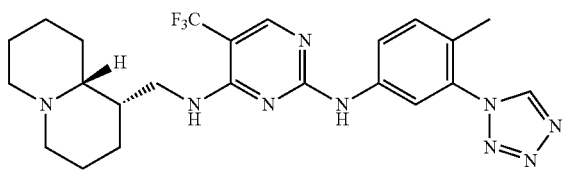

Compound 101 was prepared as described in Example 1.
MS (ES) 488 (M+H).

Example 83

1-(5-(4-(((1S,9aR)-octahydro-1H-quinolizin-1-yl)methylamino)-5-(trifluoromethyl)pyrimidin-2-ylamino)-2-cyclopropyl-4-fluorophenyl)-4-methyl-1H-tetrazol-5(4H)-one (Compound 102, Bis-Formate Salt)

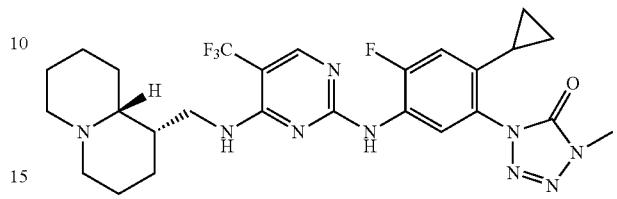

Compound 102 was prepared as described in Example 1.
$^1$H NMR (300 MHz, dmso) δ 8.64 (s, 1H), 8.19-8.08 (m, 1H), 7.71-7.59 (m, 1H), 7.42-7.24 (m, 1H), 7.03 (d, J=11.3 Hz, 1H), 3.60 (s, 3H), 3.42-2.88 (m, 4H), 2.50-2.33 (m, 3H), 2.19-1.86 (m, 2H), 1.85-1.06 (m, 10H), 0.96-0.84 (m, 2H), 0.76-0.61 (m, 2H); MS (ES) 562 (M+H).

Example 84

N2-(4-fluoro-3-(5-methyl-1H-tetrazol-1-yl)phenyl)-5-(trifluoromethyl)-N4-(((1S,9aR)-octahydro-1H-quinolizin-1-yl)methyl)pyrimidine-2,4-diamine (Compound 103, Bis-Trifluoroacetate Salt)

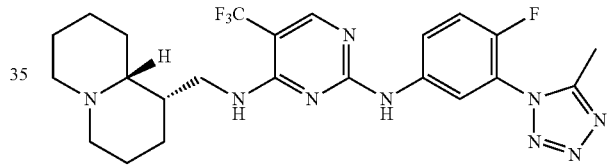

Compound 103 was prepared as described in Example 1.
$^1$H NMR (300 MHz, dmso) δ 9.63 (s, 1H), 9.30-9.03 (m, 1H), 8.39-8.23 (m, 1H), 8.04-7.88 (m, 1H), 7.88-7.71 (m, 1H), 7.70-7.53 (m, 1H), 3.59-3.36 (m, 1H), 3.36-3.19 (m, 2H), 3.20-2.67 (m, 4H), 2.49 (s, 3H), 2.26-1.97 (m, 1H), 1.94-0.84 (m, 10H); MS (ES) 506 (M+H).

Example 85

N2-(2-fluoro-5-(5-methyl-1H-tetrazol-1-yl)phenyl)-5-(trifluoromethyl)-N4-(((1S,9aR)-octahydro-1H-quinolizin-1-yl)methyl)pyrimidine-2,4-diamine (Compound 104, Bis-Trifluoroacetate Salt)

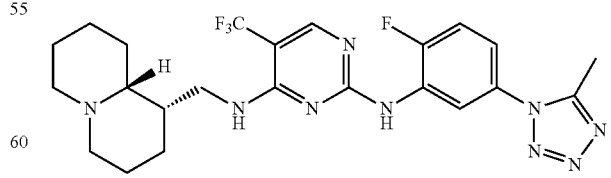

Compound 104 was prepared as described in Example 1.
$^1$H NMR (300 MHz, dmso) δ 9.21-8.86 (m, 1H), 8.17-7.70 (m, 1H), 7.69-7.47 (m, 1H), 7.21 (ddd, J=11.2, 8.6, 2.5 Hz, 1H), 6.95 (dt, J=7.8, 2.6 Hz, 1H), 6.80-6.66 (m, 1H), 3.59-

2.66 (m, 7H), 2.49 (s, 3H), 2.35-2.04 (m, 1H), 1.98-1.19 (m, 6H), 1.17-0.92 (m, 3H), 0.87-0.65 (m, 1H); MS (ES) 506 (M+H).

Example 86

5-(trifluoromethyl)-N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine (Compound 105, Bis-Trifluoroacetate Salt)

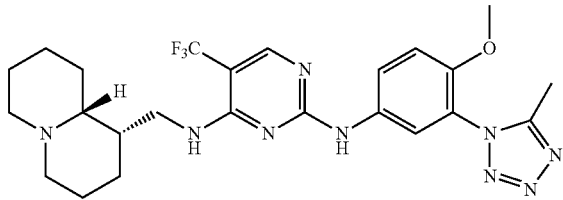 [SMILES: COc1ccc(Nc2ncc(C(F)(F)F)c(NC[C@@H]3CCCN4CCCC[C@H]34)n2)cc1-n1nnnc1C]

Compound 105 was prepared as described in Example 1.
¹H NMR (300 MHz, dmso) δ 9.53-9.33 (m, 1H), 8.73-8.47 (m, 1H), 8.38 (d, J=2.5 Hz, 1H), 7.75-7.59 (m, 2H), 7.36 (dd, J=8.7, 3.4 Hz, 2H), 3.81 (s, 3H), 3.55-3.37 (m, 1H), 3.36-3.20 (m, 2H), 3.20-2.71 (m, 4H), 2.37 (s, 3H), 2.21-1.84 (m, 1H), 1.84-1.04 (m, 9H), 0.90 (s, 1H); MS (ES) 518 (M+H).

Example 87

5-(trifluoromethyl)-N4-(((1S,9aR)-octahydro-1H-quinolizin-1-yl)methyl)-N2-(3-methoxy-5-(5-methyl-1H-tetrazol-1-yl)phenyl)pyrimidine-2,4-diamine (Compound 106, Bis-Formate Salt)

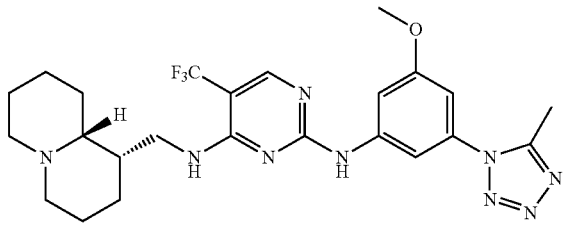

Compound 106 was prepared as described in Example 1.
MS (ES) 518 (M+H).

Example 88

3-(4-(((1S,9aR)-octahydro-1H-quinolizin-1-yl)methylamino)-5-(trifluoromethyl)pyrimidin-2-ylamino)benzonitrile (Compound 107, Bis-Formate Salt)

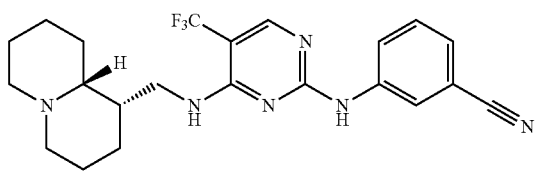 [SMILES: N#Cc1cccc(Nc2ncc(C(F)(F)F)c(NC[C@@H]3CCCN4CCCC[C@H]34)n2)c1]

Compound 107 was prepared as described in Example 1.
¹H NMR (300 MHz, dmso) δ 8.69 (s, 1H), 8.31-8.16 (m, 1H), 8.08-7.95 (m, 1H), 7.81 (s, 1H), 7.64-7.49 (m, 2H), 3.49-3.30 (m, 1H), 3.24-3.04 (m, 3H), 3.01-2.70 (m, 1H), 2.44-2.23 (m, 2H), 2.22-1.26 (m, 11H); MS (ES) 431 (M+H).

Example 89

5-(4-(((1S,9aR)-octahydro-1H-quinolizin-1-yl)methylamino)-5-(trifluoromethyl)pyrimidin-2-ylamino)-2-methylbenzonitrile (Compound 108, Bis-Formate Salt)

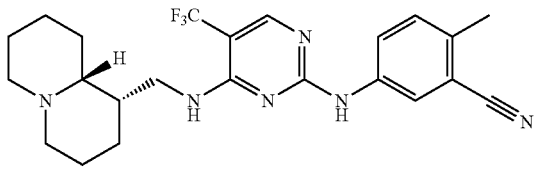

Compound 108 was prepared as described in Example 1.
¹H NMR (300 MHz, dmso) δ 8.35-8.12 (m, 1H), 7.64 (t, J=11.8 Hz, 1H), 7.46 (d, J=7.4 Hz, 1H), 7.38 (t, J=8.5 Hz, 1H), 7.07 (dd, J=13.7, 8.1 Hz, 1H), 6.82-6.71 (m, 1H), 3.65-3.22 (m, 3H), 3.22-2.95 (m, 2H), 2.90-2.62 (m, 2H), 2.26 (s, 3H), 2.23-2.12 (m, 1H), 2.12-1.77 (m, 4H), 1.75-0.93 (m, 6H); MS (ES) 445 (M+H).

Example 90

5-(4-(((1S,9aR)-octahydro-1H-quinolizin-1-yl)methylamino)-5-(trifluoromethyl)pyrimidin-2-ylamino)-2-cyclopropylbenzonitrile (Compound 109, Bis-Formate Salt)

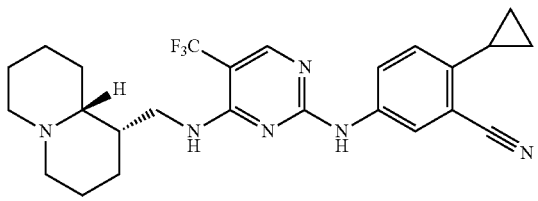 [SMILES: N#Cc1cc(Nc2ncc(C(F)(F)F)c(NC[C@@H]3CCCN4CCCC[C@H]34)n2)ccc1C1CC1]

Compound 109 was prepared as described in Example 1.
¹H NMR (300 MHz, dmso) δ 8.60 (s, 1H), 8.30-8.15 (m, 1H), 7.98-7.80 (m, 1H), 7.80-7.58 (m, 1H), 7.45 (dd, J=8.0, 2.6 Hz, 1H), 7.13-6.99 (m, 1H), 3.44-2.92 (m, 7H), 2.21-2.00 (m, 2H), 1.98-1.18 (m, 12H), 1.17-0.98 (m, 2H), 0.85-0.67 (m, 2H); MS (ES) 471 (M+H).

Example 91

5-(4-(((1S,9aR)-octahydro-1H-quinolizin-1-yl)methylamino)-5-(trifluoromethyl)pyrimidin-2-ylamino)-2-cyclopropyl-4-fluorobenzonitrile (Compound 110, Bis-Formate Salt)

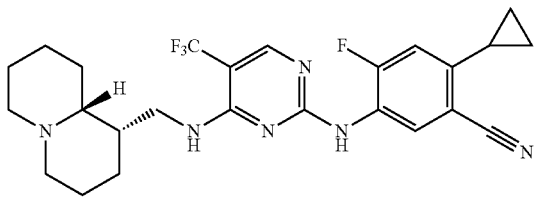 [SMILES: N#Cc1cc(Nc2ncc(C(F)(F)F)c(NC[C@@H]3CCCN4CCCC[C@H]34)n2)c(F)cc1C1CC1]

Compound 110 was prepared as described in Example 1.
MS (ES) 489 (M+H).

Example 92

5-(trifluoromethyl)-N4-(((1S,9aR)-octahydro-1H-quinolizin-1-yl)methyl)-N2-(3,5-dimethoxyphenyl)pyrimidine-2,4-diamine (Compound 111, Bis-Formate Salt)

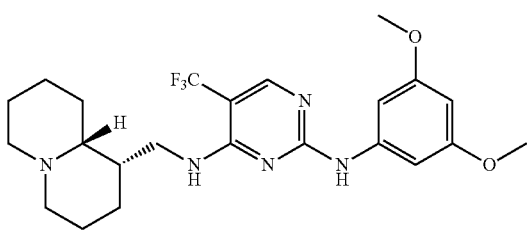

Compound 111 was prepared as described in Example 1.
¹H NMR (300 MHz, dmso) δ 8.34-7.96 (m, 1H), 7.44 (s, 1H), 7.07 (s, 1H), 6.78 (s, 1H), 6.28 (s, 1H), 3.71 (s, 3H), 3.61-2.96 (m, 4H), 2.95-2.56 (m, 3H), 2.26 (s, 3H), 2.19-1.87 (m, 2H), 1.86-1.16 (m, 9H); MS (ES) 466 (M+H).

Example 93

5-(4-(((1S,9aR)-octahydro-1H-quinolizin-1-yl)methylamino)-5-(trifluoromethyl)pyrimidin-2-ylamino)benzo[d]oxazol-2(3H)-one (Compound 112, Bis-Formate Salt)

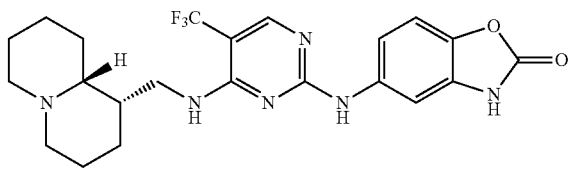 [SMILES: O=c1[nH]c2cc(Nc3ncc(C(F)(F)F)c(NC[C@@H]4CCCN5CCCC[C@H]45)n3)ccc2o1]

Compound 112 was prepared as described in Example 1.
MS (ES) 463 (M+H).

Example 94

4-(((1S,9aR)-octahydro-1H-quinolizin-1-yl)methylamino)-2-(4-methoxy-3-(5-methyl-1H-tetrazol-1-yl)phenylamino)pyrimidine-5-carbonitrile (Compound 113, Bis-Formate Salt)

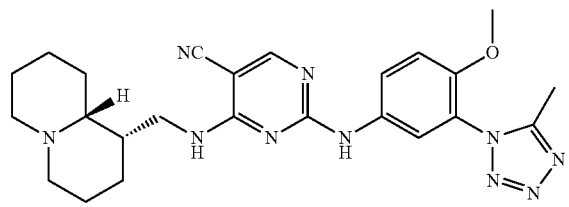 [SMILES: COc1ccc(Nc2ncc(C#N)c(NC[C@@H]3CCCN4CCCC[C@H]34)n2)cc1-n1nnnc1C]

Compound 113 was prepared as described in Example 1.
¹H NMR (300 MHz, dmso) δ 10.18-9.54 (m, 1H), 9.33-8.67 (m, 1H), 8.42-8.27 (m, 1H), 7.99-7.69 (m, 2H), 7.37-7.19 (m, 1H), 3.77 (s, 3H), 3.71-3.38 (m, 1H), 3.20-3.03 (m, 2H), 3.02-2.73 (m, 1H), 2.44-2.32 (m, 3H), 2.26 (s, 3H), 2.21-2.02 (m, 2H), 1.99-1.03 (m, 9H); MS (ES) 475 (M+H).

Example 95

4-(((1S,9aR)-octahydro-1H-quinolizin-1-yl)methylamino)-2-(4-fluoro-3-(5-methyl-1H-tetrazol-1-yl)phenylamino)pyrimidine-5-carbonitrile (Compound 114, Bis-Formate Salt)

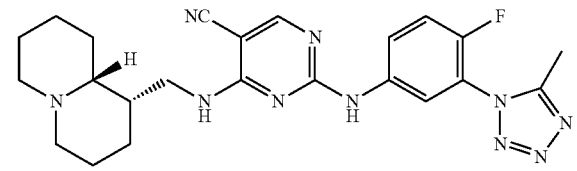

Compound 114 was prepared as described in Example 1.
¹H NMR (300 MHz, dmso) δ 10.29-9.82 (m, 1H), 9.32-8.70 (m, 1H), 8.47-8.34 (m, 1H), 8.14-8.02 (m, 1H), 8.01-7.83 (m, 1H), 7.67-7.50 (m, 1H), 3.62 (dd, J=4.4, 3.7 Hz, 1H), 3.54-3.22 (m, 4H), 3.23-3.05 (m, 1H), 3.03-2.74 (m, 1H), 2.49 (s, 3H), 2.22-2.07 (m, 1H), 2.02-1.08 (m, 10H); MS (ES) 463 (M+H).

Example 96

4-(((1S,9aR)-octahydro-1H-quinolizin-1-yl)methylamino)-2-(3-methoxy-5-(5-methyl-1H-tetrazol-1-yl)phenylamino)pyrimidine-5-carbonitrile (Compound 115, Bis-Formate Salt)

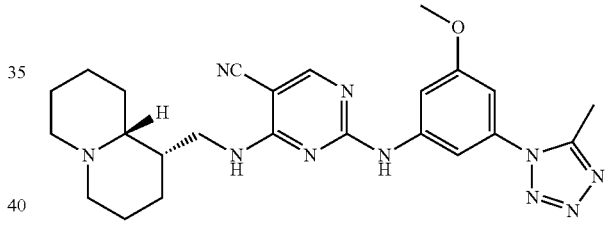

Compound 115 was prepared as described in Example 1.
¹H NMR (300 MHz, dmso) δ 10.03 (s, 1H), 9.34-8.70 (m, 1H), 8.50-8.26 (m, 1H), 7.99 (s, 1H), 7.59 (s, 1H), 7.04-6.88 (m, 1H), 3.79 (s, 3H), 3.55-3.35 (m, 3H), 3.26-3.06 (m, 3H), 3.05-2.74 (m, 1H), 2.56 (s, 3H), 2.38-2.14 (m, 3H), 2.03-1.07 (m, 8H); MS (ES) 475 (M+H).

Example 97

4-(((1S,9aR)-octahydro-1H-quinolizin-1-yl)methylamino)-2-(4-cyclopropyl-2-fluoro-5-(1H-tetrazol-1-yl)phenylamino)pyrimidine-5-carbonitrile (Compound 116, Bis-Formate Salt)

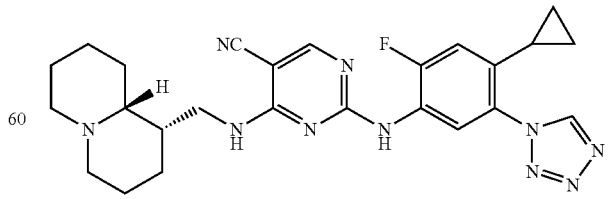

Compound 116 was prepared as described in Example 1.
¹H NMR (300 MHz, dmso) δ 9.95-9.76 (m, 1H), 9.71-9.40 (m, 1H), 8.33 (s, 1H), 7.99-7.78 (m, 1H), 7.69 (d, J=6.1 Hz, 1H), 7.28-7.12 (m, 1H), 3.58-3.40 (m, 1H), 3.37-3.00 (m, 3H), 3.00-2.72 (m, 3H), 2.19-1.94 (m, 1H), 1.93-1.27 (m, 8H), 1.28-0.99 (m, 2H), 0.89-0.74 (m, 2H), 0.74-0.58 (m, 2H); MS (ES) 489 (M+H).

Example 98

4-(((1S,9aR)-octahydro-1H-quinolizin-1-yl)methylamino)-2-(4-methyl-3-(1H-tetrazol-1-yl)phenylamino)pyrimidine-5-carbonitrile (Compound 117)

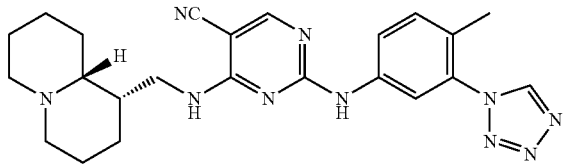 [SMILES: Cc1ccc(Nc2ncc(C#N)c(NC[C@@H]3CCCN4CCCC[C@H]34)n2)cc1-n1cnnn1]

Compound 117 was prepared as described in Example 1.
$^1$H NMR (300 MHz, dmso) δ 10.12-9.76 (m, 1H), 8.41-8.24 (m, 1H), 7.96 (d, J=2.3 Hz, 1H), 7.77 (d, J=8.2 Hz, 1H), 7.38 (d, J=8.6 Hz, 1H), 3.61-3.15 (m, 3H), 2.85-2.56 (m, 4H), 2.06 (s, 3H), 1.99-0.99 (m, 11H); MS (ES) 445 (M+H).

Example 99

4-(((1S,9aR)-octahydro-1H-quinolizin-1-yl)methylamino)-2-(2-fluoro-5-(5-methyl-1H-tetrazol-1-yl)phenylamino)pyrimidine-5-carbonitrile (Compound 118)

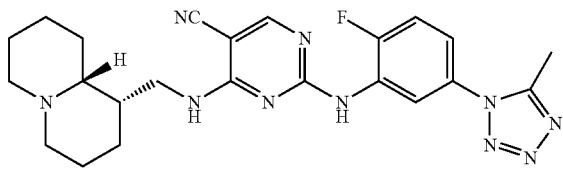 [SMILES: Cc1nnnn1-c1ccc(F)c(Nc2ncc(C#N)c(NC[C@@H]3CCCN4CCCC[C@H]34)n2)c1]

Compound 118 was prepared as described in Example 1.
$^1$H NMR (300 MHz, cdcl$_3$) δ 8.66 (d, J=5.1 Hz, 1H), 8.16 (s, 1H), 7.68 (d, J=8.1 Hz, 1H), 7.24 (d, J=9.2 Hz, 1H), 7.07 (d, J=8.1 Hz, 1H), 7.00 (dd, J=7.5, 4.4 Hz, 1H), 3.70-3.48 (m, 3H), 3.39-2.98 (m, 4H), 2.27 (s, 3H), 2.23-1.89 (m, 1H), 1.88-1.06 (m, 10H); MS (ES) 463 (M+H).

Example 100

4-(((1S,9aR)-octahydro-1H-quinolizin-1-yl)methylamino)-2-(3-cyano-4-methylphenylamino)pyrimidine-5-carbonitrile (Compound 119)

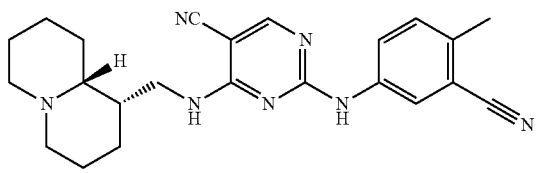

Compound 119 was prepared as described in Example 1.
$^1$H NMR (300 MHz, dmso) δ 9.91 (s, 1H), 8.33 (d, J=2.6 Hz, 2H), 8.08 (s, 1H), 7.82 (dd, J=8.5, 2.2 Hz, 1H), 7.31 (d, J=8.5 Hz, 1H), 3.70-3.44 (m, 2H), 3.45-3.17 (m, 3H), 2.81-2.61 (m, 2H), 2.39 (s, 3H), 2.02-1.57 (m, 6H), 1.56-1.23 (m, 4H), 1.23-1.02 (m, 1H); MS (ES) 402 (M+H).

Example 101

4-(((1S,9aR)-octahydro-1H-quinolizin-1-yl)methylamino)-2-(3-cyano-4-cyclopropylphenylamino)pyrimidine-5-carbonitrile (Compound 120)

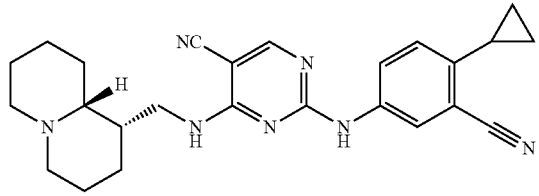

Compound 120 was prepared as described in Example 1.
$^1$H NMR (300 MHz, dmso) δ 9.90 (s, 1H), 8.32 (d, J=1.7 Hz, 1H), 8.04 (s, 1H), 7.83 (d, J=8.7 Hz, 1H), 6.99 (dd, J=8.7, 1.5 Hz, 1H), 3.67-3.45 (m, 2H), 3.44-3.12 (m, 3H), 2.73 (d, J=10.2 Hz, 2H), 2.15-2.01 (m, 1H), 2.01-1.56 (m, 6H), 1.56-1.24 (m, 4H), 1.24-1.10 (m, 1H), 1.05 (td, J=6.5, 1.9 Hz, 2H), 0.73 (t, J=5.5 Hz, 2H); MS (ES) 428 (M+H).

Example 102

4-(((1S,9aR)-octahydro-1H-quinolizin-1-yl)methylamino)-2-(3,5-dimethoxyphenylamino)pyrimidine-5-carbonitrile (Compound 121)

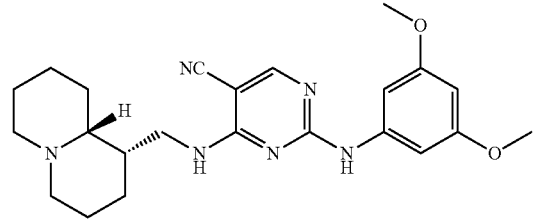 [SMILES: COc1cc(Nc2ncc(C#N)c(NC[C@@H]3CCCN4CCCC[C@H]34)n2)cc(OC)c1]

Compound 121 was prepared as described in Example 1.
$^1$H NMR (300 MHz, dmso) δ 9.63 (s, 1H), 8.39-8.16 (m, 2H), 7.00 (t, J=2.4 Hz, 2H), 6.14 (t, J=2.2 Hz, 1H), 3.70 (s, 6H), 3.66-3.48 (m, 4H), 2.82-2.62 (m, 3H), 2.06-1.57 (m, 6H), 1.56-1.26 (m, 4H), 1.25-1.03 (m, 1H); MS (ES) 423 (M+H).

Example 103

4-(((1S,9aR)-octahydro-1H-quinolizin-1-yl)methylamino)-2-(3-(5-cyclopropyl-1H-tetrazol-1-yl)-4-fluorophenylamino)pyrimidine-5-carbonitrile (Compound 122, Bis-Formate Salt)

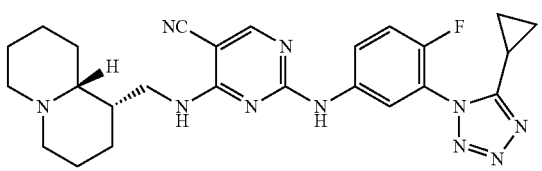 [SMILES: N#Cc1cnc(Nc2ccc(F)c(-n3nnnc3C3CC3)c2)nc1NC[C@@H]1CCCN2CCCC[C@H]12]

Compound 122 was prepared as described in Example 1.
$^1$H NMR (300 MHz, dmso) δ 8.47-8.29 (m, 2H), 8.21-8.10 (m, 2H), 7.94 (dd, J=8.3, 3.9 Hz, 1H), 7.54 (t, J=9.5 Hz, 1H), 3.56-3.40 (m, 4H), 2.82-2.64 (m, 3H), 2.10-1.99 (m, 1H), 1.98-1.77 (m, 4H), 1.77-1.23 (m, 7H), 1.23-0.99 (m, 4H); MS (ES) 489 (M+H).

Example 104

4-(((1S,9aR)-octahydro-1H-quinolizin-1-yl)methylamino)-2-(5-(5-cyclopropyl-1H-tetrazol-1-yl)-2-fluorophenylamino)pyrimidine-5-carbonitrile (Compound 123, Bis-Formate Salt)

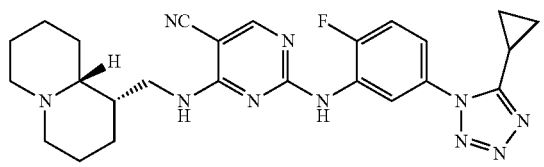 [SMILES: N#Cc1cnc(Nc2cc(-n3nnnc3C3CC3)ccc2F)nc1NC[C@@H]1CCCN2CCCC[C@H]12]

Compound 123 was prepared as described in Example 1.
$^1$H NMR (300 MHz, dmso) δ 9.59 (s, 1H), 8.36-8.15 (m, 2H), 8.13-8.03 (m, 1H), 7.56-7.48 (m, 2H), 3.46-3.23 (m, 3H), 2.68 (s, 4H), 2.02 (dd, J=10.6, 5.4 Hz, 1H), 1.96-1.69 (m, 4H), 1.70-1.39 (m, 4H), 1.39-0.95 (m, 7H); MS (ES) 489 (M+H).

Example 105

4-(((1S,9aR)-octahydro-1H-quinolizin-1-yl)methylamino)-2-(4-chloro-3-(5-cyclopropyl-1H-tetrazol-1-yl)phenylamino)pyrimidine-5-carbonitrile (Compound 124, Bis-Formate Salt)

Compound 124 was prepared as described in Example 1.
$^1$H NMR (300 MHz, dmso) δ 8.38 (t, J=7.7 Hz, 1H), 8.25-8.08 (m, 2H), 7.96 (d, J=8.7 Hz, 1H), 7.73 (d, J=8.9 Hz, 1H), 7.46 (d, J=6.8 Hz, 1H), 7.09 (d, J=8.4 Hz, 1H), 3.37-2.85 (m, 5H), 2.33-2.20 (m, 2H), 2.17-1.99 (m, 1H), 1.91-1.64 (m, 5H), 1.64-1.21 (m, 7H), 1.21-1.01 (m, 3H); MS (ES) 506 (M+H).

Example 106

4-(((1S,9aR)-octahydro-1H-quinolizin-1-yl)methylamino)-2-(4-methoxy-3-(5-methyl-1H-tetrazol-1-yl)phenylamino)pyrimidine-5-carboxamide (Compound 125)

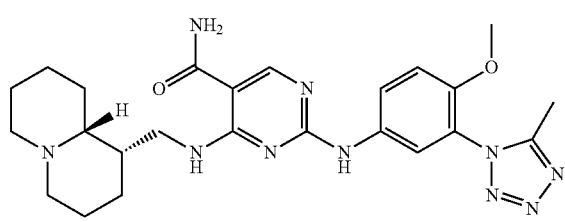 [SMILES: COc1ccc(Nc2ncc(C(N)=O)c(NC[C@@H]3CCCN4CCCC[C@H]34)n2)cc1-n1nnnc1C]

Compound 125 was prepared as described in Example 1.
$^1$H NMR (300 MHz, dmso) δ 9.58 (s, 1H), 9.23 (s, 1H), 8.48 (s, 1H), 8.02 (d, J=2.6 Hz, 1H), 7.88 (dd, J=9.1, 2.6 Hz, 1H), 7.24 (d, J=9.2 Hz, 1H), 3.75 (s, 3H), 3.65-3.51 (m, 1H), 3.49-3.35 (m, 3H), 2.67 (t, J=10.4 Hz, 3H), 2.38 (s, 3H), 1.92-1.73 (m, 2H), 1.72-1.40 (m, 4H), 1.39-1.00 (m, 5H); MS (ES) 493 (M+H).

Example 107

4-(((1S,9aR)-octahydro-1H-quinolizin-1-yl)methylamino)-2-(4-fluoro-3-(5-methyl-1H-tetrazol-1-yl)phenylamino)pyrimidine-5-carboxamide (Compound 126)

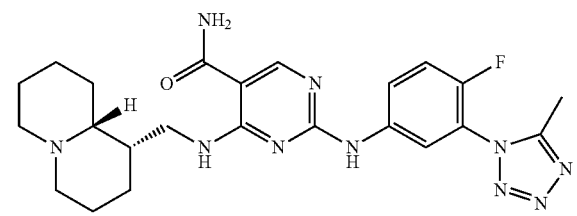 [SMILES: Cc1nnnn1-c1cc(Nc2ncc(C(N)=O)c(NC[C@@H]3CCCN4CCCC[C@H]34)n2)ccc1F]

Compound 126 was prepared as described in Example 1.
$^1$H NMR (300 MHz, dmso) δ 9.78 (s, 1H), 9.22 (s, 1H), 8.47 (s, 1H), 8.20 (dd, J=6.7, 2.6 Hz, 1H), 7.93-7.83 (m, 1H), 7.44 (t, J=9.5 Hz, 1H), 3.60-3.46 (m, 1H), 3.46-3.20 (m, 4H), 2.72-2.56 (m, 2H), 2.45 (s, 3H), 1.90-1.69 (m, 3H), 1.70-1.48 (m, 3H), 1.49-1.35 (m, 2H), 1.35-1.15 (m, 2H), 1.15-0.95 (m, 1H); MS (ES) 481 (M+H).

Example 108

4-(((1S,9aR)-octahydro-1H-quinolizin-1-yl)methylamino)-2-(2-fluoro-5-(5-methyl-1H-tetrazol-1-yl)phenylamino)pyrimidine-5-carboxamide (Compound 127, Trifluoroacetate Salt)

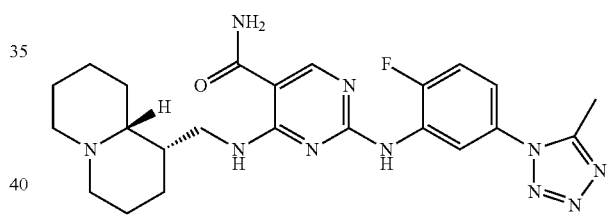

Compound 127 was prepared as described in Example 1.
$^1$H NMR (300 MHz, dmso) δ 9.18 (s, 2H), 8.49 (s, 1H), 8.22 (dd, J=6.9, 2.5 Hz, 1H), 7.55-7.44 (m, 1H), 7.43-7.34 (m, 1H), 3.58-3.44 (m, 1H), 3.33-3.06 (m, 2H), 2.81-2.63 (m, 4H), 2.55 (s, 3H), 2.07-1.80 (m, 3H), 1.75-1.40 (m, 4H), 1.38-1.01 (m, 4H); MS (ES) 481 (M+H).

Example 109

1-(5-(4-(((1S,9aR)-octahydro-1H-quinolizin-1-yl)methylamino)-5-fluoropyrimidin-2-ylamino)-2-cyclopropyl-4-methylphenyl)-4-methyl-1H-tetrazol-5(4H)-one (Compound 15)

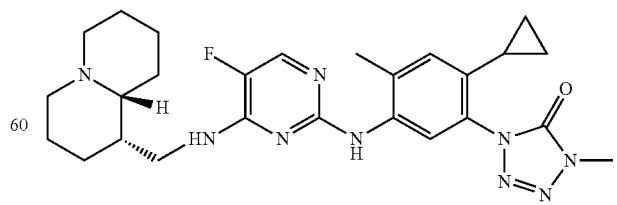

Compound 15 was prepared as described in Example 1.
$^1$H NMR (300 MHz; $d_6$-DMSO) δ 8.08 (s, 1H), 7.7 (d, J=3.9 Hz, 1H), 7.57 (s, 1H), 7.38 (m, 1H), 6.93 (s, 1H), 3.61

(s, 3H), 3.37 (m, 1H), 2.65 (m, 2H), 2.22 (s, 3H), 1.78-1.2 (m, 14H), 0.76 (d, J=8.1 Hz, 2H), 0.54 (m, 2H); m/z=508.39 (M+H)⁺.

Example 110

7-(4-(((1S,9aR)-octahydro-1H-quinolizin-1-yl)methylamino)-5-fluoropyrimidin-2-ylamino)-4-isopropyl-2,2-dimethyl-2H-benzo[b][1,4]oxazin-3(4H)-one (Compound 16)

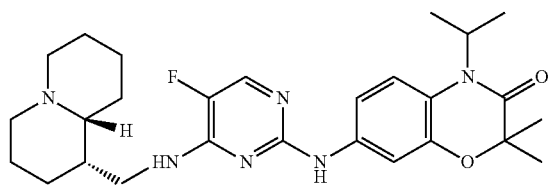 [SMILES: CC(C)N1C(=O)C(C)(C)Oc2cc(Nc3ncc(F)c(NC[C@@H]4CCCN5CCCC[C@H]45)n3)ccc21]

Compound 16 was prepared as described in Example 1.
¹H NMR (300 MHz; d₆-DMSO) δ 8.99 (s, 1H), 7.8 (d, J=3.9 Hz, 1H), 7.51 (d, J=2.1 Hz 1H), 7.42 (m, 1H), 7.31 (d, J=9.0 Hz 1H), 7.08 (d, J=9.0 Hz, 1H), 4.64 (m, 1H), 3.55 (m, 2H), 2.72 (m, 2H), 1.97-1.67 (m, 14H), 1.4 (s, 3H), 1.38, (s, 3H), 1.31 (s, 3H), 1.30 (s, 3H); m/z=497.10 (M+H)⁺, m/z=495.12 (M−H)⁻

Example 111

1-(3-(4-(((1S,9aR)-octahydro-1H-quinolizin-1-yl)methylamino)-5-fluoropyrimidin-2-ylamino)-5-methoxyphenyl)-4-methyl-1H-tetrazol-5(4H)-one (Compound 17)

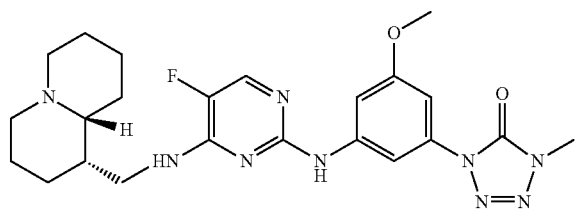 [SMILES: COc1cc(Nc2ncc(F)c(NC[C@@H]3CCCN4CCCC[C@H]34)n2)cc(-n2nnn(C)c2=O)c1]

Compound 17 was prepared as described in Example 1.
¹H NMR (300 MHz; d₆-DMSO) δ 9.27 (s, 1H), 7.9 (s, 1H), 7.85 (d, J=3.6 Hz, 1H), 7.49 (s, 1H), 7.41 (m, 1H), 6.95 (m, 1H), 3.76 (s, 3H), 3.59 (m, 1H), 3.53 (m, 2H), 2.67 (d, J=10.2 Hz, 2H), 1.88-1.28 (m, 14H); m/z=484.26 (M+H)⁺.

Example 112

7-(4-(((1S,9aR)-octahydro-1H-quinolizin-1-yl)methylamino)-5-fluoropyrimidin-2-ylamino)-4-(cyclopropylmethyl)-2,2-dimethyl-2H-benzo[b][1,4]oxazin-3(4H)-one (Compound 18)

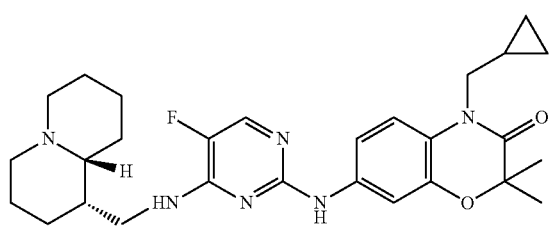 [SMILES: CC1(C)Oc2cc(Nc3ncc(F)c(NC[C@@H]4CCCN5CCCC[C@H]45)n3)ccc2N(CC2CC2)C1=O]

Compound 18 was prepared as described in Example 1.
¹H NMR (300 MHz; d₆-DMSO) δ 8.99 (s, 1H), 7.81 (d, J=3.9 Hz, 1H), 7.52 (s, 1H), 7.42 (m, 1H), 7.32 (d, J=8.7 Hz, 1H), 7.048 (d, J=8.7 Hz, 1H), 3.76 (d, J=6.6 Hz, 2H), 3.54 (s, 2H), 2.72 (d, J=10.5 Hz, 2H), 1.94 (m, 2H), 1.82 (m, 2H), 1.68 (d, J=12.0 Hz, 2H), 1.48-1.27 (9H), 0.42 (m, 2H), 0.3 (m, 2H); m/z=509.00 (M+H)⁺.

Example 113

5-fluoro-N2-(3-(trifluoromethyl)-4-morpholinophenyl)-N4-(((1S,9aR)-octahydro-1H-quinolizin-1-yl)methyl)pyrimidine-2,4-diamine (Compound 19)

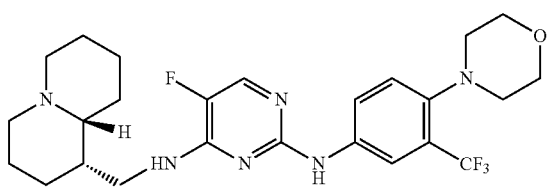 [SMILES: Fc1cnc(Nc2ccc(N3CCOCC3)c(C(F)(F)F)c2)nc1NC[C@@H]1CCCN2CCCC[C@H]12]

Compound 19 was prepared as described in Example 1.
¹H NMR (300 MHz; d₆-DMSO) δ 9.2 (s, 1H), 8.02 (s, 1H), 7.97 (d, J=9.3 Hz, 1H), 7.83 (d, J=3.3 Hz, 1H), 7.49 (m, 1H), 7.4 (d, J=9.3 Hz, 1H), 3.66 (s, 4H), 3.54 (m, 2H), 2.76 (s, 4H), 2.69 (m, 2H), 2.22 (s, 3H), 1.90-1.17 (m, 14H); m/z=509.27 (M+H)⁺.

Example 114

5-fluoro-N2-(2,2,3,3-tetrafluoro-2,3-dihydrobenzo[b][1,4]dioxin-7-yl)-N4-(((1S,9aR)-octahydro-1H-quinolizin-1-yl)methyl)pyrimidine-2,4-diamine (Compound 20)

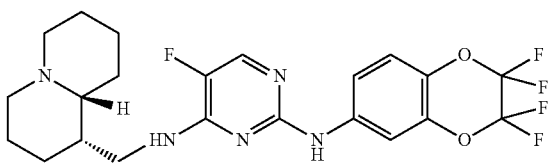 [SMILES: Fc1cnc(Nc2ccc3c(c2)OC(F)(F)C(F)(F)O3)nc1NC[C@@H]1CCCN2CCCC[C@H]12]

Compound 20 was prepared as described in Example 1.
¹H NMR (300 MHz; d₆-DMSO) δ 9.36 (s, 1H), 8.08 (d, J=2.4 Hz, 1H), 7.85 (d, J=3.6 Hz, 1H), 7.55 (m, 1H), 7.38 (d, J=6.6 Hz, 1H), 7.28 (s, 1H), 3.56 (d, J=5.1 Hz, 2H), 2.71 (d, J=10.2 Hz, 2H), 1.92-1.2 (m, 14H); ¹⁹F NMR δ −90.94, −166.2; m/z=486.2 (M+H)⁺.

Example 115

5-fluoro-N2-(3-fluoro-5-methoxyphenyl)-N4-(((1S,9aR)-octahydro-1H-quinolizin-1-yl)methyl)pyrimidine-2,4-diamine (Compound 21)

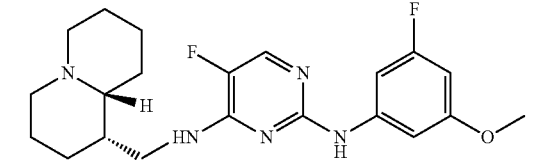 [SMILES: COc1cc(F)cc(Nc2ncc(F)c(NC[C@@H]3CCCN4CCCC[C@H]34)n2)c1]

Compound 21 was prepared as described in Example 1.
¹H NMR (300 MHz; d₆-DMSO) δ 9.15 (s, 1H), 7.85 (d, J=1.8 Hz, 1H), 7.48 (m, 1H), 7.30 (d, J=11.7 Hz, 1H), 7.13 (s, 1H), 6.27 (d, J=8.4 Hz, 1H), 3.72 (s, 3H), 3.63 (m, 2H), 2.7 (d, J=9.0 Hz, 2H), 1.93-1.2 (m, 14H), $^{19}$F NMR δ −112.14, −166.5; m/z=404.23 (M+H)$^+$.

Example 116

5-fluoro-N4-(((1S,9aR)-octahydro-1H-quinolizin-1-yl)methyl)-N2-(4-methoxy-3-(oxazol-5-yl)phenyl)pyrimidine-2,4-diamine (Compound 22)

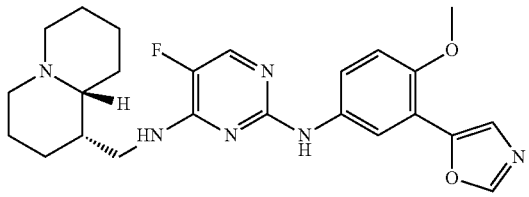 [SMILES: COc1ccc(Nc2ncc(F)c(NC[C@@H]3CCCN4CCCC[C@H]34)n2)cc1-c1cnco1]

Compound 22 was prepared as described in Example 1.
$^1$H NMR (300 MHz; d$_6$-DMSO) δ 8.91 (s, 1H), 8.39 (s, 1H), 8.1 (d, J=2.1 Hz, 1H), 7.79 (d, J=3.9 Hz, 1H), 7.58 (d, J=8.7 Hz, 1H), 7.48 (s, 1H), 7.41 (m, 1H), 6.99 (d, J=9.0 Hz, 1H), 3.86 (s, 3H), 3.54 (m, 2H), 2.65 (m, 2H), 1.85-1.26 (m, 14H); m/z=453.31 (M+H)$^+$.

Example 117

N2-(4-cyclopropyl-2-fluoro-5-(5-methyl-1H-tetrazol-1-yl)phenyl)-5-fluoro-N4-(((1S,9aR)-octahydro-1H-quinolizin-1-yl)methyl)pyrimidine-2,4-diamine (Compound 23)

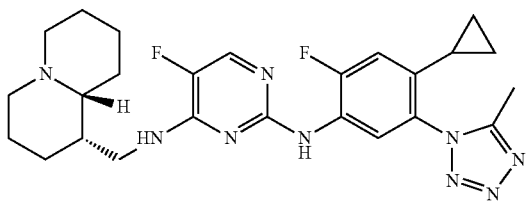 [SMILES: Cc1nnnn1-c1cc(Nc2ncc(F)c(NC[C@@H]3CCCN4CCCC[C@H]34)n2)c(F)cc1C1CC1]

Compound 23 was prepared as described in Example 1.
$^1$H NMR (300 MHz; d$_6$-DMSO) δ 8.54 (s, 1H), 7.91 (d, J=7.2 Hz, 1H), 7.78 (d, J=3.6 Hz, 1H), 7.46 (s, 1H), 7.05 (d, J=11.7 Hz, 1H), 3.37 (m, 2H), 2.71 (m, 2H), 2.67 (m, 2H), 2.41 (s, 3H), 1.82-1.12 (m, 14H), 0.75 (m, 2H), 0.65 (m, 2H); m/z=496.24 (M+H)$^+$.

Example 118

N2-[3-(1,1-dioxo-isothiazolidin-2-yl)-4-fluoro-phenyl]-5-fluoro-N4-(((1S,9aR)-octahydro-1H-quinolizin-1-yl)methyl)-pyrimidine-2,4-diamine (Compound 24)

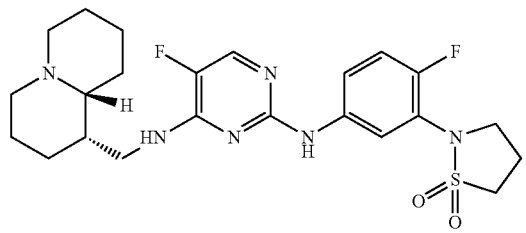 [SMILES: O=S1(=O)CCCN1c1cc(Nc2ncc(F)c(NC[C@@H]3CCCN4CCCC[C@H]34)n2)ccc1F]

Compound 24 was prepared as described in Example 1.
$^1$H NMR (300 MHz; d$_6$-DMSO) δ 9.07 (s, 1H), 8.54 (s, 1H), 8.21 (s, 1H), 7.76 (d, J=7.5 Hz, 1H), 7.71-7.66 (m, 1H), 7.46 (m, 1H), 7.1 (t, J=9.3 Hz, 1H), 3.71 (t, J=6.6 Hz, 2H), 3.5 (m, 2H), 3.37 (t, J=7.5 Hz, 2H), 2.31 (d, J=11.7 Hz, 2H), 2.41 (t, J=7.2 Hz, 2H), 1.94-1.27 (m, 14H); m/z=493.32 (M+H)$^+$.

Example 119

7-(4-(((1S,9aR)-octahydro-1H-quinolizin-1-yl)methylamino)-5-fluoropyrimidin-2-ylamino)-4-(3-fluoropropyl)-2,2-dimethyl-2H-benzo[b][1,4]oxazin-3(4H)-one (Compound 25)

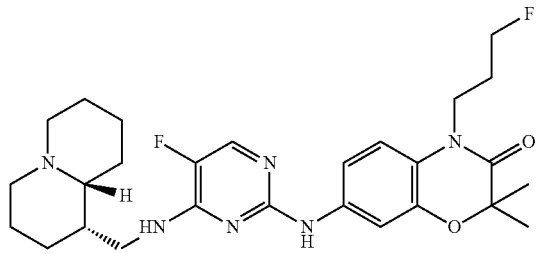 [SMILES: CC1(C)Oc2cc(Nc3ncc(F)c(NC[C@@H]4CCCN5CCCC[C@H]45)n3)ccc2N(CCCF)C1=O]

Compound 25 was prepared as described in Example 1.
$^1$H NMR (300 MHz; d$_6$-DMSO) δ 9.0 (s, 1H), 7.8 (d, J=3.0 Hz, 1H), 7.54 (s, 1H), 7.42 (m, 1H), 7.31 (d, J=8.4 Hz, 1H), 6.97 (d, J=9.0 Hz, 1H), 4.55 (t, J=5.7 Hz, 2H), 4.39 (t, J=5.4 Hz, 2H), 3.94 (t, J=6.9 Hz, 2H), 3.55 (m, 2H), 2.70 (m, 2H), 1.97-1.29 (m, 17H), $^{19}$F NMR δ −73.4, −167.4; m/z=515.36 (M+H)$^+$.

Example 120

7-(4-(((1S,9aR)-octahydro-1H-quinolizin-1-yl)methylamino)-5-fluoropyrimidin-2-ylamino)-4-(cyclopropylmethyl)-2H-benzo[b][1,4]oxazin-3(4H)-one (Compound 26)

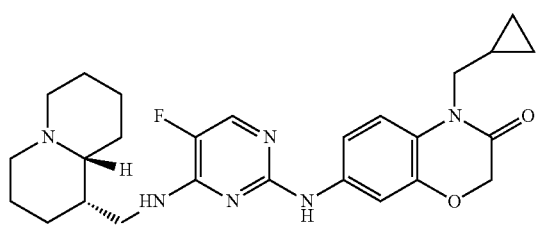 [SMILES: O=C1COc2cc(Nc3ncc(F)c(NC[C@@H]4CCCN5CCCC[C@H]45)n3)ccc2N1CC1CC1]

Compound 26 was prepared as described in Example 1.
$^1$H NMR (300 MHz; d$_6$-DMSO) δ 9.0 (s, 1H), 7.81 (d, J=3.9 Hz, 1H), 7.5-7.36 (m, 3H), 7.09 (d, J=8.7 Hz, 1H), 4.55 (s, 2H), 3.76 (m, 2H), 3.54 (m, 2H), 2.70 (m, 2H), 1.78-1.2 (m, 14H), 0.425 (m, 2H), 0.31 (m, 2H); m/z=481.26 (M+H)$^+$.

Example 121

7-(4-(((1S,9aR)-octahydro-1H-quinolizin-1-yl)methylamino)-5-fluoropyrimidin-2-ylamino)-4-ethyl-2,2-difluoro-2H-pyrido[3,2-b][1,4]oxazin-3(4H)-one (Compound 27)

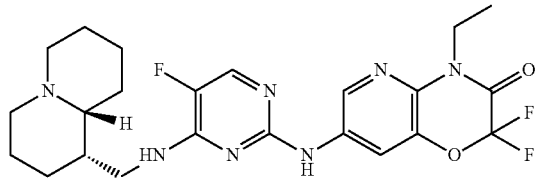 [SMILES: CCN1C(=O)C(F)(F)Oc2cc(Nc3ncc(F)c(NC[C@@H]4CCCN5CCCC[C@H]45)n3)cnc21]

Compound 27 was prepared as described in Example 1.
$^1$H NMR (300 MHz; d$_6$-DMSO) δ 9.49 (s, 1H), 8.56 (d, J=2.4 Hz, 1H), 8.28 (d, J=2.4 Hz, 1H), 7.87 (d, J=3.6 Hz, 1H), 7.65 (m, 1H), 4.09 (q, J=7.2 Hz, 2H), 3.58 (m, 2H), 2.72 (d, J=10.5 Hz, 2H), 1.95-1.26 (m, 14H), 1.19 (t, J=6.6 Hz, 2H), $^{19}$F NMR δ −73.9, −165.9; m/z=492.35 (M+H)$^+$.

Example 122

N2-(5-(1-methyl-1H-tetrazol-5-yloxy)-4-cyclopropyl-2-fluorophenyl)-5-fluoro-N4-(((1S,9aR)-octahydro-1H-quinolizin-1-yl)methyl)pyrimidine-2,4-diamine (Compound 28, Formate Salt)

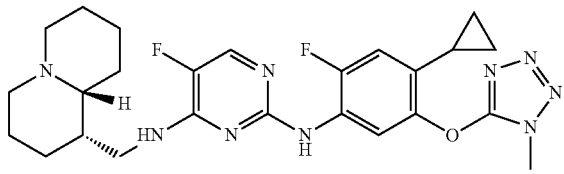 [SMILES: Cn1nnnc1Oc1cc(Nc2ncc(F)c(NC[C@@H]3CCCN4CCCC[C@H]34)n2)c(F)cc1C1CC1]

Compound 28 was prepared as described in Example 1.

$^1$H NMR (300 MHz; d$_6$-DMSO) δ 8.23 (m, 1H), 7.77 (s, 1H), 7.27 (s, 1H), 3.51 (bs, 2H), 4.2 (s, 3H), 3.51 (s, 3H), 3.17 (d, J=11.7 Hz, 2H), 1.98-1.36 (m, 14H), 0.86 (d, J=8.4 Hz, 2H), 0.64 (d, J=5.1 Hz, 2H); m/z=512.29 (M+H)$^+$.

Example 123

5-fluoro-N2-(3-pentafluorosulfanyl-6-fluoro-phenyl)-N4-(((1S,9aR)-octahydro-1H-quinolizin-1-yl)methyl)pyrimidine-2,4-diamine (Compound 29)

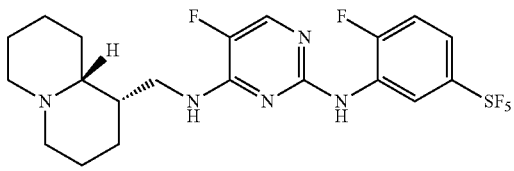

Compound 29 was prepared as described in Example 1.

Mono-SNAr product (75 mg, 1.0 eq), 3 ml of isopropyl alcohol, p-Toluenesulfonic acid monohydrate (1.5 eq) and the desired aniline (1.5 eq) were used and the reaction was heated at 70° C. overnight. After purification by preparative HPLC, the mixture was partitioned between 1M NaOH (30 mL) and EtOAc (30 mL). The aqueous layer was extracted with EtOAc (2×20 mL) and the combined organic extracts were dried (Na$_2$SO$_4$), filtered and the solvent removed under vacuum to leave a crude residue. The residue was lyophilized from MeCN/H$_2$O to give the product as a solid. Compound 29 was obtained as a single enantiomer (and single diastereomer); purity=99.26% by LC/MS; m/z=500.29 (M+H)$^+$. $^1$H NMR (300 MHz; d$_6$-DMSO) δ 8.72 (s, 1H), 8.46 (dd, J=6.9, 2.7 Hz, 1H), 7.83 (d, J=3.8 Hz, 1H), 7.58-7.53 (m, 2H), 7.40 (q, J=13.8 Hz, 1H), 3.43 (t, J=5.9 Hz, 2H), 2.74-2.62 (m, 2H), 1.91-1.55 (m, 7H), 1.49-1.06 (m, 7H); $^{19}$F NMR (300 MHz; d$_6$-DMSO) δ −112.6 (m), −117.2, −135.1, −135.6, −166.2; m/z=500.29 (M+H)$^+$.

Example 124

5-fluoro-N2-(3-pentafluorosulfanyl-5-fluoro-phenyl)-N4-(((1S,9aR)-octahydro-1H-quinolizin-1-yl)methyl)pyrimidine-2,4-diamine (Compound 30)

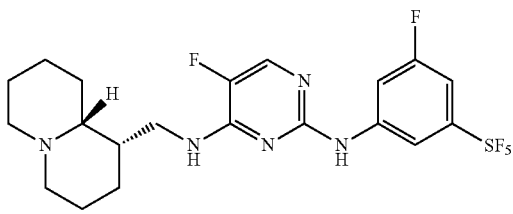

Compound 30 was prepared as described in Example 1.

Mono-SNAr product (75 mg, 1.0 eq), 3 ml of isopropyl alcohol, p-Toluenesulfonic acid monohydrate (1.5 eq) and the desired aniline (1.5 eq) were used and the reaction was heated at 70° C. overnight. After purification by preparative HPLC, the mixture was partitioned between 1M NaOH (30 mL) and EtOAc (30 mL). The aqueous layer was extracted with EtOAc (2×20 mL) and the combined organic extracts were dried (Na$_2$SO$_4$), filtered and the solvent removed under vacuum to leave a residue. The residue was lyophilized from MeCN/H$_2$O to give the product (73 mg, 58%) as a solid. Compound 30 was obtained as a single enantiomer (and single diastereomer); purity=99.67% by LC/MS; m/z=500.29 (M+H)$^+$. $^1$H NMR (300 MHz; d$_6$-DMSO) δ 9.63 (s, 1H), 8.13 (d, J=11.8 Hz, 1H), 8.06 (s, 1H), 7.91 (d, J=3.7 Hz, 1H), 7.63 (br. d, J=5.1 Hz, 1H), 7.27 (dt, J=8.9, 1.9 Hz, 1H), 3.51-3.58 (m, 2H), 2.74 (br. d, J=10.6 Hz, 2H), 1.93-1.65 (m, 7H), 1.45-1.13 (m, 7H); $^{19}$F NMR (300 MHz; d$_6$-DMSO) δ −109.7 (t), −113.7 (m), −136.1, −136.7, −165.1; m/z=500.29 (M+H)$^+$.

Example 125

7-(4-(((1S,9aR)-octahydro-1H-quinolizin-1-yl)methylamino)-5-fluoropyrimidin-2-ylamino)-4-(cyclopropylmethyl)-2,2-dimethyl-2H-pyrido[3,2-b][1,4]oxazin-3(4H)-one (Compound 31)

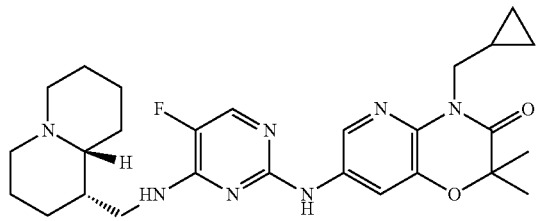 [SMILES: CC1(C)Oc2cc(Nc3ncc(F)c(NC[C@@H]4CCCN5CCCC[C@H]45)n3)cnc2N(CC2CC2)C1=O]

Compound 31 was prepared as described in Example 1.

$^1$H NMR (300 MHz; d$_6$-DMSO) δ 9.19 (s, 1H), 8.38 (d, J=2.4 Hz, 1H), 7.84 (d, J=3.6 Hz, 1H), 7.52 (s, 1H), 4.07 (d, J=5.4 Hz, 1H), 3.86 (d, J=6.9 Hz, 2H), 3.56 (m, 1H), 3.15 (d, J=4.5 Hz, 2H), 2.7 (m, 2H), 1.95-1.2 (m, 14H), 1.4 (s, 6H), 0.38 (m, 2H), 0.3 (m, 2H); m/z=509.99 (M+H)$^+$.

Example 126

General Scheme for the Preparation of 5-(4-(((1S, 9aR)-octahydro-1H-quinolizin-9-yl)methylamino)-5-chloropyrimidin-2-ylamino)-2-cyclopropylbenzonitrile (Compound 5, Formate Salt)

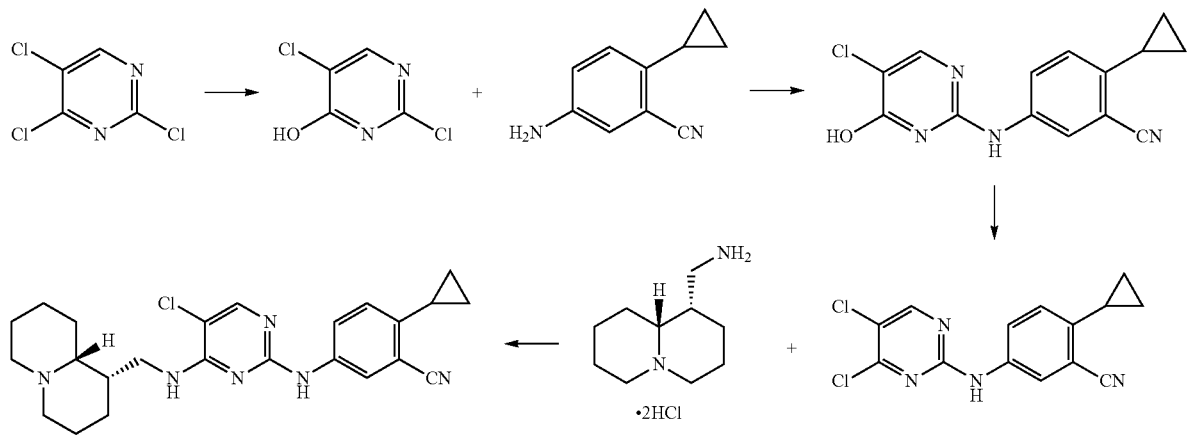

Preparation of 2,5-dichloropyrimidin-4-ol

2,4,5-trichloropyrimidine (16.7 g, 91.0 mmol) was added to a tared, sealed flask and weighed. The oil was dissolved in 54 mL THF and cooled to 0° C. 1M aqueous NaOH solution (182 mL, 182 mmol) was added dropwise via an addition funnel, keeping the reaction at 0° C. This was allowed to warm to room temperature and concentrated to remove THF. Additional water was added to maintain dissolution. The pH was adjusted to 6 with a small quantity of HCl, and the aqueous was washed 3 times with ethyl acetate. The pH was then brought below 1 with more HCl, and extracted six times with ethyl acetate. This layer was washed with brine and dried over sodium sulfate. Product solution was filtered, concentrated, and dried on the high vacuum to give 14.1 g of 2,5-dichloropyrimidin-4-ol as an oil (96%).

$^1$H NMR (300 MHz; d$_6$-DMSO) δ 8.24 (s, 1H); m/z=165 (M+H)$^+$.

Preparation of 5-amino-2-cyclopropylbenzonitrile

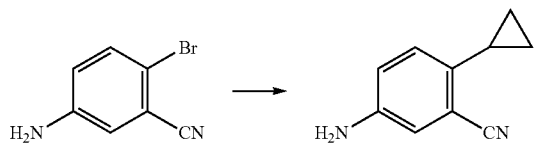 [SMILES: N#Cc1cc(N)ccc1Br ; N#Cc1cc(N)ccc1C1CC1]

5-amino-2-bromobenzonitrile (5.0 g, 25.4 mmol), cyclopropylboronic acid (4.36 g, 50.8 mmol), Cs$_2$CO$_3$ (49.62 g, 152.3 mmol), and tricyclohexylphosphine (2.85 g, 10.2 mmol) were weighed out and added to a large reaction tube with magnetic stir bar. Toluene (120 mL) and water (40 mL) were added, and the reaction was subjected to vigorous subsurface nitrogen sparging. Pd(OAc)$_2$ (1.14 g, 5.1 mmol) was weighed out and added, the tube was sealed under nitrogen, and the reaction was heated overnight at 110° C. This was then filtered with water and ethyl acetate washings. The combined washings were treated with saturated aqueous NaHCO$_3$ and the layers were separated. The aqueous was extracted 4 more times with ethyl acetate, and the combined organic layer was washed twice with brine and dried over sodium sulfate.

After filtration, concentration, and drying on the high vacuum, 7.65 g was obtained of 5-amino-2-cyclopropylbenzonitrile containing tricyclohexylphosphine derived byproducts. This was used without further purification.

$^1$H NMR (300 MHz; d$_6$-DMSO) δ 6.94-6.58 (m, 3H), 5.34 (s, 2H), 1.98-1.90 (m, 1H), 0.91 (qd, 2H), 0.73-0.43 (m, 2H); m/z=159 (M+H)$^+$.

Preparation of 5-(5-chloro-4-hydroxypyrimidin-2-ylamino)-2-cyclopropylbenzonitrile

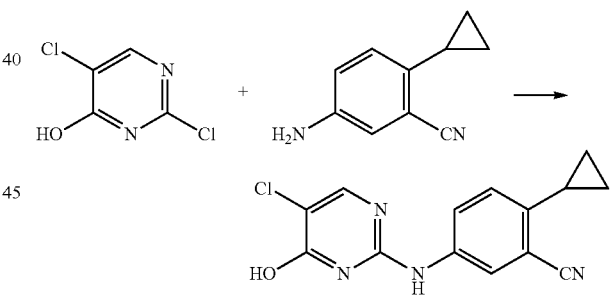

5-amino-2-cyclopropylbenzonitrile (25.4 mmol; from the previous reaction) was transferred to a large reaction tube with magnetic stir bar in 250 mL isopropyl alcohol. 2,5-dichloropyrimidin-4-ol (4.20 g, 25.5 mmol) and p-toluenesulfonic acid monohydrate (14.50 g, 76.2 mmol) were weighed out and added. This was heated overnight at 110° C. After that time, it was allowed to cool to room temperature and an orange precipitate was filtered off. The filtrate was concentrated to half volume, and a second precipitate crashed out which was filtered off. Again, the filtrate was concentrated to half volume and a third precipitate crashed out which was filtered off. Finally, further concentration crashed out a fourth precipitate which was collected and washed with hexane. This was dried on high vacuum to give 5.63 g of 5-(5-chloro-4-hydroxypyrimidin-2-ylamino)-2-cyclopropylbenzonitrile as a tosylate salt, containing 1.2 equivalents of p-toluenesulfonic acid (45% yield).

$^1$H NMR (300 MHz; d$_6$-DMSO) δ 8.03 (d, 1H), 7.99 (s, 1H), 7.62 (dd, 1H), 7.47 (d, 2.4H-tosylate), 7.11 (d, 2.4H-tosylate), 7.05 (d, 1H), 2.27 (s, 3.6H-tosylate), 2.09 (td, 1H), 1.10-1.00 (m, 2H), 0.84-0.65 (m, 2H); m/z=287 (M+H)$^+$.

Preparation of 5-(4,5-dichloropyrimidin-2-ylamino)-2-cyclopropylbenzonitrile

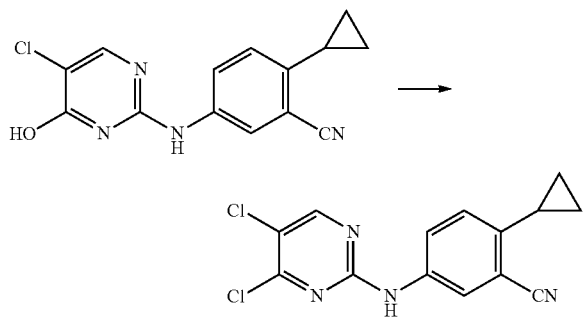

5-(5-chloro-4-hydroxypyrimidin-2-ylamino)-2-cyclopropylbenzonitrile, containing 1.2 equivalents of p-toluenesulfonic acid (1.00 g, 2.03 mmol) was weighed out and added to a flask with a magnetic stir bar. This was suspended in 11 mL POCl$_3$ and the reaction was heated at reflux for 3 hours. This was evaporated, then quenched with cold 10% aqueous Na$_2$CO$_3$. The mixture was extracted 4 times with ethyl acetate and the combined organic layer was dried over sodium sulfate. This was filtered, concentrated onto a plug of silica, and purified by column chromatography. Pure product was concentrated and dried on the high vacuum to give 493 mg of 5-(4,5-dichloropyrimidin-2-ylamino)-2-cyclopropylbenzonitrile (80% yield, accounting for the mass of p-toluenesulfonic acid present in the starting material).

$^1$H NMR (300 MHz; d$_6$-DMSO) δ 10.40 (s, 1H), 8.67 (s, 1H), 8.04 (d, 1H), 7.76 (dd, 1H), 7.06 (d, 1H), 2.16-2.02 (m, 1H), 1.10-0.99 (m, 2H), 0.84-0.71 (m, 2H); m/z=305 (M+H)$^+$.

Preparation of 5-(4-(((1S,9aR)-octahydro-1H-quinolizin-9-yl)methylamino)-5-chloropyrimidin-2-ylamino)-2-cyclopropylbenzonitrile (Compound 5, Formate Salt)

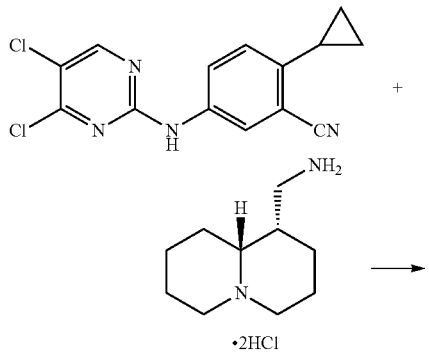

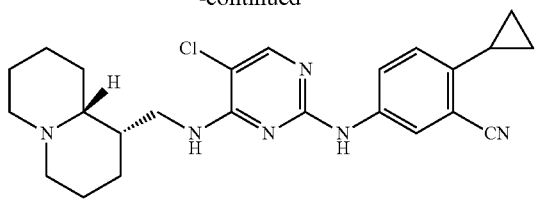

(((1S,9aR)-octahydro-1H-quinolizin-9-yl)methanamine, di-HCl salt (55.4 mg, 0.23 mmol) was weighed out and added to a reaction vial with a magnetic stir bar. 5-(4,5-dichloropyrimidin-2-ylamino)-2-cyclopropylbenzonitrile (35.0 mg, 0.12 mmol) was weighed out and added followed by addition of 3 mL isopropyl alcohol and then diisopropylethylamine (0.120 mL, 0.69 mmol). This was heated overnight at 110° C. The solvent was evaporated and the residue purified by preparative HPLC to obtain 26.5 mg of pure Compound 5 as a mono-formic acid salt (48% yield).

$^1$H NMR (300 MHz; d$_6$-DMSO) δ 9.37 (s, 1H), 8.17 (s, 1H), 8.10 (s, 1H), 7.94 (s, 1H), 7.81 (dd, 1H), 7.64 (t, 1H), 6.96 (d, 1H), 3.56 (t, 2H), 2.80 (d, 2H), 2.25-1.89 (m, 5H), 1.89-1.76 (m, 1H), 1.74-1.41 (m, 6H), 1.35 (d, 2H), 1.20 (d, 1H), 1.02 (dt, 2H), 0.88-0.56 (m, 2H); m/z=437 (M+H)$^+$.

Example 127

Preparation 1-(5-(4-(((1S,9aR)-octahydro-1H-quinolizin-1-yl)methylamino)-5-fluoropyrimidin-2-ylamino)-2-(oxetan-3-yloxy)phenyl)-4-methyl-1H-tetrazol-5(4H)-one (Compound 14)

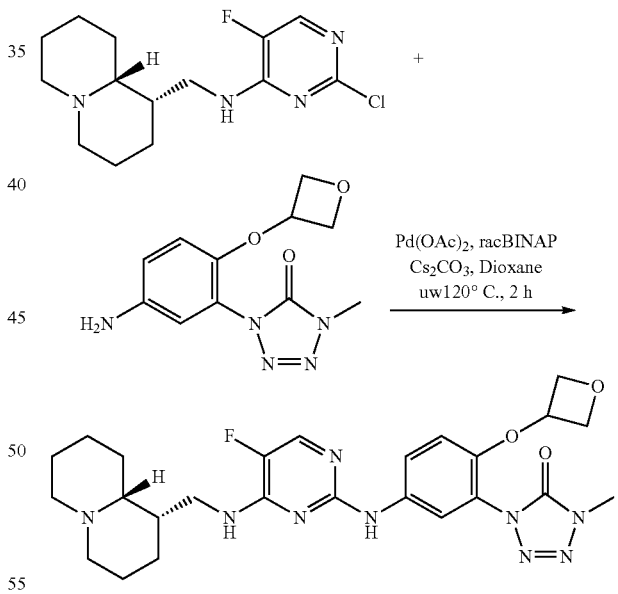

To a microwave vial, was added 2-chloro-5-fluoro-N-(((1S,9aR)-octahydro-1H-quinolizin-1-yl)methyl)pyrimidin-4-amine (prepared according to Example 1; 400 mg, 1.34 mmol, 1 equiv), 1-(5-amino-2-(oxetan-3-yloxy)phenyl)-4-methyl-1H-tetrazol-5(4H)-one (prepared as described in WO2011/068898, the disclosure of which is incorporated herein by reference; 493 mg, 1.87 mmol, 1.4 equiv), rac-BINAP (181 mg, 0.291 mmol, 0.217 equiv), Cs$_2$CO$_3$ (1.31 g, 4.02 mmol, 3 equiv), Pd(OAc)$_2$ (26 mg, 0.116 mmol, 0.0870 equiv), and dioxane (10 mL). The microwave vial was capped and sonicated under vacuum for 5 min. The reaction mixture was heated in the microwave at 120° C. for 2 h. The cooled reaction mixture was filtered using a pad of celite and rinsed with dioxane, and the filtrate was concentrated. The crude product was purified by flash chromatography and eluted with DCM:2M NH₃/MeOH=100:0 to 94:4 using 1% 2M NH₃/MeOH increments to provide the desired product Compound 14 1-(5-(4-(((1S,9aR)-octahydro-1H-quinolizin-1-yl)methylamino)-5-fluoropyrimidin-2-ylamino)-2-(oxetan-3-yloxy)phenyl)-4-methyl-1H-tetrazol-5(4H)-one (535 mg, 76%) as a solid.

¹H NMR (300 MHz; d₆-DMSO) δ 9.10 (s, 1H), 7.92 (s, 1H), 7.71-7.81 (m, 2H), 7.45 (bs, 1H), 6.77-6.81 (d, 1H, J=9.3 Hz), 5.22-5.27 (p, 1H, J=4.8 Hz), 4.80-4.84 (t, 2H, J=6 Hz), 4.40-4.44 (t, 2H, J=5.4 Hz), 3.62 (s, 3H), 3.48 (bs, 2H), 2.69 (bs, 2H), 1.06-2.99 (m, 14H); ¹⁹F NMR (282 MHz; d₆-DMSO) δ −167.2 (s); m/z=526 (M+H)⁺.

Example 128

General Scheme for the Preparation of N2-(4,4-dimethyl-4H-5-oxa-1,2,3,9b-tetraaza-cyclopenta[a]naphthalen-8-yl)-5-fluoro-N4-(((1S,9aR)-octahydro-1H-quinolizin-1-yl)methyl)-pyrimidine-2,4-diamine (Compound 98)

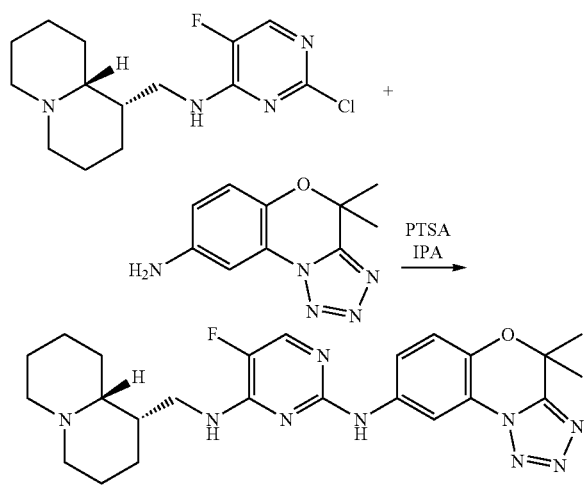

Preparation of the nitro tetrazole (4,4-dimethyl-8-nitro-4H-benzo[b]tetrazolo[1,5-d][1,4]oxazine)

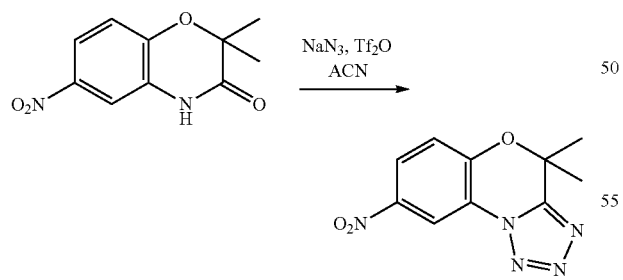

A suspension of 2,2-dimethyl-6-nitro-2H-benzo[b][1,4]oxazin-3(4H)-one (1.00 g, 4.50 mmol, 1 equiv) and sodium azide (1.76 g, 27.0 mmol, 6 equiv) in ACN (50 mL) under argon was cooled to −10° C. (external temperature). While maintaining the temperature at −10° C., trifluoromethanesulfonic anhydride (2.27 mL, 3.81 g, 13.5 mmol, 3 equiv) was added slowly dropwise. The reaction was allowed to warm to RT overnight. TLC, LCMS indicated a 1:1 ratio of reactant: product. Reaction was cooled to −10° C., and was slowly quenched with ice-cold saturated NaHCO₃ and diluted with EtOAc. The layers were separated, and the organic layer was washed with water 1x, dried over Na₂SO₄, and concentrated to dryness. The crude product was purified by flash chromatography and eluted with DCM to afford the product nitro tetrazole (609 mg, 55%) as a white solid and recovered 450 mg of reactant.

¹H NMR (300 MHz; d₆-DMSO) δ 8.60-8.61 (d, 1H, J=2.4 Hz), 8.28-8.31 (m, 1H), 7.46-7.49 (d, 1H, J=9 Hz), 1.83 (s, 3H); m/z=248 (M+H)⁺.

Preparation of the Amine Tetrazole (4,4-dimethyl-4H-benzo[b]tetrazolo[1,5-d][1,4]oxazin-8-amine)

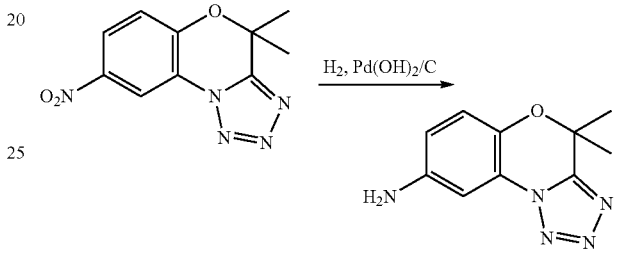

A Parr vessel was charged with the nitro tetrazole (330 mg, 1.33 mmol), EtOH (4 mL), and 20% Pd(OH)₂/C (33 mg, 10% by weight of the starting nitro compound) giving a suspension. The vessel was sealed, degassed, and back-filled with H₂ (×3). The vessel was then charged with 40 psi H₂ and allowed to shake for 3 h. LCMS analysis indicated a 10:90 ratio of hydroxamine:product. Additional catalyst was added 20% Pd(OH)₂/C (33 mg, 10% by weight of the starting nitro compound) and allowed to shake for 1 h. LCMS analysis indicated a 10:90 ratio of hydroxamine:product. The reaction mixture was filtered through a pad of celite, and the pad of celite was rinsed with MeOH. The filtrate was evaporated to dryness. The crude product was absorbed onto silica gel and purified by flash chromatography and eluted with hex:EtOAc=100:0 to 30%-40% EtOAc using 10% EtOAc increments to afford the product amine tetrazole (269 mg, 93%) as a white solid.

¹H NMR (300 MHz; d₆-DMSO) δ 7.12-7.13 (d, 1H, J=2.7 Hz), 6.93-6.95 (d, 1H, J=8.7 Hz), 6.58-6.61 (dd, 1H, J=2.4 Hz, J=8.7 Hz), 5.33 (bs, 2H), 1.69 (s, 3H); m/z=218 (M+H)⁺.

Preparation of N2-(4,4-dimethyl-4H-5-oxa-1,2,3,9b-tetraaza-cyclopenta[a]naphthalen-8-yl)-5-fluoro-N4-(((1S,9aR)-octahydro-1H-quinolizin-1-yl)methyl)-pyrimidine-2,4-diamine (Compound 98)

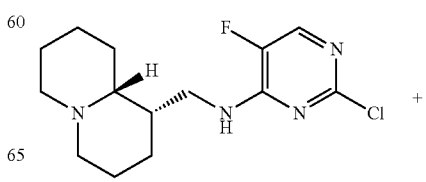

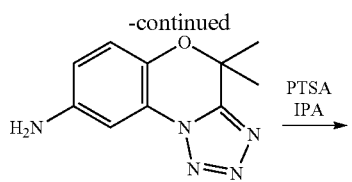

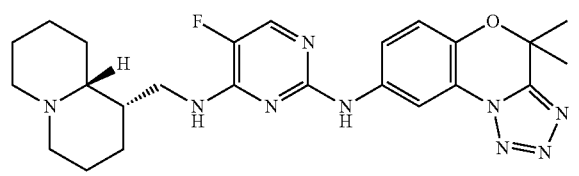

A mixture of 2-chloro-5-fluoro-N-(((1S,9aR)-octahydro-1H-quinolizin-1-yl)methyl)pyrimidin-4-amine (prepared as described in Example 1; 42 mg, 0.142 mmol, 1 equiv), amine tetrazole (37 mg, 0.170 mmol, 1.2 equiv), and PTSA monohydrate (27 mg, 1.42 mmol, 1 equiv) in IPA (2 mL) was heated to 70° C. for 3 d. LCMS indicated 1% unreacted 2-chloro-5-fluoro-N-(((1S,9aR)-octahydro-1H-quinolizin-1-yl)methyl)pyrimidin-4-amine. After cooling the reaction to ambient temperature, 3-amino benzoic acid (20 mg, 0.142 mmol, 1 equiv) was added and heated to 70° C. overnight to scavenge the unreacted pyrimidine. After cooling to ambient temperature, the crude mixture was concentrated to dryness. The residue was taken in ice-cold water, EtOAc, and aqueous 1N NaOH. The aqueous and organic layers were partitioned, and the organic layer washed with 1N NaOH (1×5 mL). The organic layer was dried (Na$_2$SO$_4$), filtered, and the solvent removed under vacuum. The crude product was purified by prepTLC using DCM:2M NH$_3$/MeOH=1:1 to provide the desired product Compound 98 (56 mg, 83%) as a solid.

$^1$H NMR (300 MHz; d$_6$-DMSO) δ 9.27 (s, 1H), 8.53 (s, 1H), 7.85-7.87 (m, 1H), 7.51-7.61 (m, 2H), 7.07-7.15 (d, 1H, J=9 Hz), 3.49-3.58 (m, 2H), 2.51-2.74 (m, 2H), 0.986-2.09 (m, 20H); $^{19}$F NMR (282 MHz; d$_6$-DMSO) δ −166.8 (s); m/z=480 (M+H)$^+$.

Example 129

2-((2-fluoro-4-hydroxy-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 128)

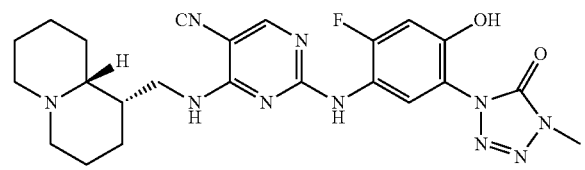

Compound 128 was prepared as described in Example 1. MS (ES) 495 (M+H).

Example 130

2-((2-fluoro-4-(2-methoxyethoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 129, Formate Salt)

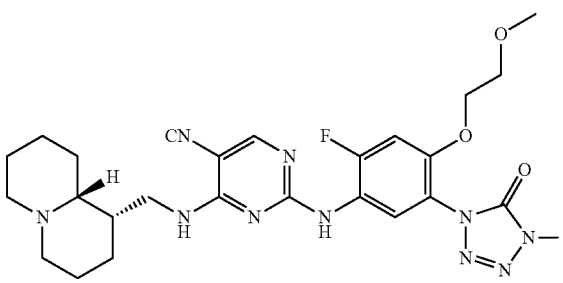

Compound 129 was prepared as described in Example 1. MS (ES) 533 (M+H).

Example 131

2-((2-fluoro-5-(4-methyl-5-oxo-4,5-dihydro-1H-tetrazol-1-yl)-4-((3-methyloxetan-3-yl)methoxy)phenyl)amino)-4-((((1S,9aR)-octahydro-2H-quinolizin-1-yl)methyl)amino)pyrimidine-5-carbonitrile (Compound 130, Formate Salt)

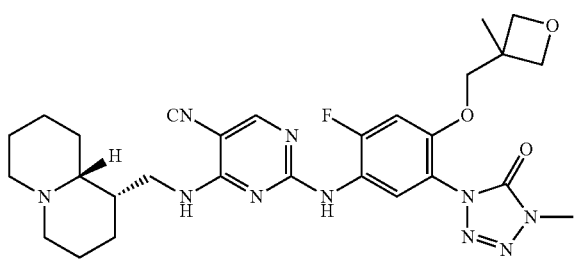

Compound 130 was prepared as described in Example 1. MS (ES) 579 (M+H).

Example 132

2-((4-((1,4-dioxan-2-yl)methoxy)-2-fluoro-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 131, Formate Salt)

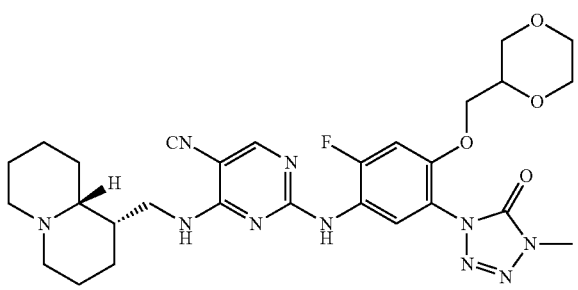

Compound 131 was prepared as described in Example 1. MS (ES) 595 (M+H).

Example 133

2-((4-(2,3-dihydroxypropoxy)-2-fluoro-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 132, TFA Salt)

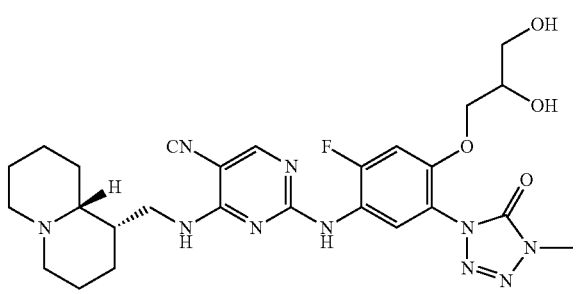

Compound 132 was prepared as described in Example 1. MS (ES) 569 (M+H).

Example 134

2-((2-fluoro-4-(2-(2-methoxyethoxy)ethoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 133, Formate Salt)

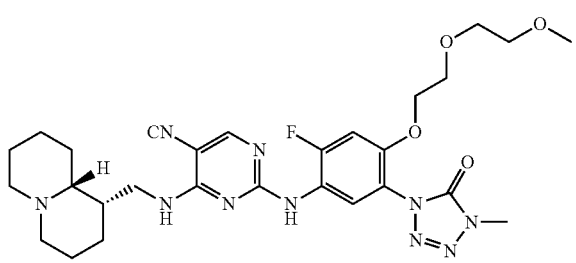

Compound 133 was prepared as described in Example 1. MS (ES) 597 (M+H).

Example 135

2-((2-fluoro-5-(4-methyl-5-oxo-4,5-dihydro-1H-tetrazol-1-yl)-4-(3,3,3-trifluoro-2-hydroxy-2-(trifluoromethyl)propoxy)phenyl)amino)-4-((((1S,9aR)-octahydro-2H-quinolizin-1-yl)methyl)amino)pyrimidine-5-carbonitrile (Compound 134, Formate Salt)

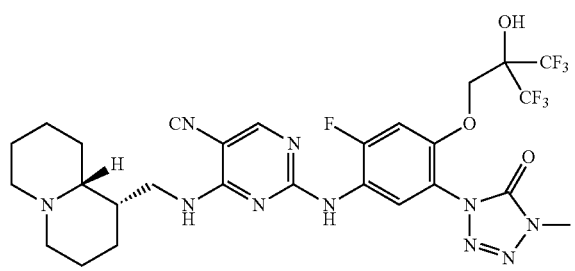

Compound 134 was prepared as described in Example 1. MS (ES) 675 (M+H).

Example 136

2-((2-fluoro-4-(2-hydroxyethoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 135)

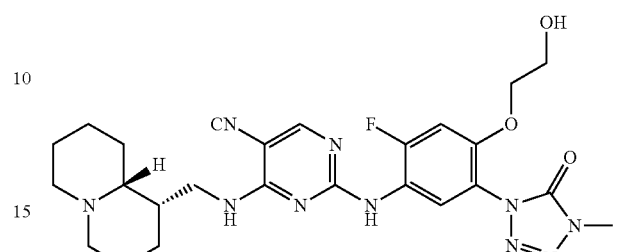

Compound 135 was prepared as described in Example 1. MS (ES) 539 (M+H).

Example 137

2-((2-fluoro-4-(2-hydroxypropoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 136, Formate Salt)

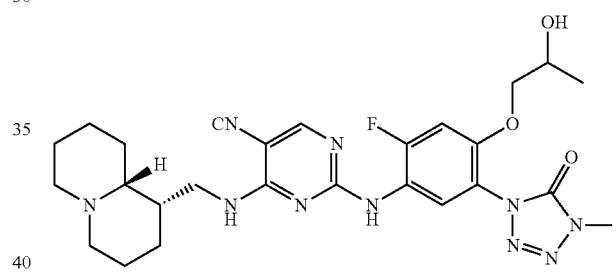

Compound 136 was prepared as described in Example 1. MS (ES) 553 (M+H).

Example 138

2-((2-fluoro-4-(2-hydroxyethoxy-1,1,2,2-d4)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 137)

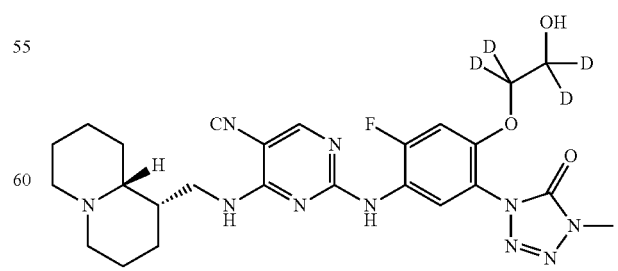

Compound 137 was prepared as described in Example 1. MS (ES) 543 (M+H).

Example 139

2-(4-((5-fluoro-4-((((1S,9aR)-octahydro-2H-quinolizin-1-yl)methyl)amino)pyrimidin-2-yl)amino)-2-(1H-tetrazol-1-yl)phenoxy)ethan-1-ol (Compound 138)

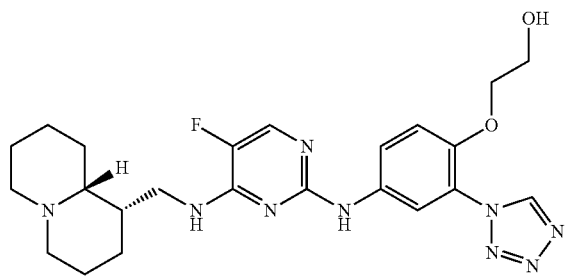 [SMILES: OCCOc1ccc(Nc2ncc(F)c(NC[C@@H]3CCCN4CCCC[C@H]34)n2)cc1-n1cnnn1]

Compound 138 was prepared as described in Example 1. MS (ES) 484 (M+H).

Example 140

2-(4-((5-chloro-4-((((1S,9aR)-octahydro-2H-quinolizin-1-yl)methyl)amino)pyrimidin-2-yl)amino)-2-(1H-tetrazol-1-yl)phenoxy)ethan-1-ol (Compound 139)

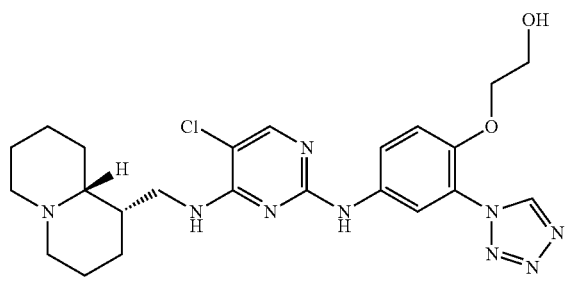 [SMILES: OCCOc1ccc(Nc2ncc(Cl)c(NC[C@@H]3CCCN4CCCC[C@H]34)n2)cc1-n1cnnn1]

Compound 139 was prepared as described in Example 1. MS (ES) 501 (M+H).

Example 141

2-((4-(2-hydroxyethoxy)-3-(1H-tetrazol-1-yl)phenyl)amino)-4-((((1S,9aR)-octahydro-2H-quinolizin-1-yl)methyl)amino)pyrimidine-5-carbonitrile (Compound 140)

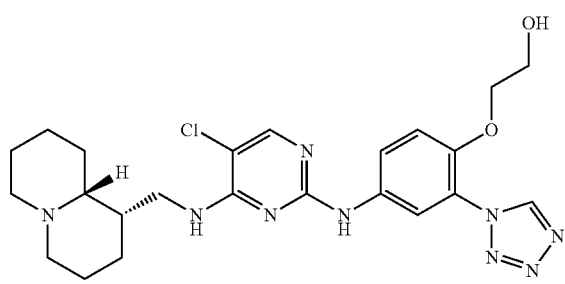 [SMILES: OCCOc1ccc(Nc2ncc(Cl)c(NC[C@@H]3CCCN4CCCC[C@H]34)n2)cc1-n1cnnn1]

Compound 140 was prepared as described in Example 1. MS (ES) 491 (M+H).

Example 142

2-(4-((4-((((1S,9aR)-octahydro-2H-quinolizin-1-yl)methyl)amino)pyrimidin-2-yl)amino)-2-(1H-tetrazol-1-yl)phenoxy)ethan-1-ol (Compound 141)

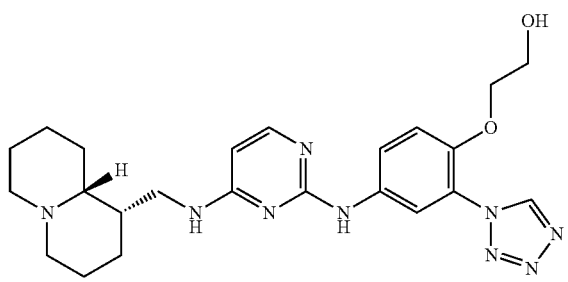 [SMILES: OCCOc1ccc(Nc2nccc(NC[C@@H]3CCCN4CCCC[C@H]34)n2)cc1-n1cnnn1]

Compound 141 was prepared as described in Example 1. MS (ES) 466 (M+H).

Example 143

2-((2-fluoro-4-((S)-2-hydroxypropoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 142)

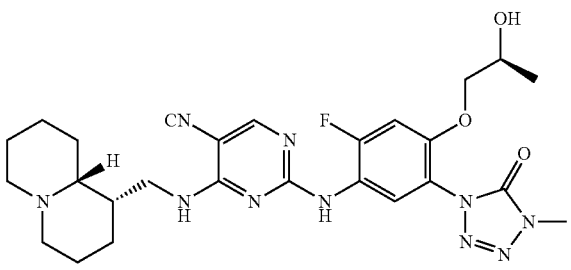

Compound 142 was prepared as described in Example 1. MS (ES) 553 (M+H).

Example 144

2-((2-fluoro-4-((R)-2-hydroxypropoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 143, Formate Salt)

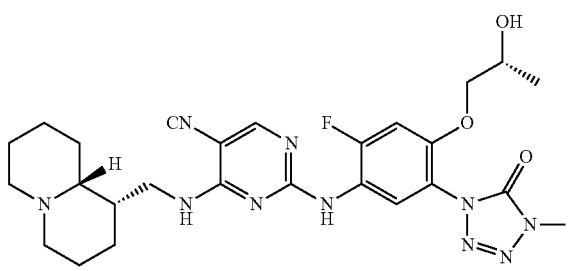

Compound 143 was prepared as described in Example 1. MS (ES) 553 (M+H).

Example 145

2-((3-cyano-4-(2-hydroxypropoxy)phenyl)amino)-4-(((((1S,9aR)-octahydro-2H-quinolizin-1-yl)methyl)amino)pyrimidine-5-carbonitrile (Compound 144, Formate Salt)

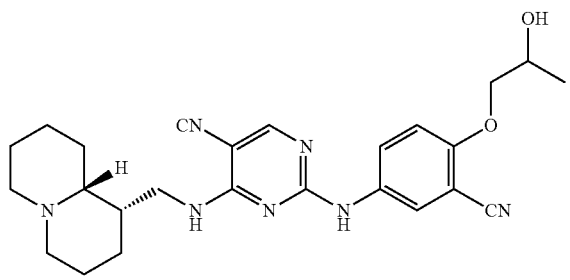

Compound 144 was prepared as described in Example 1. MS (ES) 462 (M+H).

Example 146

5-((5-fluoro-4-(((((1S,9aR)-octahydro-2H-quinolizin-1-yl)methyl)amino)pyrimidin-2-yl)amino)-2-(2-hydroxypropoxy)benzonitrile (Compound 145, Formate Salt)

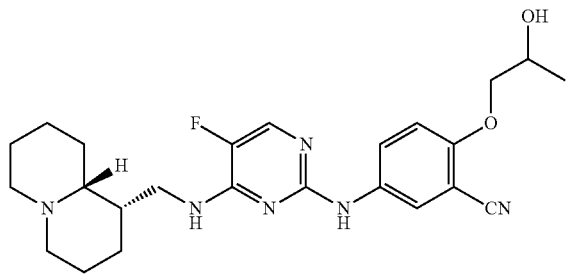 [SMILES: CC(O)COc1ccc(Nc2ncc(F)c(NC[C@@H]3CCCN4CCCC[C@H]34)n2)cc1C#N]

Compound 145 was prepared as described in Example 1. MS (ES) 455 (M+H).

Example 147

1-(5-((5-chloro-4-(((((1S,9aR)-octahydro-2H-quinolizin-1-yl)methyl)amino)pyrimidin-2-yl)amino)-4-fluoro-2-hydroxyphenyl)-4-methyl-1,4-dihydro-5H-tetrazol-5-one (Compound 146)

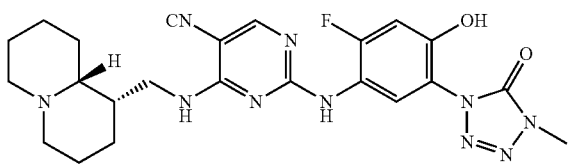

Compound 146 was prepared as described in Example 1. MS (ES) 504 (M+H).

Example 148

1-(5-((5-fluoro-4-(((((1S,9aR)-octahydro-2H-quinolizin-1-yl)methyl)amino)pyrimidin-2-yl)amino)-4-fluoro-2-hydroxyphenyl)-4-methyl-1,4-dihydro-5H-tetrazol-5-one (Compound 147)

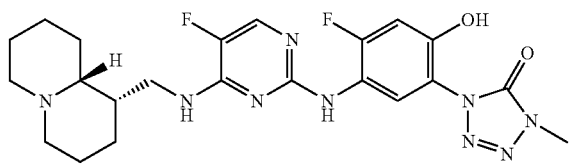 [SMILES: Cn1nnn(-c2cc(Nc3ncc(F)c(NC[C@@H]4CCCN5CCCC[C@H]45)n3)c(F)cc2O)c1=O]

Compound 147 was prepared as described in Example 1. MS (ES) 488 (M+H).

Example 149

1-(4-fluoro-5-((5-fluoro-4-(((((1S,9aR)-octahydro-2H-quinolizin-1-yl)methyl)amino)pyrimidin-2-yl)amino)-2-((1-hydroxy-2-methylpropan-2-yl)oxy)phenyl)-4-methyl-1,4-dihydro-5H-tetrazol-5-one (Compound 148)

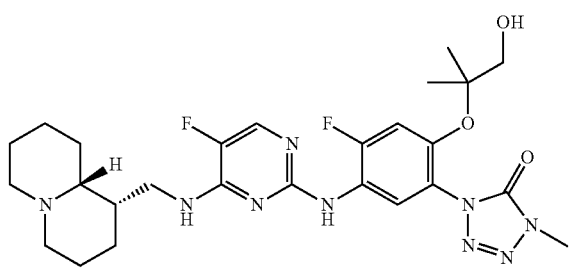 [SMILES: Cn1nnn(-c2cc(Nc3ncc(F)c(NC[C@@H]4CCCN5CCCC[C@H]45)n3)c(F)cc2OC(C)(C)CO)c1=O]

Compound 148 was prepared as described in Example 1. MS (ES) 560 (M+H).

Example 150

1-(4-fluoro-5-((5-fluoro-4-(((((1S,9aR)-octahydro-2H-quinolizin-1-yl)methyl)amino)pyrimidin-2-yl)amino)-2-((S)-2-hydroxypropoxy)phenyl)-4-methyl-1,4-dihydro-5H-tetrazol-5-one (Compound 149)

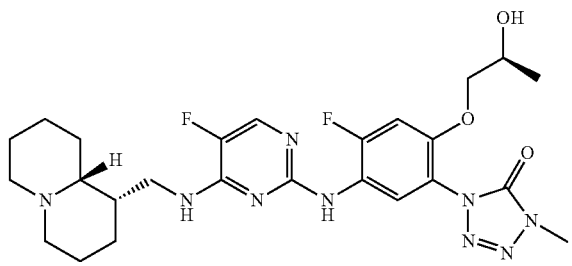 [SMILES: C[C@H](O)COc1cc(F)c(Nc2ncc(F)c(NC[C@@H]3CCCN4CCCC[C@H]34)n2)cc1-n1nnn(C)c1=O]

Compound 149 was prepared as described in Example 1. MS (ES) 546 (M+H).

Example 151

Ethyl 2-(4-((5-cyano-4-((((1S,9aR)-octahydro-2H-quinolizin-1-yl)methyl)amino)pyrimidin-2-yl)amino)-5-fluoro-2-(4-methyl-5-oxo-4,5-dihydro-1H-tetrazol-1-yl)phenoxy)-2-methylpropanoate (Compound 150)

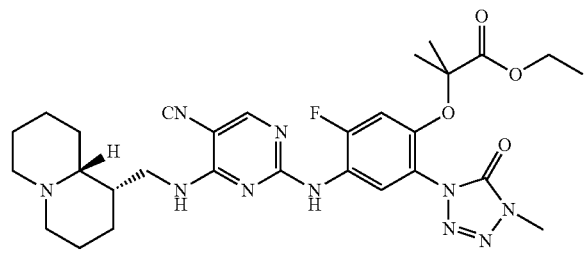

Compound 150 was prepared as described in Example 1. MS (ES) 609 (M+H).

Example 152

2-((2-fluoro-4-((1-hydroxy-2-methylpropan-2-yl)oxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 151)

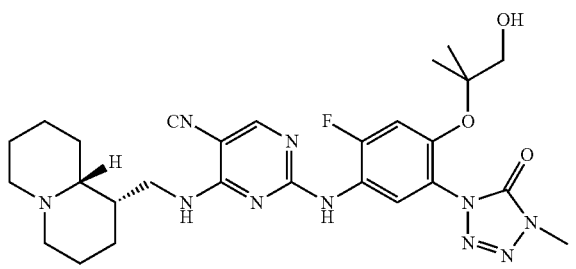

Compound 151 was prepared as described in Example 1. MS (ES) 567 (M+H).

Example 153

1-(5-((5-chloro-4-((((1S,9aR)-octahydro-2H-quinolizin-1-yl)methyl)amino)pyrimidin-2-yl)amino)-4-fluoro-2-((S)-2-hydroxypropoxy)phenyl)-4-methyl-1,4-dihydro-5H-tetrazol-5-one (Compound 152)

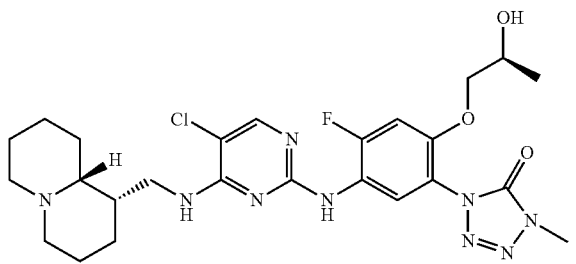 [SMILES: C[C@H](O)COc1cc(F)c(Nc2ncc(Cl)c(NC[C@@H]3CCCN4CCCC[C@H]34)n2)cc1-n1nnn(C)c1=O]

Compound 152 was prepared as described in Example 1. MS (ES) 563 (M+H).

Example 154

1-(5-((5-chloro-4-((((1S,9aR)-octahydro-2H-quinolizin-1-yl)methyl)amino)pyrimidin-2-yl)amino)-4-fluoro-2-((1-hydroxy-2-methylpropan-2-yl)oxy)phenyl)-4-methyl-1,4-dihydro-5H-tetrazol-5-one (Compound 153)

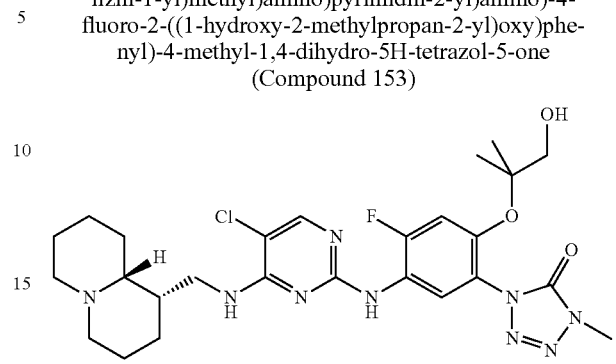

Compound 153 was prepared as described in Example 1. MS (ES) 577 (M+H).

Example 155

1-(4-fluoro-5-((5-fluoro-4-((((1S,9aR)-octahydro-2H-quinolizin-1-yl)methyl)amino)pyrimidin-2-yl)amino)-2-(2-hydroxy-2-methylpropoxy)phenyl)-4-methyl-1,4-dihydro-5H-tetrazol-5-one (Compound 154)

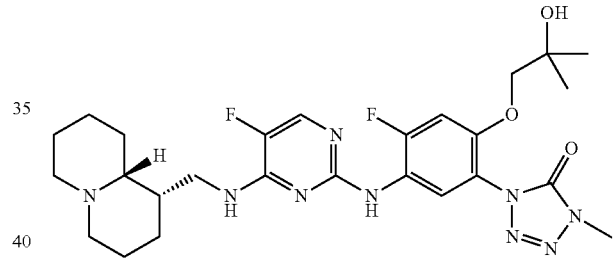

Compound 154 was prepared as described in Example 1. MS (ES) 560 (M+H).

Example 156

1-(5-((5-chloro-4-((((1S,9aR)-octahydro-2H-quinolizin-1-yl)methyl)amino)pyrimidin-2-yl)amino)-4-fluoro-2-(2-hydroxy-2-methylpropoxy)phenyl)-4-methyl-1,4-dihydro-5H-tetrazol-5-one (Compound 155)

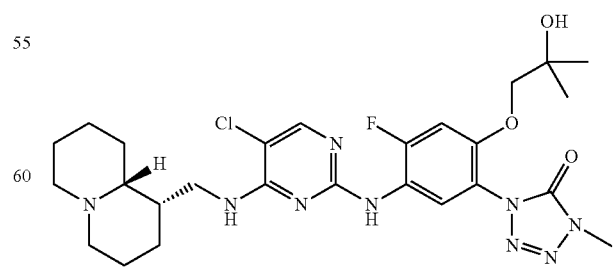

Compound 155 was prepared as described in Example 1. MS (ES) 577 (M+H).

Example 157

2-((2-fluoro-4-(2-hydroxy-2-methylpropoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile (Compound 156)

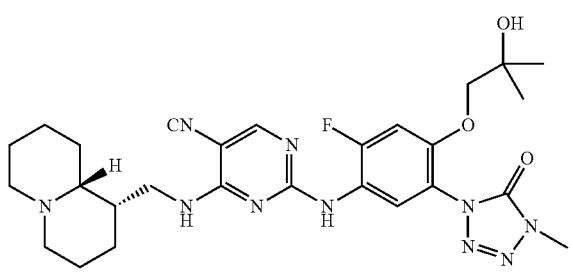

Compound 156 was prepared as described in Example 1. MS (ES) 567 (M+H).

BIOLOGICAL EXAMPLES

Example 158

PKC Assay

The inhibition of PKC-alpha, PKC-beta, PKC-delta, PKC epsilon and PKC-theta activity is determined via ELISA as follows: NUNC MAXISORP (#436110) or Costar High Binding (#3922) plates are coated with 0.01 mg/ml Neutravidin (Pierce #PI-31000) in 1×PBS (100 µL/well) for 18-24 hours at 4° C. When ready to be used, plates are washed with 1×PBST and then blocked with 2% BSA in 1×PBST (100 µL/well) for a minimum of 1 hour at room temperature. The reactions are conducted in a volume of 60 µL/well. When ready to begin, the plates are washed with 1×PBST to remove the 2% BSA blocking solution. Reaction solution containing the necessary buffer components as well as the appropriate concentrations of ATP and peptide substrate is then added to each well (see Table 3). Appropriate concentrations of test compound is then added— with the volume added should taking into consideration the DMSO tolerance of the kinases being about 0.2%. The reaction is then initiated by the addition of kinase — the approximate final concentration of which is listed in Table 3 (the concentration may vary depending on the batch to batch variability in the activity of enzymes). After allowing the reaction to stand at room temperature for 20 minutes, the plates are then washed with 1×PBST.

After removal of the reaction mixture from the plate and washing with 1×PBST, an antibody developing solution containing a 1:10,000 dilution of the appropriate primary and secondary antibodies (Table 3) in a 0.1% BSA solution in 1×PBST is then added to each well (100 µL/well). This is then allowed to stand at room temperature for a minimum of 1 hour. After this time, the plates are again washed with 1×PBST. The SuperSignal ELISA Pico Chemiluminescent substrate (Pierce #PI-37069) was then added (100 µL/well) and the plate is read on a luminescence plate reader.

Example 159

PKC Assay

Alternatively, the inhibition of PKC activity is measured by monitoring the production of phosphorylated peptide by fluorescence polarization at different concentrations of the inhibitor. Reactions are carried out in 96-well plate format with a total volume of 20 µL containing 20 mM HEPES, pH 7.4, 5 mM $MgCl_2$, 0.2 mM $CaCl_2$, 1 mM DTT, 0.02% Brij-35, 0.1 mg/ml phosphatidylserine, 0.02 mg/ml dioleoyl-sn-glycerol and 5 µM each of ATP and the peptide substrate. Compounds are first diluted serially in DMSO and then transferred to a solution containing the above concentrations of HEPES, $MgCl_2$, $CaCl_2$, DTT, and Brij-35 to yield 5× compound solutions in 2% DMSO, which is then added to the reaction solution. Reactions are initiated by the addition of PKC at a typical concentration as described in Table 4, and then allowed to incubate at room temperature for 20 minutes. At the end of this time, a combination of quench (EDTA) and detection (peptide tracer and antibody) reagents is added using the protocol of Invitrogen P2748. After a 30 minutes period of incubation, the amount of phosphorylated peptide generated is measured by fluorescence polarization (Ex=485 nm, Em=535 nm) using a Tecan Polarian instrument.

TABLE 4

| Peptide substrate | SEQ ID | Enzyme source | Typical enzyme concentration |
|---|---|---|---|
| PKC theta | RFARKGSLRQKNV | Seq ID No. 1 | Upstate Biotechnologies, Temecula, CA, cat. #14-444 | 40 ng/ml |
| PKC epsilon | RFARKGSLRQKNV | Seq ID No. 1 | Upstate Biotechnologies, | 50 ng/ml |

TABLE 3

| Kinase | Buffer components | [ATP] (uM) | [peptide] (uM) | Time (min) | 1° and 2° antibodies | Notes |
|---|---|---|---|---|---|---|
| PKCs α: ~8 ng/ml β: ~16 ng/ml δ: ~13 ng/ml ε: ~13 ng/ml θ: ~8 ng/ml | 20 mM HePes pH 7.4 5 mM $MgCl_2$ 0.2 mM $CaCl_2$ 1 mM DTT 0.05% Chaps | 1 µm | 1 µm PKC peptide (biotin-RFARKGSLRQKNV) (Invitrogen #P2760) | 20 min | Rabbit pSer PKC substrate Ab (Cell Signaling #2261); HRP-goat a-rabbit (Jackson Immunoresearch #111-035-003) | 0.15 mg/ml DAG (Sigma #D0138) 0.75 mg/ml Phosphoserine (Sigma #P6641) DMSO tolerance ~0.2% |

TABLE 4-continued

| Peptide substrate | SEQ ID | Enzyme source | Typical enzyme concentration |
|---|---|---|---|
| | | Temecula, CA, cat. #14-518 | |

Example 160

Calcium Influx

HEK-FLPTREX cells are stably transfected with pcDNA5/FRT/TO+hTRPV4a, rat TRPV1-HA or rTRPA1-HA are grown in Dulbecco's Modified Eagle's Medium (DMEM) containing 10% tetracycline-free fetal bovine serum, hygromycin (50 µg/ml) and blasticidin (10 µg/ml). Cells are treated with tetracycline (0.1 µg/ml, 20 h) to induce TRP expression. DRG from thoracic and lumbar spinal cord of rats or mice were minced in cold Hank's Balanced Salt Solution (HBSS) and incubated for 60 at 37° C. in DMEM containing 1 mg/ml of collagenase type IA and 0.1 mg/ml of DNAse type IV, pelleted and incubated with 0.25% trypsin for 30 minutes. Neurons are pelleted, suspended in DMEM containing 10% fetal bovine serum, 10% horse serum, 100 U/ml penicillin, 0.1 mg/ml streptomycin, 2 mM glutamine, dissociated by gentle trituration until the solution appears cloudy and homogeneous and plated on glass coverslips coated with PolyOnitine/laminin. Neurons are cultured for 3-4 days before the experiment.

Cells grown on coverslips or on a 96 multiwell plate are incubated in HBSS (pH 7.4) containing Ca2+ and Mg2+, 20 mM HEPES buffer, 0.1% BSA, 100 U/ml penicillin, 100 µg/ml streptomycin, with 2.5-5 µM Fura-2AM (Invitrogen) for 20-45 minutes at 37° C. Cells are washed and fluorescence is measured at 340 nm and 380 nm excitation and 510 nm emission in a F-2500 spectrophotometer, or in a Flexstation 3 Microplate Reader III (for the measurement of the calcium in the cell population) or using a Zeiss Axiovert microscope, an ICCD video camera and a video microscopy acquisition program (for the measurement of the calcium influx in the single neurons). Substances are injected directly into the chamber (20 ml into 2 ml, for the spectrophotometer; 20 ml in 200 ml for the Flexstation, 50 ml in 350 ml in the chamber for the single cells).

Example 161

In Vivo Hyperplasia

Mechanical pain is quantified as the number of times the hind paw is withdrawn in response to 5 applications of a 0.173 mN von Frey hair. Responses are expressed as a percentage (e.g. 3 withdrawals out of 5 are recorded as 60%) and mechanical hyperalgesia defined as increase in the percentage of withdrawal compared to basal measurement. 2) Mechanical pain is quantified using the 'up-down paradigm', determining the 50% response threshold to the von Frey filaments applied to the mid-plantar surface for 5 s or until a withdrawal response occurred. Von Frey filaments are in this range of intensities: 1.65, 2.44, 2.83, 3.22, 3.61, 3.84, 4.08.

Thermal hyperalgesia is assessed in mice using a plantar test apparatus and quantified as the latency of paw withdrawal to a radiant heat. Thermal hyperalgesia is defined as a decrease in the withdrawal latency compared to the basal measurement. After measuring basal level mice, under light halothane anesthesia (5%), are injected with testing compound into the left or right paws (5-10 µl intraplantar injection) and paw withdrawal measurements repeated at different time point. To assess PAR2 TRPV1, TRPV4 and TRPA1 mediated hyperalgesia and potentiation of TRPV-mediated responses, mice are treated with PAR2-AP for 15 minutes followed by capsaicin, 4αPDD or HNE. To assess the role of protein kinases, the antagonists or the corresponding vehicles are injected 20-30 minutes before the challenge with agonists. The effects induced by the different treatments are evaluated within the same rat comparing the responses recorded in the right paw (receiving for example saline, or vehicle) with the responses obtained in the left paw (receiving for example PAR2-AP or 4αPDD).

Formalin induced hyperalgesia is assessed using 5% solution of formalin administered by intradermal injection into the dorsal surface of the mouse or rat forepaw to induce a painful behavior. Pain is accessed on a four-level scale related to posture: 0, normal posture; 1, with the injected paw remaining on the ground but not supporting the animal; 2, with the injected paw clearly raised; and 3, with the injected paw being licked, nibbled, or shaken. Animals are observed and scored for behavior at 3 minutes after the injection (defined as initial phase that results from the direct stimulation of nociceptors), and then at 30-60 minutes after the injection (defined as second phase that involves a period of sensitization during which inflammatory phenomena occur). The nociceptive behavioral score for each 3-minutes interval is calculated as the weighted average of the number of seconds spent in each behavior. 2.5% solution of formalin is administered by intraplantar injection and thermal and mechanical pain measured as described above after 30-60 minutes. To assess the role of protein kinases, antagonists or their vehicles (control) are injected into the right paws 20-30 minutes before formalin. Nociceptive behavior will be scored for each rats and compared to control.

Example 162

IL-2 ELISA, Human Primary T Cell, Anti CD3+CD28+

Compounds 1-156 were tested in a whole cell functional assay for PKC mediated IL-2 production as follows. Human primary T cell isolation and culture: Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 minutes at 4° C. at 1750 rpm. The cells at the serum: ficoll interface were recovered and washed twice with 5 volumes of PBS. These freshly isolated human peripheral blood mononuclear cells were cultured in Yssel's medium containing 40 U/ml IL2 in a flask pre-coated with 1 µg/ml aCD3 and 5 µg/ml aCD28 (Anti-Human CD3, BD Pharmingen Catalog #555336, Anti-Human CD28, Beckman Coulter Catalog #1M1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/ml IL-2. The primary T-cells were then washed twice with PBS to remove the IL-2.

Primary T cell stimulation and IL2 ELISA: Human primary T cells (100,000 cells per well) were pre-incubated with or without test compound in Yssel's medium for 1 hour at 37°

C. Cells were then stimulated by transferring them to round-bottom 96-well plates pre-coated with 1 μg/ml aCD3 and 5 μg/ml αCD28. For counter assay, cells were instead stimulated by adding 8× stock solutions of PMA and ionomycin in Yssels (for final concentrations of 0.5 ng/ml PMA and 0.1 uM ionomycin, both from Calbiochem). Cells were incubated at 37° C. for 24 hours before 100 μL supernatants were harvested for quantification of IL-2 by ELISA using Human IL-2 Duoset ELISA Kit from R and D Systems, Cat. #DY202E. Compounds 1-156 blocked IL-2 production with an $IC_{50}$ of less than 30 micromolar.

$IC_{50}$ data (micromolar) is shown in Table 5 below.

TABLE 5

| Compound | IL2 ELISA, Human primary T cell, anti-CD3 + CD28, 8 pt (μM) |
|---|---|
| 1 | 0.1069 |
| 2 | 0.3718 |
| 3 | 1.68 |
| 4 | 0.1419 |
| 5 | 0.1201 |
| 6 | 0.0889 |
| 7 | 0.4279 |
| 8 | 0.1057 |
| 9 | 0.1947 |
| 10 | 0.5944 |
| 11 | 1.079 |
| 12 | 0.8891 |
| 13 | 4.48 |
| 14 | 0.2011 |
| 15 | 10.65 |
| 16 | 0.7025 |
| 17 | 0.4052 |
| 18 | 0.1265 |
| 19 | 0.5536 |
| 20 | 1.075 |
| 21 | 0.7019 |
| 22 | 0.6972 |
| 23 | 0.0663 |
| 24 | 3.45 |
| 25 | 0.8529 |
| 26 | 0.1694 |
| 27 | 0.6518 |
| 28 | 1.815 |
| 29 | 1.803 |
| 30 | 0.6716 |
| 31 | 0.3592 |
| 32 | 0.1587 |
| 33 | 0.1173 |
| 34 | 0.6696 |
| 35 | 0.0542 |
| 36 | 0.1124 |
| 37 | 0.0872 |
| 38 | 0.1264 |
| 39 | 0.4177 |
| 40 | 0.2666 |
| 41 | 0.0723 |
| 42 | 0.3481 |
| 43 | 0.4122 |
| 44 | 1.18 |
| 45 | 0.224 |
| 46 | 1.12 |
| 47 | 0.6487 |
| 48 | 3.815 |
| 49 | 0.8967 |
| 50 | 1.996 |
| 51 | 0.5315 |
| 52 | 0.4423 |
| 53 | 2.526 |
| 54 | 1.098 |
| 55 | 0.6073 |
| 56 | 3.797 |
| 57 | 3.586 |
| 58 | 18.62 |
| 59 | 0.16 |

TABLE 5-continued

| Compound | IL2 ELISA, Human primary T cell, anti-CD3 + CD28, 8 pt (μM) |
|---|---|
| 60 | 1.356 |
| 61 | 1.979 |
| 62 | 1.872 |
| 63 | 1.161 |
| 64 | 0.4593 |
| 65 | 0.0728 |
| 66 | 1.479 |
| 67 | 1.077 |
| 68 | 0.95 |
| 69 | 0.265 |
| 70 | 1.53 |
| 71 | 3.747 |
| 72 | 1.271 |
| 73 | 3.269 |
| 74 | 2.194 |
| 75 | 2.912 |
| 76 | 6.448 |
| 77 | 2.418 |
| 78 | 2.241 |
| 79 | 5.354 |
| 80 | 2.484 |
| 81 | 1.308 |
| 82 | 1.306 |
| 83 | 3.872 |
| 84 | 15.4 |
| 85 | 3.314 |
| 86 | 11.04 |
| 87 | 8.257 |
| 88 | 12.73 |
| 89 | 14.58 |
| 90 | 9.82 |
| 91 | 7.943 |
| 92 | 9.457 |
| 93 | 3.922 |
| 94 | 2.573 |
| 95 | 1.74 |
| 96 | 4.981 |
| 97 | 5.41 |
| 98 | 0.0774 |
| 99 | 0.0509 |
| 100 | 4.214 |
| 101 | 10.69 |
| 102 | 12.64 |
| 103 | 26.55 |
| 104 | 26.8 |
| 105 | 11.75 |
| 106 | 21.47 |
| 107 | 17.07 |
| 108 | 41.2 |
| 109 | 6.576 |
| 110 | 10.71 |
| 111 | 12.5 |
| 112 | 21.72 |
| 113 | 0.018 |
| 114 | 0.0365 |
| 115 | 0.0225 |
| 116 | 0.0074 |
| 117 | 0.0117 |
| 118 | 0.076 |
| 119 | 0.0357 |
| 120 | 0.0093 |
| 121 | 0.1414 |
| 122 | 0.0206 |
| 123 | 0.0418 |
| 124 | 0.0031 |
| 125 | 1.784 |
| 126 | 1.602 |
| 127 | 0.8239 |
| 128 | 1.937 |
| 129 | 1.336 |
| 130 | 0.4443 |
| 131 | 1.305 |
| 132 | 1.238 |
| 133 | 0.9923 |
| 134 | 0.9084 |

TABLE 5-continued

| Compound | IL2 ELISA, Human primary T cell, anti-CD3 + CD28, 8 pt (μM) |
|---|---|
| 135 | 5008 |
| 136 | 0.1761 |
| 137 | 9999 |
| 138 | 0.0493 |
| 139 | 0.0175 |
| 140 | 0.0276 |
| 141 | 3.549 |
| 142 | 0.0662 |
| 143 | 0.1468 |
| 144 | 12.39 |
| 145 | 4.628 |
| 146 | 1.976 |
| 147 | 5.06 |
| 148 | 1.592 |
| 149 | 0.2655 |
| 150 | 1.139 |
| 151 | 0.3055 |
| 152 | 0.0898 |
| 153 | 0.8319 |
| 154 | 0.1877 |
| 155 | 0.1358 |
| 156 | 0.0276 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

---

What is claimed is:

1. A compound of formula (I):

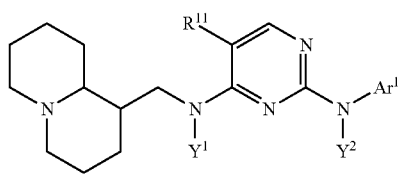

wherein
$R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, alkylthioalkylene, substituted alkylthioalkylene, and $SF_5$;

$Y^1$ and $Y^2$ are independently selected from hydrogen and alkyl; and $Ar^1$ is selected from aryl, substituted aryl, heteroaryl, and substituted heteroaryl;

or a pharmaceutically acceptable salt or stereoisomer thereof.

2. The compound of claim 1, wherein $Ar^1$ is aryl or substituted aryl.

3. The compound of claim 1, wherein $Ar^1$ is heteroaryl or substituted heteroaryl.

4. The compound of claim 1, wherein the compound is of formula (II)

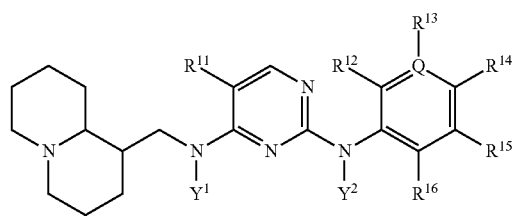

wherein
$R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, alkylthioalkylene, substituted alkylthioalkylene, and $SF_5$;

$Y^1$ and $Y^2$ are independently selected from hydrogen and alkyl;

Q is C or N; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl;

or a pharmaceutically acceptable salt or stereoisomer thereof.

5. The compound of claim 4, wherein Q is C.

6. The compound of claim 4, wherein Q is N and $R^{13}$ is absent.

7. The compound of claim 4, wherein $R^{12}$, $R^{13}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

8. The compound of claim 4, wherein the formula is

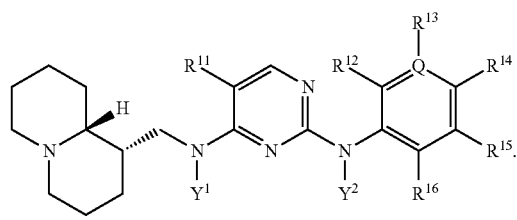

(IIa)

9. The compound of claim 8, wherein Q is C.

10. The compound of claim 8, wherein Q is N and $R^{13}$ is absent.

11. The compound of claim 8, wherein $R^{12}$, $R^{13}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

12. The compound of claim 4, wherein the compound is of formula (III)

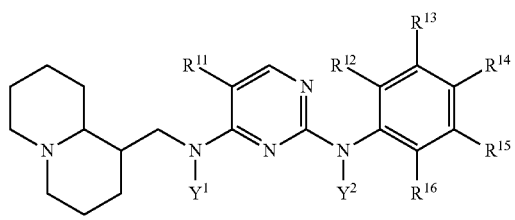

(III)

wherein
$R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, alkylthioalkylene, substituted alkylthioalkylene, and $SF_5$;

$Y^1$ and $Y^2$ are independently selected from hydrogen and alkyl; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl;

or a pharmaceutically acceptable salt or stereoisomer thereof.

13. The compound of claim 12, wherein $R^{12}$, $R^{13}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

14. The compound of claim 12, wherein the formula is

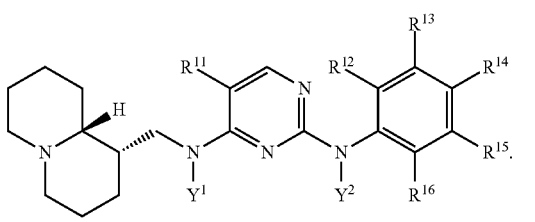

(IIIa)

15. The compound of claim 4, whrein the compound is of formula (IV)

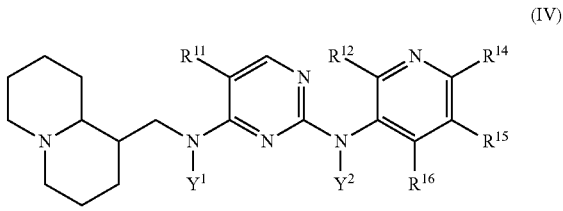

(IV)

wherein
$R^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, alkylthioalkylene, substituted alkylthioalkylene, and $SF_5$;

Y¹ and Y² are independently selected from hydrogen and alkyl; and $R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl;

or a pharmaceutically acceptable salt or stereoisomer thereof.

16. The compound of claim 15, wherein $R^{12}$, $R^{14}$, $R^{15}$, and $R^{16}$ are independently selected from hydrogen, alkyl, substituted alkyl, halogen, cyano, alkoxy, substituted alkoxy, sulfur pentafluoride, aryl, substituted aryl, cycloalkyl, substituted cycloalkyl, heteroaryl, substituted heteroaryl, heterocyclyl, and substituted heterocyclyl, or $R^{14}$ and $R^{15}$ together with the carbon atoms to which they are attached form aryl, substituted aryl, heteroaryl, substituted heteroaryl, heterocyclyl, or substituted heterocyclyl.

17. The compound of claim 15, wherein the formula is

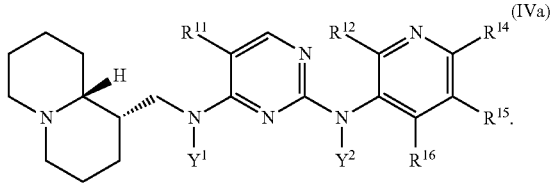

18. The compound of claim 1, wherein $R^{11}$ is selected from hydrogen, alkyl, substituted alkyl, alkoxy, substituted alkoxy, amino, substituted amino, cyano, halogen, acyl and aminoacyl.

19. The compound of claim 1, wherein Y¹ and Y² are hydrogen.

20. The compound of claim 1, wherein the compound is selected from:
Compound 1: 5-(4-(((1S,9aR)-octahydro-1H-quinolizin-1-yl)methylamino)-5-fluoropyrimidin-2-ylamino)-2-cyclopropylbenzonitrile;
Compound 2: N2-(4-cyclopropyl-2-fluoro-5-(1H-tetrazol-1-yl)phenyl)-5-fluoro-N4-(((1S,9aR) -octahydro-1H-quinolizin-1-yl)methyl)pyrimidine-2,4-diamine;
Compound 3: 1-(5-(4-(((1S,9aR)-octahydro-1H-quinolizin-1-yl)methylamino)-5-fluoropyrimidin-2-ylamino)-2-cyclopropyl-4-fluorophenyl)-4-methyl-1H-tetrazol-5(4H)-one;
Compound 4: 5-fluoro-N4-(((1S,9aR)-octahydro-1H-quinolizin-1-yl)methyl)-N2-(4-methyl-3-(1H-tetrazol-1-yl)phenyl)pyrimidine-2,4-diamine;
Compound 5: 5-(4-(((1S,9aR)-octahydro-1H-quinolizin-9-yl)methylamino)-5-chloropyrimidin-2-ylamino)-2-cyclopropylbenzonitrile;
Compound 6: 5-fluoro-N4-(((1S,9aR)-octahydro-1H-quinolizin-1-yl)methyl)-N2-(4-methoxy-3-(5-methyl-1H-tetrazol-1-yl)phenyl)pyrimidine-2,4diamine;
Compound 7: 5-fluoro-N2-(2-fluoro-5-(5-methyl-1H-tetrazol-1-yl)phenyl)-N4-(((1S,9aR)-octahydro -1H-quinolizin-1-yl)methyl)pyrimidine-2,4-diamine;
Compound 8: 5-fluoro-N2-(4-fluoro-3-(5-methyl-1H-tetrazol-1-yl)phenyl)-N4-(((1S,9aR)-octahydro -1H-quinolizin-1-yl)methyl)pyrimidine-2,4-diamine;
Compound 9: 5-(4-(((1S,9aR)-octahydro-1H-quinolizin-1-yl)methylamino)-5-fluoropyrimidin-2-ylamino)-2-methylbenzonitrile;
Compound 10: 3-(4-(((1S,9aR)-octahydro-1H-quinolizin-1-yl)methylamino)-5-fluoropyrimidin-2-ylamino)benzonitrile;
Compound 11: 5-fluoro-N4-(((1S,9aR)-octahydro-1H-quinolizin-1-yl)methyl)-N2-(3,5-dimethoxyphenyl)pyrimidine-2,4-diamine;
Compound 12: 5-(4-(((1S,9aR)-octahydro-1H-quinolizin-1-yl)methylamino)-5-fluoropyrimidin-2-ylamino)-2-cyclopropyl-4-fluorobenzonitrile;
Compound 13: 5-fluoro-N4-(((1S,9aR)-octahydro-1H-quinolizin-1-yl)methyl)-N2-phenylpyrimidine-2,4-diamine;
Compound 14: 1-(5-(4-(((1S,9aR)-octahydro-1H-quinolizin-1-yl)methylamino)-5-fluoropyrimidin-2-ylamino)-2-(oxetan-3-yloxy)phenyl)-4-methyl-1H-tetrazol-5(4H)-one;
Compound 15: 1-(5-(4-(((1S,9aR)-octahydro-1H-quinolizin-1-yl)methylamino)-5-fluoropyrimidin-2-ylamino)-2-cyclopropyl-4-methylphenyl)-4-methyl-1H-tetrazol-5(4H)-one;
Compound 16: 7-(4-(((1S,9aR)-octahydro-1H-quinolizin-1-yl)methylamino)-5-fluoropyrimidin-2-ylamino)-4-isopropyl-2,2-dimethyl-2H-benzo[b][1,4]oxazin-3 (4H)-one;
Compound 17: 1-(3-(4-(((1S,9aR)-octahydro-1H-quinolizin-1-yl)methylamino)-5-fluoropyrimidin-2-ylamino)-5-methoxyphenyl)-4-methyl-1H-tetrazol-5 (4H)-one;
Compound 18: 7-(4-(((1S,9aR)-octahydro-1H-quinolizin-1-yl)methylamino)-5-fluoropyrimidin-2-ylamino)-4-(cyclopropylmethyl)-2,2-dimethyl-2H-benzo[b][1,4] oxazin-3(4H)-one;
Compound 19: 5-fluoro-N2-(3-(trifluoromethyl)-4-morpholinophenyl)-N4-(((1S,9aR)-octahydro-1H-quinolizin-1-yl)methyl)pyrimidine-2,4-diamine;
Compound 20: 5-fluoro-N2-(2,2,3,3-tetrafluoro-2,3-dihydrobenzo[b][1,4]dioxin-7-yl)-N4-(((1S,9aR)-octahydro-1H-quinolizin-1-yl)methyl)pyrimidine-2,4-diamine;
Compound 21: 5-fluoro-N2-(3-fluoro-5-methoxyphenyl)-N4-(((1S,9aR)-octahydro-1H-quinolizin-1-yl)methyl)pyrimidine-2,4-diamine;
Compound 22: 5-fluoro-N4-(((1S,9aR)-octahydro-1H-quinolizin-1-yl)methyl)-N2-(4-methoxy-3-(oxazol-5-yl)phenyl)pyrimidine-2,4-diamine;
Compound 23: N2-(4-cyclopropyl-2-fluoro-5-(5-methyl-1H-tetrazol-1-yl)phenyl)-5-fluoro-N4-(((1S,9aR)-octahydro-1H-quinolizin-1-yl)methyl)pyrimidine-2,4-diamine;
Compound 24: N2-[3-(1,1-dioxo-isothiazolidin-2-yl)-4-fluoro-phenyl]-5-fluoro-N4-(((1S,9aR) -octahydro-1H-quinolizin-1-yl)methyl)-pyrimidine-2,4-diamine;
Compound 25: 7-(4-(((1S,9aR)-octahydro-1H-quinolizin-1-yl)methylamino)-5-fluoropyrimidin-2-ylamino)-4-(3-fluoropropyl)-2,2-dimethyl-2H-benzo[b][1,4]oxazin-3(4H)-one;

Compound 26: 7-(4-(((1S,9aR)-octahydro-1H-quinolizin-1-yl)methylamino)-5-fluoropyrimidin-2-ylamino)-4-(cyclopropylmethyl)-2H-benzo[b][1,4]oxazin-3(4H)-one;

Compound 27: 7-(4-(((1S,9aR)-octahydro-1H-quinolizin-1-yl)methylamino)-5-fluoropyrimidin-2-ylamino)-4-ethyl-2,2-difluoro-2H-pyrido[3,2-b][1,4]oxazin-3(4H)-one;

Compound 28: N2-(5-(1-methyl-1H-tetrazol-5-yloxy)-4-cyclopropyl-2-fluorophenyl)-5-fluoro-N 4-(((1S,9aR)-octahydro-1H-quinolizin-1-yl)methyl)pyrimidine-2,4-diamine;

Compound 29: 5-fluoro-N2-(3-pentafluorosulfanyl-6-fluoro-phenyl)-N4-(((1S,9aR)-octahydro-1H-quinolizin-1-yl)methyl)pyrimidine-2,4-diamine;

Compound 30: 5-fluoro-N2-(3-pentafluorosulfanyl-5-fluoro-phenyl)-N4-(((1S,9aR)-octahydro-1H-quinolizin-1-yl)methyl)pyrimidine-2,4-diamine;

Compound 31: 7-(4-(((1S,9aR)-octahydro-1H-quinolizin-1-yl)methylamino)-5-fluoropyrimidin-2-ylamino)-4-(cyclopropylmethyl)-2,2-dimethyl-2H-pyrido[3,2-b][1,4]oxazin-3(4H)-one;

Compound 32: 5-chloro-N2-(4-cyclopropyl-2-fluoro-5-(1H-tetrazol-1-yl)phenyl)-N4-(((1S,9aR)-octahydro-1H-quinolizin-1-yl)methyl)pyrimidine-2,4-diamine;

Compound 33: 5-chloro-N4-(((1S,9aR)-octahydro-1H-quinolizin-1-yl)methyl)-N2-(4-methyl-3-(1H-tetrazol-1-yl)phenyl)pyrimidine-2,4-diamine;

Compound 34: 1-(5-(4-(((1S,9aR)-octahydro-1H-quinolizin-1-yl)methylamino)-5-chloropyrimidin-2-ylamino)-2-cyclopropyl-4-fluorophenyl)-4-methyl-1H-tetrazol-5(4H)-one;

Compound 35: 5-chloro-N2-(4-fluoro-3-(5-methyl-1H-tetrazol-1-yl)phenyl)-N4-(((1S,9aR)-octahydro-1H-quinolizin-1-yl)methyl)pyrimidine-2,4-diamine;

Compound 36: 5-chloro-N2-(2-fluoro-5-(5-methyl-1H-tetrazol-1-yl)phenyl)-N4-(((1S,9aR)-octahydro-1H-quinolizin-1-yl)methyl)pyrimidine-2,4-diamine;

Compound 37: 5-chloro-N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine;

Compound 38: 5-chloro-N4-(((1S,9aR)-octahydro-1H-quinolizin-1-yl)methyl)-N2-(3-methoxy-5-(5-methyl-1H-tetrazol-1-yl)phenyl)pyrimidine-2,4-diamine;

Compound 39: 3-(4-(((1S,9aR)-octahydro-1H-quinolizin-1-yl)methylamino)-5-chloropyrimidin-2-ylamino)benzonitrile;

Compound 40: 5-(4-(((1S,9aR)-octahydro-1H-quinolizin-1-yl)methylamino)-5-chloropyrimidin-2-ylamino)-2-methylbenzonitrile;

Compound 41: 5-(4-(((1S,9aR)-octahydro-1H-quinolizin-1-yl)methylamino)-5-chloropyrimidin-2-ylamino)-2-cyclopropylbenzonitrile;

Compound 42: 5-(4-(((1S,9aR)-octahydro-1H-quinolizin-1-yl)methylamino)-5-chloropyrimidin-2-ylamino)-2-cyclopropyl-4-fluorobenzonitrile;

Compound 43: 5-chloro-N4-(((1S,9aR)-octahydro-1H-quinolizin-1-yl)methyl)-N2-(3,5-dimethoxyphenyl)pyrimidine-2,4-diamine;

Compound 44: 5-(4-(((1S,9aR)-octahydro-1H-quinolizin-1-yl)methylamino)-5-chloropyrimidin-2-ylamino)benzo[d]oxazol-2(3H)-one;

Compound 45: N2-(5-(5-cyclopropyl-1H-tetrazol-1-yl)-2-fluorophenyl)-5-fluoro-N4-(((1S,9aR)-octahydro-1H-quinolizin-1-yl)methyl)pyrimidine-2,4-diamine;

Compound 46: N2-(4-cyclopropyl-2-fluoro-5-(1H-tetrazol-1-yl)phenyl)-N4-(((1S,9aR)-octahydro-1H-quinolizin-1-yl)methyl)pyrimidine-2,4-diamine;

Compound 47: N4-(((1S,9aR)-octahydro-1H-quinolizin-1-yl)methyl)-N2-(4-methyl-3-(1H-tetrazol-1-yl)phenyl)pyrimidine-2,4-diamine;

Compound 48: 1-(5-(4-(((1S,9aR)-octahydro-1H-quinolizin-1-yl)methylamino)pyrimidin-2-ylamino)-2-cyclopropyl-4-fluorophenyl)-4-methyl-1H-tetrazol-5(4H)-one;

Compound 49: N2-(4-fluoro-3-(5-methyl-1H-tetrazol-1-yl)phenyl)-N4-(((1S,9aR)-octahydro-1H-quinolizin-1-yl)methyl)pyrimidine-2,4-diamine;

Compound 50: N2-(2-fluoro-5-(5-methyl-1H-tetrazol-1-yl)phenyl)-N4-(((1S,9aR)-octahydro-1H-quinolizin-1-yl)methyl)pyrimidine-2,4-diamine;

Compound 51: N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine;

Compound 52: N4-(((1S,9aR)-octahydro-1H-quinolizin-1-yl)methyl)-N2-(3-methoxy-5-(5-methyl-1H-tetrazol-1-yl)phenyl)pyrimidine-2,4-diamine;

Compound 53: 3-(4-(((1S,9aR)-octahydro-1H-quinolizin-1-yl)methylamino)pyrimidin-2-ylamino)benzonitrile;

Compound 54: 5-(4-(((1S,9aR)-octahydro-1H-quinolizin-1-yl)methylamino)pyrimidin-2-ylamino)-2-methylbenzonitrile;

Compound 55: 5-(4-(((1S,9aR)-octahydro-1H-quinolizin-1-yl)methylamino)pyrimidin-2-ylamino)-2-cyclopropylbenzonitrile;

Compound 56: 5-(4-(((1S,9aR)-octahydro-1H-quinolizin-1-yl)methylamino)pyrimidin-2-ylamino)-2-cyclopropyl-4-fluorobenzonitrile;

Compound 57: N4-(((1S,9aR)-octahydro-1H-quinolizin-1-yl)methyl)-N2-(3,5-dimethoxyphenyl)pyrimidine-2,4-diamine;

Compound 58: 5-(4-(((1S,9aR)-octahydro-1H-quinolizin-1-yl)methylamino)pyrimidin-2-ylamino)benzo[d]oxazol-2(3H)-one;

Compound 59: N2-(4-cyclopropyl-2-fluoro-5-(1H-tetrazol-1-yl)phenyl)-N4-(((1S,9aR)-octahydro-1H-quinolizin-1-yl)methyl)-5-methylpyrimidine-2,4-diamine;

Compound 60: N4-(((1S,9aR)-octahydro-1H-quinolizin-1-yl)methyl)-5-methyl-N2-(4-methyl-3-(1H-tetrazol-1-yl)phenyl)pyrimidine-2,4-diamine;

Compound 61: 1-(5-(4-(((1S,9aR)-octahydro-1H-quinolizin-1-yl)methylamino)-5-methylpyrimidin-2-ylamino)-2-cyclopropyl-4-fluorophenyl)-4-methyl-1H-tetrazol-5(4H)-one;

Compound 62: N2-(4-fluoro-3-(5-methyl-1H-tetrazol-1-yl)phenyl)-N4-(((1S,9aR)-octahydro-1H-quinolizin-1-yl)methyl)-5-methylpyrimidine-2,4-diamine;

Compound 63: N2-(2-fluoro-5-(5-methyl-1H-tetrazol-1-yl)phenyl)-N4-(((1S,9aR)-octahydro-1H-quinolizin-1-yl)methyl)-5-methylpyrimidine-2,4-diamine;

Compound 64: N4-(((1S,9aR)-octahydro-1H-quinolizin-1-yl)methyl)-N2-(4-methoxy-3-(5-methyl-1H-tetrazol-1-yl)phenyl)-5-methylpyrimidine-2,4-diamine;

Compound 65: N4-(((1S,9aR)-octahydro-1H-quinolizin-1-yl)methyl)-N2-(3-methoxy-5-(5-methyl-1H-tetrazol-1-yl)phenyl)-5-methylpyrimidine-2,4-diamine;

Compound 66: 3-(4-(((1S,9aR)-octahydro-1H-quinolizin-1-yl)methylamino)-5-methylpyrimidin-2-ylamino)benzonitrile;

Compound 67: 5-(4-(((1S,9aR)-octahydro-1H-quinolizin-1-yl)methylamino)-5-methylpyrimidin-2-ylamino)-2-methylbenzonitrile;

Compound 68: 5-(4-(((1S,9aR)-octahydro-1H-quinolizin-1-yl)methylamino)-5-methylpyrimidin-2-ylamino)-2-cyclopropylbenzonitrile;

Compound 69: 5-(4-(((1S,9aR)-octahydro-1H-quinolizin-1-yl)methylamino)-5-methylpyrimidin-2-ylamino)-2-cyclopropyl-4-fluorobenzonitrile;

Compound 70: N4-(((1S,9aR)-octahydro-1H-quinolizin-1-yl)methyl)-N2-(3,5-dimethoxyphenyl)-5-methylpyrimidine-2,4-diamine;

Compound 71: 5-(4-(((1S,9aR)-octahydro-1H-quinolizin-1-yl)methylamino)-5-methylpyrimidin-2-ylamino)benzo[d]oxazol-2(3H)-one;

Compound 72: N2-(4-cyclopropyl-2-fluoro-5-(1H-tetrazol-1-yl)phenyl)-N4-(((1S,9aR)-octahydro-1H-quinolizin-1-yl)methyl)-5-methoxypyrimidine-2,4-diamine;

Compound 73: N4-(((1S,9aR)-octahydro-1H-quinolizin-1-yl)methyl)-5-methoxy-N2-(4-methyl-3-(1H-tetrazol-1-yl)phenyl)pyrimidine-2,4-diamine;

Compound 74: 1-(5-(4-(((1S,9aR)-octahydro-1H-quinolizin-1-yl)methylamino)-5-methoxypyrimidin-2-ylamino)-2-cyclopropyl-4-fluorophenyl)-4-methyl-1H-tetrazol-5(4H)-one;

Compound 75: N2-(4-fluoro-3-(5-methyl-1H-tetrazol-1-yl)phenyl)-N4-(((1S,9aR)-octahydro-1H-quinolizin-1-yl)methyl)-5-methoxypyrimidine-2,4-diamine;

Compound 76: N2-(2-fluoro-5-(5-methyl-1H-tetrazol-1-yl)phenyl)-N4-(((1S,9aR)-octahydro-1H-quinolizin-1-yl)methyl)-5-methoxypyrimidine-2,4-diamine;

Compound 77: N4-(((1S,9aR)-octahydro-1H-quinolizin-1-yl)methyl)-5-methoxy-N2-(4-methoxy-3-(5-methyl-1H-tetrazol-1-yl)phenyl)pyrimidine-2,4-diamine;

Compound 78: N4-(((1S,9aR)-octahydro-1H-quinolizin-1-yl)methyl)-5-methoxy-N2-(3-methoxy-5-(5-methyl-1H-tetrazol-1-yl)phenyl)pyrimidine-2,4-diamine;

Compound 79: 3-(4-(((1S,9aR)-octahydro-1H-quinolizin-1-yl)methylamino)-5-methoxypyrimidin-2-ylamino)benzonitrile;

Compound 80: 5-(4-(((1S,9aR)-octahydro-1H-quinolizin-1-yl)methylamino)-5-methoxypyrimidin-2-ylamino)-2-methylbenzonitrile;

Compound 81: 5-(4-(((1S,9aR)-octahydro-1H-quinolizin-1-yl)methylamino)-5-methoxypyrimidin-2-ylamino)-2-cyclopropylbenzonitrile;

Compound 82: 5-(4-(((1S,9aR)-octahydro-1H-quinolizin-1-yl)methylamino)-5-methoxypyrimidin-2-ylamino)-2-cyclopropyl-4-fluorobenzonitrile;

Compound 83: N4-(((1S,9aR)-octahydro-1H-quinolizin-1-yl)methyl)-5-methoxy-N2-(3,5-dimethoxyphenyl)pyrimidine-2,4-diamine;

Compound 84: 5-(4-(((1S,9aR)-octahydro-1H-quinolizin-1-yl)methylamino)-5-methoxypyrimidin-2-ylamino)benzo[d]oxazol-2(3H)-one;

Compound 85: N2-(4-cyclopropyl-2-fluoro-5-(1H-tetrazol-1-yl)phenyl)-N4-(((1S,9aR)-octahydro-1H-quinolizin-1-yl)methyl)-N5,N5-dimethylpyrimidine-2,4,5-triamine;

Compound 86: N4-(((1S,9aR)-octahydro-1H-quinolizin-1-yl)methyl)-N5,N5-dimethyl-N2-(4-methyl-3-(1H-tetrazol-1-yl)phenyl)pyrimidine-2,4,5-triamine;

Compound 87: 1-(5-(4-(((1S,9aR)-octahydro-1H-quinolizin-1-yl)methylamino)-5-(dimethylamino)pyrimidin-2-ylamino)-2-cyclopropyl-4-fluorophenyl)-4-methyl-1H-tetrazol-5(4H)-one;

Compound 88: N2-(4-fluoro-3-(5-methyl-1H-tetrazol-1-yl)phenyl)-N4-(((1S,9aR)-octahydro-1H-quinolizin-1-yl)methyl)-N5,N5-dimethylpyrimidine-2,4,5-triamine;

Compound 89: N2-(2-fluoro-5-(5-methyl-1H-tetrazol-1-yl)phenyl)-N4-(((1S,9aR)-octahydro-1H-quinolizin-1-yl)methyl)-N5,N5-dimethylpyrimidine-2,4,5-triamine;

Compound 90: N4-(((1S,9aR)-octahydro-1H-quinolizin-1-yl)methyl)-N2-(4-methoxy-3-(5-methyl-1H-tetrazol-1-yl)phenyl)-N5,N5-dimethylpyrimidine-2,4,5-triamine;

Compound 91: N4-(((1S,9aR)-octahydro-1H-quinolizin-1-yl)methyl)-N2-(3-methoxy-5-(5-methyl-1H-tetrazol-1-yl)phenyl)-N5,N5-dimethylpyrimidine-2,4,5-triamine;

Compound 92: 3-(4-(((1S,9aR)-octahydro-1H-quinolizin-1-yl)methylamino)-5-(dimethylamino)pyrimidin-2-ylamino)benzonitrile;

Compound 93: 5-(4-(((1S,9aR)-octahydro-1H-quinolizin-1-yl)methylamino)-5-(dimethylamino)pyrimidin-2-ylamino)-2-methylbenzonitrile;

Compound 94: 5-(4-(((1S,9aR)-octahydro-1H-quinolizin-1-yl)methylamino)-5-(dimethylamino)pyrimidin-2-ylamino)-2-cyclopropylbenzonitrile;

Compound 95: 5-(4-(((1S,9aR)-octahydro-1H-quinolizin-1-yl)methylamino)-5-(dimethylamino)pyrimidin-2-ylamino)-2-cyclopropyl-4-fluorobenzonitrile;

Compound 96: N4-(((1S,9aR)-octahydro-1H-quinolizin-1-yl)methyl)-N2-(3,5-dimethoxyphenyl)-N5,N5-dimethylpyrimidine-2,4,5-triamine;

Compound 97: 5-(4-(((1S,9aR)-octahydro-1H-quinolizin-1-yl)methylamino)-5-(dimethylamino)pyrimidin-2-ylamino)benzo[d]oxazol-2(3H)-one;

Compound 98: N2-(4,4-dimethyl-4H-5-oxa-1,2,3,9b-tetraaza-cyclopenta[a]naphthalen-8-yl)-5-fluoro-N4-(((1S,9aR)-octahydro-1H-quinolizin-1-yl)methyl)-pyrimidine-2,4-diamine;

Compound 99: 4-(((1S,9aR)-octahydro-1H-quinolizin-1-yl)methylamino)-2-(4-cyclopropyl-2-fluoro-5-(4,5-dihydro-4-methyl-5-oxotetrazol-1-yl)phenylamino)pyrimidine-5-carbonitrile;

Compound 100: N2-(4-cyclopropyl-2-fluoro-5-(1H-tetrazol-1-yl)phenyl)-5-(trifluoromethyl)-N4-(((1S,9aR)-octahydro-1H-quinolizin-1-yl)methyl)pyrimidine-2,4-diamine;

Compound 101: 5-(trifluoromethyl)-N4-(((1S,9aR)-octahydro-1H-quinolizin-1-yl)methyl)-N2-(4-methyl-3-(1H-tetrazol-1-yl)phenyl)pyrimidine-2,4-diamine;

Compound 102: 1-(5-(4-(((1S,9aR)-octahydro-1H-quinolizin-1-yl)methylamino)-5-(trifluoromethyl)pyrimidin-2-ylamino)-2-cyclopropyl-4-fluorophenyl)-4-methyl-1H-tetrazol-5(4H)-one;

Compound 103: N2-(4-fluoro-3-(5-methyl-1H-tetrazol-1-yl)phenyl)-5-(trifluoromethyl)-N4-(((1S,9aR)-octahydro-1H-quinolizin-1-yl)methyl)pyrimidine-2,4-diamine;

Compound 104: N2-(2-fluoro-5-(5-methyl-1H-tetrazol-1-yl)phenyl)-5-(trifluoromethyl)-N4-(((1S,9aR)-octahydro-1H-quinolizin-1-yl)methyl)pyrimidine-2,4-diamine;

Compound 105: 5-(trifluoromethyl)-N4-(((1S,9aR)-octahydro-1H-quinolizin-1-yl)methyl)-N2-(4-methoxy-3-(5-methyl-1H-tetrazol-1-yl)phenyl)pyrimidine-2,4-diamine;

Compound 106: 5-(trifluoromethyl)-N4-(((1S,9aR)-octahydro-1H-quinolizin-1-yl)methyl)-N2-(3-methoxy-5-(5-methyl-1H-tetrazol-1-yl)phenyl)pyrimidine-2,4-diamine;

Compound 107: 3-(4-(((1S,9aR)-octahydro-1H-quinolizin-1-yl)methylamino)-5-(trifluoromethyl)pyrimidin-2-ylamino)benzonitrile;

Compound 108: 5-(4-(((1S,9aR)-octahydro-1H-quinolizin-1-yl)methylamino)-5-(trifluoromethyl)pyrimidin-2-ylamino)-2-methylbenzonitrile;

Compound 109: 5-(4-(((1S,9aR)-octahydro-1H-quinolizin-1-yl)methylamino)-5-(trifluoromethyl)pyrimidin-2-ylamino)-2-cyclopropylbenzonitrile;

Compound 110: 5-(4-(((1S,9aR)-octahydro-1H-quinolizin-1-yl)methylamino)-5-(trifluoromethyl)pyrimidin-2-ylamino)-2-cyclopropyl-4-fluorobenzonitrile;

Compound 111: 5-(trifluoromethyl)-N4-(((1S,9aR)-octahydro-1H-quinolizin-1-yl)methyl)-N2-(3,5-dimethoxyphenyl)pyrimidine-2,4-diamine;

Compound 112: 5-(4-(((1S,9aR)-octahydro-1H-quinolizin-1-yl)methylamino)-5-(trifluoromethyl)pyrimidin-2-ylamino)benzo[d]oxazol-2(3H)-one;

Compound 113: 4-(((1S,9aR)-octahydro-1H-quinolizin-1-yl)methylamino)-2-(4-methoxy-3-(5-methyl-1H-tetrazol-1-yl)phenylamino)pyrimidine-5-carbonitrile;

Compound 114: 4-(((1S,9aR)-octahydro-1H-quinolizin-1-yl)methylamino)-2-(4-fluoro-3-(5-methyl-1H-tetrazol-1-yl)phenylamino)pyrimidine-5-carbonitrile;

Compound 115: 4-(((1S,9aR)-octahydro-1H-quinolizin-1-yl)methylamino)-2-(3-methoxy-5-(5-methyl-1H-tetrazol-1-yl)phenylamino)pyrimidine-5-carbonitrile;

Compound 116: 4-(((1S,9aR)-octahydro-1H-quinolizin-1-yl)methylamino)-2-(4-cyclopropyl-2-fluoro-5-(1H-tetrazol-1-yl)phenylamino)pyrimidine-5-carbonitrile;

Compound 117: 4-(((1S,9aR)-octahydro-1H-quinolizin-1-yl)methylamino)-2-(4-methyl-3-(1H-tetrazol-1-yl)phenylamino)pyrimidine-5-carbonitrile;

Compound 118: 4-(((1S,9aR)-octahydro-1H-quinolizin-1-yl)methylamino)-2-(2-fluoro-5-(5-methyl-1H-tetrazol-1-yl)phenylamino)pyrimidine-5-carbonitrile;

Compound 119: 4-(((1S,9aR)-octahydro-1H-quinolizin-1-yl)methylamino)-2-(3-cyano-4-methylphenylamino)pyrimidine-5-carbonitrile;

Compound 120: 4-(((1S,9aR)-octahydro-1H-quinolizin-1-yl)methylamino)-2-(3-cyano-4-cyclopropylphenylamino)pyrimidine-5-carbonitrile;

Compound 121: 4-(((1S,9aR)-octahydro-1H-quinolizin-1-yl)methylamino)-2-(3,5-dimethoxyphenylamino)pyrimidine-5-carbonitrile;

Compound 122: 4-(((1S,9aR)-octahydro-1H-quinolizin-1-yl)methylamino)-2-(3-(5-cyclopropyl-1H-tetrazol-1-yl)-4-fluorophenylamino)pyrimidine-5-carbonitrile;

Compound 123: 4-(((1S,9aR)-octahydro-1H-quinolizin-1-yl)methylamino)-2-(5-(5-cyclopropyl-1H-tetrazol-1-yl)-2-fluorophenylamino)pyrimidine-5-carbonitrile;

Compound 124: 4-(((1S,9aR)-octahydro-1H-quinolizin-1-yl)methylamino)-2-(4-chloro-3-(5-cyclopropyl-1H-tetrazol-1-yl)phenylamino)pyrimidine-5-carbonitrile;

Compound 125: 4-(((1S,9aR)-octahydro-1H-quinolizin-1-yl)methylamino)-2-(4-methoxy-3-(5-methyl-1H-tetrazol-1-yl)phenylamino)pyrimidine-5-carboxamide;

Compound 126: 4-(((1S,9aR)-octahydro-1H-quinolizin-1-yl)methylamino)-2-(4-fluoro-3-(5-methyl-1H-tetrazol-1-yl)phenylamino)pyrimidine-5-carboxamide;

Compound 127: 4-(((1S,9aR)-octahydro-1H-quinolizin-1-yl)methylamino)-2-(2-fluoro-5-(5-methyl-1H-tetrazol-1-yl)phenylamino)pyrimidine-5-carboxamide;

Compound 128: 2-((2-fluoro-4-hydroxy-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 129: 2-((2-fluoro-4-(2-methoxyethoxy)-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 130: 2-((2-fluoro-5-(4-methyl-5-oxo-4,5-dihydro-1H-tetrazol-1-yl)-4-((3-methyloxetan-3-yl)methoxy)phenyl)amino)-4-(((((1S,9aR)-octahydro-2H-quinolizin-1-yl)methyl)amino)pyrimidine-5-carbonitrile;

Compound 131: 2-((4-((1,4-dioxan-2-yl)methoxy)-2-fluoro-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 132: 2-((4-(2,3-dihydroxypropoxy)-2-fluoro-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 133: 2-((2-fluoro-4-(2-(2-methoxyethoxy)ethoxy)-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 134: 2-((2-fluoro-5-(4-methyl-5-oxo-4,5-dihydro-1H-tetrazol-1-yl)-4-(3,3,3-trifluoro-2-hydroxy-2-(trifluoromethyl)propoxy)phenyl)amino)-4-(((((1S,9aR)-octahydro-2H-quinolizin-1-yl)methyl)amino)pyrimidine-5-carbonitrile;

Compound 135: 2-((2-fluoro-4-(2-hydroxyethoxy)-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 136: 2-((2-fluoro-4-(2-hydroxypropoxy)-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 137: 2-((2-fluoro-4-(2-hydroxyethoxy-1,1,2,2-d4)-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 138: 2-(4-((5-fluoro-4-(((((1S,9aR)-octahydro-2H-quinolizin-1-yl)methyl)amino)pyrimidin-2-yl)amino)-2-(1H-tetrazol-1-yl)phenoxy)ethan-1-ol;

Compound 139: 2-(4-((5-chloro-4-(((((1S,9aR)-octahydro-2H-quinolizin-1-yl)methyl)amino)pyrimidin-2-yl)amino)-2-(1H-tetrazol-1-yl)phenoxy)ethan-1-ol;

Compound 140: 2-((4-(2-hydroxyethoxy)-3-(1H-tetrazol-1-yl)phenyl)amino)-4-(((((1S,9aR)-octahydro-2H-quinolizin-1-yl)methyl)amino)pyrimidine-5-carbonitrile;

Compound 141: 2-(4-((4-(((((1S,9aR)-octahydro-2H-quinolizin-1-yl)methyl)amino)pyrimidin-2-yl)amino)-2-(1H-tetrazol-1-yl)phenoxy)ethan-1-ol;

Compound 142: 2-((2-fluoro-4-((S)-2-hydroxypropoxy)-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 143: 2-((2-fluoro-4-((R)-2-hydroxypropoxy)-5-(4-methyl-5-oxo-4,5-dihydro-1H-tetrazol-1-yl)phenyl)amino)-4-(((((1S,9aR)-octahydro-2H-quinolizin-1-yl)methyl)amino)pyrimidine-5-carbonitrile;

Compound 144: 2-((3-cyano-4-(2-hydroxypropoxy)phenyl)amino)-4-(((((1S,9aR)-octahydro-2H-quinolizin-1-yl)methyl)amino)pyrimidine-5-carbonitrile;

Compound 145: 5-((5-fluoro-4-(((((1S,9aR)-octahydro-2H-quinolizin-1-yl)methyl)amino)pyrimidin-2-yl)amino)-2-(2-hydroxypropoxy)benzonitrile;

Compound 146: 1-(5-((5-chloro-4-(((((1S,9aR)-octahydro-2H-quinolizin-1-yl)methyl)amino)pyrimidin-2-yl)amino)-4-fluoro-2-hydroxyphenyl)-4-methyl-1,4-dihydro-5H-tetrazol-5-one;

Compound 147: 1-(5-((5-fluoro-4-((((1S,9aR)-octahydro-2H-quinolizin-1-yl)methyl)amino)pyrimidin-2-yl)amino)-4-fluoro-2-hydroxyphenyl)-4-methyl-1,4-dihydro-5H-tetrazol-5-one;

Compound 148: 1-(4-fluoro-5-((5-fluoro-4-((((1S,9aR)-octahydro-2H-quinolizin-1-yl)methyl)amino)pyrimidin-2-yl)amino)-2-((1-hydroxy-2-methylpropan-2-yl)oxy)phenyl)-4-methyl-1,4-dihydro-5H-tetrazol-5-one;

Compound 149: 1-(4-fluoro-5-((5-fluoro-4-((((1S,9aR)-octahydro-2H-quinolizin-1-yl)methyl)amino)pyrimidin-2-yl)amino)-2-((S)-2-hydroxypropoxy)phenyl)-4-methyl-1,4-dihydro-5H-tetrazol-5-one;

Compound 150: ethyl 2-(4-((5-cyano-4-((((1S,9aR)-octahydro-2H-quinolizin-1-yl)methyl)amino)pyrimidin-2-yl)amino)-5-fluoro-2-(4-methyl-5-oxo-4,5-dihydro-1H-tetrazol-1-yl)phenoxy)-2-methylpropanoate;

Compound 151: 2-((2-fluoro-4-((1-hydroxy-2-methylpropan-2-yl)oxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile;

Compound 152: 1-(5-((5-chloro-4-((((1S,9aR)-octahydro-2H-quinolizin-1-yl)methyl)amino)pyrimidin-2-yl)amino)-4-fluoro-2-((S)-2-hydroxypropoxy)phenyl)-4-methyl-1,4-dihydro-5H-tetrazol-5-one;

Compound 153: 1-(5-((5-chloro-4-((((1S,9aR)-octahydro-2H-quinolizin-1-yl)methyl)amino)pyrimidin-2-yl)amino)-4-fluoro-2-((1-hydroxy-2-methylpropan-2-yl)oxy)phenyl)-4-methyl-1,4-dihydro-5H-tetrazol-5-one;

Compound 154: 1-(4-fluoro-5-((5-fluoro-4-((((1S,9aR)-octahydro-2H-quinolizin-1-yl)methyl)amino)pyrimidin-2-yl)amino)-2-(2-hydroxy-2-methylpropoxy)phenyl)-4-methyl-1,4-dihydro-5H-tetrazol-5-one;

Compound 155: 1-(5-((5-chloro-4-((((1S,9aR)-octahydro-2H-quinolizin-1-yl)methyl)amino)pyrimidin-2-yl)amino)-4-fluoro-2-(2-hydroxy-2-methylpropoxy)phenyl)-4-methyl-1,4-dihydro-5H-tetrazol-5-one; and Compound 156: 2-((2-fluoro-4-(2-hydroxy-2-methylpropoxy)-5-(4-methyl-5-oxo-4,5-dihydro-1H-tetrazol-1-yl)phenyl)amino)-4-((((1S,9aR)-octahydro-2H-quinolizin-1-yl)methyl)amino)pyrimidine-5-carbonitrile.

21. A pharmaceutical composition comprising a compound of claim 1 and a pharmaceutically acceptable carrier.

22. A method for making a compound according to the formula

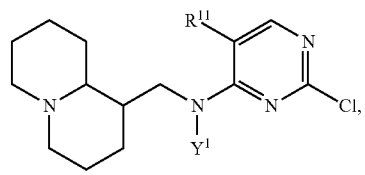

wherein

R$^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, alkylthioalkylene, substituted alkylthioalkylene, and SF$_5$; and Y$^1$ is selected from hydrogen and alkyl;

the method comprising contacting a compound of the formula

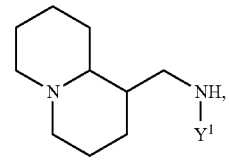

with a compound of the formula:

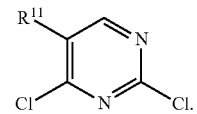

23. A method for making a compound according to the formula

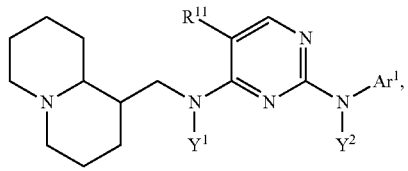

wherein

R$^{11}$ is selected from hydrogen, alkyl, substituted alkyl, cycloalkyl, substituted cycloalkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, substituted alkynyl, aryl, substituted aryl, heteroaryl, substituted heteroaryl, alkylthioalkylene, substituted alkylthioalkylene, and SF$_5$;

Y$^1$ and Y$^2$ are independently selected from hydrogen and alkyl; and

Ar$^1$ is selected from aryl, substituted aryl, heteroaryl, and substituted heteroaryl;

the method comprising contacting a compound of the formula

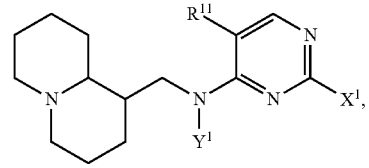

wherein X$^1$ is a halogen;

with a compound of the formula HNY$^2$Ar$^1$.

24. The method of claim 23, wherein the reaction is run in a polar aprotic or polar protic solvent.

25. The method of claim 23, wherein Ar$^1$ is aryl or substituted aryl.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic amino acid sequence

<400> SEQUENCE: 1

Arg Phe Ala Arg Lys Gly Ser Leu Arg Gln Lys Asn Val
1               5                   10